US005591764A

United States Patent [19]

Fahmy et al.

[11] Patent Number: 5,591,764

[45] Date of Patent: Jan. 7, 1997

[54] N-ACYLATED PYRAZOLINES

[75] Inventors: Mohamed A. H. Fahmy, deceased, late of Wilmington, by Salwa Fahmy, executor; Charles R. Harrison, Newark; George P. Lahm, Wilmington; Thomas M. Stevenson, Newark, all of Del.

[73] Assignee: E. I. Du Pont de Nemours and Company, Wilmington, Del.

[21] Appl. No.: 468,394

[22] Filed: Jun. 6, 1995

Related U.S. Application Data

[62] Division of Ser. No. 279,377, Jul. 22, 1994, Pat. No. 5,491,162, which is a continuation of Ser. No. 4,860, Jan. 15, 1993, abandoned, which is a division of Ser. No. 659,402, Mar. 12, 1991, Pat. No. 5,196,408, which is a continuation-in-part of Ser. No. 304,011, Jan. 25, 1989, abandoned, which is a continuation-in-part of Ser. No. 249,882, Sep. 27, 1988, abandoned.

[51] Int. Cl.$^6$ .......................... A01N 43/56; C07D 231/06

[52] U.S. Cl. .......................... 514/403; 514/326; 546/211; 548/364.1; 548/379.4

[58] Field of Search .......................... 548/379.4; 514/403

[56] References Cited

U.S. PATENT DOCUMENTS

| | | |
|---|---|---|
| 4,070,365 | 1/1978 | van Daalen et al. . |
| 4,156,007 | 5/1979 | van Daalen et al. . |
| 4,174,393 | 11/1979 | van Daalen et al. . |
| 4,407,813 | 10/1983 | Ozawa et al. . |
| 4,439,440 | 3/1984 | van Hes et al. . |
| 4,572,914 | 2/1986 | van Hes et al. . |
| 4,663,341 | 5/1987 | Jacobson . |
| 4,960,784 | 10/1990 | Lahm . |
| 5,006,524 | 4/1991 | Lahm . |

FOREIGN PATENT DOCUMENTS

| | | |
|---|---|---|
| 0113213 | 7/1984 | European Pat. Off. . |
| 0153127 | 8/1985 | European Pat. Off. . |
| 0286346 | 10/1988 | European Pat. Off. . |
| 0300692 | 1/1989 | European Pat. Off. . |
| WO88/05046 | 7/1988 | WIPO . |
| WO88/07994 | 10/1988 | WIPO . |

OTHER PUBLICATIONS

Grosscurt et al, *J. Agric. Food Chem.*, 27(2), 406–409, 1979.

*Primary Examiner*—Robert W. Ramsuer

[57] ABSTRACT

N-sulfenylated and N-acylated pyrazoline arthropodicides, compositions containing them and methods for controlling arthropods by applying compounds of the invention to them or to their environment. The pyrazolines are selected from those of Formulae I to III wherein $R_1$, $R_2$, $R_3$, Q, A, B, J, K, Y, m, n and p are as defined in the text:

I $(R_2)_n$ $(R_3)_p$ H H N N C O N Q $(R_1)_m$

II $(R_2)_n$ $(R_3)_p$ N N H H C O N Y $(R_1)_m$

III $(R_2)_n$ A B J K N N N O Z $(R_1)_m$

4 Claims, No Drawings

N-ACYLATED PYRAZOLINES

This is a division of application Ser. No. 08/279,377, filed Jul. 22, 1994, which now U.S. Pat. No. 5,491,162, is a continuation of U.S. Ser. No. 08/004,860, filed Jan. 15, 1993, now abandoned, which in turn is a divisional of U.S. Ser. No. 07/659,402, filed Mar. 12, 1991, now U.S. Pat. No. 5,196,408, which is a continuation-in-part of U.S. Ser. No. 07/304,011 filed Jan. 25, 1989, now abandoned, which in turn is a continuation-in-part of U.S. Ser. No. 07/249,882 filed Sep. 27, 1988, now abandoned.

BACKGROUND OF THE INVENTION

The following publications disclose pyrazolines:

| | |
|---|---|
| U.S. Pat. No. 4,070,365 | EPA 21,506 |
| U.S. Pat. No. 4,156,007 | EPA 58,424 |
| U.S. Pat. No. 4,174,393 | EPA 65,334 |
| U.S. Pat. No. 4,663,341 | EPA 113,213 |
| WO 88/05046 | EPA 153,127 |
| WO 88/07994 | EPA 286,346 |
| WO 89/00562 | EPA 300,692 |
| Grosscurt et al., J. Agric. Food Chem., Vol. 27, No. 2 (1979). | |

SUMMARY OF THE INVENTION

This invention pertains to compounds of Formulae I, II and III, including all geometric and stereoisomers, agriculturally suitable salts thereof, compositions containing them and their use as arthropodicides in agricultural and home uses, Hereafter, the compounds, isomers and salts are referred to as compound(s) for the sake of simplicity. The compounds are:

I

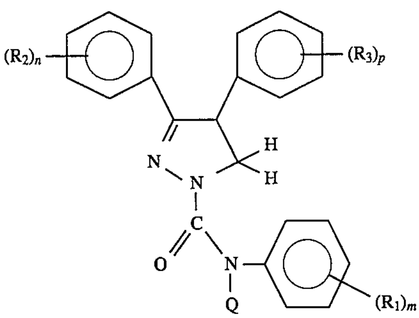

II

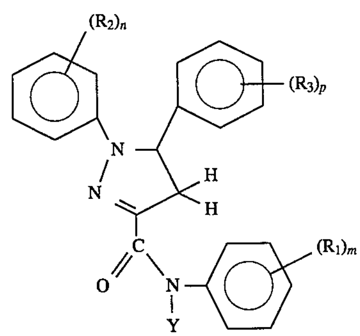

-continued

III

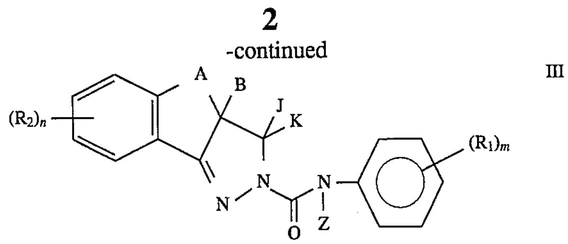

wherein

A is a 1, 2 or 3-atom bridge comprising 0 to 3 carbon atoms, 0 to 1 oxygen atoms, $NR_6$, or S(O)q, wherein each carbon individually can be substituted with 1 to 2 substituents selected from 1 to 2 halogen, $C_1$ to $C_6$ alkyl, $C_2$ to $C_4$ alkoxycarbonyl or phenyl optionally substituted with 1 to 3 substituents independently selected from W and one of the carbon atoms can be combined into the group C(O) or C(S);

B is H, $C_1$ to $C_6$ alkyl, $C_4$ to $C_7$ cycloalkyl alkyl, $C_3$ to $C_6$ cycloalkyl optionally substituted with 1 to 2 halogens or 1 to 2 $CH_3$; $C_1$ to $C_6$ haloalkyl, $C_2$ to $C_6$ alkenyl, $C_2$ to $C_6$ haloalkenyl, $C_2$ to $C_6$ alkynyl, $OR_7$, $C_2$ to $C_6$ alkoxyalkyl, $C_2$ to $C_6$ cyanoalkyl, $C_3$ to $C_8$ alkoxycarbonylalkyl, $CO_2R_4$, $C(O)R_4$, $C(O)NR_4R_5$, $C(S)NR_4R_5$, $C(S)R_4$, $C(S)SR_4$, phenyl, phenyl substituted by $(R_{14})p$, benzyl, or benzyl substituted with 1 to 3 substituents independently selected from W;

J is H, $C_1$ to $C_4$ alkyl or phenyl optionally substituted with W;

K is H or $CH_3$;

q is 0, 1 or 2;

$R_1$, $R_2$, $R_3$ and $R_{14}$ are independently selected from $R_4$, halogen, CN, $N_3$, SCN, $NO_2$, $OR_4$, $SR_4$, $S(O)R_4$, $S(O)_2R_4$, $OC(O)R_4$, $OS(O)_2R_4$, $CO_2R_4$, $C(O)R_4$, $C(O)NR_4R_5$, $S(O)_2NR_4R_5$, $NR_4R_5$, $NR_5C(O)R_4$, $OC(O)NHR_4$, $NR_5C(O)NHR_4$ and $NR_5S(O)_2R_4$; or when m, n or p is 2, $R_1$, $R_2$, $R_3$ or $R_{14}$ can independently be taken together as $OCH_2O$, $OCH_2CH_2O$ or $CH_2CH_2O$, to form a 5 or 6-membered ring, each of which can be independently substituted with 1 to 4 halogen atoms or 1 to 2 methyl groups;

$R_4$ is selected from H, $C_1$ to $C_6$ alkyl, $C_3$ to $C_6$ cycloalkyl, $C_3$ to $C_8$ alkoxycarbonylalkyl, $C_3$ to $C_6$ alkenyl, $C_3$ to $C_6$ alkynyl, $C_1$ to $C_6$ haloalkyl, $C_3$ to $C_6$ haloalkenyl, $C_1$ to $C_6$ alkyl substituted with CN, $CO_2CH_3$, $CO_2CH_2CH_3$, $OCH_3$, $OCH_2CH_3$, $SCH_3$, $SCH_2CH_3$ or $NO_2$, or $R_4$ is phenyl or benzyl, either optionally substituted with W; or $R_4$ and $R_5$ can be taken together as $(CH_2)_4$, $(CH_2)_5$ or $CH_2CH_2OCH_2CH_2$;

$R_5$ is selected from H, $C_1$ to $C_4$ alkyl, $C_3$ to $C_4$ alkenyl, $C_3$ to $C_4$ alkynyl or $C_1$ to $C_4$ haloalkyl;

m, n and p are independently 1 to 3;

W is halogen, CN, $NO_2$, $C_1$ to $C_2$ alkyl, $C_1$ to $C_2$ haloalkyl, $C_1$ to $C_2$ alkoxy, $C_1$ to $C_2$ haloalkoxy, $C_1$ to $C_2$ alkylthio, $C_1$ to $C_2$ haloalkylthio, $C_1$ to $C_2$ alkylsulfonyl or $C_1$ to $C_2$ haloalkylsulfonyl;

$R_6$ is H, $C_1$ to $C_4$ alkyl, $C_1$ to $C_4$ haloalkyl, $C_2$ to $C_4$ alkenyl, $C_2$ to $C_4$ haloalkenyl, phenyl optionally substituted with W or benzyl optionally substituted with W;

$R_7$ is H, $C_1$ to $C_4$ alkyl, $C_2$ to $C_4$ alkenyl, $C_2$ to $C_4$ alkynyl, $C_2$ to $C_4$ alkylcarbonyl, $C_2$ to $C_4$ alkoxycarbonyl or $C_1$–$C_4$ alkylsulfonyl;

Q is SX, $C_2$ to $C_{22}$ alkoxycarbonyl, $C_2$ to $C_{22}$ haloalkoxycarbonyl, $C_7$ to $C_{15}$ phenoxycarbonyl optionally substituted with 1 to 3 substituents selected from W; $C_7$ to $C_{15}$ phenyl carbonyl optionally substituted with 1 to 3 substituents independently selected from W; $C_2$ to $C_{22}$ alkyl carbonyl, $C_2$ to $C_{22}$ haloalkyl carbonyl, CHO, $C(O)CO_2R_5$, or $C_8$ to $C_{12}$ benzyloxycarbonyl optionally substituted with 1 to 3 substituents independently selected from W; when Q is other than SX, $R_3$ is other than $CO_2R_4$, $C(O)R_4$, $SO_2NR_4R_5$ or $CONR_4R_5$;

Y is $C_5$ to $C_{22}$ alkyl, $C_2$ to $C_{22}$ haloalkyl, $C_5$ to $C_{22}$ alkoxyalkyl, $C_4$ to $C_{22}$ alkoxyalkoxyalkyl, $C_5$ to $C_{12}$ alkylthio, $C_5$ to $C_{12}$ haloalkylthio, $C_5$ to $C_{22}$ alkylcarbonyl, $C_5$ to $C_{22}$ haloalkylcarbonyl, $C_5$ to $C_{22}$ alkoxycarbonyl, $C_3$ to $C_{22}$ haloalkoxycarbonyl, or SX;

Z is $C_7$ to $C_{22}$ alkyl, $C_2$ to $C_{22}$ haloalkyl, $C_7$ to $C_{22}$ alkoxyalkyl, $C_4$ to $C_{22}$ alkoxyalkoxyalkyl, $C_7$ to $C_{12}$ alkylthio, $C_7$ to $C_{12}$ haloalkylthio, $C_7$ to $C_{22}$ alkylcarbonyl, $C_7$ to $C_{22}$ haloalkylcarbonyl, $C_7$ to $C_{22}$ alkoxycarbonyl, $C_3$ to $C_{22}$ haloalkoxycarbonyl, $C_7$ to $C_{15}$ phenylcarbonyl optionally substituted by 1 to 3 substituents independently selected from W; or SX;

X is $NR_8C(=O)R_9$, X₁

$NR_8S(O)_aR_9$, X₂

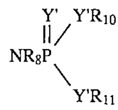

X₃

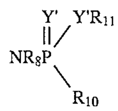

X₄

$C(=O)R_9$ X₅

$P(=O)(OR_{10})(OR_{11})$ X₆

$NR_8R_{12}$ X₇ or $SR_{10}$ X₈

$R_8$ and $R_{12}$ are independently $C_1$ to $C_6$ alkyl, $C_1$ to $C_6$ haloalkyl, $C_3$ to $C_6$ cycloalkyl, $C_4$ to $C_7$ cycloalkylalkyl, phenyl optionally substituted by 1 to 2 substituents selected from W, benzyl optionally substituted by 1 to 2 substituents independently selected from W, phenethyl optionally substituted by 1 to 2 substituents independently selected from W, $C_2$ to $C_6$ cyanoalkyl, $C_2$ to $C_6$ alkoxyalkyl, $C_3$ to $C_8$ alkoxycarbonylalkyl, $C_4$ to $C_8$ dialkylaminocarbonylalkyl; or $R_8$ and $R_{12}$ can be taken together as $(CH_2)_4$, $(CH_2)_5$ or $(CH_2)_2O(CH_2)_2$, $R_9$ is F, $C_1$ to $C_{22}$ alkyl, $C_3$ to $C_6$ cycloalkyl, $C_3$ to $C_6$ cycloalkoxy, $C_2$ to $C_8$ dialkylamino, $C_1$ to $C_6$ haloalkyl, phenyl or phenoxy either optionally substituted by 1 to 2 substituents independently selected from W; $C_1$ to $C_{22}$ alkoxy, $C_1$ to $C_4$ alkoxy substituted by cyano, nitro, $C_2$ to $C_4$ alkoxy, $C_4$ to $C_8$ alkoxyalkoxy, $C_1$ to $C_2$ alkylthio, $C_2$ to $C_3$ alkoxycarbonyl, $C_3$ to $C_5$ dialkylaminocarbonyl, phenyl or 1 to 6 halogens; or $R_9$ is morpholino, piperidino or pyrrolidino, 1-naphthoxy, 2,2-dimethyl-2,3-dihydrobenzofuranoxy-7 or $ON{=}C(CH_3)SCH_3$;

$R_{10}$ and $R_{11}$ are independently $C_1$ to $C_4$ alkyl, $C_2$ to $C_4$ haloalkyl or phenyl optionally substituted by 1 to 2 substituents independently selected from W; or $R_{10}$ and $R_{11}$ can be taken together as $(CH_2)_2$, $(CH_2)_3$ or $CH_2C(CH_3)_2CH_2$;

Y' is S or O; and a is 0 to 2.

Preferred compounds A are those of Formula I, II or III wherein:

$R_1$, $R_2$, $R_3$ and $R_{14}$ are independently $R_4$, $CO_2R_4$, halogen, CN, $NO_2$, $OR_4$, $SR_4$, $S(O)R_4$, $S(O)_2R_4$ or $NR_4R_5$, or when m, n or p is 2;

$R_1$, $R_2$, $R_3$ or $R_{14}$ can be taken together as $OCH_2O$, $OCH_2CH_2O$ or $CH_2CH_2O$, each of which can be substituted with 1 to 4 halogen atoms or 1 to 2 methyl groups;

$R_4$ is $C_1$ to $C_2$ alkyl, $C_3$ to $C_4$ alkenyl, $C_1$ to $C_2$ haloalkyl, $C_3$ to $C_4$ haloalkenyl or phenyl optionally substituted with halogen;

$R_5$ is H or $C_1$ to $C_2$ alkyl;

Q is SX, CHO, $C_2$ to $C_6$ alkoxycarbonyl, $C_2$ to $C_6$ haloalkoxycarbonyl, $C_2$ to $C_6$ alkylcarbonyl, $C_2$ to $C_4$ haloalkylcarbonyl, $C_7$ to $C_{10}$ phenoxycarbonyl, $C_7$ to $C_{10}$ phenylcarbonyl or $C_8$ to $C_{10}$ benzyloxycarbonyl each phenoxy, phenyl or benzyloxy group optionally substituted with 1 to 2 substituents selected from W;

X is $X_1$, $X_2$, $X_3$, $X_4$ or $X_5$;

$R_8$ and $R_{12}$ are independently $C_1$ to $C_6$ alkyl, $C_1$ to $C_6$ haloalkyl, $C_5$ to $C_6$ cycloalkyl, $C_3$ to $C_8$ alkoxycarbonylalkyl, phenyl, benzyl or phenethyl, each optionally independently substituted with W; or $R_8$ and $R_{12}$ can be taken together as $(CH_2)_4$, $(CH_2)_5$ or $(CH_2)_2O(CH_2)_2$;

$R_{10}$ and $R_{11}$ are independently $C_1$ to $C_3$ alkyl or phenyl;

a is 2;

Formula III is

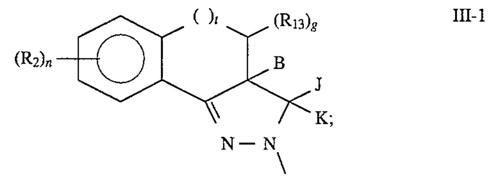

III-1

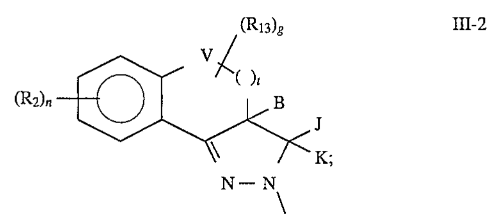

III-2

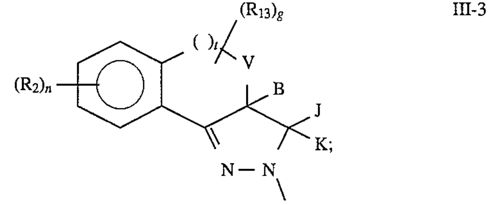

III-3

-continued

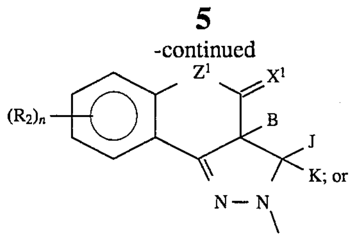

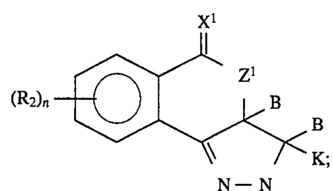

X' is O or S;

t is 0, 1 or 2;

V is O, $S(O)_q$, or $NR_6$;

Z' is O or $NR_6$;

$R_{13}$ is H, halogen, $C_1$ to $C_6$ alkyl, $C_2$ to $C_4$ alkoxycarbonyl, phenyl or phenyl substituted by 1 to 3 substituents independently selected from W; and g is 0, 1 or 2.

Preferred compounds B are compounds A wherein:

$R_1$ is halogen, CN, $NO_2$, $OCF_2H$, $OCF_3$, $OCH_2CF_3$, $OCF_2CF_2H$, $CF_3$ or when m is 2 then $R_1$ may be taken together as $CH_2C(CH_3)_2O$ or $CF_2CF_2O$ to form a 5 membered ring;

$R_2$ is H, halogen, CN, $NO_2$, $OCH_3$, $OCF_2H$, $OCH_2CF_3$, $OCF_3$, $SCH_3$, $SCF_2H$, $SCF_3$, $CF_3$, $OCF_2CF_2H$ or phenoxy;

$R_3$ and $R_{14}$ are independently $R_2$ or $CO_2R_4$;

Q is SX, $C_2$ to $C_4$ alkoxycarbonyl, $C_2$ to $C_4$ alkylcarbonyl, $C_7$ to $C_8$ phenylcarbonyl or CHO;

X is $X_1$, $X_2$ or $X_3$;

$R_8$ is $C_1$ to $C_4$ alkyl, $CF_3$, cyclohexyl, phenyl optionally substituted with W or benzyl optionally substituted by W;

$R_9$ is F, $C_1$ to $C_{22}$ alkyl, $C_1$ to $C_6$ haloalkyl, phenyl or phenoxy optionally substituted by W; $C_1$ to $C_{22}$ alkoxy, dimethylamino or $C_1$ to $C_4$ alkoxy substituted with $NO_2$, $C_2$ to $C_4$ alkoxy or 1 to 6 halogens;

m, n or p are independently 1 to 2 and one substituent is in the 4-position and

B is H, $C_1$–$C_4$ alkyl, $CO_2R_4$, $C(O)R_4$ or phenyl optionally substituted by $(R_{14})p$.

Preferred compounds C are preferred compounds B wherein:

X is $X_1$;

$R_8$ is $C_1$ to $C_4$ alkyl;

$R_9$ is $C_1$ to $C_{22}$ alkoxy;

Formula III is III-1 or III-2;

V is O or $CH_2$;

t is 1; and $R_{13}$ is H.

Preferred compounds D are preferred compounds B wherein:

X is $X_2$;

$R_8$ is $C_1$ to $C_4$ alkyl or phenyl optionally substituted with $CH_3$ or Cl; and $R_9$ is $C_1$ to $C_6$ alkyl, $C_1$ to $C_6$ haloalkyl, dimethylamino or phenyl optionally substituted with $CH_3$ or Cl.

Preferred compounds E are preferred compounds C of Formula I.

Preferred compounds F are preferred compounds B of Formula II.

Preferred compounds G are preferred compounds B of Formula III.

Specifically preferred are the compounds:

H. methyl 3,4-di-(4-chlorophenyl)-1-[[N-[[(ethoxycarbonyl)(1-methylethyl)amino]thio]-N-[4-(trifluoromethyl)phenyl]amino]carbonyl]-4,5-dihydro-1H-pyrazole of preferred E;

I. N-acetyl-3,4-bis(4-chloropheny)-4,5-dihydro-N-[4-(trifluoromethyl) phenyl]-1H-pyrazole-1-carboxamide of preferred F; and J. methyl 7-chloro-3,3a,4,5-tetrahydro-2-[[N-[[N-methyl-N-[octadecyloxy)carbonyl]amino]thio]-N-[4-(trifluoromethyl)-phenyl]amino]carbonyl]-2H-benz[g]indazole-3a-carboxylate of preferred G.

DETAILS OF THE INVENTION

Compounds of Formulae I, II and III can be prepared by the reaction of a pyrazoline compound of Formula V, VI or VII with a sulfenyl halide of Formula IV.

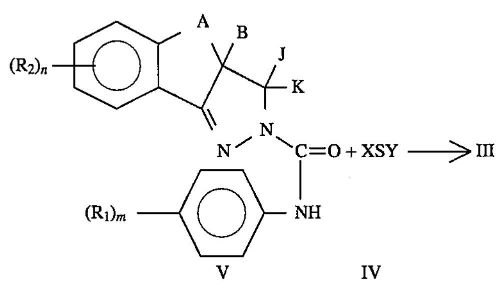

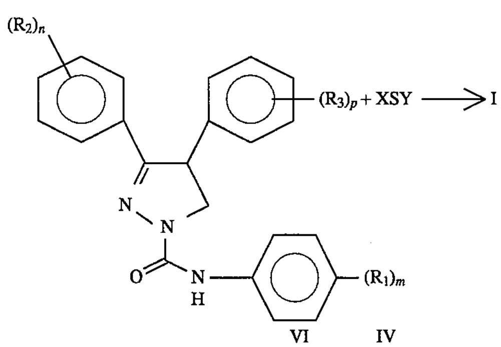

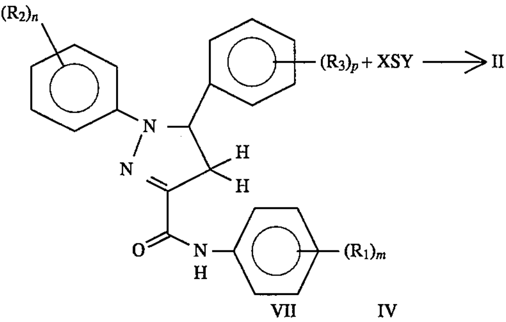

wherein

Y in Formula IV represents a halogen such as chloro, bromo, or iodo.

The treatment of V, VI or VII with IV is carried out by mixing the two reagents in the presence of a base and a solvent. Suitable bases are the tertiary amines such as triethylamine or pyridine. Alkali metal bases such as sodium hydride or potassium tert-butoxide or organo lithium bases such as aryl or alkyllithium also can be utilized.

Suitable solvents include methylene chloride, tetrahydrofuran or ether. In some cases, the base can also be used as the solvent, e.g., pyridine. In most cases, it is desirable to mix compounds of Formula V, VI or VII and the desired base at a low temperature of about 5° C. to −70° C. which is held at this temperature during treatment with the appropriate amount of compounds of Formula IV. The mixture is then warmed to room temperature to complete the reaction. Generally, it is desirable to employ a moderate stoichiometric excess, up to 10% of the base and compounds of Formula IV relative to compounds of Formula V, VI or VII. Water should be excluded from the reaction mixture by using anhydrous reagents and conducting the treatment in a nitrogen atmosphere. The product is isolated and purified by conventional techniques as demonstrated in Example 1. The pyrazoline precursors of Formula V, VI, and VII are compounds that can be prepared by methods known to those skilled in the art. The methods of pyrazoline synthesis have been recently reviewed by El-Rayyes and Al-Awadi in "Synthesis" page 1028 to 1042, November 1985.

Compounds of Formula V wherein B═H can be prepared by the following sequence of reactions as shown in Scheme 1.

SCHEME I

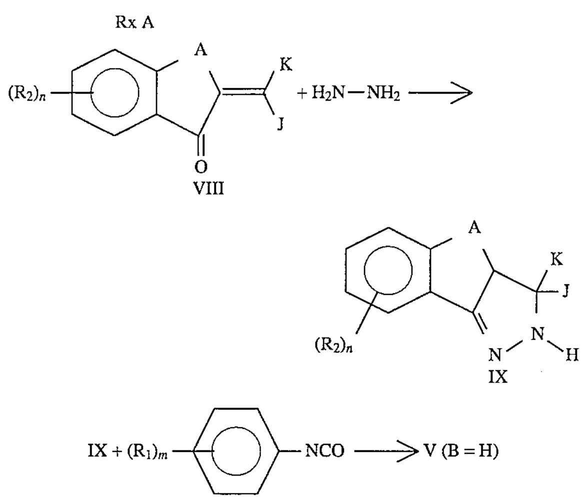

In another embodiment, certain compounds of Formula V wherein B is other than H can be prepared directly from compounds of Formula V wherein B is H by further treatment with a base and the appropriate type of electrophile as illustrated by Scheme 2.

SCHEME 2

SCHEME 2

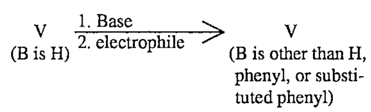

Compounds of Formula V where B is also phenyl or substituted phenyl can be prepared by reaction of a substituted ketone of Formula X with hydrazine as shown in Scheme 3.

SCHEME 3

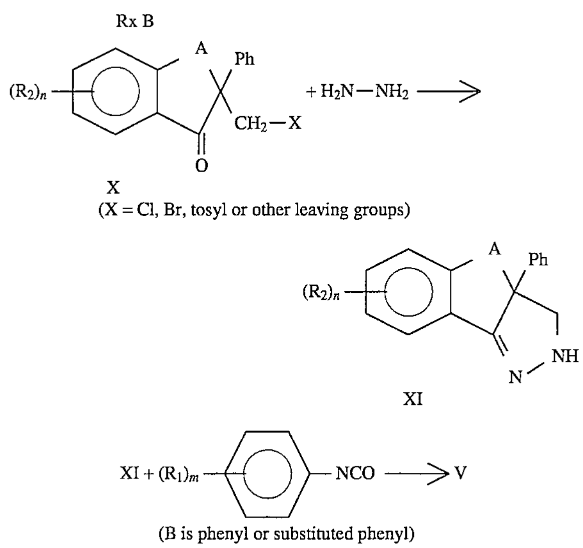

For compounds of Formula VI, Grosscurt et al., have published the synthesis of 3,4-diphenyl-1-phenylcarbamoyl-2-pyrazolines in Journal of Agricultural and Food Chemistry, 27:406–409 (1979). Similar methods of synthesis are also presented in U.S. Pat. No. 4,633,341. Compounds of Formula VII have been prepared using procedures indicated in PCT WO 88/05046.

Sulfenyl halides of the type XSY (Formula IV) wherein X and Y are as specified in this disclosure are known in the literature. A review article by Kule in Synthesis, 561, (1970) describes the chemistry and preparation of the majority of sulfenyl halides utilized in this invention. The synthesis of N-chlorosulfenylcarbamates was described in U.S. Pat. No. 3,843,689. Other sulfenyl halides can be prepared by the general procedures described in these literature examples or obvious modifications thereof.

Compounds of Formula I (Q is other than SX) are synthesized from compounds of Formula VI. Reaction of compounds of Formula VI in the presence of an acid acceptor with electrophilic carbonyl-containing reagents results in substitution on nitrogen. Strong bases known to deprotonate ureas such as potassium t-butoxide, potassium hydride and sodium hydride are the preferred acid acceptors in the process. Suitable electrophiles include, but are not restricted to, acyl halides, acid anhydrides, carbonates, and chloroformates. The reaction sequence is normally run in the temperature range of −10° to 25° C., but can be run at temperatures as high as 110° C. or as low as −50° C. in certain cases. Solvents which are not deprotonated under the conditions of the reaction such as tetrahydrofuran, dimethylformamide, dimethoxyethane, and diethyl ether are preferred. The electrophiles used in this process are well known to those skilled in the art and are generally commercially available.

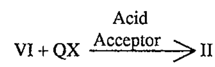

$$\text{VI} + \text{QX} \xrightarrow[\text{Acceptor}]{\text{Acid}} \text{II}$$

wherein:

QX is selected from acyl halides, chloroformates and acid anhydrides.

The following Examples illustrate the invention.

EXAMPLE 1

3,3a, 4,5-Tetrahydro-3a-methoxycarbonyl-N-[4-(trifluoromethyl)pheny]-N-[N'-(1-methylethyl)-N'-(ethoxycarbonyl)aminosulfenyl]-2H-benz[g]indazole-2-carboxamide Step A: 3,3a,4,5-Tetrahydro-N-[4-(trifluoromethyl)phenyl]-2H-benz[g]indazole-2-carboxamide A mixture of 10.0 g of α-tetralone, 2.0 g of paraformaldehyde, 6.5 g of dimethylamine hydrochloride and 1.75 ml of conc. HCl in 20 ml of ethanol was heated at reflux for 24 h, cooled to room temperature and then partitioned between ether and water. The aqueous extracts were made basic with 1N aqueous NaOH and extracted with ether. The ether extracts were dried over magnesium sulfate and concentrated to 12.3 g of a yellow oil. The residual oil was dissolved in 40 ml of n-propyl alcohol, combined with 6.7 ml of hydrazine hydrate and heated at reflux for 1 h. The reaction mixture was then concentrated under vacuum, partitioned between 5% aqueous $NaHCO_3$ and methylene chloride and dried over magnesium sulfate. To the methylene chloride extracts were added 12.5 g of 4-trifluoromethylphenyl isocyanate and the mixture was then refluxed one hour, cooled to room temperature and concentrated to 26.1 g of a brown oil. Chromatography on silica gel followed by trituration with ether afforded 11.78 g of the title compound as a tan powder, m.p. 149°–151° C.

$^1$H NMR ($CDCl_3$), δ1.9 (m,1H), 2.4 (m, 1H), 3.0 (m, 2H), 3.5 (m,2H), 4.4 (m,1H), 7.3 (m,3H), 7.58 (d,2H), 7.65 (d,2H), 8.0 (d,2H), 8.3 (bs,1H).

Step B: 3,3a, 4,5-tetrahydro-3a-methoxycarbonyl-N-[4'-(trifluoromethyl)phenyl]-2H-benz[g]indazole-2-carboxamide To a solution of 0.9 ml of diisopropylamine in 10 ml of THF, at −78° C., was added 2.3 ml of 2.5M n-butyl lithium in hexane and the mixture was stirred for 5 mins. To this solution was added a solution of 1.0 g of the title compound of Step A in 5 ml of THF. The reaction was warmed to 0° C., recooled to −78° C. and then 0.75 ml of methyl chloroformate was added. The reaction mixture was then stirred for 24 h, with gradual warming to room temperature, quenched with 0.5 ml of glacial acetic acid, and poured into a 5% solution of aqueous $NaHCO_3$. The mixture was extracted with chloroform, dried over magnesium sulfate and concentrated. Chromatography on silica gel with 30% ethyl acetate hexane afforded 0.25 g of the title compound, m.p. 177° to 180° C.

$^1$H NMR ($CDCl_3$), δ2.1 (m,1H), 2.7 (m,1H), 3.0 (m,2H), 3.71 (s,3H), 3.76 (d,1H), 4.58 (d,1H), 7.3 (m,3H), 7.57 (d,2H), 7.66 (d,2H), 8.0 (d,1H), 8.22 (s,1H).

Step C: Ethyl (1-methylethyl)carbamate

To a solution of ethyl chloroformate (21.7 g, 0.2 mol) in 200 ml ether cooled to 0° C. was added dropwise 35.7 ml of isopropylamine with stirring and cooling. After complete addition of the amine, the reaction mixture was stirred at room temperature for an additional 0.5 hour. The reaction mixture was filtered, and the ether solution was washed with water, and dried over magnesium sulfate. Evaporation of the ether and distillation of the residue in a Kugelrohr apparatus resulted in 22.6 g of the title compound B.p.: 50°–66° C. (bath temperature) at 1.5 mm Hg.

Step D: Ethyl (chlorosulfenyl)(1-methylethyl)carbamate

To a solution of ethyl (1-methylethyl)carbamate (13.1 g, 0.1 mol) in 100 ml methylene chloride cooled to 0° C. was added sulfur dichloride (11.3 g, 0.11 mol) in one portion. While maintaining the temperature of the mixture at 0° C., pyridine (8.7 g, 0.11 mol) was added dropwise over eleven minutes. After complete addition of the pyridine the temperature was allowed to rise to room temperature and stirring was continued for additional 1.5 hours. The mixture was let stand overnight. Methylene chloride was evaporated under vacuum and 100 ml hexane was added. Filteration of the pyridine hydrochloride and evaporation of hexane resulted in an orange oil which was distilled in a Kugelrohr apparatus to give 12.5 g of the title compound Bp: 64°–80° (bath temperature) at 1.4 mm Hg.

Step E: 3,3a, 4,5-Tetrahydro-3a-methoxycarbonyl-N-[4-(trifluoromethyl)phenyl]-N-[N'-(1-methylethyl)-N'-(ethoxycarbonyl)aminosulfenyl]-2H-benz[g]indazole-2-carboxamide To a solution of the title compound of Step B (2.0 g, 4.8 mmol) in 50 ml methylene chloride cooled to 0° C. was added triethylamine (1.0 g, 0.01 mol) and ethyl (chlorosulfenyl) (1-methylethyl)carbamate from Step D (1.4 g, 7.7 mmol). The mixture was allowed to warm to room temperature and stirred for one hour. The crude mixture was purified by silica column chromatography using ether-hexane (1:2) as eluent. The title compound (2.38 g) was obtained in about 90% purity (mp: 130°–134°). Extraction of the product with ether-hexane (2:1) gave 1.8 g of highly pure material mp: 139°–140° C.

$^1$H NMR ($CDCl_3$); δ0.92 (t,3H), 1.26 (d,3H), 1.35 (d,3H), 1.95 (m, 1H), 2.7 (m,1H), 2.95 (m,2H), 3.67 (s,3H), 3.8 (m,3H), 4.5 (m,2H), 7.2 (m,3H), 7.45 (d,3H), 7.65 (d,2H).

EXAMPLE 2

3,3a, 4,5-Tetrahydro-3a-methoxycarbonyl-N-[4-(trifluoromethyl)phenyl]-N-(1-methylpropoxylcarbonylsulfenyl)-2H-benz[g]indazole-2-carboxamide.

Step A: (1-methylpropoxycarbonyl)sulfenyl chloride

Chlorocarbonylsulfenyl chloride (13.1 g, 0.1 mol) was mixed with 2-butanol (6.7 g, 0.09 mol)and warmed to about 35° to 40° C. for one hour. Distillation resulted in the tithe compound (5.93 g) Bp. 70° C./0.8 mm Hg. NMR spectrum was consistent with the structure.

Step B: 3,3a, 4,5-Tetrahydro-3a-methoxycarbonyl-N-[4-(trifluoromethyl)phenyl]-N-(1-methylpropoxycarbonylsulfenyl)-2H-benz[g]indazole-2-carboxamide.

To a solution of the title compound of Step B (Example 1) (0.4 g, 0.96 mmol) in 5 ml methylene chloride was added triethylamine (0.12 g) and cooled to 0° C. To this solution was added (1-methylpropoxycarbonyl)sulfenyl chloride (Step A) (0.2 g, 0.0012 mol). The mixture was stirred at room temperature for one hour. At this stage thin layer chromatography indicated only partial conversion, therefor, addition- al amounts of (1-methylpropoxycarbonyl)sulfenyl chloride (0.2 g) and triethylamine (0.12 g) was added and the mixture was let stand overnight. The reaction mixture was subjected to silica gel column chromatography using hexane-ether (7:1) as eluent. The title compound was obtained (0.22 g) in high purity; m.p.: 125°–126° C.

$^1$H NMR ($CDCl_3$): δ0.9 (m,3H), 1.3 (m,3H), 1.6 (m, 2H), 1.9 (m, 1H), 2.8 (m,3H), 3.67 (s,3H), 3.8 (d,1H), 4.5 (d,1H), 5.0 (m,1H), 7.05 (m,3H), 7.25 (m,1H), 7.5 (d,2H), 7.57 (d,2H).

EXAMPLE 3

3,3 a,4,5-Tetrahydro-3a-methoxycarbonyl-N-[4-trifluoromethyl)phenyl]-N-(dibutylaminosulfenyl)-2H-benz[g]indazole-2-carboxamide Step A: N,N'-bis-(dibutylamino)disulfide To a solution of dibutylamine (52 g, 0.4 mol) in 200 ml hexane cooled to 0° C. was added sulfur monochloride (13.5 g, 0.1 mol) dropwise with stirring over a period of 20 minutes. The reaction mixture was warmed up to room temperature and stirring was continued for 30 minutes. The reaction mixture was filtered and hexane was evaporated to yield 30.1 g of the title compound.

Step B: Dibutylaminosulfenylchloride

To a solution of N,N'-bis-(dibutylamino)disulfide (13.2 g, 0.05 mol) in 12 ml carbontetrachloride was added. Sulfuryl chloride (6.75 g, 0.05 mol) was added dropwise at ambient temperature. Then heated to about 60° C. for 10 minutes, and distilled to give the title compound (7.55 g) as a yellow liquid. Bp: 80°–87° C. at 0.6 mm Hg.

Step C: 3,3a,4,5-Tetrahydro-3a-methoxycarbonyl-N-[4-(trifluoromethyl)phenyl]-N-(dibutylaminosulfenyl)-2H-benz[g]indazole-2-carboxamide.

To a solution of the title compound of Step B (Example 1) (0.4 g, 0.96 mmol) in 8 ml methylene chloride cooled to 0° C. was added triethylamine (0.15 g) and dibutylaminosulfenylchloride (0.2 g). The reaction mixture was, warmed to room temperature and stirred for one hour. The mixture was subjected to silica gel column chromatography using hexane-ether (6:1) as the eluent. The title compound was obtained (0.24 g) in high purity.

$^1H$ NMR ($CDCl_3$): δ0.7 to 1.7 (m,14H), 1.9 (m,1H), 2.6 to 3.1 (m,7H), 3.67 (s,3H), 3.75 (d,1H), 4.45 (d,1H), 7.1 (m,3H), 7.25 (m,1H), 7.4 (d,2H), 7.6 (d,2H).

EXAMPLE 4

7-Chloro-3,3a,4,5-tetrahydro-3a-methoxycarbonyl-N-[4-(trifluoromethyl)phenyl]-N-[N'-(methyl)-N'-(hexoxycarbonyl)aminosulfenyl]-2H-benz[g]indazole-2-carboxamide Step A: ((2-(3-chlorophenyl)ethyl)methanesulfonate To a 0° C. solution of 30.0 g of 3-chlorophenethyl alcohol and 15.3 ml of methane sulfonyl chloride in 150 ml of THF was added, dropwise, a solution of 28.0 ml of triethylamine in 50 ml of THF. The reaction was warmed to room temperature, stirred overnight, and then filtered. The filtrate was partitioned between aqueous sodium bicarbonate and ether. The organic extracts were then dried over magnesium sulfate, filtered and concentrated under reduced pressure to afford 45.93 g of a clear, colorless oil.

Step B: 3-chlorobenzenebutanoic acid

To a mixture of 8.0 g of 60% sodium hydride in 300 ml of THF, under $N_2$, was added dropwise a solution of 31.0 ml of diethyl malonate in 50 ml of THF. Upon complete addition of the diethyl malonate, a pale yellow homogeneous solution was obtained. To this was added a solution of 45.93 g of the sulfonate from Step A and the mixture was then heated at reflux overnight. The reaction was then cooled to room temperature, poured into 400 ml of 1N HCl, and extracted with ether. The ether extracts were dried over magnesium sulfate, filtered and concentrated under reduced pressure to afford 68.9 g of a yellow oil. The crude oil was dissolved in 400 ml of methanol, 100 ml of $H_2O$ and 40 ml of 50% aqueous NaOH. The reaction was stirred overnight and the methanol was then removed at reduced pressure. The crude residue was partitioned between $H_2O$ and ether, the aqueous extracts were acidified with concentrated HCl and then extracted several times with ether. The ether extracts were dried over magnesium sulfate, filtered and concentrated to afford 51.7 g of a yellow oil. The crude residue was dissolved in 200 ml of toluene and heated at reflux for 4 days under $N_2$ to effect decarboxylation. After this time toluene was removed by concentration at reduced pressure to afford 35.72 g of a yellow oil. $^1H$ NMR analysis of the crude product was consistent with 3-chlorobenzene- butenoic acid of purity estimated to be 80%. The crude product was used without further purification directly in the next step.

Step C: 6-chloro-3,4-dihydro-1(2H)-naphthalenone

A mixture of 35.72 of the product from Step B and 50 ml of thionyl chloride was heated at reflux for 2 hours and then stirred at room temperature for 18 hours. After this time thionyl chloride was removed at reduced pressure and the product was dissolved in carbon tetrachloride and concentrated at reduced pressure. The residue was dissolved in 150 ml of dichloroethane cooled to 0° C. and 28 g of aluminum chloride was added portionwise over about 1 hr in approximately 3 g portions. After stirring for 3 hrs the reaction was poured over a mixture of ice/1N HCl and extracted three times with methylene chloride. The organic extracts were dried over magnesium sulfate and concentrated to approximately 30 g of a brown oil. Chromatography on silica gel with 10% ethyl acetate/hexane afforded 17.83 g of 6-chloro-3,4-dihydro-1(2H)-naphthalenone as a brown oil. $^1H$ NMR was consistent with the structure.

Step D: 7-chloro-3,3a,4-5-tetrahydro-N-[4-(trifluoromethyl)phenyl]-2H-benz[g]-indazole-2-carboxamide A mixture of 6-chloro-3,4-dihydro-1(2H)-naphthalenone (Step C), 2.5 g of dimethylamine hydrochloride, 1.0 g of paraformaldehyde, 0.7 ml of concentrated HCl and 15 ml of ethanol was combined and heated at reflux for 18 hrs. The reaction was then concentrated at reduced pressure and partitioned between $H_2O$ and ether. The aqueous extracts were made baic with 1N NaOH and then extracted three times with ether. The ether extracts were dried over magnesium Sulfate and concentrated to 4.64 g of a yellow oil. This compound was dissolved fin 25 ml of ethanol and 1.5 ml of hydrazine hydrate was added followed by 5 to 6 drops of 50% sodium hydroxide. The reaction was then heated at reflux, under $N_2$, for 2 to 3 hrs after which time it was cooled and most of the ethanol was removed by concentration at reduced pressure. The crude residue was partitioned between saturated aqueous sodium bicarbonate and methylene chloride. The methylene chloride extracts were dried over magnesium sulfate and filtered. The methylene chloride extracts were then combined with 3.5 g of 4-trifluoromethylphenyl isocyanate and stirred under $N_2$ overnight. The reaction was then concentrated and the crude residue triturated with ether to afford 3.35 g of the title compound as a white powder, m.p. 196° to 199° C.

$^1H$ NMR ($CDCl_3$) δ1.9 (m,1H), 2.2 (m,1H), 3.0 (m,2H), 3.5 (m,2H), 4.43 (m,1H), 7.24 (m,2H), 7.55 (d,2H), 7.67 (d,2H), 7.92 (d,1H), 8.20 (s,1H).

Step E: 7-chloro-3,3a,4,5-tetrahydro-3a-methoxycarbonyl-N-[4-(trifluoromethyl)phenyl]-2H-benz[g]indazole-2-carboxamide A solution of 50 ml of THF and 6.7 ml of diisopropylamine was cooled under $N_2$ to −78° C. and then 17.5 ml of 2.5M n-butyllithium in hexane was added. After 5 min, a solution of 7.8 g of the title compound of Step D in 15 ml of THF was added dropwise and the dark red solution that formed was stirred at −78° C. for an additional 15 min. After this time a solution of 4.6 ml of methyl chloroformate in 10 ml of THF was added dropwise and the red color dissipated rapidly. The reaction was warmed to room temperature and after 1 hr quenched with 5% aqueous sodium bicarbonate. The reaction mixture was partitioned between ether and 5% aqueous sodium bicarbonate. The ether extracts were dried over magnesium sulfate and concentrated to 14.1 g of a yellow oily solid. The crude product was triturated with ether and the resulting white precipitate was filtered and dried to afford 5.56 g of the title compound as a white solid, m.p. 234° to 236° C.

$^1$H NMR($CDCl_3$) δ2.1 (m,1H), 2.75 (m,1H), 2.95 (m,2H), 3.71 (s,3H), 3.75 (d,1H, J=6 Hz), 4.59 (d,1H, J=6 Hz), 7.25 (m,2H), 7.57 (d,2H), 7.66 (d,2H), 7.94 (d,1H), 8.18 (d,1H).

Step F: 7-chloro-3,3a,4,5-tetrahydro-3a-methoxycarbonyl-N-[4-(trifluoromethyl)phenyl]-N-[N'-(methyl)-N'-(hexoxy-carbonyl)aminosulfenyl]-2H-benz[g]indazole-2-carboxamide To a suspension of the title compound of Step E above (2.2 g, 0.005 mol) in 25 ml methylene chloride cooled to 0° C. was added triethylamine (1.0 g) and hexyl (chlorosulfenyl)(methyl)carbamate, (prepared in a manner similar to Example 1, Step D), (2.5 g 75% pure) dropwise at 0° C. The mixture was stirred at room temperature for additional one hour. The reaction mixture was concentrated under high vacuum and subjected to silica gel column chromatography using hexane-ether (1:1) as an eluent. The title compound (2.5 g) was obtained, melting point 128°–129° C. in high purity.

$^1$H NMR ($CDCl_3$) δ0.87 (t,3H), 1.18 (m,8H), 1.9(m,1H), 2.8 (m,3H), 3.5 (s,3H), 3.66 (s,3H), 3.7 (m,3H), 4.5 (d,1H), 7.05 (m,3H), 7.35 (d,2H), 7.6 (d,2H).

Using the procedures described in Examples 1 to 4 with obvious modifications, the compounds exemplified in Examples 5 to 28 were prepared.

TABLE A

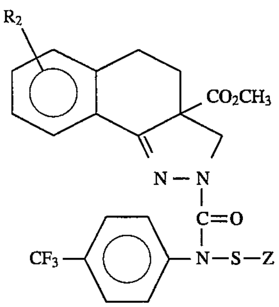

| Example | $R_2$ | Z | m.p. °C. | $^1$H NMR (δ in ppm) in $CDCl_3$ |
|---|---|---|---|---|
| 5 | H | $N(CH_3)C(O)OC_4H_9$ | 134 | 1.0(t, 3H), 1.2(m, 4H), 1.9(m, 1H), 2.6–3(m, 3H), 3.5(s, 3H), 3.66(s, 3H), 3.7(m, 2H), 3.75(d, 1H), 4.45(d, 1H), 7.1(m, 3H), 7.25(m, 1H), 7.35(d, 2H), 7.6(d, 2H). |
| 6 | H | $N(CH_3)C(O)OC_2H_5$ | 121–123 | 0.88(t, 3H), 1.9(m, 1H), 2.6–3(m, 3H), 3.5(s, 3H), 3.66(s, 3H), 3.8(m, 3H), 4.47(d, 1H), 7.11(m, 3H), 7.25(m, 1H), 7.35(d, 2H), 7.6(d, 2H). |
| 7 | 6-F | $N(CH_3)C(O)OC_4H_9$ | 120 | 0.83(t, 3H), 1.2(m, 4H), 1.85(m, 1H), 2.7(m, 2H), 3.0(m, 1H), 3.5(s, 3H), 3.66(s, 3H), 3.75(m, 3H), 4.5(d, 1H), 7.0(m, 3H), 7.35(d, 2H), 7.6(d, 3H). |
| 8 | H | $N(CH_3)C(O)OcycloC_6H_{11}$ | 175–176 | 0.6–1.7(m, 10H), 1.9(m, 1H), 2.6–3.0(m, 3H), 3.51(s, 3H), 3.65(s, 3H), 3.75(d, 1H), 4.35(m, 1H), 4.45(d, 1H), 7.1(m, 3H), 7.25(m, 1H), 7.35(d, 2H), 7.6(d, 2H). |
| 9 | H | $N(CH_3)C(O)OC_8H_{17}$ | 144–145 | 0.88(t, 3H), 1.21(m, 12H), 1.9(m, 1H), 2.7(m, 1H), 2.9(m, 2H), 3.5(m, 3H), 3.65(m, 3H), 3.75(m, 3H), 4.5(d, 1H), 7.1(m, 3H), 7.25(m, 1H), 7.35(d, 2H), 7.6(d, 2H). |
| 10 | H | $N(CH_3)C(O)OC_{10}H_{21}$ | 76–78 | 0.88(t, 3H), 1.25(m, 16H), 1.9(m, 1H), 2.7(m, 1H), 2.9(m, 2H), 3.5(s, 3H), 3.66(s, 3H), 3.75(m, 3H), 4.5(d, 1H), 7.15(m, 3H), |

TABLE A-continued

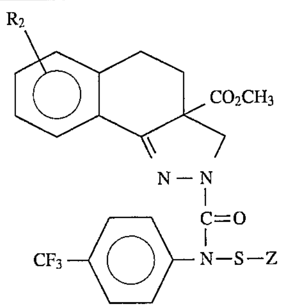

| Example | $R_2$ | Z | m.p. °C. | $^1$H NMR (δ in ppm) in $CDCl_3$ |
|---|---|---|---|---|
| | | | | 7.25(m, 1H), 7.35(d, 2H), 7.6(d, 2H). |
| 11 | 6-F | N-[CH($CH_3$)$_2$]C(O)O$C_2H_5$ | 143.5 | 0.91(t, 3H), 1.27(d, 3H), 1.35(d, 3H), 1.9(m, 1H), 2.75(m, 2H), 3.05(m, 1H), 3.67(s, 3H), 3.75(m, 3H), 4.5(m, 2H), 7.25(m, 3H), 7.45(d, 2H), 7.6(d, 2H), |
| 12 | H | N($CH_3$)C(O)O$C_{12}H_{25}$ | — | 0.88(t, 3H), 1.26(m, 20H), 1.9(m, 1H), 2.7(m, 1H), 2.9(m, 2H), 3.5(s, 3H), 3.66(s, 3H), 3.75(m, 3H), 4.5(d, 1H), 7.1(m, 3H), 7.25(m, 1H), 7.35(d, 2H), 7.6(d, 2H). |
| 13 | H | N($CH_3$)C(O)O$C_6H_{13}$ | — | 0.88(t, 3H), 1.26(m, 8H), 1.9(m, 1H), 2.7(m, 1H), 2.9(m, 2H), 3.51(s, 3H), 3.66(s, 3H), 3.75(m, 3H), 4.5(d, 2H), 7.1(m, 3H), 7.25(m, 1H), 7.35(d, 2H), 7.6(d, 2H). |
| 14 | 7-Cl | C(O)O-sec-$C_4H_9$ | 132 | 0.88(t, 3H), 1.3(m, 3H), 1.6(m, 2H), 1.9(m, 1H), 2.6–3.0(m, 3H), 3.88(s, 3H), 3.8(d, 1H), 4.5(d, 1H), 5.0(m, 1H), 7.0(m, 3H), 7.35(d, 2H), 7.6(d, 2H). |
| 15 | 7-Cl | N-[CH($CH_3$)$_2$]C(O)O$C_2H_5$ | 152 | 0.9(t, 3H), 1.26(d, 3H), 1.35(d, 3H), 1.9(m, 1H), 2.7(m, 1H), 2.9(m, 2H), 3.67(s, 3H), 3.8(m, 3H), 4.5(m, 2H), 7.14(m, 2H), 7.4(m, 3H), 7.6(d, 2H). |
| 16 | 7-Cl | N($CH_3$)C(O)O$C_2H_5$ | — | 0.88(t, 3H), 1.9(m, 1H), 2.65(m, 1H), 2.9(m, 2H), 3.49(s, 3H), 3.66(s, 3H), 3.8(m, 3H), 4.5(d, 1H), 7.07(m, 3H), 7.35(d, 2H), 7.6(d, 2H). |
| 17 | 7-Cl | N($CH_3$)C(O)O$C_8H_{17}$ | 103–106 | 0.88(t, 3H), 1.23(m, 12H), 1.9(m, 1H), 2.65(m, 1H), 2.85(m, 2H), 3.5(s, 3H), 3.66(s, 3H), 3.75(m, 3H), 4.45(d, 1H), 7.05(m, 3H), 7.35(d, 2H), 7.6(d, 2H). |
| 18 | 6-F | C(O)O-sec-$C_4H_9$ | 125–126 | 0.9(m, 3H), 1.3(m, 5H), 1.9(m, 1H), 2.75(m, 2H), 3.0(m, 1H), 3.7(s, 3H), 3.8(d, 1H), 4.5(d, 1H), 5.0(m, 1H), 6.8(m, 1H), 7.05(m, 2H), 7.45(d, 2H), 7.6(d, 2H). |
| 19 | 7-Cl | N($CH_3$)C(O)O$C_4H_9$ | 125–127 | 0.82(m, 3H), 1.2(m, 4H), 1.9(m, 1H), 2.65(m, 1H), 2.85(m, 2H), 3.5(s, 3H), 3.66(s, 3H), 3.75(m, 3H), 4.45(d, 1H), 7.05(m, 3H), 7.35(d, 2H), 7.6(d, 2H). |
| 20 | 7-Cl | N[CH($CH_3$)$_2$]C(O)O$C_4H_9$ | — | 0.84(t, 3H), 1.25(m, 10H), 1.9(m, H), 2.65(m, 1H), |

TABLE A-continued

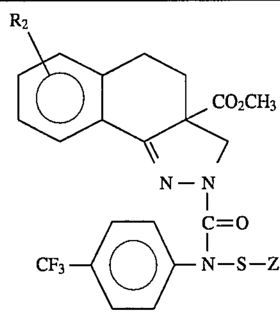

| Example | $R_2$ | Z | m.p. °C. | $^1$H NMR (δ in ppm) in $CDCl_3$ |
|---|---|---|---|---|
| | | | | 3.66(s, 3H), 3.7(m, 3H), 4.45(m, 2H), 7.15(m, 2H), 7.4(m, 3H), 7.6(d, 2H). |
| 21 | 7-Cl | $N(CH_3)C(O)OC_{12}H_{25}$ | — | 0.88(t, 3H), 1.2(m, 20H), 1.9(m, 1H), 2.65(m, 1H), 2.9(m, 2H), 3.5(s, 3H), 3.67(s, 3H), 3.75(m, 3H), 4.5(d, 1H), 7.05(m, 3H), 7.35(d, 2H), 7.6(d, 2H). |
| 22 | 7-Cl | $N(CH_3)C(O)O$-cyclo$C_6H_{11}$ | 87–91 | 0.8–1.7(Broad m, 10H), 2.65(m, 1H), 2.9(m, 2H), 3.51(s, 3H), 3.66(s, 3H), 3.75(d, 1H), 4.35(m, 1H), 4.45(d, 1H), 7.05(m, 3H), 7.35(d, 2H), 7.6(d, 2H). |
| 23 | 7-Cl | $N(CH_3)C(O)O(CH_2)_2OC_4H_9$ | — | 0.9(t, 3H), 1.4(m, 4H) 1.9(m, 1H), 2.7(m, 1H) 2.9(m, 2H), 3.3(m, 4H) 3.5(s, 3H), 3.67(s, 3H), 3.9(m, 3H), 4.5(d, 1H), 7.1(m, 3H), 7.4(d, 2H), 7.6(d, 2H). |
| 24 | 7-Cl | $N(CH_3)C(O)OC_{14}H_{29}$ | — | 0.87(t, 3H), 1.26(m, 24H), 1.9(m, 1H), 2.65(m, 1H), 2.9(m, 2H), 3.5(s, 3H), 3.68(s, 3H), 3.75(m, 3H), 4.47(d, 1H), 7.05(m, 3H), 7.35(d, 2H), 7.57(d, 2H). |
| 25 | 7-Cl | $N(CH_3)C(O)OC_{16}H_{33}$ | — | 0.87(t, 3H), 1.26(m, 28H), 1.9(m, 1H), 2.65(m, 1H), 2.9(m, 2H), 3.5(s, 3H), 3.67(s, 3H), 3.75(m, 3H), 4.47(d, 1H), 7.05(m, 3H), 7.35(d, 2H), 7.6(d, 2H). |
| 26 | 7-Cl | $N(CH_3)C(O)OC_{18}H_{37}$ | — | 0.9(t, 3H), 1.26(m, 32H), 1.9(m, 1H), 2.65(m, 1H), 2.9(m, 2H), 3.5(s, 3H), 3.67(m, 3H), 3.75(m, 3H), 4.5(d, 1H), 7.05(m, 3H), 7.35(d, 2H), 7.6(d, 2H). |
| 27 | 7-Cl | $N(CH_3)C(O)OC_{22}H_{45}$ | — | 0.88(t, 3H), 1.26(m, 40H), 1.9(m, 1H), 2.65(m, 1H), 2.9(m, 2H), 3.5(s, 3H), 3.65(m, 3H), 3.75(m, 3H), 4.48(d, 1H), 7.06(m, 3H), 7.35(d, 2H), 7.6(d, 2H). |
| 28 | 7-Cl | $N(CH_3)C(O)O(CH_2)_2O(CH_2)_2OC_4H_9$ | — | 0.91(t, 3H), 1.4(m, 4H), 1.9(m, 1H), 2.7(m, 1H), 2.9(m, 2H), 3.5(s, 3H), 3.67(s, 3H), 3.7(m, 9H), 4.0(m, 1H), 4.2(m, 1H), 4.5(d, 1H), 7.6(m, 3H), 7.4(d, 2H), 7.6(d, 2H). |

EXAMPLE 29

1-(4-chlorophenyl)-5-(4-fluorophenyl)-4,5-dihydro-N-[4-(trifluoromethyl)phenyl]-N-[N'-(1-methylethyl)-N'-(ethoxycarbonyl)aminothiol]-1H-pyrazole-3-carboxamide Step A: Ethyl (chlorosulfenyl) (1-methylethyl)carbamate To a solution of ethyl (1-methylethyl)carbamate (13.1 g, 0.1 mol) in 100 ml of methylene chloride cooled to 0° C. was added sulfur dichloride (11.3 g, 0.11 mol) in one portion. While maintaining the temperature of the mixture at 0° C., pyridine (8.7 g, 0.11 mol) was added dropwise over eleven minutes. After complete addition of the pyridine the temperature was allowed to rise to room temperature and stirring was continued for additional 1.5 hours. The mixture was let stand overnight. Methylene chloride was evaporated under vacuum and 100 ml hexane was added. Filteration of pyridine hydrochloride and evaporation of hexane resulted in an orange oil which was distilled in a Kugelrohr apparatus to give 12.5 g of the title Compound B.P.: 64°–80° (bath temp.)

Step B: 1-(4-chlorophenyl)-5-(4-fluorophenyl)-4,5-dihydro-N-[4-(trifluoromethyl)phenyl]-N-[N'-(1-methylethyl)-N'-(ethoxycarbonyl)aminothiol]-1H-pyrazole-3-carboxamide To a solution of 1-(4-chlorophenyl)-5-(4-fluorophenyl)-4,5-dihydro-N-[4-(trifluoromethyl)phenyl]-1H-pyrazole-3-carboxamide (0.95 g, 0.002 mol) in 10 ml of methylene chloride cooled to 0° C. was added triethylamine (0.25 g) followed by the title compound of Step A (0.5 g, 0.0025 mol). The reaction mixture was allowed to warm to room temperature with stirring for one hour. Methylene chloride (50 ml) was added and the mixture was washed with water, dried over magnesium sulfate and filtered. The solvent was evaporated and the residue was purified by silica gel column chromatograph using hexane:ether (2:1) as the eluent. Obtained 1.0 g of the title compound, m.p.: 136°–137° C., H-NMR ($CDCl_3$); δ7.7 (d,2H), 7.4 (δ, 2H), 7.0 (m, 6H), 6.3 (d, 2H), 5.2 (d of d, 1H), 4.5 (m, 1H), 3.75 (m, 3H), 3.05 (d of d, 1H) 1.3 (d of d, 6H), 0.87 (t, 3H).

EXAMPLE 30

3,4-bis-(4-chlorophenyl)-N-[4-(trifluoromethyl) phenyl]-N-[N'-(1-methylethyl)-N'-(ethoxycarbonyl) aminothiol]4,5-dihydro-1H-pyrazole-1-carboxamide To a solution of 3,4-bis-(4-chlorophenyl)-N-[4-(trifluoromethyl)phenyl)]-4,5-dihydro-1H-pyrazole-1-carboxamide (0.466 g, 0.001 mol) in 5 ml of methylene chloride cooled to 0° C. was added 0.3 g of triethylamine and ethyl (chlorosulfenyl)(1-methylethyl)carbamate (0.5 g). The mixture was allowed to warm to room temperature and let stand overnight. 20 ml $CH_2Cl_2$ was added and the mixture was washed with water and dried over $MgSO_4$ and filtered. The solvent was evaporated under vacuum. The residue was purified by silica gel column chromatography using $CH_2Cl_2$:Butylchloride mixture (1:1) as a primary eluent followed by ether. The title compound was obtained in high purity (0.28 g), m.p.: 65°–68° C.

$^1$H-NMR ($CDCl_3$), δ7.65 (d, 2H), 7.5 (d, 2H), 7.27 (d, 2H), 7.17 (S, 4H), 7.0 (d, 2H), 4.6–4.3 (m, 3H), 3.95 (d of d, 1H), 3.8 (q, 2H), 1.3 (m, 6H), 0.95 (t, 3H).

The following additional Examples (Tables B and C) employed procedures similar to those described in the previous Examples 29 and 30 or in the disclosed literature.

TABLE B

| Example | X | m.p. °C. | $^1$H-NMR (δ in ppm) in $CDCl_3$ |
|---|---|---|---|
| 31 | $N[CH(CH_3)_2]C(O)OC_4H_9$ | 165–170 | 7.23(d, 2H), 7.4(d, 2H), 7.0(M, 6H), 6.3(d, 2H), 5.2(d of d, 1H), 4.5 (M, 1H), 3.75(M, 3H), 3.1(d of d, 1H), 1.4–1.1 (M, 10H), .85(t, 3H) |
| 32 | $N[CH(CH_3)(C_2H_5)]C(O)OC_2H_5$ | — | 7.23(d, 2H), 7.4(d, 2H), 7.0(M, 6H), 6.3(d, 2H), 5.2(d of d, 1H), 4.5 (M, 1H), 3.75(M, 3H), 3.1(d of d, 1H), 1.8–1.1 (M, 5H), 0.9(M, 6H). |
| 33 | $C(O)OCH(CH_3)(C_2H_5)$ | 159–161 | 7.25(d, 2H), 7.55(d, 2H), 7.0(M, 6H), 6.25(d, 2H), 5.2(d of d, 1H), 5.0 (M, 1H), 3.75(d of d, 1H), 3.1(d of d, 1H), 1.65(M, 2H), 1.28(d, 3H), 0.9(t, 3H). |
| 34 | $N(CH_3)C(O)O(cycloC_6H_{11})$ | 147–150 | 7.2(d, 2H), 7.4(d, 2H), 7.0(M, 6H), 6.3(d, 2H), 5.2(d of d, 1H), 4.3 (M, 1H), 3.7(d of d, 1H), |

TABLE B-continued

| Example | X | m.p. °C. | $^1$H-NMR (δ in ppm) in $CDCl_3$ |
|---|---|---|---|
| | | | 3.5(5, 3H), 3.2(d of d, 1H), 1.8–0.9(M, 10H). |

TABLE C

| EXAMPLE | Q | $R_3$ | $R_1$ | m.p. °C. | $^1$H-NMR (δ in ppm) |
|---|---|---|---|---|---|
| 35 | $S-N(CH_3)C(O)O$-sec-$C_4H_9$ | Cl | $CF_3$ | 83–84 | 7.8–6.9(m, 12H), 4.6–4.3(M, 3H), 4.0 (M, 1H), 3.52(S, 3H), 1.25(M, 2H), 1.0–0.7(M, 6H). |
| 36 | $S-C(O)O$-sec-$C_4H_9$ | Cl | $CF_3$ | 78–80 | 7.7–7.0(M, 12H), 5.0 (M, 1H), 4.45(M, 2H), 4.0(M, 1H), 1.6(M, 2H), 1.3(d, 3H), 0.9(t, 3H). |
| 37 | $S-C(O)O$-sec-$C_4H_9$ | Cl | Cl | 66–69 | 7.4–6.9(M, 12H), 5.0 (M, 1H), 4.5(M, 2H), 4.0(M, 1H), 1.6(M, 2H), 1.28(d, 3H), 0.9(M, 3H). |
| 38 | $CO_2CH_3$ | Cl | $CF_3$ | 151–154 | 7.7–7.0(m, 12H), 4.7 (d, d, 1H), 4.5(d, d, 1H), 4.1(d, d, 1H), 3.86(s, 3H). |
| 39 | $COCH_3$ | F | $CF_3$ | 157–159 | 7.7–7.0(m, 12H), 4.7 (d, d, 1H), 4.5(d, d, 1H), 4.1(d, d, 1H), 3.86(s, 3H). |
| 40 | $S-N(CH(CH_3)_2)SO_2C_2H_5$ | Cl | $CF_3$ | oil | 7.65(m, 2H), 7.25(m, 4H), 7.05(m, 1H), 4.6–3.9 (m, 3H), 3/65(m, 1H), 3.03 (q, 2H), 1.36(t, 3H), 1.24(d, 6H). |
| 41 | $COCH_3$ | Cl | $CF_3$ | 166–168 | 7.6–7.0(m, 12H), 4.7–4.0(m, 3H), 2.3(s, 3H). |
| 42 | $COCH_3$ | F | Cl | 187–190 | 7.5–7.0(m, 12H), 4.6(m, 1H), 4.4(m, 1H), 4.0(m, 1H), 2.26(s, 3H). |
| 43 | $COCH_3$ | F | Br | 181–186 | 7.6–7.0(m, 12H), 4.65(m, 1H), 4.4(m, 1H), 4.0(m, 1H), 2.25(s, 3H). |
| 44 | $CO_2Me$ | F | $CF_3$ | 80–86 | |
| 45 | COPh | F | $CF_3$ | 176–179 | |
| 46 | COEt | Cl | $CF_3$ | 169–170 | |
| 47 | EtCOCO | Cl | $CF_3$ | 166–167 | |
| 48 | CO-n-Bu | Cl | $CF_3$ | 60–62 | |
| 49 | $COCH_3$ | Cl | Cl | 205–206 | |

TABLE C-continued

| EXAMPLE | Q | $R_3$ | $R_1$ | m.p. °C. | $^1$H-NMR (δ in ppm) |
|---|---|---|---|---|---|
| 50 | COEt | Cl | Cl | 157–158 | |
| 51 | $CO_2Me$ | Cl | Cl | 162–166 | |
| 52 | 4-ClPhCO | Cl | $CF_3$ | 209–211 | |
| 53 | t-BuCO | Cl | $CF_3$ | 140–145 | |
| 54 | PhOCO | Cl | $CF_3$ | 150–155 | |

EXAMPLE 55

N-acetyl-3,4-bis(4-chlorophenyl)-4,5-dihydro-N-[4-(trifluoromethyl)phenyl]-1H-pyrazole-1-carboxamide The compound of Step D of Example 6 (0.65 g) was dissolved in tetrahydrofuran (20 ml) and treated with 60% sodium hydride in oil (0.12 g). After the evolution of hydrogen was complete (30 minutes), acetic anhydride (0.6 ml) was added and the mixture was stirred at room temperature for 16 hours. The reaction was diluted with saturated aqueous ammonium chloride solution (15 ml) and ethyl acetate (30 ml). The organic layer was dried with magnesium sulfate and evaporated. The residue was subjected to chromatography on silica gel with hexanes/ethyl acetate (3:1) as eluent. Addition of methanol (10 ml) to the product gave, after filtration, the title compound (0.4 g). m.p. 166° to 168° C.

NMR ($CDCl_3$) 7.6–7.0 (m, ArH, 12H), 4.7–4.0 (m, 3H, CH and $CH_2$), 2.3 (s, $COCH_3$, 3H).

TABLE 1

| $R_1$ | $R_2$ | B | $R_8$ | $R_9$ |
|---|---|---|---|---|
| 4-$CF_3$ | 5-Cl | H | Me | OEt |
| 4-$CF_3$ | 5-Cl | Me | Me | OEt |
| 4-$CF_3$ | H | $CO_2Me$ | Me | OEt |
| 4-Cl | H | $CO_2Me$ | Me | OEt |

TABLE 1-continued

| $R_1$ | $R_2$ | B | $R_8$ | $R_9$ |
|---|---|---|---|---|
| 4-Br | H | $CO_2Me$ | Me | OEt |
| 4-$OCF_3$ | H | $CO_2Me$ | Me | OEt |
| 4-$CF_3$ | 5-Cl | $CO_2Me$ | Me | OEt |
| 4-Cl | 5-Cl | $CO_2Me$ | Me | OEt |
| 4-$OCF_3$ | 5-Cl | $CO_2Me$ | Me | OEt |
| 4-$CF_3$ | 5-$CF_3$ | $CO_2Me$ | Me | OEt |
| 4-$CF_3$ | 5-F | $CO_2Me$ | Me | OEt |
| 4-$CF_3$ | 5-Cl | Ph | Me | OEt |
| 4-$CF_3$ | 5-Cl | 4-Cl−Ph | Me | OEt |
| 4-$CF_3$ | 5-Cl | $CO_2Et$ | Me | OEt |
| 4-$CF_3$ | 5-Cl | H | Me | O-n-Bu |
| 4-$CF_3$ | 4-F | H | Me | O-n-Bu |
| 4-$CF_3$ | H | Me | Me | O-n-Bu |
| 4-$CF_3$ | 5-Cl | Me | Me | O-n-Bu |
| 4-$CF_3$ | 5-Br | Me | Me | O-n-Bu |
| 4-$CF_3$ | 4-F | Me | Me | O-n-Bu |
| 4-$CF_3$ | H | $CO_2Me$ | Me | O-n-Bu |
| 4-Cl | H | $CO_2Me$ | Me | O-n-Bu |
| 4-Br | H | $CO_2Me$ | Me | O-n-Bu |
| 4-$OCF_3$ | H | $CO_2Me$ | Me | O-n-Bu |
| 4-$CF_3$ | 5-Cl | $CO_2Me$ | Me | O-n-Bu |
| 4-Cl | 5-Cl | $CO_2Me$ | Me | O-n-Bu |
| 4-Br | 5-Cl | $CO_2Me$ | Me | O-n-Bu |
| 4-$OCF_3$ | 5-Cl | $CO_2Me$ | Me | O-n-Bu |
| 4-$CF_3$ | 5-Br | $CO_2Me$ | Me | O-n-Bu |
| 4-Cl | 5-Br | $CO_2Me$ | Me | O-n-Bu |
| 4-Br | 5-Br | $CO_2Me$ | Me | O-n-Bu |
| 4-$OCF_3$ | 5-Br | $CO_2Me$ | Me | O-n-Bu |
| 4-$CF_3$ | 4-F | $CO_2Me$ | Me | O-n-Bu |
| 4-Cl | 4-F | $CO_2Me$ | Me | O-n-Bu |

TABLE 1-continued

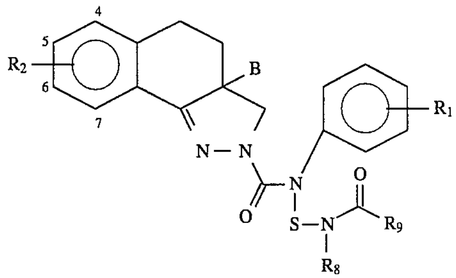

| $R_1$ | $R_2$ | B | $R_8$ | $R_9$ |
|---|---|---|---|---|
| 4-Br | 4-F | $CO_2Me$ | Me | O-n-Bu |
| 4-$OCF_3$ | 4-F | $CO_2Me$ | Me | O-n-Bu |
| 4-$CF_3$ | 5-$CF_3$ | $CO_2Me$ | Me | O-n-Bu |
| 4-$CF_3$ | 5-F | $CO_2Me$ | Me | O-n-Bu |
| 4-$CF_3$ | 5-Cl | Ph | Me | O-n-Bu |
| 4-$CF_3$ | 5-Cl | 4-Cl—Ph | Me | O-n-Bu |
| 4-$CF_3$ | 5-Cl | $CO_2Et$ | Me | O-n-Bu |
| 4-$CF_3$ | 5-Cl | Me | Me | O-n-hexyl |
| 4-$CF_3$ | H | $CO_2Me$ | Me | O-n-hexyl |
| 4-Cl | H | $CO_2Me$ | Me | O-n-hexyl |
| 4-Br | H | $CO_2Me$ | Me | O-n-hexyl |
| 4-$OCF_3$ | H | $CO_2Me$ | Me | O-n-hexyl |
| 4-$CF_3$ | 5-Cl | $CO_2Me$ | Me | O-n-hexyl |
| 4-Cl | 5-Cl | $CO_2Me$ | Me | O-n-hexyl |
| 4-Br | 5-Cl | $CO_2Me$ | Me | O-n-hexyl |
| 4-$OCF_3$ | 5-Cl | $CO_2Me$ | Me | O-n-hexyl |
| 4-$CF_3$ | 5-Br | $CO_2Me$ | Me | O-n-hexyl |
| 4-Cl | 5-Br | $CO_2Me$ | Me | O-n-hexyl |
| 4-Br | 5-Br | $CO_2Me$ | Me | O-n-hexyl |
| 4-$OCF_3$ | 5-Br | $CO_2Me$ | Me | O-n-hexyl |
| 4-$CF_3$ | 4-F | $CO_2Me$ | Me | O-n-hexyl |
| 4-Cl | 4-F | $CO_2Me$ | Me | O-n-hexyl |
| 4-Br | 4-F | $CO_2Me$ | Me | O-n-hexyl |
| 4-$OCF_3$ | 4-F | $CO_2Me$ | Me | O-n-hexyl |
| 4-$CF_3$ | 5-$CF_3$ | $CO_2Me$ | Me | O-n-hexyl |
| 4-$CF_3$ | 5-F | $CO_2Me$ | Me | O-n-hexyl |
| 4-$CF_3$ | 5-Cl | Ph | Me | O-n-hexyl |
| 4-$CF_3$ | 5-Cl | 4-Cl—Ph | Me | O-n-hexyl |
| 4-$CF_3$ | 5-Cl | $CO_2Et$ | Me | O-n-hexyl |
| 4-$CF_3$ | 5-Cl | Me | Me | O-n-octyl |
| 4-$CF_3$ | H | $CO_2Me$ | Me | O-n-octyl |
| 4-Cl | H | $CO_2Me$ | Me | O-n-octyl |
| 4-Br | H | $CO_2Me$ | Me | O-n-octyl |
| 4-$OCF_3$ | H | $CO_2Me$ | Me | O-n-octyl |
| 4-$CF_3$ | 5-Cl | $CO_2Me$ | Me | O-n-octyl |
| 4-Cl | 5-Cl | $CO_2Me$ | Me | O-n-octyl |
| 4-Br | 5-Cl | $CO_2Me$ | Me | O-n-octyl |
| 4-$OCF_3$ | 5-Cl | $CO_2Me$ | Me | O-n-octyl |
| 4-$CF_3$ | 5-Br | $CO_2Me$ | Me | O-n-octyl |
| 4-Cl | 5-Br | $CO_2Me$ | Me | O-n-octyl |
| 4-Br | 5-Br | $CO_2Me$ | Me | O-n-octyl |
| 4-$OCF_3$ | 5-Br | $CO_2Me$ | Me | O-n-octyl |
| 4-$CF_3$ | 4-F | $CO_2Me$ | Me | O-n-octyl |
| 4-Cl | 4-F | $CO_2Me$ | Me | O-n-octyl |
| 4-Br | 4-F | $CO_2Me$ | Me | O-n-octyl |
| 4-$OCF_3$ | 4-F | $CO_2Me$ | Me | O-n-octyl |
| 4-$CF_3$ | 5-$CF_3$ | $CO_2Me$ | Me | O-n-octyl |
| 4-$CF_3$ | 5-F | $CO_2Me$ | Me | O-n-octyl |
| 4-$CF_3$ | 5-Cl | Ph | Me | O-n-octyl |
| 4-$CF_3$ | 5-Cl | 4-Cl—Ph | Me | O-n-octyl |
| 4-$CF_3$ | 5-Cl | $CO_2Et$ | Me | O-n-octyl |
| 4-$CF_3$ | 5-Cl | Me | Me | O-n-decyl |
| 4-$CF_3$ | H | $CO_2Me$ | Me | O-n-decyl |
| 4-Cl | H | $CO_2Me$ | Me | O-n-decyl |
| 4-Br | H | $CO_2Me$ | Me | O-n-decyl |
| 4-$OCF_3$ | H | $CO_2Me$ | Me | O-n-decyl |
| 4-$CF_3$ | 5-Cl | $CO_2Me$ | Me | O-n-decyl |
| 4-Cl | 5-Cl | $CO_2Me$ | Me | O-n-decyl |
| 4-Br | 5-Cl | $CO_2Me$ | Me | O-n-decyl |
| 4-$OCF_3$ | 5-Cl | $CO_2Me$ | Me | O-n-decyl |
| 4-$CF_3$ | 5-Br | $CO_2Me$ | Me | O-n-decyl |
| 4-Cl | 5-Br | $CO_2Me$ | Me | O-n-decyl |
| 4-Br | 5-Br | $CO_2Me$ | Me | O-n-decyl |
| 4-$OCF_3$ | 5-Br | $CO_2Me$ | Me | O-n-decyl |

TABLE 1-continued

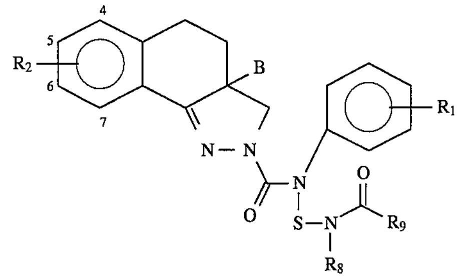

| $R_1$ | $R_2$ | B | $R_8$ | $R_9$ |
|---|---|---|---|---|
| 4-$CF_3$ | 4-F | $CO_2Me$ | Me | O-n-decyl |
| 4-Cl | 4-F | $CO_2Me$ | Me | O-n-decyl |
| 4-Br | 4-F | $CO_2Me$ | Me | O-n-decyl |
| 4-$OCF_3$ | 4-F | $CO_2Me$ | Me | O-n-decyl |
| 4-$CF_3$ | 5-$CF_3$ | $CO_2Me$ | Me | O-n-decyl |
| 4-$CF_3$ | 5-F | $CO_2Me$ | Me | O-n-decyl |
| 4-$CF_3$ | 5-Cl | Ph | Me | O-n-decyl |
| 4-$CF_3$ | 5-Cl | 4-Cl—Ph | Me | O-n-decyl |
| 4-$CF_3$ | 5-Cl | $CO_2Et$ | Me | O-n-decyl |
| 4-$CF_3$ | 5-Cl | Me | Me | O-n-dodecyl |
| 4-$CF_3$ | H | $CO_2Me$ | Me | O-n-dodecyl |
| 4-Cl | H | $CO_2Me$ | Me | O-n-dodecyl |
| 4-Br | H | $CO_2Me$ | Me | O-n-dodecyl |
| 4-$OCF_3$ | H | $CO_2Me$ | Me | O-n-dodecyl |
| 4-$CF_3$ | 5-Cl | $CO_2Me$ | Me | O-n-dodecyl |
| 4-Cl | 5-Cl | $CO_2Me$ | Me | O-n-dodecyl |
| 4-Br | 5-Cl | $CO_2Me$ | Me | O-n-dodecyl |
| 4-$OCF_3$ | 5-Cl | $CO_2Me$ | Me | O-n-dodecyl |
| 4-$CF_3$ | 5-Br | $CO_2Me$ | Me | O-n-dodecyl |
| 4-Cl | 5-Br | $CO_2Me$ | Me | O-n-dodecyl |
| 4-Br | 5-Br | $CO_2Me$ | Me | O-n-dodecyl |
| 4-$OCF_3$ | 5-Br | $CO_2Me$ | Me | O-n-dodecyl |
| 4-$CF_3$ | 4-F | $CO_2Me$ | Me | O-n-dodecyl |
| 4-Cl | 4-F | $CO_2Me$ | Me | O-n-dodecyl |
| 4-Br | 4-F | $CO_2Me$ | Me | O-n-dodecyl |
| 4-$OCF_3$ | 4-F | $CO_2Me$ | Me | O-n-dodecyl |
| 4-$CF_3$ | 5-$CF_3$ | $CO_2Me$ | Me | O-n-dodecyl |
| 4-$CF_3$ | 5-F | $CO_2Me$ | Me | O-n-dodecyl |
| 4-$CF_3$ | 5-Cl | Ph | Me | O-n-dodecyl |
| 4-$CF_3$ | 5-Cl | 4-Cl—Ph | Me | O-n-dodecyl |
| 4-$CF_3$ | 5-Cl | $CO_2Et$ | Me | O-n-dodecyl |
| 4-$CF_3$ | 5-Cl | Me | Me | O-sec-Bu |
| 4-$CF_3$ | H | $CO_2Me$ | Me | O-sec-Bu |
| 4-Cl | H | $CO_2Me$ | Me | O-sec-Bu |
| 4-Br | H | $CO_2Me$ | Me | O-sec-Bu |
| 4-$OCF_3$ | H | $CO_2Me$ | Me | O-sec-Bu |
| 4-$CF_3$ | 5-Cl | $CO_2Me$ | Me | O-sec-Bu |
| 4-Cl | 5-Cl | $CO_2Me$ | Me | O-sec-Bu |
| 4-Br | 5-Cl | $CO_2Me$ | Me | O-sec-Bu |
| 4-$OCF_3$ | 5-Cl | $CO_2Me$ | Me | O-sec-Bu |
| 4-$CF_3$ | 5-Br | $CO_2Me$ | Me | O-sec-Bu |
| 4-Cl | 5-Br | $CO_2Me$ | Me | O-sec-Bu |
| 4-Br | 5-Br | $CO_2Me$ | Me | O-sec-Bu |
| 4-$OCF_3$ | 5-Br | $CO_2Me$ | Me | O-sec-Bu |
| 4-$CF_3$ | 4-F | $CO_2Me$ | Me | O-sec-Bu |
| 4-Cl | 4-F | $CO_2Me$ | Me | O-sec-Bu |
| 4-Br | 4-F | $CO_2Me$ | Me | O-sec-Bu |
| 4-$OCF_3$ | 4-F | $CO_2Me$ | Me | O-sec-Bu |
| 4-$CF_3$ | 5-$CF_3$ | $CO_2Me$ | Me | O-sec-Bu |
| 4-$CF_3$ | 5-F | $CO_2Me$ | Me | O-sec-Bu |
| 4-$CF_3$ | 5-Cl | Ph | Me | O-sec-Bu |
| 4-$CF_3$ | 5-Cl | 4-Cl—Ph | Me | O-sec-Bu |
| 4-$CF_3$ | 5-Cl | $CO_2Et$ | Me | O-sec-Bu |
| 4-$CF_3$ | 5-Cl | Me | Me | $OCH_2CH_2OEt$ |
| 4-$CF_3$ | H | $CO_2Me$ | Me | $OCH_2CH_2OEt$ |
| 4-Cl | H | $CO_2Me$ | Me | $OCH_2CH_2OEt$ |
| 4-Br | H | $CO_2Me$ | Me | $OCH_2CH_2OEt$ |
| 4-$OCF_3$ | H | $CO_2Me$ | Me | $OCH_2CH_2OEt$ |
| 4-$CF_3$ | 5-Cl | $CO_2Me$ | Me | $OCH_2CH_2OEt$ |
| 4-Cl | 5-Cl | $CO_2Me$ | Me | $OCH_2CH_2OEt$ |
| 4-Br | 5-Cl | $CO_2Me$ | Me | $OCH_2CH_2OEt$ |
| 4-$OCF_3$ | 5-Cl | $CO_2Me$ | Me | $OCH_2CH_2OEt$ |
| 4-$CF_3$ | 5-Br | $CO_2Me$ | Me | $OCH_2CH_2OEt$ |
| 4-Cl | 5-Br | $CO_2Me$ | Me | $OCH_2CH_2OEt$ |

TABLE 1-continued

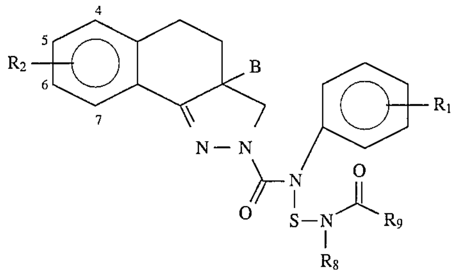

| $R_1$ | $R_2$ | B | $R_8$ | $R_9$ |
|---|---|---|---|---|
| 4-Br | 5-Br | $CO_2Me$ | Me | $OCH_2CH_2OEt$ |
| 4-$OCF_3$ | 5-Br | $CO_2Me$ | Me | $OCH_2CH_2OEt$ |
| 4-$CF_3$ | 4-F | $CO_2Me$ | Me | $OCH_2CH_2OEt$ |
| 4-Cl | 4-F | $CO_2Me$ | Me | $OCH_2CH_2OEt$ |
| 4-Br | 4-F | $CO_2Me$ | Me | $OCH_2CH_2OEt$ |
| 4-$OCF_3$ | 4-F | $CO_2Me$ | Me | $OCH_2CH_2OEt$ |
| 4-$CF_3$ | 5-$CF_3$ | $CO_2Me$ | Me | $OCH_2CH_2OEt$ |
| 4-$CF_3$ | 5-F | $CO_2Me$ | Me | $OCH_2CH_2OEt$ |
| 4-$CF_3$ | 5-Cl | Ph | Me | $OCH_2CH_2OEt$ |
| 4-$CF_3$ | 5-Cl | 4-Cl—Ph | Me | $OCH_2CH_2OEt$ |
| 4-$CF_3$ | 5-Cl | $CO_2Et$ | Me | $OCH_2CH_2OEt$ |
| 4-$CF_3$ | 5-Cl | Me | Me | $OCH_2CCl_3$ |
| 4-$CF_3$ | H | $CO_2Me$ | Me | $OCH_2CCl_3$ |
| 4-Cl | H | $CO_2Me$ | Me | $OCH_2CCl_3$ |
| 4-Br | H | $CO_2Me$ | Me | $OCH_2CCl_3$ |
| 4-$OCF_3$ | H | $CO_2Me$ | Me | $OCH_2CCl_3$ |
| 4-$CF_3$ | 5-Cl | $CO_2Me$ | Me | $OCH_2CCl_3$ |
| 4-Cl | 5-Cl | $CO_2Me$ | Me | $OCH_2CCl_3$ |
| 4-Br | 5-Cl | $CO_2Me$ | Me | $OCH_2CCl_3$ |
| 4-$OCF_3$ | 5-Cl | $CO_2Me$ | Me | $OCH_2CCl_3$ |
| 4-$CF_3$ | 5-Br | $CO_2Me$ | Me | $OCH_2CCl_3$ |
| 4-Cl | 5-Br | $CO_2Me$ | Me | $OCH_2CCl_3$ |
| 4-Br | 5-Br | $CO_2Me$ | Me | $OCH_2CCl_3$ |
| 4-$OCF_3$ | 5-Br | $CO_2Me$ | Me | $OCH_2CCl_3$ |
| 4-$CF_3$ | 4-F | $CO_2Me$ | Me | $OCH_2CCl_3$ |
| 4-Cl | 4-F | $CO_2Me$ | Me | $OCH_2CCl_3$ |
| 4-Br | 4-F | $CO_2Me$ | Me | $OCH_2CCl_3$ |
| 4-$OCF_3$ | 4-F | $CO_2Me$ | Me | $OCH_2CCl_3$ |
| 4-$CF_3$ | 5-$CF_3$ | $CO_2Me$ | Me | $OCH_2CCl_3$ |
| 4-$CF_3$ | 5-F | $CO_2Me$ | Me | $OCH_2CCl_3$ |
| 4-$CF_3$ | 5-Cl | Ph | Me | $OCH_2CCl_3$ |
| 4-$CF_3$ | 5-Cl | 4-Cl—Ph | Me | $OCH_2CCl_3$ |
| 4-$CF_3$ | 5-Cl | $CO_2Et$ | Me | $OCH_2CCl_3$ |
| 4-$CF_3$ | 5-Cl | Me | Me | $OCH_2CF_3$ |
| 4-$CF_3$ | H | $CO_2Me$ | Me | $OCH_2CF_3$ |
| 4-Cl | H | $CO_2Me$ | Me | $OCH_2CF_3$ |
| 4-Br | H | $CO_2Me$ | Me | $OCH_2CF_3$ |
| 4-$OCF_3$ | H | $CO_2Me$ | Me | $OCH_2CF_3$ |
| 4-$CF_3$ | 5-Cl | $CO_2Me$ | Me | $OCH_2CF_3$ |
| 4-Cl | 5-Cl | $CO_2Me$ | Me | $OCH_2CF_3$ |
| 4-Br | 5-Cl | $CO_2Me$ | Me | $OCH_2CF_3$ |
| 4-$OCF_3$ | 5-Cl | $CO_2Me$ | Me | $OCH_2CF_3$ |
| 4-$CF_3$ | 5-Br | $CO_2Me$ | Me | $OCH_2CF_3$ |
| 4-Cl | 5-Br | $CO_2Me$ | Me | $OCH_2CF_3$ |
| 4-Br | 5-Br | $CO_2Me$ | Me | $OCH_2CF_3$ |
| 4-$OCF_3$ | 5-Br | $CO_2Me$ | Me | $OCH_2CF_3$ |
| 4-$CF_3$ | 4-F | $CO_2Me$ | Me | $OCH_2CF_3$ |
| 4-Cl | 4-F | $CO_2Me$ | Me | $OCH_2CF_3$ |
| 4-Br | 4-F | $CO_2Me$ | Me | $OCH_2CF_3$ |
| 4-$OCF_3$ | 4-F | $CO_2Me$ | Me | $OCH_2CF_3$ |
| 4-$CF_3$ | 5-$CF_3$ | $CO_2Me$ | Me | $OCH_2CF_3$ |
| 4-$CF_3$ | 5-F | $CO_2Me$ | Me | $OCH_2CF_3$ |
| 4-$CF_3$ | 5-Cl | Ph | Me | $OCH_2CF_3$ |
| 4-$CF_3$ | 5-Cl | 4-Cl—Ph | Me | $OCH_2CF_3$ |
| 4-$CF_3$ | 5-Cl | $CO_2Et$ | Me | $OCH_2CF_3$ |
| 4-$CF_3$ | 5-Cl | Me | Me | $OCH_2CO_2Et$ |
| 4-$CF_3$ | H | $CO_2Me$ | Me | $OCH_2CO_2Et$ |
| 4-Cl | H | $CO_2Me$ | Me | $OCH_2CO_2Et$ |
| 4-Br | H | $CO_2Me$ | Me | $OCH_2CO_2Et$ |
| 4-$OCF_3$ | H | $CO_2Me$ | Me | $OCH_2CO_2Et$ |
| 4-$CF_3$ | 5-Cl | $CO_2Me$ | Me | $OCH_2CO_2Et$ |
| 4-Cl | 5-Cl | $CO_2Me$ | Me | $OCH_2CO_2Et$ |
| 4-Br | 5-Cl | $CO_2Me$ | Me | $OCH_2CO_2Et$ |
| 4-$OCF_3$ | 5-Cl | $CO_2Me$ | Me | $OCH_2CO_2Et$ |

TABLE 1-continued

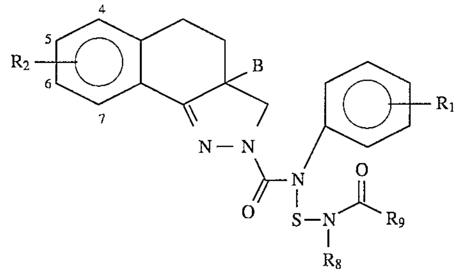

| $R_1$ | $R_2$ | B | $R_8$ | $R_9$ |
|---|---|---|---|---|
| 4-$CF_3$ | 5-Br | $CO_2Me$ | Me | $OCH_2CO_2Et$ |
| 4-Cl | 5-Br | $CO_2Me$ | Me | $OCH_2CO_2Et$ |
| 4-Br | 5-Br | $CO_2Me$ | Me | $OCH_2CO_2Et$ |
| 4-$OCF_3$ | 5-Br | $CO_2Me$ | Me | $OCH_2CO_2Et$ |
| 4-$CF_3$ | 4-F | $CO_2Me$ | Me | $OCH_2CO_2Et$ |
| 4-Cl | 4-F | $CO_2Me$ | Me | $OCH_2CO_2Et$ |
| 4-Br | 4-F | $CO_2Me$ | Me | $OCH_2CO_2Et$ |
| 4-$OCF_3$ | 4-F | $CO_2Me$ | Me | $OCH_2CO_2Et$ |
| 4-$CF_3$ | 5-$CF_3$ | $CO_2Me$ | Me | $OCH_2CO_2Et$ |
| 4-$CF_3$ | 5-F | $CO_2Me$ | Me | $OCH_2CO_2Et$ |
| 4-$CF_3$ | 5-Cl | Ph | Me | $OCH_2CO_2Et$ |
| 4-$CF_3$ | 5-Cl | 4-Cl—Ph | Me | $OCH_2CO_2Et$ |
| 4-$CF_3$ | 5-Cl | $CO_2Et$ | Me | $OCH_2CO_2Et$ |
| 4-$CF_3$ | H | H | Me | F |
| 4-$CF_3$ | 5-Cl | H | Me | F |
| 4-$CF_3$ | 5-Br | H | Me | F |
| 4-$CF_3$ | 4-F | H | Me | F |
| 4-$CF_3$ | H | Me | Me | F |
| 4-$CF_3$ | 5-Cl | Me | Me | F |
| 4-$CF_3$ | 5-Br | Me | Me | F |
| 4-$CF_3$ | 4-F | Me | Me | F |
| 4-$CF_3$ | H | $CO_2Me$ | Me | F |
| 4-Cl | H | $CO_2Me$ | Me | F |
| 4-Br | H | $CO_2Me$ | Me | F |
| 4-$OCF_3$ | H | $CO_2Me$ | Me | F |
| 4-$CF_3$ | 5-Cl | $CO_2Me$ | Me | F |
| 4-Cl | 5-Cl | $CO_2Me$ | Me | F |
| 4-Br | 5-Cl | $CO_2Me$ | Me | F |
| 4-$OCF_3$ | 5-Cl | $CO_2Me$ | Me | F |
| 4-$CF_3$ | 5-Br | $CO_2Me$ | Me | F |
| 4-Cl | 5-Br | $CO_2Me$ | Me | F |
| 4-Br | 5-Br | $CO_2Me$ | Me | F |
| 4-$OCF_3$ | 5-Br | $CO_2Me$ | Me | F |
| 4-$CF_3$ | 4-F | $CO_2Me$ | Me | F |
| 4-Cl | 4-F | $CO_2Me$ | Me | F |
| 4-Br | 4-F | $CO_2Me$ | Me | F |
| 4-$OCF_3$ | 4-F | $CO_2Me$ | Me | F |
| 4-$CF_3$ | 5-$CF_3$ | $CO_2Me$ | Me | F |
| 4-$CF_3$ | 5-F | $CO_2Me$ | Me | F |
| 4-$CF_3$ | 5-Cl | Ph | Me | F |
| 4-$CF_3$ | 5-Cl | 4-Cl—Ph | Me | F |
| 4-$CF_3$ | 5-Cl | $CO_2Et$ | Me | F |
| 4-$CF_3$ | 5-Cl | $CO_2Me$ | Me | piperidino |
| 4-$CF_3$ | 4-F | Me | Me | piperidino |
| 4-$CF_3$ | Cl | $CO_2Me$ | Me | morpholino |
| 4-$OCF_3$ | Cl | $CO_2Me$ | Me | morpholino |
| 4-$CF_3$ | 5-Cl | $CO_2Me$ | Me | n-Pr |
| 4-$OCF_3$ | 5-Cl | $CO_2Me$ | Me | n-Pr |
| 4-$CF_3$ | 5-Br | $CO_2Me$ | Me | sec-Bu |
| 4-Cl | 5-Br | $CO_2Me$ | Me | sec-Bu |
| 4-Br | 5-Br | $CO_2Me$ | Me | sec-Bu |
| 4-$OCF_3$ | 5-Br | $CO_2Me$ | Me | sec-Bu |
| 4-$CF_3$ | 4-F | $CO_2Me$ | Me | 4-Cl—Ph |
| 4-Cl | 4-F | $CO_2Me$ | Me | 4-Cl—Ph |
| 4-Br | 4-F | $CO_2Me$ | Me | 4-Cl—Ph |
| 4-$OCF_3$ | 4-F | $CO_2Me$ | Me | 4-Cl—Ph |
| 4-$CF_3$ | 5-Cl | Me | Et | $OCH_2CCl_3$ |
| 4-$CF_3$ | H | $CO_2Me$ | Et | $NEt_2$ |
| 4-Cl | H | $CO_2Me$ | Et | $NEt_2$ |
| 4-Br | H | $CO_2Me$ | Et | $NEt_2$ |
| 4-$OCF_3$ | H | $CO_2Me$ | Et | $NEt_2$ |
| 4-$CF_3$ | 5-Cl | $CO_2Me$ | Et | 2,6-di-Me-morpholino |
| 4-Cl | 5-Cl | $CO_2Me$ | Et | 2,6-di-Me-morpholino |
| 4-Br | 5-Cl | $CO_2Me$ | Et | 2,6-di-Me-morpholino |

TABLE 1-continued

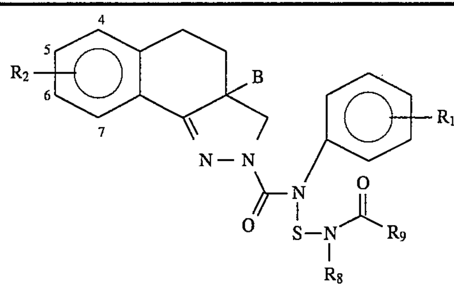

| $R_1$ | $R_2$ | B | $R_8$ | $R_9$ |
|---|---|---|---|---|
| 4-$OCF_3$ | 5-Cl | $CO_2Me$ | Et | 2,6-di-Me-morpholino |
| 4-$CF_3$ | 5-Cl | Me | iPr | OEt |
| 4-$CF_3$ | H | $CO_2Me$ | iPr | OEt |
| 4-Cl | H | $CO_2Me$ | iPr | OEt |
| 4-Br | H | $CO_2Me$ | iPr | OEt |
| 4-$OCF_3$ | H | $CO_2Me$ | iPr | OEt |
| 4-$CF_3$ | 5-Cl | $CO_2Me$ | iPr | OEt |
| 4-Cl | 5-Cl | $CO_2Me$ | iPr | OEt |
| 4-Br | 5-Cl | $CO_2Me$ | iPr | OEt |
| 4-$OCF_3$ | 5-Cl | $CO_2Me$ | iPr | OEt |
| 4-$CF_3$ | 5-Br | $CO_2Me$ | iPr | OEt |
| 4-Cl | 5-Br | $CO_2Me$ | iPr | OEt |
| 4-Br | 5-Br | $CO_2Me$ | iPr | OEt |
| 4-$OCF_3$ | 5-Br | $CO_2Me$ | iPr | OEt |
| 4-$CF_3$ | 4-F | $CO_2Me$ | iPr | OEt |
| 4-Cl | 4-F | $CO_2Me$ | iPr | OEt |
| 4-Br | 4-F | $CO_2Me$ | iPr | OEt |
| 4-$OCF_3$ | 4-F | $CO_2Me$ | iPr | OEt |
| 4-$CF_3$ | 5-$CF_3$ | $CO_2Me$ | iPr | OEt |
| 4-$CF_3$ | 5-F | $CO_2Me$ | iPr | OEt |
| 4-$CF_3$ | 5-Cl | Ph | iPr | OEt |
| 4-$CF_3$ | 5-Cl | 4-Cl—Ph | iPr | OEt |
| 4-$CF_3$ | 5-Cl | $CO_2Et$ | iPr | OEt |
| 4-$CF_3$ | 5-Cl | $CO_2Me$ | Me | ON=$(CH_3)SCH_3$ |
| 4-$CF_3$ | 5-Cl | $CO_2Me$ | Me | 2,3-dihydro-2,2-dimethylbenzofuranyl oxy-7 |
| 4-$CF_3$ | 5-Cl | $CO_2Me$ | Me | 1-naphthoxy |
| 4-$CF_3$ | 5-Cl | Me | iPr | O-n-Bu |
| 4-$CF_3$ | H | $CO_2Me$ | iPr | O-n-Bu |
| 4-Cl | H | $CO_2Me$ | iPr | O-n-Bu |
| 4-Br | H | $CO_2Me$ | iPr | O-n-Bu |
| 4-$OCF_3$ | H | $CO_2Me$ | iPr | O-n-Bu |
| 4-$CF_3$ | 5-Cl | $CO_2Me$ | iPr | O-n-Bu |
| 4-Cl | 5-Cl | $CO_2Me$ | iPr | O-n-Bu |
| 4-Br | 5-Cl | $CO_2Me$ | iPr | O-n-Bu |
| 4-$OCF_3$ | 5-Cl | $CO_2Me$ | iPr | O-n-Bu |
| 4-$CF_3$ | 5-Br | $CO_2Me$ | iPr | O-n-Bu |
| 4-Cl | 5-Br | $CO_2Me$ | iPr | O-n-Bu |
| 4-Br | 5-Br | $CO_2Me$ | iPr | O-n-Bu |
| 4-$OCF_3$ | 5-Br | $CO_2Me$ | iPr | O-n-Bu |
| 4-$CF_3$ | 4-F | $CO_2Me$ | iPr | O-n-Bu |
| 4-Cl | 4-F | $CO_2Me$ | iPr | O-n-Bu |
| 4-Br | 4-F | $CO_2Me$ | iPr | O-n-Bu |
| 4-$OCF_3$ | 4-F | $CO_2Me$ | iPr | O-n-Bu |
| 4-$CF_3$ | 5-$CF_3$ | $CO_2Me$ | iPr | O-n-Bu |
| 4-$CF_3$ | 5-F | $CO_2Me$ | iPr | O-n-Bu |
| 4-$CF_3$ | 5-Cl | Ph | iPr | O-n-Bu |
| 4-$CF_3$ | 5-Cl | 4-Cl—Ph | iPr | O-n-Bu |
| 4-$CF_3$ | 5-Cl | $CO_2Et$ | iPr | O-n-Bu |
| 4-$CF_3$ | H | $CO_2Me$ | iPr | $OCH_2CO_2Me$ |
| 4-$CF_3$ | 5-Cl | $CO_2Me$ | iPr | $OCH_2CO_2Me$ |
| 4-$CF_3$ | 5-Br | $CO_2Me$ | iPr | $OCH_2CO_2Me$ |
| 4-$CF_3$ | 4-F | $CO_2Me$ | iPr | $OCH_2CO_2Me$ |
| 4-$CF_3$ | H | $CO_2Me$ | iPr | $NMe_2$ |
| 4-Cl | H | $CO_2Me$ | iPr | $NMe_2$ |
| 4-Br | H | $CO_2Me$ | iPr | $NMe_2$ |
| 4-$OCF_3$ | H | $CO_2Me$ | iPr | $NMe_2$ |
| 4-$CF_3$ | 5-Cl | $CO_2Me$ | iPr | $NEt_2$ |
| 4-Cl | 5-Cl | $CO_2Me$ | iPr | $NEt_2$ |
| 4-Br | 5-Cl | $CO_2Me$ | iPr | $NEt_2$ |
| 4-$OCF_3$ | 5-Cl | $CO_2Me$ | iPr | $NEt_2$ |
| 4-$CF_3$ | 5-Br | $CO_2Me$ | iPr | piperidino |
| 4-Cl | 5-Br | $CO_2Me$ | iPr | piperidino |

TABLE 1-continued

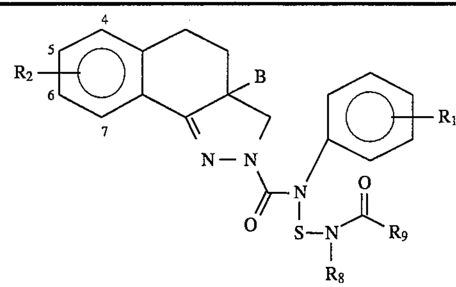

| $R_1$ | $R_2$ | B | $R_8$ | $R_9$ |
|---|---|---|---|---|
| 4-Br | 5-Br | $CO_2Me$ | iPr | piperidino |
| 4-$OCF_3$ | 5-Br | $CO_2Me$ | iPr | piperidino |
| 4-$CF_3$ | 4-F | $CO_2Me$ | iPr | Et |
| 4-Cl | 4-F | $CO_2Me$ | iPr | Et |
| 4-Br | 4-F | $CO_2Me$ | iPr | Et |
| 4-$OCF_3$ | 4-F | $CO_2Me$ | iPr | Et |
| 4-$CF_3$ | H | H | $CH_2Ph$ | OEt |
| 4-$CF_3$ | 5-Cl | H | $CH_2Ph$ | O-n-octyl |
| 4-$CF_3$ | 5-Br | H | $CH_2Ph$ | $OCH_2CO_2Et$ |
| 4-$CF_3$ | H | Me | $CH_2Ph$ | $NEt_2$ |
| 4-$CF_3$ | 5-Cl | Me | $CH_2Ph$ | morpholino |
| 4-$CF_3$ | 5-Br | Me | $CH_2Ph$ | 4-Cl—Ph |
| 4-$CF_3$ | 4-F | Me | $CH_2Ph$ | Et |
| 4-$CF_3$ | H | $CO_2Me$ | $CH_2Ph$ | O-n-Bu |
| 4-Cl | H | $CO_2Me$ | $CH_2Ph$ | O-iPr |
| 4-Br | H | $CO_2Me$ | $CH_2Ph$ | $OCH_2CF_3$ |
| 4-$OCF_3$ | H | $CO_2Me$ | $CH_2Ph$ | $NMe_2$ |
| 4-$CF_3$ | 5-Cl | $CO_2Me$ | $CH_2Ph$ | piperidino |
| 4-Cl | 5-Cl | $CO_2Me$ | $CH_2Ph$ | Ph |
| 4-Br | 5-Cl | $CO_2Me$ | $CH_2Ph$ | 4-$NO_2$—Ph |
| 4-$OCF_3$ | 5-Cl | $CO_2Me$ | $CH_2Ph$ | Bu |
| 4-$CF_3$ | 5-Br | $CO_2Me$ | $CH_2Ph$ | O-n-hexyl |
| 4-Cl | 5-Br | $CO_2Me$ | $CH_2Ph$ | O-sec-Bu |
| 4-Br | 5-Br | $CO_2Me$ | $CH_2Ph$ | $OCH_2CH_2OEt$ |
| 4-$OCF_3$ | 5-Br | $CO_2Me$ | $CH_2Ph$ | $NMe_2$ |
| 4-$CF_3$ | 4-F | $CO_2Me$ | $CH_2Ph$ | 2,6-di-Me-morpholino |
| 4-Cl | 4-F | $CO_2Me$ | $CH_2Ph$ | 3-Br—Ph |
| 4-Br | 4-F | $CO_2Me$ | $CH_2Ph$ | 4-Me—Ph |
| 4-$OCF_3$ | 4-F | $CO_2Me$ | $CH_2Ph$ | nPr |
| 4-$CF_3$ | 5-$CF_3$ | $CO_2Me$ | $CH_2Ph$ | Me |
| 4-$CF_3$ | 5-F | $CO_2Me$ | $CH_2Ph$ | OEt |
| 4-$CF_3$ | 5-Cl | Ph | $CH_2Ph$ | O-n-Bu |
| 4-$CF_3$ | 5-Cl | 4-Cl—Ph | $CH_2Ph$ | O-n-octyl |
| 4-$CF_3$ | 5-Cl | $CO_2Et$ | $CH_2Ph$ | $OCH_2CCl_3$ |

TABLE 2

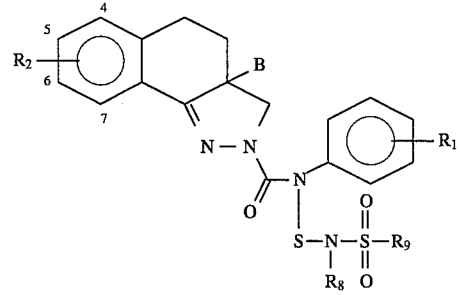

| $R_1$ | $R_2$ | B | $R_8$ | $R_9$ |
|---|---|---|---|---|
| 4-$CF_3$ | H | $CO_2Me$ | Me | $NMe_2$ |
| 4-Cl | H | $CO_2Me$ | Me | $NMe_2$ |
| 4-Br | H | $CO_2Me$ | Me | $NMe_2$ |
| 4-$OCF_3$ | H | $CO_2Me$ | Me | $NMe_2$ |
| 4-$CF_3$ | 5-Cl | $CO_2Me$ | Me | $NMe_2$ |
| 4-Cl | 5-Cl | $CO_2Me$ | Me | $NMe_2$ |
| 4-Br | 5-Cl | $CO_2Me$ | Me | $NMe_2$ |
| 4-$OCF_3$ | 5-Cl | $CO_2Me$ | Me | $NMe_2$ |
| 4-$CF_3$ | 5-Br | $CO_2Me$ | Me | $NMe_2$ |

TABLE 2-continued

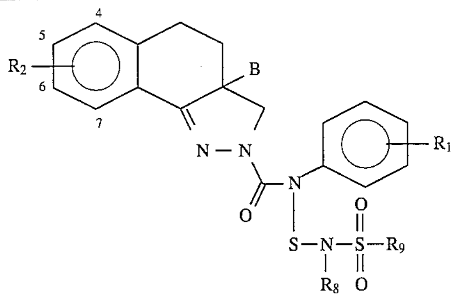

| $R_1$ | $R_2$ | B | $R_8$ | $R_9$ |
|---|---|---|---|---|
| 4-Cl | 5-Br | $CO_2Me$ | Me | $NMe_2$ |
| 4-Br | 5-Br | $CO_2Me$ | Me | $NMe_2$ |
| $4\text{-}OCF_3$ | 5-Br | $CO_2Me$ | Me | $NMe_2$ |
| $4\text{-}CF_3$ | 4-F | $CO_2Me$ | Me | $NMe_2$ |
| 4-Cl | 4-F | $CO_2Me$ | Me | $NMe_2$ |
| 4-Br | 4-F | $CO_2Me$ | Me | $NMe_2$ |
| $4\text{-}OCF_3$ | 4-F | $CO_2Me$ | Me | $NMe_2$ |
| $4\text{-}CF_3$ | $5\text{-}CF_3$ | $CO_2Me$ | Me | $NMe_2$ |
| $4\text{-}CF_3$ | 5-F | $CO_2Me$ | Me | $NMe_2$ |
| $4\text{-}CF_3$ | 5-Cl | Ph | Me | $NMe_2$ |
| $4\text{-}CF_3$ | 5-Cl | 4-Cl-Ph | Me | $NMe_2$ |
| $4\text{-}CF_3$ | 5-Cl | $CO_2Et$ | Me | $NMe_2$ |
| $4\text{-}CF_3$ | H | $CO_2Me$ | Me | $NEt_2$ |
| 4-Cl | H | $CO_2Me$ | Me | $NEt_2$ |
| 4-Br | H | $CO_2Me$ | Me | $NEt_2$ |
| $4\text{-}OCF_3$ | H | $CO_2Me$ | Me | $NEt_2$ |
| $4\text{-}CF_3$ | 5-Cl | $CO_2Me$ | Me | $NEt_2$ |
| 4-Cl | 5-Cl | $CO_2Me$ | Me | $NEt_2$ |
| 4-Br | 5-Cl | $CO_2Me$ | Me | $NEt_2$ |
| $4\text{-}OCF_3$ | 5-Cl | $CO_2Me$ | Me | $NEt_2$ |
| $4\text{-}CF_3$ | 5-Br | $CO_2Me$ | Me | $NEt_2$ |
| 4-Cl | 5-Br | $CO_2Me$ | Me | $NEt_2$ |
| 4-Br | 5-Br | $CO_2Me$ | Me | $NEt_2$ |
| $4\text{-}OCF_3$ | 5-Br | $CO_2Me$ | Me | $NEt_2$ |
| $4\text{-}CF_3$ | 4-F | $CO_2Me$ | Me | $NEt_2$ |
| 4-Cl | 4-F | $CO_2Me$ | Me | piperidino |
| 4-Br | 4-F | $CO_2Me$ | Me | piperidino |
| $4\text{-}OCF_3$ | 4-F | $CO_2Me$ | Me | piperidino |
| $4\text{-}CF_3$ | $5\text{-}CF_3$ | $CO_2Me$ | Me | piperidino |
| $4\text{-}CF_3$ | 5-F | $CO_2Me$ | Me | piperidino |
| $4\text{-}CF_3$ | 5-Cl | Ph | Me | piperidino |
| $4\text{-}CF_3$ | 5-Cl | 4-Cl-Ph | Me | piperidino |
| $4\text{-}CF_3$ | 5-Cl | $CO_2Et$ | Me | piperidino |
| $4\text{-}CF_3$ | H | $CO_2Me$ | Me | $C_2H_5$ |
| $4\text{-}CF_3$ | 5-Cl | $CO_2Me$ | Me | $C_2H_5$ |
| $4\text{-}CF_3$ | 5-Br | $CO_2Me$ | Me | $C_2H_5$ |
| $4\text{-}CF_3$ | 4-F | $CO_2Me$ | Me | $C_2H_5$ |
| $4\text{-}CF_3$ | H | $CO_2Me$ | Me | n-hexyl |
| 4-Cl | H | $CO_2Me$ | Me | n-hexyl |
| 4-Br | H | $CO_2Me$ | Me | n-hexyl |
| $4\text{-}OCF_3$ | H | $CO_2Me$ | Me | n-hexyl |
| $4\text{-}CF_3$ | 5-Cl | $CO_2Me$ | Me | Ph |
| 4-Cl | 5-Cl | $CO_2Me$ | Me | Ph |
| 4-Br | 5-Cl | $CO_2Me$ | Me | Ph |
| $4\text{-}OCF_3$ | 5-Cl | $CO_2Me$ | Me | Ph |
| $4\text{-}CF_3$ | 5-Br | $CO_2Me$ | Me | 4-Cl-Ph |
| 4-Cl | 5-Br | $CO_2Me$ | Me | 4-Cl-Ph |
| 4-Br | 5-Br | $CO_2Me$ | Me | 4-Cl-Ph |
| $4\text{-}OCF_3$ | 5-Br | $CO_2Me$ | Me | 4-Cl-Ph |
| $4\text{-}CF_3$ | 4-F | $CO_2Me$ | Me | 4-Me-Ph |
| 4-Cl | 4-F | $CO_2Me$ | Me | 4-Me-Ph |
| 4-Br | 4-F | $CO_2Me$ | Me | 4-Me-Ph |
| $4\text{-}OCF_3$ | 4-F | $CO_2Me$ | Me | 4-Me-Ph |
| $4\text{-}CF_3$ | $5\text{-}CF_3$ | $CO_2Me$ | Me | n-Bu |
| $4\text{-}CF_3$ | 5-F | $CO_2Me$ | Me | n-Bu |
| $4\text{-}CF_3$ | 5-Cl | Ph | Me | n-Bu |
| $4\text{-}CF_3$ | 5-Cl | 4-Cl-Ph | Me | n-Bu |
| $4\text{-}CF_3$ | 5-Cl | $CO_2Et$ | Me | n-Bu |
| $4\text{-}CF_3$ | H | H | Et | $NMe_2$ |
| $4\text{-}CF_3$ | 5-Cl | H | Et | $NMe_2$ |
| $4\text{-}CF_3$ | 5-Br | H | Et | $NMe_2$ |
| $4\text{-}CF_3$ | 4-F | H | Et | $NMe_2$ |
| $4\text{-}CF_3$ | H | Me | Et | $NEt_2$ |
| $4\text{-}CF_3$ | 5-Cl | Me | Et | $NEt_2$ |
| $4\text{-}CF_3$ | 5-Br | Me | Et | $NEt_2$ |
| $4\text{-}CF_3$ | 4-F | Me | Et | $NEt_2$ |
| $4\text{-}CF_3$ | 5-Cl | $CO_2Me$ | Et | morpholino |
| 4-Cl | 5-Cl | $CO_2Me$ | Et | morpholino |
| 4-Br | 5-Cl | $CO_2Me$ | Et | morpholino |
| $4\text{-}OCF_3$ | 5-Cl | $CO_2Me$ | Et | morpholino |
| $4\text{-}CF_3$ | 5-Cl | $CO_2Me$ | Et | iPr |
| 4-Cl | 5-Cl | $CO_2Me$ | Et | iPr |
| 4-Br | 5-Cl | $CO_2Me$ | Et | iPr |
| $4\text{-}OCF_3$ | 5-Cl | $CO_2Me$ | Et | iPr |
| $4\text{-}CF_3$ | 5-Br | $CO_2Me$ | Et | n-Bu |
| 4-Cl | 5-Br | $CO_2Me$ | Et | n-Bu |
| 4-Br | 5-Br | $CO_2Me$ | Et | n-Bu |
| $4\text{-}OCF_3$ | 5-Br | $CO_2Me$ | Et | n-Bu |
| $4\text{-}CF_3$ | 4-F | $CO_2Me$ | Et | Ph |
| 4-Cl | 4-F | $CO_2Me$ | Et | Ph |
| 4-Br | 4-F | $CO_2Me$ | Et | Ph |
| $4\text{-}OCF_3$ | 4-F | $CO_2Me$ | Et | Ph |
| $4\text{-}CF_3$ | H | $CO_2Me$ | iPr | $NMe_2$ |
| 4-Cl | H | $CO_2Me$ | iPr | $NMe_2$ |
| 4-Br | H | $CO_2Me$ | iPr | $NMe_2$ |
| $4\text{-}OCF_3$ | H | $CO_2Me$ | iPr | $NMe_2$ |
| $4\text{-}CF_3$ | 5-Cl | $CO_2Me$ | iPr | $NMe_2$ |
| 4-Cl | 5-Cl | $CO_2Me$ | iPr | $NMe_2$ |
| 4-Br | 5-Cl | $CO_2Me$ | iPr | $NMe_2$ |
| $4\text{-}OCF_3$ | 5-Cl | $CO_2Me$ | iPr | $NMe_2$ |
| $4\text{-}CF_3$ | 5-Br | $CO_2Me$ | iPr | $NMe_2$ |
| 4-Cl | 5-Br | $CO_2Me$ | iPr | $NMe_2$ |
| 4-Br | 5-Br | $CO_2Me$ | iPr | $NMe_2$ |
| $4\text{-}OCF_3$ | 5-Br | $CO_2Me$ | iPr | $NMe_2$ |
| $4\text{-}CF_3$ | 4-F | $CO_2Me$ | iPr | $NMe_2$ |
| 4-Cl | 4-F | $CO_2Me$ | iPr | $NMe_2$ |
| 4-Br | 4-F | $CO_2Me$ | iPr | $NMe_2$ |
| $4\text{-}OCF_3$ | 4-F | $CO_2Me$ | iPr | $NMe_2$ |
| $4\text{-}CF_3$ | $5\text{-}CF_3$ | $CO_2Me$ | iPr | $NMe_2$ |
| $4\text{-}CF_3$ | 5-F | $CO_2Me$ | iPr | $NMe_2$ |
| $4\text{-}CF_3$ | 5-Cl | Ph | iPr | $NMe_2$ |
| $4\text{-}CF_3$ | 5-Cl | 4-Cl-Ph | iPr | $NMe_2$ |
| $4\text{-}CF_3$ | 5-Cl | $CO_2Et$ | iPr | $NMe_2$ |
| $4\text{-}CF_3$ | H | $CO_2Me$ | iPr | 2,6-di-Me-morpholino |
| $4\text{-}CF_3$ | 5-Cl | $CO_2Me$ | iPr | 2,6-di-Me-morpholino |
| $4\text{-}CF_3$ | 5-Br | $CO_2Me$ | iPr | 2,6-di-Me-morpholino |
| $4\text{-}CF_3$ | 4-F | $CO_2Me$ | iPr | 2,6-di-Me-morpholino |
| $4\text{-}CF_3$ | H | $CO_2Me$ | iPr | piperidino |
| $4\text{-}OCF_3$ | H | $CO_2Me$ | iPr | piperidino |
| $4\text{-}CF_3$ | 5-Cl | $CO_2Me$ | iPr | Et |
| 4-Cl | 5-Cl | $CO_2Me$ | iPr | Et |
| 4-Br | 5-Cl | $CO_2Me$ | iPr | Et |
| $4\text{-}OCF_3$ | 5-Cl | $CO_2Me$ | iPr | Et |
| $4\text{-}CF_3$ | 5-Br | $CO_2Me$ | iPr | n-Bu |
| 4-Cl | 5-Br | $CO_2Me$ | iPr | n-Bu |
| 4-Br | 5-Br | $CO_2Me$ | iPr | n-Bu |
| $4\text{-}OCF_3$ | 5-Br | $CO_2Me$ | iPr | n-Bu |
| $4\text{-}CF_3$ | 4-F | $CO_2Me$ | iPr | Ph |
| 4-Cl | 4-F | $CO_2Me$ | iPr | Ph |
| 4-Br | 4-F | $CO_2Me$ | iPr | Ph |
| $4\text{-}OCF_3$ | 4-F | $CO_2Me$ | iPr | Ph |
| $4\text{-}CF_3$ | $5\text{-}CF_3$ | $CO_2Me$ | iPr | 4-Cl-Ph |

TABLE 2-continued

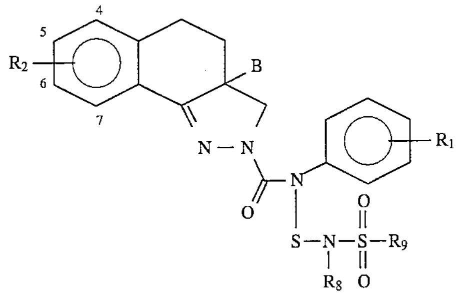

TABLE 2-continued

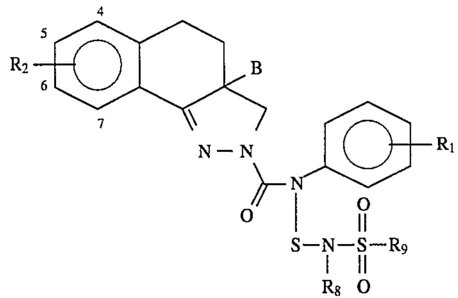

| $R_1$ | $R_2$ | B | $R_8$ | $R_9$ |
|---|---|---|---|---|
| 4-$CF_3$ | 5-F | $CO_2Me$ | iPr | 4-Cl—Ph |
| 4-$CF_3$ | 5-Cl | Ph | iPr | 4-Cl—Ph |
| 4-$CF_3$ | 5-Cl | 4-Cl—Ph | iPr | 4-Cl—Ph |
| 4-$CF_3$ | 5-Cl | $CO_2Et$ | iPr | 4-Cl—Ph |

TABLE 3

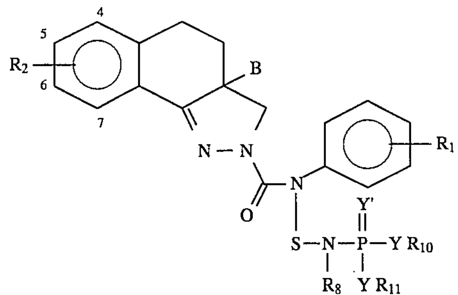

| $R_1$ | $R_2$ | B | $R_8$ | Y' | $Y'R_{10}$ | $Y'R_{11}$ |
|---|---|---|---|---|---|---|
| 4-$CF_3$ | H | $CO_2Me$ | tBu | S | OEt | OEt |
| 4-Cl | H | $CO_2Me$ | tBu | S | OEt | OEt |
| 4-Br | H | $CO_2Me$ | tBu | S | OEt | OEt |
| 4-$OCF_3$ | H | $CO_2Me$ | tBu | S | OEt | OEt |
| 4-$CF_3$ | 5-Cl | $CO_2Me$ | tBu | S | OEt | OEt |
| 4-Cl | 5-Cl | $CO_2Me$ | tBu | S | OEt | OEt |
| 4-Br | 5-Cl | $CO_2Me$ | tBu | S | OEt | OEt |
| 4-$OCF_3$ | 5-Cl | $CO_2Me$ | tBu | S | OEt | OEt |
| 4-$CF_3$ | 5-Br | $CO_2Me$ | tBu | S | OEt | OEt |
| 4-Cl | 5-Br | $CO_2Me$ | tBu | S | OEt | OEt |
| 4-Br | 5-Br | $CO_2Me$ | tBu | S | OEt | OEt |
| 4-$OCF_3$ | 5-Br | $CO_2Me$ | tBu | S | OEt | OEt |
| 4-$CF_3$ | 4-F | $CO_2Me$ | tBu | S | OEt | OEt |
| 4-Cl | 4-F | $CO_2Me$ | tBu | S | OEt | OEt |
| 4-Br | 4-F | $CO_2Me$ | tBu | S | OEt | OEt |
| 4-$OCF_3$ | 4-F | $CO_2Me$ | tBu | S | OEt | OEt |
| 4-$CF_3$ | 5-$CF_3$ | $CO_2Me$ | tBu | S | OEt | OEt |
| 4-$CF_3$ | 5-F | $CO_2Me$ | tBu | S | OEt | OEt |
| 4-$CF_3$ | 5-Cl | Ph | tBu | S | OEt | OEt |
| 4-$CF_3$ | 5-Cl | 4-Cl—Ph | tBu | S | OEt | OEt |
| 4-$CF_3$ | 5-Cl | $CO_2Et$ | tBu | S | OEt | OEt |
| 4-$CF_3$ | H | $CO_2Me$ | tBu | S | $OCH_2C(Me)_2CH_2O$ | |
| 4-Cl | H | $CO_2Me$ | tBu | S | $OCH_2C(Me)_2CH_2O$ | |
| 4-Br | H | $CO_2Me$ | tBu | S | $OCH_2C(Me)_2CH_2O$ | |
| 4-$OCF_3$ | H | $CO_2Me$ | tBu | S | $OCH_2C(Me)_2CH_2O$ | |
| 4-$CF_3$ | 5-Cl | $CO_2Me$ | tBu | S | $OCH_2C(Me)_2CH_2O$ | |
| 4-Cl | 5-Cl | $CO_2Me$ | tBu | S | $OCH_2C(Me)_2CH_2O$ | |
| 4-Br | 5-Cl | $CO_2Me$ | tBu | S | $OCH_2C(Me)_2CH_2O$ | |
| 4-$OCF_3$ | 5-Cl | $CO_2Me$ | tBu | S | $OCH_2C(Me)_2CH_2O$ | |
| 4-$CF_3$ | 5-Br | $CO_2Me$ | tBu | S | $OCH_2C(Me)_2CH_2O$ | |
| 4-Cl | 5-Br | $CO_2Me$ | tBu | S | $OCH_2C(Me)_2CH_2O$ | |
| 4-Br | 5-Br | $CO_2Me$ | tBu | S | $OCH_2C(Me)_2CH_2O$ | |
| 4-$OCF_3$ | 5-Br | $CO_2Me$ | tBu | S | $OCH_2C(Me)_2CH_2O$ | |
| 4-$CF_3$ | 4-F | $CO_2Me$ | tBu | S | $OCH_2C(Me)_2CH_2O$ | |
| 4-Cl | 4-F | $CO_2Me$ | tBu | S | $OCH_2C(Me)_2CH_2O$ | |
| 4-Br | 4-F | $CO_2Me$ | tBu | S | $OCH_2C(Me)_2CH_2O$ | |
| 4-$OCF_3$ | 4-F | $CO_2Me$ | tBu | S | $OCH_2C(Me)_2CH_2O$ | |
| 4-$CF_3$ | 5-$CF_3$ | $CO_2Me$ | tBu | S | $OCH_2C(Me)_2CH_2O$ | |

TABLE 3-continued

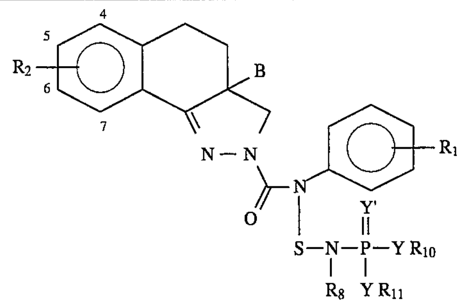

| $R_1$ | $R_2$ | B | $R_8$ | Y' | $Y'R_{10}$ | $Y'R_{11}$ |
|---|---|---|---|---|---|---|
| 4-$CF_3$ | 5-F | $CO_2Me$ | tBu | S | $OCH_2C(Me)_2CH_2O$ | |
| 4-$CF_3$ | 5-Cl | Ph | tBu | S | $OCH_2C(Me)_2CH_2O$ | |
| 4-$CF_3$ | 5-Cl | 4-Cl—Ph | tBu | S | $OCH_2C(Me)_2CH_2O$ | |
| 4-$CF_3$ | 5-Cl | $CO_2Et$ | tBu | S | $OCH_2C(Me)_2CH_2O$ | |
| 4-$CF_3$ | H | $CO_2Me$ | tBu | S | $OCH_2CH_2CH_2O$ | |
| 4-Cl | H | $CO_2Me$ | tBu | S | $OCH_2CH_2CH_2O$ | |
| 4-Br | H | $CO_2Me$ | tBu | S | $OCH_2CH_2CH_2O$ | |
| 4-$OCF_3$ | H | $CO_2Me$ | tBu | S | $OCH_2CH_2CH_2O$ | |
| 4-$CF_3$ | 5-Cl | $CO_2Me$ | tBu | S | $OCH_2CH_2CH_2O$ | |
| 4-Cl | 5-Cl | $CO_2Me$ | tBu | S | $OCH_2CH_2CH_2O$ | |
| 4-Br | 5-Cl | $CO_2Me$ | tBu | S | $OCH_2CH_2CH_2O$ | |
| 4-$OCF_3$ | 5-Cl | $CO_2Me$ | tBu | S | $OCH_2CH_2CH_2O$ | |
| 4-$CF_3$ | 5-Br | $CO_2Me$ | tBu | S | $OCH_2CH_2CH_2O$ | |
| 4-Cl | 5-Br | $CO_2Me$ | tBu | S | $OCH_2CH_2CH_2O$ | |
| 4-Br | 5-Br | $CO_2Me$ | tBu | S | $OCH_2CH_2CH_2O$ | |
| 4-$OCF_3$ | 5-Br | $CO_2Me$ | tBu | S | $OCH_2CH_2CH_2O$ | |
| 4-$CF_3$ | 4-F | $CO_2Me$ | tBu | S | $OCH_2CH_2CH_2O$ | |
| 4-Cl | 4-F | $CO_2Me$ | tBu | S | $OCH_2CH_2CH_2O$ | |
| 4-Br | 4-F | $CO_2Me$ | tBu | S | $OCH_2CH_2CH_2O$ | |
| 4-$OCF_3$ | 4-F | $CO_2Me$ | tBu | S | $OCH_2CH_2CH_2O$ | |
| 4-$CF_3$ | 5-$CF_3$ | $CO_2Me$ | tBu | S | $OCH_2CH_2CH_2O$ | |
| 4-$CF_3$ | 5-F | $CO_2Me$ | tBu | S | $OCH_2CH_2CH_2O$ | |
| 4-$CF_3$ | 5-Cl | Ph | tBu | S | $OCH_2CH_2CH_2O$ | |
| 4-$CF_3$ | 5-Cl | 4-Cl—Ph | tBu | S | $OCH_2CH_2CH_2O$ | |
| 4-$CF_3$ | 5-Cl | $CO_2Et$ | tBu | S | $OCH_2CH_2CH_2O$ | |
| 4-$CF_3$ | H | $CO_2Me$ | tBu | S | $OCH_2CH_2O$ | |
| 4-Cl | H | $CO_2Me$ | tBu | S | $OCH_2CH_2O$ | |
| 4-Br | H | $CO_2Me$ | tBu | S | $OCH_2CH_2O$ | |
| 4-$OCF_3$ | H | $CO_2Me$ | tBu | S | $OCH_2CH_2O$ | |
| 4-$CF_3$ | 5-Cl | $CO_2Me$ | tBu | S | $OCH_2CH_2O$ | |
| 4-Cl | 5-Cl | $CO_2Me$ | tBu | S | $OCH_2CH_2O$ | |
| 4-Br | 5-Cl | $CO_2Me$ | tBu | S | $OCH_2CH_2O$ | |
| 4-$OCF_3$ | 5-Cl | $CO_2Me$ | tBu | S | $OCH_2CH_2O$ | |
| 4-$CF_3$ | 5-Br | $CO_2Me$ | tBu | S | $OCH_2CH_2O$ | |
| 4-Cl | 5-Br | $CO_2Me$ | tBu | S | $OCH_2CH_2O$ | |
| 4-Br | 5-Br | $CO_2Me$ | tBu | S | $OCH_2CH_2O$ | |
| 4-$OCF_3$ | 5-Br | $CO_2Me$ | tBu | S | $OCH_2CH_2O$ | |
| 4-$CF_3$ | 4-F | $CO_2Me$ | tBu | S | $OCH_2CH_2O$ | |
| 4-Cl | 4-F | $CO_2Me$ | tBu | S | $OCH_2CH_2O$ | |
| 4-Br | 4-F | $CO_2Me$ | tBu | S | $OCH_2CH_2O$ | |
| 4-$OCF_3$ | 4-F | $CO_2Me$ | tBu | S | $OCH_2CH_2O$ | |
| 4-$CF_3$ | 5-$CF_3$ | $CO_2Me$ | tBu | S | $OCH_2CH_2O$ | |
| 4-$CF_3$ | 5-F | $CO_2Me$ | tBu | S | $OCH_2CH_2O$ | |
| 4-$CF_3$ | 5-Cl | Ph | tBu | S | $OCH_2CH_2O$ | |
| 4-$CF_3$ | 5-Cl | 4-Cl—Ph | tBu | S | $OCH_2CH_2O$ | |
| 4-$CF_3$ | 5-Cl | $CO_2Et$ | tBu | S | $OCH_2CH_2O$ | |
| 4-$CF_3$ | H | $CO_2Me$ | iPr | S | OEt | OEt |
| 4-Cl | H | $CO_2Me$ | iPr | S | OEt | OEt |
| 4-Br | H | $CO_2Me$ | iPr | S | OEt | OEt |
| 4-$OCF_3$ | H | $CO_2Me$ | iPr | S | OEt | OEt |
| 4-$CF_3$ | 5-Cl | $CO_2Me$ | iPr | S | OEt | OEt |
| 4-Cl | 5-Cl | $CO_2Me$ | iPr | S | OEt | OEt |
| 4-Br | 5-Cl | $CO_2Me$ | iPr | S | OEt | OEt |
| 4-$OCF_3$ | 5-Cl | $CO_2Me$ | iPr | S | OEt | OEt |
| 4-$CF_3$ | 5-Br | $CO_2Me$ | iPr | S | OEt | OEt |
| 4-Cl | 5-Br | $CO_2Me$ | iPr | S | OEt | OEt |
| 4-Br | 5-Br | $CO_2Me$ | iPr | S | OEt | OEt |
| 4-$OCF_3$ | 5-Br | $CO_2Me$ | iPr | S | OEt | OEt |
| 4-$CF_3$ | 4-F | $CO_2Me$ | iPr | S | OEt | OEt |
| 4-Cl | 4-F | $CO_2Me$ | iPr | S | OEt | OEt |
| 4-Br | 4-F | $CO_2Me$ | iPr | S | OEt | OEt |
| 4-$OCF_3$ | 4-F | $CO_2Me$ | iPr | S | OEt | OEt |
| 4-$CF_3$ | 5-$CF_3$ | $CO_2Me$ | iPr | S | OEt | OEt |

TABLE 3-continued

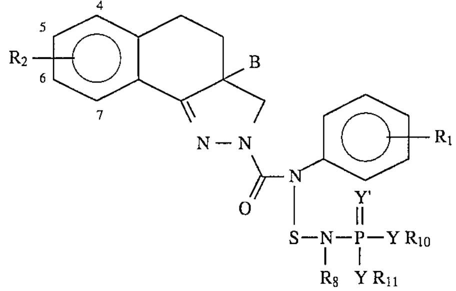

| $R_1$ | $R_2$ | B | $R_8$ | Y' | $Y'R_{10}$ | $Y'R_{11}$ |
|---|---|---|---|---|---|---|
| 4-$CF_3$ | 5-F | $CO_2Me$ | iPr | S | OEt | OEt |
| 4-$CF_3$ | 5-Cl | Ph | iPr | S | OEt | OEt |
| 4-$CF_3$ | 5-Cl | 4-Cl—Ph | iPr | S | OEt | OEt |
| 4-$CF_3$ | 5-Cl | $CO_2Et$ | iPr | S | OEt | OEt |
| 4-$CF_3$ | H | $CO_2Me$ | iPr | S | $OCH_2C(Me)_2CH_2O$ | |
| 4-Cl | H | $CO_2Me$ | iPr | S | $OCH_2C(Me)_2CH_2O$ | |
| 4-Br | H | $CO_2Me$ | iPr | S | $OCH_2C(Me)_2CH_2O$ | |
| 4-$OCF_3$ | H | $CO_2Me$ | iPr | S | $OCH_2C(Me)_2CH_2O$ | |
| 4-$CF_3$ | 5-Cl | $CO_2Me$ | iPr | S | $OCH_2C(Me)_2CH_2O$ | |
| 4-Cl | 5-Cl | $CO_2Me$ | iPr | S | $OCH_2C(Me)_2CH_2O$ | |
| 4-Br | 5-Cl | $CO_2Me$ | iPr | S | $OCH_2C(Me)_2CH_2O$ | |
| 4-$OCF_3$ | 5-Cl | $CO_2Me$ | iPr | S | $OCH_2C(Me)_2CH_2O$ | |
| 4-$CF_3$ | 5-Br | $CO_2Me$ | iPr | S | $OCH_2C(Me)_2CH_2O$ | |
| 4-Cl | 5-Br | $CO_2Me$ | iPr | S | $OCH_2C(Me)_2CH_2O$ | |
| 4-Br | 5-Br | $CO_2Me$ | iPr | S | $OCH_2C(Me)_2CH_2O$ | |
| 4-$OCF_3$ | 5-Br | $CO_2Me$ | iPr | S | $OCH_2C(Me)_2CH_2O$ | |
| 4-$CF_3$ | 4-F | $CO_2Me$ | iPr | S | $OCH_2C(Me)_2CH_2O$ | |
| 4-Cl | 4-F | $CO_2Me$ | iPr | S | $OCH_2C(Me)_2CH_2O$ | |
| 4-Br | 4-F | $CO_2Me$ | iPr | S | $OCH_2C(Me)_2CH_2O$ | |
| 4-$OCF_3$ | 4-F | $CO_2Me$ | iPr | S | $OCH_2C(Me)_2CH_2O$ | |
| 4-$CF_3$ | 5-$CF_3$ | $CO_2Me$ | iPr | S | $OCH_2C(Me)_2CH_2O$ | |
| 4-$CF_3$ | 5-F | $CO_2Me$ | iPr | S | $OCH_2C(Me)_2CH_2O$ | |
| 4-$CF_3$ | 5-Cl | Ph | iPr | S | $OCH_2C(Me)_2CH_2O$ | |
| 4-$CF_3$ | 5-Cl | 4-Cl—Ph | iPr | S | $OCH_2C(Me)_2CH_2O$ | |
| 4-$CF_3$ | 5-Cl | $CO_2Et$ | iPr | S | $OCH_2C(Me)_2CH_2O$ | |
| 4-$CF_3$ | H | $CO_2Me$ | Me | S | OEt | OEt |
| 4-Cl | H | $CO_2Me$ | Me | S | OEt | OEt |
| 4-Br | H | $CO_2Me$ | Me | S | OEt | OEt |
| 4-$OCF_3$ | H | $CO_2Me$ | Me | S | OEt | OEt |
| 4-$CF_3$ | 5-Cl | $CO_2Me$ | Me | S | OEt | OEt |
| 4-Cl | 5-Cl | $CO_2Me$ | Me | S | OEt | OEt |
| 4-Br | 5-Cl | $CO_2Me$ | Me | S | OEt | OEt |
| 4-$OCF_3$ | 5-Cl | $CO_2Me$ | Me | S | OEt | OEt |
| 4-$CF_3$ | 5-Br | $CO_2Me$ | Me | S | OEt | OEt |
| 4-Cl | 5-Br | $CO_2Me$ | Me | S | OEt | OEt |
| 4-Br | 5-Br | $CO_2Me$ | Me | S | OEt | OEt |
| 4-$OCF_3$ | 5-Br | $CO_2Me$ | Me | S | OEt | OEt |
| 4-$CF_3$ | 4-F | $CO_2Me$ | Me | S | OEt | OEt |
| 4-Cl | 4-F | $CO_2Me$ | Me | S | OEt | OEt |
| 4-Br | 4-F | $CO_2Me$ | Me | S | OEt | OEt |
| 4-$OCF_3$ | 4-F | $CO_2Me$ | Me | S | OEt | OEt |
| 4-$CF_3$ | 5-$CF_3$ | $CO_2Me$ | Me | S | OEt | OEt |
| 4-$CF_3$ | 5-F | $CO_2Me$ | Me | S | OEt | OEt |
| 4-$CF_3$ | 5-Cl | Ph | Me | S | OEt | OEt |
| 4-$CF_3$ | 5-Cl | 4-Cl—Ph | Me | S | OEt | OEt |
| 4-$CF_3$ | H | $CO_2Me$ | tBu | O | OEt | OEt |
| 4-Cl | H | $CO_2Me$ | tBu | O | OEt | OEt |
| 4-Br | H | $CO_2Me$ | tBu | O | OEt | OEt |
| 4-$OCF_3$ | H | $CO_2Me$ | tBu | O | OEt | OEt |
| 4-$CF_3$ | 5-Cl | $CO_2Me$ | tBu | O | OEt | OEt |
| 4-Cl | 5-Cl | $CO_2Me$ | tBu | O | OEt | OEt |
| 4-Br | 5-Cl | $CO_2Me$ | tBu | O | OEt | OEt |
| 4-$OCF_3$ | 5-Cl | $CO_2Me$ | tBu | O | OEt | OEt |
| 4-$CF_3$ | 5-Br | $CO_2Me$ | tBu | O | OEt | OEt |
| 4-Cl | 5-Br | $CO_2Me$ | tBu | O | OEt | OEt |
| 4-Br | 5-Br | $CO_2Me$ | tBu | O | OEt | OEt |
| 4-$OCF_3$ | 5-Br | $CO_2Me$ | tBu | O | OEt | OEt |
| 4-$CF_3$ | 4-F | $CO_2Me$ | tBu | O | OEt | OEt |
| 4-Cl | 4-F | $CO_2Me$ | tBu | O | OEt | OEt |
| 4-Br | 4-F | $CO_2Me$ | tBu | O | OEt | OEt |
| 4-$OCF_3$ | 4-F | $CO_2Me$ | tBu | O | OEt | OEt |
| 4-$CF_3$ | 5-$CF_3$ | $CO_2Me$ | tBu | O | OEt | OEt |
| 4-$CF_3$ | 5-F | $CO_2Me$ | tBu | O | OEt | OEt |

TABLE 3-continued

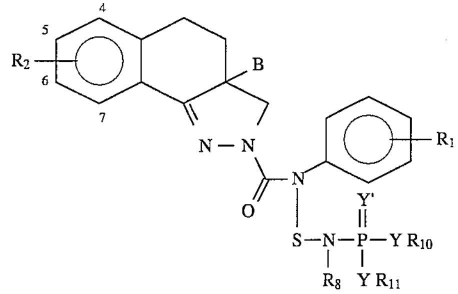

| $R_1$ | $R_2$ | B | $R_8$ | Y' | $Y'R_{10}$ | $Y'R_{11}$ |
|---|---|---|---|---|---|---|
| 4-$CF_3$ | 5-Cl | Ph | tBu | O | OEt | OEt |
| 4-$CF_3$ | 5-Cl | 4-Cl—Ph | tBu | O | OEt | OEt |
| 4-$CF_3$ | 5-Cl | $CO_2Et$ | tBu | O | OEt | OEt |
| 4-$CF_3$ | H | $CO_2Me$ | tBu | O | $OCH_2C(Me)_2CH_2O$ | |
| 4-Cl | H | $CO_2Me$ | tBu | O | $OCH_2C(Me)_2CH_2O$ | |
| 4-Br | H | $CO_2Me$ | tBu | O | $OCH_2C(Me)_2CH_2O$ | |
| 4-$OCF_3$ | H | $CO_2Me$ | tBu | O | $OCH_2C(Me)_2CH_2O$ | |
| 4-$CF_3$ | 5-Cl | $CO_2Me$ | tBu | O | $OCH_2C(Me)_2CH_2O$ | |
| 4-Cl | 5-Cl | $CO_2Me$ | tBu | O | $OCH_2C(Me)_2CH_2O$ | |
| 4-Br | 5-Cl | $CO_2Me$ | tBu | O | $OCH_2C(Me)_2CH_2O$ | |
| 4-$OCF_3$ | 5-Cl | $CO_2Me$ | tBu | O | $OCH_2C(Me)_2CH_2O$ | |
| 4-$CF_3$ | 5-Br | $CO_2Me$ | tBu | O | $OCH_2C(Me)_2CH_2O$ | |
| 4-Cl | 5-Br | $CO_2Me$ | tBu | O | $OCH_2C(Me)_2CH_2O$ | |
| 4-Br | 5-Br | $CO_2Me$ | tBu | O | $OCH_2C(Me)_2CH_2O$ | |
| 4-$OCF_3$ | 5-Br | $CO_2Me$ | tBu | O | $OCH_2C(Me)_2CH_2O$ | |
| 4-$CF_3$ | 4-F | $CO_2Me$ | tBu | O | $OCH_2C(Me)_2CH_2O$ | |
| 4-Cl | 4-F | $CO_2Me$ | tBu | O | $OCH_2C(Me)_2CH_2O$ | |
| 4-Br | 4-F | $CO_2Me$ | tBu | O | $OCH_2C(Me)_2CH_2O$ | |
| 4-$OCF_3$ | 4-F | $CO_2Me$ | tBu | O | $OCH_2C(Me)_2CH_2O$ | |
| 4-$CF_3$ | 5-$CF_3$ | $CO_2Me$ | tBu | O | $OCH_2C(Me)_2CH_2O$ | |
| 4-$CF_3$ | 5-F | $CO_2Me$ | tBu | O | $OCH_2C(Me)_2CH_2O$ | |
| 4-$CF_3$ | 5-Cl | Ph | tBu | O | $OCH_2C(Me)_2CH_2O$ | |
| 4-$CF_3$ | 5-Cl | 4-Cl—Ph | tBu | O | $OCH_2C(Me)_2CH_2O$ | |
| 4-$CF_3$ | 5-Cl | $CO_2Et$ | tBu | O | $OCH_2C(Me)_2CH_2O$ | |

TABLE 4

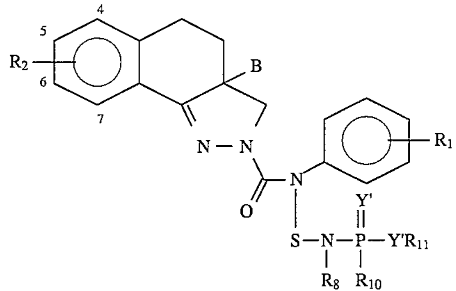

| $R_1$ | $R_2$ | B | $R_8$ | Y' | $R_{10}$ | $Y'R_{11}$ |
|---|---|---|---|---|---|---|
| 4-$CF_3$ | H | $CO_2Me$ | iPr | O | Et | OEt |
| 4-Cl | H | $CO_2Me$ | iPr | O | Et | OEt |
| 4-Br | H | $CO_2Me$ | iPr | O | Et | OEt |
| 4-$OCF_3$ | H | $CO_2Me$ | iPr | O | Et | OEt |
| 4-$CF_3$ | 5-Cl | $CO_2Me$ | iPr | O | Et | OEt |
| 4-Cl | 5-Cl | $CO_2Me$ | iPr | O | Et | OEt |
| 4-Br | 5-Cl | $CO_2Me$ | iPr | O | Et | OEt |
| 4-$OCF_3$ | 5-Cl | $CO_2Me$ | iPr | O | Et | OEt |
| 4-$CF_3$ | 5-Br | $CO_2Me$ | iPr | O | Et | OEt |
| 4-Cl | 5-Br | $CO_2Me$ | iPr | O | Et | OEt |
| 4-Br | 5-Br | $CO_2Me$ | iPr | O | Et | OEt |
| 4-$OCF_3$ | 5-Br | $CO_2Me$ | iPr | O | Et | OEt |
| 4-$CF_3$ | 4-F | $CO_2Me$ | iPr | O | Et | OEt |
| 4-Cl | 4-F | $CO_2Me$ | iPr | O | Et | OEt |
| 4-Br | 4-F | $CO_2Me$ | iPr | O | Et | OEt |
| 4-$OCF_3$ | 4-F | $CO_2Me$ | iPr | O | Et | OEt |
| 4-$CF_3$ | 5-$CF_3$ | $CO_2Me$ | iPr | O | Et | OEt |
| 4-$CF_3$ | 5-F | $CO_2Me$ | iPr | O | Et | OEt |

TABLE 4-continued

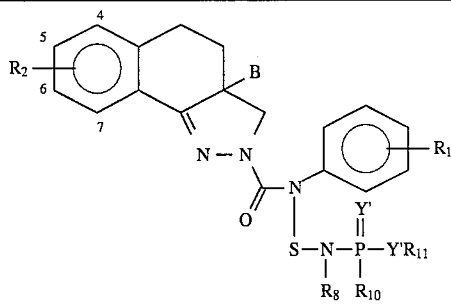

| $R_1$ | $R_2$ | B | $R_8$ | Y' | $R_{10}$ | Y'$R_{11}$ |
|---|---|---|---|---|---|---|
| 4-$CF_3$ | 5-Cl | Ph | iPr | O | Et | OEt |
| 4-$CF_3$ | 5-Cl | 4-Cl—Ph | iPr | O | Et | OEt |
| 4-$CF_3$ | 5-Cl | $CO_2Et$ | iPr | O | Et | OEt |
| 4-$CF_3$ | H | $CO_2Me$ | iPr | O | Et | O-iPr |
| 4-Cl | H | $CO_2Me$ | iPr | O | Et | O-iPr |
| 4-Br | H | $CO_2Me$ | iPr | O | Et | O-iPr |
| 4-$OCF_3$ | H | $CO_2Me$ | iPr | O | Et | O-iPr |
| 4-$CF_3$ | 5-Cl | $CO_2Me$ | iPr | O | Et | O-iPr |
| 4-Cl | 5-Cl | $CO_2Me$ | iPr | O | Et | O-iPr |
| 4-Br | 5-Cl | $CO_2Me$ | iPr | O | Et | O-iPr |
| 4-$OCF_3$ | 5-Cl | $CO_2Me$ | iPr | O | Et | O-iPr |
| 4-$CF_3$ | 5-Br | $CO_2Me$ | iPr | O | Et | O-iPr |
| 4-Cl | 5-Br | $CO_2Me$ | iPr | O | Et | O-iPr |
| 4-Br | 5-Br | $CO_2Me$ | iPr | O | Et | O-iPr |
| 4-$OCF_3$ | 5-Br | $CO_2Me$ | iPr | O | Et | O-iPr |
| 4-$CF_3$ | 4-F | $CO_2Me$ | iPr | O | Et | O-iPr |
| 4-Cl | 4-F | $CO_2Me$ | iPr | O | Et | O-iPr |
| 4-Br | 4-F | $CO_2Me$ | iPr | O | Et | O-iPr |
| 4-$OCF_3$ | 4-F | $CO_2Me$ | iPr | O | Et | O-iPr |
| 4-$CF_3$ | 5-$CF_3$ | $CO_2Me$ | iPr | O | Et | O-iPr |
| 4-$CF_3$ | 5-F | $CO_2Me$ | iPr | O | Et | O-iPr |
| 4-$CF_3$ | 5-Cl | Ph | iPr | O | Et | O-iPr |
| 4-$CF_3$ | 5-Cl | 4-Cl—Ph | iPr | O | Et | O-iPr |
| 4-$CF_3$ | 5-Cl | $CO_2Et$ | iPr | O | Et | O-iPr |
| 4-$CF_3$ | H | $CO_2Me$ | iPr | O | Et | OPh |
| 4-Cl | H | $CO_2Me$ | iPr | O | Et | OPh |
| 4-Br | H | $CO_2Me$ | iPr | O | Et | OPh |
| 4-$OCF_3$ | H | $CO_2Me$ | iPr | O | Et | OPh |
| 4-$CF_3$ | 5-Cl | $CO_2Me$ | iPr | O | Et | OPh |
| 4-Cl | 5-Cl | $CO_2Me$ | iPr | O | Et | OPh |
| 4-Br | 5-Cl | $CO_2Me$ | iPr | O | Et | OPh |
| 4-$OCF_3$ | 5-Cl | $CO_2Me$ | iPr | O | Et | OPh |
| 4-$CF_3$ | 5-Br | $CO_2Me$ | iPr | O | Et | OPh |
| 4-Cl | 5-Br | $CO_2Me$ | iPr | O | Et | OPh |
| 4-Br | 5-Br | $CO_2Me$ | iPr | O | Et | OPh |
| 4-$OCF_3$ | 5-Br | $CO_2Me$ | iPr | O | Et | OPh |
| 4-$CF_3$ | 4-F | $CO_2Me$ | iPr | O | Et | OPh |
| 4-Cl | 4-F | $CO_2Me$ | iPr | O | Et | OPh |
| 4-Br | 4-F | $CO_2Me$ | iPr | O | Et | OPh |
| 4-$OCF_3$ | 4-F | $CO_2Me$ | iPr | O | Et | OPh |
| 4-$CF_3$ | 5-$CF_3$ | $CO_2Me$ | iPr | O | Et | OPh |
| 4-$CF_3$ | 5-F | $CO_2Me$ | iPr | O | Et | OPh |
| 4-$CF_3$ | 5-Cl | Ph | iPr | O | Et | OPh |
| 4-$CF_3$ | 5-Cl | 4-Cl—Ph | iPr | O | Et | OPh |
| 4-$CF_3$ | 5-Cl | $CO_2Et$ | iPr | O | Et | OPh |
| 4-Br | 4-F | $CO_2Me$ | iPr | O | Ph | OEt |
| 4-$OCF_3$ | 4-F | $CO_2Me$ | iPr | O | Ph | OEt |
| 4-$CF_3$ | 5-$CF_3$ | $CO_2Me$ | iPr | O | Ph | OEt |
| 4-$CF_3$ | 5-F | $CO_2Me$ | iPr | O | Ph | OEt |
| 4-$CF_3$ | 5-Cl | Ph | iPr | O | Ph | OEt |
| 4-$CF_3$ | 5-Cl | 4-Cl—Ph | iPr | O | Ph | OEt |
| 4-$CF_3$ | 5-Cl | $CO_2Et$ | iPr | O | Ph | OEt |
| 4-$CF_3$ | H | $CO_2Me$ | tBu | O | Et | OEt |
| 4-Cl | H | $CO_2Me$ | tBu | O | Et | OEt |
| 4-Br | H | $CO_2Me$ | tBu | O | Et | OEt |
| 4-$OCF_3$ | H | $CO_2Me$ | tBu | O | Et | OEt |

TABLE 4-continued

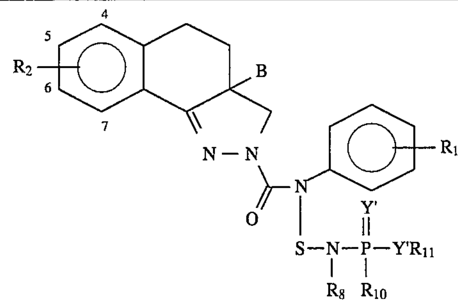

| $R_1$ | $R_2$ | B | $R_8$ | Y' | $R_{10}$ | Y'$R_{11}$ |
|---|---|---|---|---|---|---|
| 4-$CF_3$ | 5-Cl | $CO_2Me$ | tBu | O | Et | OEt |
| 4-Cl | 5-Cl | $CO_2Me$ | tBu | O | Et | OEt |
| 4-Br | 5-Cl | $CO_2Me$ | tBu | O | Et | OEt |
| 4-$OCF_3$ | 5-Cl | $CO_2Me$ | tBu | O | Et | OEt |
| 4-$CF_3$ | 5-Br | $CO_2Me$ | tBu | O | Et | OEt |
| 4-Cl | 5-Br | $CO_2Me$ | tBu | O | Et | OEt |
| 4-Br | 5-Br | $CO_2Me$ | tBu | O | Et | OEt |
| 4-$OCF_3$ | 5-Br | $CO_2Me$ | tBu | O | Et | OEt |
| 4-$CF_3$ | 4-F | $CO_2Me$ | tBu | O | Et | OEt |
| 4-Cl | 4-F | $CO_2Me$ | tBu | O | Et | OEt |
| 4-Br | 4-F | $CO_2Me$ | tBu | O | Et | OEt |
| 4-$OCF_3$ | 4-F | $CO_2Me$ | tBu | O | Et | OEt |
| 4-$CF_3$ | 5-$CF_3$ | $CO_2Me$ | tBu | O | Et | OEt |
| 4-$CF_3$ | 5-F | $CO_2Me$ | tBu | O | Et | OEt |
| 4-$CF_3$ | 5-Cl | Ph | tBu | O | Et | OEt |
| 4-$CF_3$ | 5-Cl | 4-Cl—Ph | tBu | O | Et | OEt |
| 4-$CF_3$ | 5-Cl | $CO_2Et$ | tBu | O | Et | OEt |
| 4-$CF_3$ | H | $CO_2Me$ | tBu | O | Et | O-iPr |
| 4-Cl | H | $CO_2Me$ | tBu | O | Et | O-iPr |
| 4-Br | H | $CO_2Me$ | tBu | O | Et | O-iPr |
| 4-$OCF_3$ | H | $CO_2Me$ | tBu | O | Et | O-iPr |
| 4-$CF_3$ | 5-Cl | $CO_2Me$ | tBu | O | Et | O-iPr |
| 4-Cl | 5-Cl | $CO_2Me$ | tBu | O | Et | O-iPr |
| 4-Br | 5-Cl | $CO_2Me$ | tBu | O | Et | O-iPr |
| 4-$OCF_3$ | 5-Cl | $CO_2Me$ | tBu | O | Et | O-iPr |
| 4-$CF_3$ | 5-Br | $CO_2Me$ | tBu | O | Et | O-iPr |
| 4-Cl | 5-Br | $CO_2Me$ | tBu | O | Et | O-iPr |
| 4-Br | 5-Br | $CO_2Me$ | tBu | O | Et | O-iPr |
| 4-$OCF_3$ | 5-Br | $CO_2Me$ | tBu | O | Et | O-iPr |
| 4-$CF_3$ | 4-F | $CO_2Me$ | tBu | O | Et | O-iPr |
| 4-Cl | 4-F | $CO_2Me$ | tBu | O | Et | O-iPr |
| 4-Br | 4-F | $CO_2Me$ | tBu | O | Et | O-iPr |
| 4-$OCF_3$ | 4-F | $CO_2Me$ | tBu | O | Et | O-iPr |
| 4-$CF_3$ | 5-$CF_3$ | $CO_2Me$ | tBu | O | Et | O-iPr |
| 4-$CF_3$ | 5-F | $CO_2Me$ | tau | O | Et | O-iPr |
| 4-$CF_3$ | 5-Cl | Ph | tBu | O | Et | O-iPr |
| 4-$CF_3$ | 5-Cl | 4-Cl—Ph | tBu | O | Et | O-iPr |
| 4-$CF_3$ | 5-Cl | $CO_2Et$ | tBu | O | Et | O-iPr |
| 4-$CF_3$ | H | $CO_2Me$ | tBu | S | Et | OPh |
| 4-Cl | H | $CO_2Me$ | tBu | S | Ph | OEt |
| 4-Br | H | $CO_2Me$ | tBu | S | Ph | O-iPr |
| 4-$OCF_3$ | H | $CO_2Me$ | tBu | S | Ph | OPh |
| 4-Br | 5-Br | $CO_2Me$ | iPr | S | iPr | OEt |
| 4-$OCF_3$ | 5-Br | $CO_2Me$ | iPr | S | iPr | O-iPr |
| 4-$CF_3$ | 4-F | $CO_2Me$ | iPr | S | iPr | OPh |
| 4-Cl | 4-F | $CO_2Me$ | iPr | S | nPr | OEt |
| 4-Br | 4-F | $CO_2Me$ | iPr | S | nPr | O-iPr |
| 4-$OCF_3$ | 4-F | $CO_2Me$ | iPr | S | nPr | OPh |
| 4-$CF_3$ | 5-$CF_3$ | $CO_2Me$ | tBu | S | Me | OEt |
| 4-$CF_3$ | 5-F | $CO_2Me$ | tBu | S | Me | O-iPr |
| 4-$CF_3$ | 5-Cl | Ph | tBu | S | Me | OPh |
| 4-$CF_3$ | 5-Cl | 4-Cl—Ph | tBu | S | Me | O-sec-Bu |
| 4-$CF_3$ | 5-Cl | $CO_2Et$ | tBu | S | Me | O-nPr |

TABLE 5

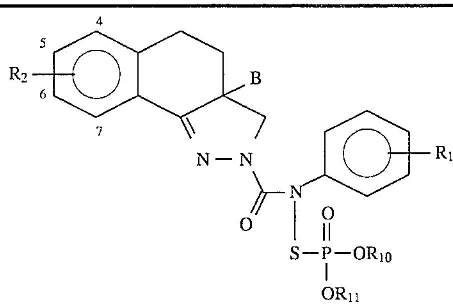

| $R_1$ | $R_2$ | B | $R_{10}$ | $R_{11}$ |
|---|---|---|---|---|
| 4-$CF_3$ | H | $CO_2Me$ | Et | Et |
| 4-Cl | H | $CO_2Me$ | Et | Et |
| 4-Br | H | $CO_2Me$ | Et | Et |
| 4-$OCF_3$ | H | $CO_2Me$ | Et | Et |
| 4-$CF_3$ | 5-Cl | $CO_2Me$ | Et | Et |
| 4-Cl | 5-Cl | $CO_2Me$ | Et | Et |
| 4-Br | 5-Cl | $CO_2Me$ | Et | Et |
| 4-$OCF_3$ | 5-Cl | $CO_2Me$ | Et | Et |
| 4-$CF_3$ | 5-Br | $CO_2Me$ | Et | Et |
| 4-Cl | 5-Br | $CO_2Me$ | Et | Et |
| 4-Br | 5-Br | $CO_2Me$ | Et | Et |
| 4-$OCF_3$ | 5-Br | $CO_2Me$ | Et | Et |
| 4-$CF_3$ | 4-F | $CO_2Me$ | Et | Et |
| 4-Cl | 4-F | $CO_2Me$ | Et | Et |
| 4-Br | 4-F | $CO_2Me$ | Et | Et |
| 4-$OCF_3$ | 4-F | $CO_2Me$ | Et | Et |
| 4-$CF_3$ | 5-$CF_3$ | $CO_2Me$ | Et | Et |
| 4-$CF_3$ | 5-F | $CO_2Me$ | Et | Et |
| 4-$CF_3$ | 5-Cl | Ph | Et | Et |
| 4-$CF_3$ | 5-Cl | 4-Cl—Ph | Et | Et |
| 4-$CF_3$ | 5-Cl | $CO_2Et$ | Et | Et |
| 4-$CF_3$ | 5-Cl | Ph | Ph | Ph |
| 4-$CF_3$ | 5-Cl | 4-Cl—Ph | Ph | Ph |
| 4-$CF_3$ | 5-Cl | $CO_2Et$ | Ph | Ph |

TABLE 6

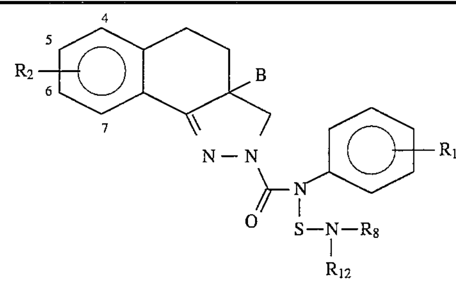

| $R_1$ | $R_2$ | B | $R_8$ | $R_{12}$ |
|---|---|---|---|---|
| 4-$CF_3$ | H | $CO_2Me$ | nBu | nBu |
| 4-Cl | H | $CO_2Me$ | nBu | nBu |
| 4-Br | H | $CO_2Me$ | nBu | nBu |
| 4-$OCF_3$ | H | $CO_2Me$ | nBu | nBu |
| 4-$CF_3$ | 5-Cl | $CO_2Me$ | nBu | nBu |
| 4-Cl | 5-Cl | $CO_2Me$ | nBu | nBu |
| 4-Br | 5-Cl | $CO_2Me$ | nBu | nBu |
| 4-$OCF_3$ | 5-Cl | $CO_2Me$ | nBu | nBu |
| 4-$CF_3$ | 5-Br | $CO_2Me$ | nBu | nBu |
| 4-Cl | 5-Br | $CO_2Me$ | nBu | nBu |
| 4-Br | 5-Br | $CO_2Me$ | nBu | nBu |
| 4-$OCF_3$ | 5-Br | $CO_2Me$ | nBu | nBu |
| 4-$CF_3$ | 4-F | $CO_2Me$ | nBu | nBu |
| 4-Cl | 4-F | $CO_2Me$ | nBu | nBu |
| 4-Br | 4-F | $CO_2Me$ | nBu | nBu |
| 4-$OCF_3$ | 4-F | $CO_2Me$ | nBu | nBu |
| 4-$CF_3$ | 5-$CF_3$ | $CO_2Me$ | nBu | nBu |
| 4-$CF_3$ | 5-F | $CO_2Me$ | nBu | nBu |
| 4-$CF_3$ | 5-Cl | Ph | nBu | nBu |
| 4-$CF_3$ | 5-Cl | 4-Cl—Ph | nBu | nBu |
| 4-$CF_3$ | 5-Cl | $CO_2Et$ | nBu | nBu |
| 4-$CF_3$ | H | $CO_2Me$ | —$CH_2CH_2CH_2CH_2CH_2$— | |
| 4-Cl | H | $CO_2Me$ | —$CH_2CH_2CH_2CH_2CH_2$— | |
| 4-Br | H | $CO_2Me$ | —$CH_2CH_2CH_2CH_2CH_2$— | |
| 4-$OCF_3$ | H | $CO_2Me$ | —$CH_2CH_2CH_2CH_2CH_2$— | |
| 4-$CF_3$ | 5-Cl | $CO_2Me$ | —$CH_2CH_2CH_2CH_2CH_2$— | |
| 4-Cl | 5-Cl | $CO_2Me$ | —$CH_2CH_2CH_2CH_2CH_2$— | |
| 4-Br | 5-Cl | $CO_2Me$ | —$CH_2CH_2CH_2CH_2CH_2$— | |
| 4-$OCF_3$ | 5-Cl | $CO_2Me$ | —$CH_2CH_2CH_2CH_2CH_2$— | |
| 4-$CF_3$ | 5-Br | $CO_2Me$ | —$CH_2CH_2CH_2CH_2CH_2$— | |
| 4-Cl | 5-Br | $CO_2Me$ | —$CH_2CH_2CH_2CH_2CH_2$— | |
| 4-Br | 5-Br | $CO_2Me$ | —$CH_2CH_2CH_2CH_2CH_2$— | |
| 4-$OCF_3$ | 5-Br | $CO_2Me$ | —$CH_2CH_2CH_2CH_2CH_2$— | |
| 4-$CF_3$ | 4-F | $CO_2Me$ | —$CH_2CH_2CH_2CH_2CH_2$— | |
| 4-Cl | 4-F | $CO_2Me$ | —$CH_2CH_2CH_2CH_2CH_2$— | |
| 4-Br | 4-F | $CO_2Me$ | —$CH_2CH_2CH_2CH_2CH_2$— | |
| 4-$OCF_3$ | 4-F | $CO_2Me$ | —$CH_2CH_2CH_2CH_2CH_2$— | |
| 4-$CF_3$ | 5-$CF_3$ | $CO_2Me$ | —$CH_2CH_2CH_2CH_2CH_2$— | |
| 4-$CF_3$ | 5-F | $CO_2Me$ | —$CH_2CH_2CH_2CH_2CH_2$— | |
| 4-$CF_3$ | 5-Cl | Ph | —$CH_2CH_2CH_2CH_2CH_2$— | |
| 4-$CF_3$ | 5-Cl | 4-Cl—Ph | —$CH_2CH_2CH_2CH_2CH_2$— | |
| 4-$CF_3$ | 5-Cl | $CO_2Et$ | —$CH_2CH_2CH_2CH_2CH_2$— | |
| 4-$CF_3$ | H | $CO_2Me$ | —$CH_2CH_2OCH_2CH_2$— | |
| 4-Cl | H | $CO_2Me$ | —$CH_2CH_2OCH_2CH_2$— | |
| 4-Br | H | $CO_2Me$ | —$CH_2CH_2OCH_2CH_2$— | |
| 4-$OCF_3$ | H | $CO_2Me$ | —$CH_2CH_2OCH_2CH_2$— | |
| 4-$CF_3$ | 5-Cl | $CO_2Me$ | —$CH_2CH_2OCH_2CH_2$— | |
| 4-Cl | 5-Cl | $CO_2Me$ | —$CH_2CH_2OCH_2CH_2$— | |
| 4-Br | 5-Cl | $CO_2Me$ | —$CH_2CH_2OCH_2CH_2$— | |
| 4-$OCF_3$ | 5-Cl | $CO_2Me$ | —$CH_2CH_2OCH_2CH_2$— | |
| 4-$CF_3$ | 5-Br | $CO_2Me$ | —$CH_2CH_2OCH_2CH_2$— | |
| 4-Cl | 5-Br | $CO_2Me$ | —$CH_2CH_2OCH_2CH_2$— | |
| 4-Br | 5-Br | $CO_2Me$ | —$CH_2CH_2OCH_2CH_2$— | |
| 4-$OCF_3$ | 5-Br | $CO_2Me$ | —$CH_2CH_2OCH_2CH_2$— | |
| 4-CF 3 | 4-F | $CO_2Me$ | —$CH_2CH_2OCH_2CH_2$— | |
| 4-Cl | 4-F | $CO_2Me$ | —$CH_2CH_2OCH_2CH_2$— | |
| 4-Br | 4-F | $CO_2Me$ | —$CH_2CH_2OCH_2CH_2$— | |
| 4-$OCF_3$ | 4-F | $CO_2Me$ | —$CH_2CH_2OCH_2CH_2$— | |
| 4-$CF_3$ | 5-$CF_3$ | $CO_2Me$ | —$CH_2CH_2OCH_2CH_2$— | |
| 4-$CF_3$ | 5-F | $CO_2Me$ | —$CH_2CH_2OCH_2CH_2$— | |
| 4-$CF_3$ | 5-Cl | Ph | —$CH_2CH_2OCH_2CH_2$— | |
| 4-$CF_3$ | 5-Cl | 4-Cl—Ph | —$CH_2CH_2OCH_2CH_2$— | |
| 4-$CF_3$ | 5-Cl | $CO_2Et$ | —$CH_2CH_2OCH_2CH_2$— | |
| 4-$CF_3$ | H | $CO_2Me$ | —$CH_2CHMeOCHMeCH_2$— | |

TABLE 6-continued

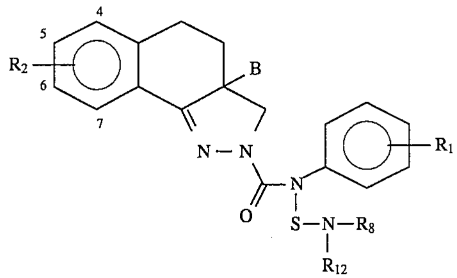

| $R_1$ | $R_2$ | B | $R_8$ | $R_{12}$ |
|---|---|---|---|---|
| 4-Cl | H | $CO_2Me$ | $-CH_2CHMeOCHMeCH_2-$ | |
| 4-Br | H | $CO_2Me$ | $-CH_2CHMeOCHMeCH_2-$ | |
| 4-$OCF_3$ | H | $CO_2Me$ | $-CH_2CHMeOCHMeCH_2-$ | |
| 4-$CF_3$ | 5-Cl | $CO_2Me$ | $-CH_2CHMeOCHMeCH_2-$ | |
| 4-Cl | 5-Cl | $CO_2Me$ | $-CH_2CHMeOCHMeCH_2-$ | |
| 4-Br | 5-Cl | $CO_2Me$ | $-CH_2CHMeOCHMeCH_2-$ | |
| 4-$OCF_3$ | 5-Cl | $CO_2Me$ | $-CH_2CHMeOCHMeCH_2-$ | |
| 4-$CF_3$ | 5-Br | $CO_2Me$ | $-CH_2CHMeOCHMeCH_2-$ | |
| 4-Cl | 5-Br | $CO_2Me$ | $-CH_2CHMeOCHMeCH_2-$ | |
| 4-Br | 5-Br | $CO_2Me$ | $-CH_2CHMeOCHMeCH_2-$ | |
| 4-$OCF_3$ | 5-Br | $CO_2Me$ | $-CH_2CHMeOCHMeCH_2-$ | |
| 4-$CF_3$ | 4-F | $CO_2Me$ | $-CH_2CHMeOCHMeCH_2-$ | |
| 4-Cl | 4-F | $CO_2Me$ | $-CH_2CHMeOCHMeCH_2-$ | |
| 4-Br | 4-F | $CO_2Me$ | $-CH_2CHMeOCHMeCH_2-$ | |
| 4-$OCF_3$ | 4-F | $CO_2Me$ | $-CH_2CHMeOCHMeCH_2-$ | |
| 4-$CF_3$ | 5-$CF_3$ | $CO_2Me$ | $-CH_2CHMeOCHMeCH_2-$ | |
| 4-$CF_3$ | 5-F | $CO_2Me$ | $-CH_2CHMeOCHMeCH_2-$ | |
| 4-$CF_3$ | 5-Cl | Ph | $-CH_2CHMeOCHMeCH_2-$ | |
| 4-$CF_3$ | 5-Cl | 4-Cl−Ph | $-CH_2CHMeOCHMeCH_2-$ | |
| 4-$CF_3$ | 5-Cl | $CO_2Et$ | $-CH_2CHMeOCHMeCH_2-$ | |
| 4-$CF_3$ | H | $CO_2Me$ | Et | cyclo-$C_6H_{11}$ |
| 4-Cl | H | $CO_2Me$ | Et | cyclo-$C_6H_{11}$ |
| 4-Br | H | $CO_2Me$ | Et | cyclo-$C_6H_{11}$ |
| 4-$OCF_3$ | H | $CO_2Me$ | Et | cyclo-$C_6H_{11}$ |
| 4-$CF_3$ | 5-Cl | $CO_2Me$ | Et | cyclo-$C_6H_{11}$ |
| 4-Cl | 5-Cl | $CO_2Me$ | Et | cyclo-$C_6H_{11}$ |
| 4-Br | 5-Cl | $CO_2Me$ | Et | cyclo-$C_6H_{11}$ |
| 4-$OCF_3$ | 5-Cl | $CO_2Me$ | Et | cyclo-$C_6H_{11}$ |
| 4-$CF_3$ | 5-Br | $CO_2Me$ | Et | cyclo-$C_6H_{11}$ |
| 4-Cl | 5-Br | $CO_2Me$ | Et | cyclo-$C_6H_{11}$ |
| 4-Br | 5-Br | $CO_2Me$ | Et | cyclo-$C_6H_{11}$ |
| 4-$OCF_3$ | 5-Br | $CO_2Me$ | Et | cyclo-$C_6H_{11}$ |
| 4-$CF_3$ | 4-F | $CO_2Me$ | Et | cyclo-$C_6H_{11}$ |
| 4-Cl | 4-F | $CO_2Me$ | Et | cyclo-$C_6H_{11}$ |
| 4-Br | 4-F | $CO_2Me$ | Et | cyclo-$C_6H_{11}$ |
| 4-$OCF_3$ | 4-F | $CO_2Me$ | Et | cyclo-$C_6H_{11}$ |
| 4-$CF_3$ | 5-$CF_3$ | $CO_2Me$ | Et | cyclo-$C_6H_{11}$ |
| 4-$CF_3$ | 5-F | $CO_2Me$ | Et | cyclo-$C_6H_{11}$ |
| 4-$CF_3$ | 5-Cl | Ph | Et | cyclo-$C_6H_{11}$ |
| 4-$CF_3$ | 5-Cl | 4-Cl−Ph | Et | cyclo-$C_6H_{11}$ |
| 4-$CF_3$ | 5-Cl | $CO_2Et$ | Et | cyclo-$C_6H_{11}$ |
| 4-$CF_3$ | H | $CO_2Me$ | iPr | $CH_2CH_2CO_2Et$ |
| 4-Cl | H | $CO_2Me$ | iPr | $CH_2CH_2CO_2Et$ |
| 4-Br | H | $CO_2Me$ | iPr | $CH_2CH_2CO_2Et$ |
| 4-$OCF_3$ | H | $CO_2Me$ | iPr | $CH_2CH_2CO_2Et$ |
| 4-$CF_3$ | 5-Cl | $CO_2Me$ | iPr | $CH_2CH_2CO_2Et$ |
| 4-Cl | 5-Cl | $CO_2Me$ | iPr | $CH_2CH_2CO_2Et$ |
| 4-Br | 5-Cl | $CO_2Me$ | iPr | $CH_2CH_2CO_2Et$ |
| 4-$OCF_3$ | 5-Cl | $C_2Me$ | iPr | $CH_2CH_2CO_2Et$ |
| 4-$CF_3$ | 5-Br | $CO_2Me$ | iPr | $CH_2CH_2CO_2Et$ |
| 4-Cl | 5-Br | $CO_2Me$ | iPr | $CH_2CH_2CO_2Et$ |
| 4-Br | 5-Br | $CO_2Me$ | iPr | $CH_2CH_2CO_2Et$ |
| 4-$OCF_3$ | 5-Br | $CO_2Me$ | iPr | $CH_2CH_2CO_2Et$ |
| 4-$CF_3$ | 4-F | $CO_2Me$ | iPr | $CH_2CH_2CO_2Et$ |
| 4-Cl | 4-F | $CO_2Me$ | iPr | $CH_2CH_2CO_2Et$ |
| 4-Br | 4-F | $CO_2Me$ | iPr | $CH_2CH_2CO_2Et$ |
| 4-$OCF_3$ | 4-F | $CO_2Me$ | iPr | $CH_2CH_2CO_2Et$ |
| 4-$CF_3$ | 5-$CF_3$ | $CO_2Me$ | iPr | $CH_2CH_2CO_2Et$ |
| 4-$CF_3$ | 5-F | $CO_2Me$ | iPr | $CH_2CH_2CO_2Et$ |
| 4-$CF_3$ | 5-Cl | Ph | iPr | $CH_2CH_2CO_2Et$ |
| 4-$CF_3$ | 5-Cl | 4-Cl−Ph | iPr | $CH_2CH_2CO_2Et$ |
| 4-$CF_3$ | 5-Cl | $CO_2Et$ | iPr | $CH_2CH_2CO_2Et$ |

TABLE 7

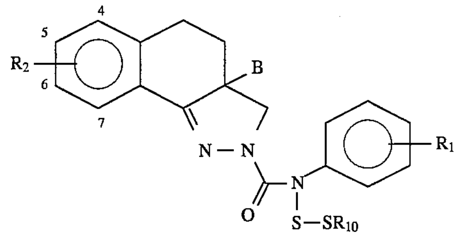

| $R_1$ | $R_2$ | B | $R_{10}$ |
|---|---|---|---|
| 4-$CF_3$ | H | $CO_2Me$ | tBu |
| 4-Cl | H | $CO_2Me$ | tBu |
| 4-Br | H | $CO_2Me$ | tBu |
| 4-$OCF_3$ | H | $CO_2Me$ | tBu |
| 4-$CF_3$ | 5-Cl | $CO_2Me$ | tBu |
| 4-Cl | 5-Cl | $CO_2Me$ | tBu |
| 4-Br | 5-Cl | $CO_2Me$ | tBu |
| 4-$OCF_3$ | 5-Cl | $CO_2Me$ | tBu |
| 4-$CF_3$ | 5-Br | $CO_2Me$ | tBu |
| 4-Cl | 5-Br | $CO_2Me$ | tBu |
| 4-Br | 5-Br | $CO_2Me$ | tBu |
| 4-$OCF_3$ | 5-Br | $CO_2Me$ | tBu |
| 4-$CF_3$ | 4-F | $CO_2Me$ | tBu |
| 4-Cl | 4-F | $CO_2Me$ | tBu |
| 4-Br | 4-F | $CO_2Me$ | tBu |
| 4-$OCF_3$ | 4-F | $CO_2Me$ | tBu |
| 4-$CF_3$ | 5-$CF_3$ | $CO_2Me$ | tBu |
| 4-$CF_3$ | 5-F | $CO_2Me$ | tBu |
| 4-$CF_3$ | 5-Cl | Ph | tBu |
| 4-$CF_3$ | 5-Cl | 4-Cl−Ph | tBu |
| 4-$CF_3$ | 5-Cl | $CO_2Et$ | tBu |
| 4-$CF_3$ | H | $CO_2Me$ | Ph |
| 4-Cl | H | $CO_2Me$ | Ph |
| 4-Br | H | $CO_2Me$ | Ph |
| 4-$OCF_3$ | H | $CO_2Me$ | Ph |
| 4-$CF_3$ | 5-Cl | $CO_2Me$ | Ph |
| 4-Cl | 5-Cl | $CO_2Me$ | Ph |
| 4-Br | 5-Cl | $CO_2Me$ | Ph |
| 4-$OCF_3$ | 5-Cl | $CO_2Me$ | Ph |
| 4-$CF_3$ | 5-Br | $CO_2Me$ | Ph |
| 4-Cl | 5-Br | $CO_2Me$ | Ph |
| 4-Br | 5-Br | $CO_2Me$ | Ph |
| 4-$OCF_3$ | 5-Br | $CO_2Me$ | Ph |
| 4-$CF_3$ | 4-F | $CO_2Me$ | Ph |
| 4-Cl | 4-F | $CO_2Me$ | Ph |
| 4-Br | 4-F | $CO_2Me$ | Ph |
| 4-$OCF_3$ | 4-F | $CO_2Me$ | Ph |
| 4-CF | 5-$CF_3$ | $CO_2Me$ | Ph |
| 4-$CF_3$ | 5-F | $CO_2Me$ | Ph |
| 4-$CF_3$ | 5-Cl | Ph | Ph |
| 4-$CF_3$ | 5-Cl | 4-Cl−Ph | Ph |
| 4-$CF_3$ | 5-Cl | $CO_2Et$ | Ph |
| 4-$CF_3$ | H | $CO_2Me$ | 4-Cl−Ph |
| 4-Cl | H | $CO_2Me$ | 4-Cl−Ph |
| 4-Br | H | $CO_2Me$ | 4-Cl−Ph |
| 4-$OCF_3$ | H | $CO_2Me$ | 4-Cl−Ph |
| 4-$CF_3$ | 5-Cl | $CO_2Me$ | 4-Cl−Ph |
| 4-Cl | 5-Cl | $CO_2Me$ | 4-Cl−Ph |
| 4-Br | 5-Cl | $CO_2Me$ | 4-Cl−Ph |
| 4-$OCF_3$ | 5-Cl | $CO_2Me$ | 4-Cl−Ph |
| 4-$CF_3$ | 5-Br | $CO_2Me$ | 4-Cl−Ph |
| 4-Cl | 5-Br | $CO_2Me$ | 4-Cl−Ph |
| 4-Br | 5-Br | $CO_2Me$ | 4-Cl−Ph |
| 4-$OCF_3$ | 5-Br | $CO_2Me$ | 4-Cl−Ph |
| 4-$CF_3$ | 4-F | $CO_2Me$ | 4-Cl−Ph |
| 4-Cl | 4-F | $CO_2Me$ | 4-Cl−Ph |
| 4-Br | 4-F | $CO_2Me$ | 4-Cl−Ph |
| 4-$OCF_3$ | 4-F | $CO_2Me$ | 4-Cl−Ph |
| 4-$CF_3$ | 5-$CF_3$ | $CO_2Me$ | 4-Cl−Ph |
| 4-$CF_3$ | 5-F | $CO_2Me$ | 4-Cl−Ph |

TABLE 8

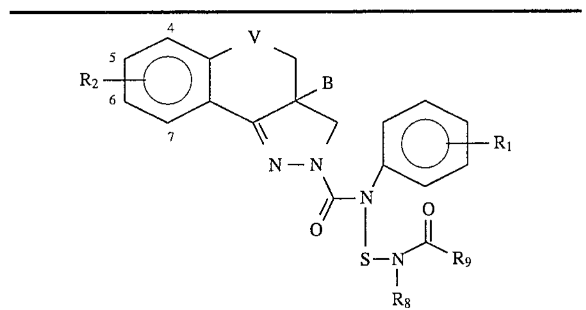

| $R_1$ | $R_2$ | B | V | $R_8$ | $R_9$ |
|---|---|---|---|---|---|
| 4-$CF_3$ | 5-Br | H | O | Me | OEt |
| 4-Cl | 5-Br | H | O | Me | OEt |
| 4-Br | 5-Br | H | O | Me | OEt |
| 4-$OCF_3$ | 5-Br | H | O | Me | OEt |
| 4-$CF_3$ | 5-Cl | H | O | Me | OEt |
| 4-Cl | 5-Cl | H | O | Me | OEt |
| 4-Br | 5-Cl | H | O | Me | OEt |
| 4-$CF_3$ | 5-$CF_3$ | H | O | Me | OEt |
| 4-$CF_3$ | 4-F | H | O | Me | OEt |
| 4-$CF_3$ | H | H | O | Me | OEt |
| 4-$CF_3$ | 5-Br | $CO_2Me$ | O | Me | OEt |
| 4-$CF_3$ | 5-Cl | $CO_2Me$ | O | Me | OEt |
| 4-$CF_3$ | 5-$CF_3$ | $CO_2Me$ | O | Me | OEt |
| 4-$CF_3$ | 4-F | $CO_2Me$ | O | Me | OEt |
| 4-$CF_3$ | H | $CO_2Me$ | O | Me | OEt |
| 4-$CF_3$ | 5-Cl | H | S | Me | OEt |
| 4-Cl | 5-Cl | H | S | Me | OEt |
| 4-Br | 5-Cl | H | S | Me | OEt |
| 4-$CF_3$ | 5-Br | H | S | Me | OEt |
| 4-$CF_3$ | 5-F | H | S | Me | OEt |
| 4-$CF_3$ | 4-Cl | H | S | Me | OEt |
| 4-$CF_3$ | 4-F | H | S | Me | OEt |
| 4-$CF_3$ | H | H | S | Me | OEt |
| 4-$CF_3$ | 5-Cl | $CO_2Me$ | S | Me | OEt |
| 4-$CF_3$ | 5-Br | $CO_2Me$ | S | Me | OEt |
| 4-$CF_3$ | 5-F | $CO_2Me$ | S | Me | OEt |
| 4-$CF_3$ | 4-Cl | $CO_2Me$ | S | Me | OEt |
| 4-$CF_3$ | 4-F | $CO_2Me$ | S | Me | OEt |
| 4-$CF_3$ | H | $CO_2Me$ | S | Me | OEt |
| 4-$CF_3$ | 5-Br | H | O | Me | O-n-Bu |
| 4-Cl | 5-Br | H | O | Me | O-n-Bu |
| 4-Br | 5-Br | H | O | Me | O-n-Bu |
| 4-$OCF_3$ | 5-Br | H | O | Me | O-n-Bu |
| 4-$CF_3$ | 5-Cl | H | O | Me | O-n-Bu |
| 4-Cl | 5-Cl | H | O | Me | O-n-Bu |
| 4-Br | 5-Cl | H | O | Me | O-n-Bu |
| 4-$CF_3$ | 5-$CF_3$ | H | O | Me | O-n-Bu |
| 4-$CF_3$ | 4-F | H | O | Me | O-n-Bu |
| 4-$CF_3$ | H | H | O | Me | O-n-Bu |
| 4-$CF_3$ | 5-Br | $CO_2Me$ | O | Me | O-n-Bu |
| 4-$CF_3$ | 5-Cl | $CO_2Me$ | O | Me | O-n-Bu |
| 4-$CF_3$ | 5-$CF_3$ | $CO_2Me$ | O | Me | O-n-Bu |
| 4-$CF_3$ | 4-F | $CO_2Me$ | O | Me | O-n-Bu |
| 4-$CF_3$ | H | $CO_2Me$ | O | Me | O-n-Bu |
| 4-$CF_3$ | 5-Cl | H | S | Me | O-n-Bu |
| 4-Cl | 5-Cl | H | S | Me | O-n-Bu |
| 4-Br | 5-Cl | H | S | Me | O-n-Bu |
| 4-$CF_3$ | 5-Br | H | S | Me | O-n-Bu |
| 4-$CF_3$ | 5-F | H | S | Me | O-n-Bu |
| 4-$CF_3$ | 4-Cl | H | S | Me | O-n-Bu |
| 4-$CF_3$ | 4-F | H | S | Me | O-n-Bu |
| 4-$CF_3$ | H | H | S | Me | O-n-Bu |
| 4-$CF_3$ | 5-Cl | $CO_2Me$ | S | Me | O-n-Bu |
| 4-$CF_3$ | 5-Br | $CO_2Me$ | S | Me | O-n-Bu |
| 4-$CF_3$ | 5-F | $CO_2Me$ | S | Me | O-n-Bu |
| 4-$CF_3$ | 4-Cl | $CO_2Me$ | S | Me | O-n-Bu |
| 4-$CF_3$ | 4-F | $CO_2Me$ | S | Me | O-n-Bu |
| 4-$CF_3$ | H | $CO_2Me$ | S | Me | O-n-Bu |
| 4-$CF_3$ | 5-Br | H | O | Me | O-n-hexyl |
| 4-Cl | 5-Br | H | O | Me | O-n-hexyl |
| 4-Br | 5-Br | H | O | Me | O-n-hexyl |
| 4-$OCF_3$ | 5-Br | H | O | Me | O-n-hexyl |
| 4-$CF_3$ | 5-Cl | H | O | Me | O-n-hexyl |

TABLE 8-continued

| $R_1$ | $R_2$ | B | V | $R_8$ | $R_9$ |
|---|---|---|---|---|---|
| 4-Cl | 5-Cl | H | O | Me | O-n-hexyl |
| 4-Br | 5-Cl | H | O | Me | O-n-hexyl |
| 4-$CF_3$ | 5-$CF_3$ | H | O | Me | O-n-hexyl |
| 4-$CF_3$ | 4-F | H | O | Me | O-n-hexyl |
| 4-$CF_3$ | H | H | O | Me | O-n-hexyl |
| 4-$CF_3$ | 5-Br | $CO_2Me$ | O | Me | O-n-hexyl |
| 4-$CF_3$ | 5-Cl | $CO_2Me$ | O | Me | O-n-hexyl |
| 4-$CF_3$ | 5-$CF_3$ | $CO_2Me$ | O | Me | O-n-hexyl |
| 4-$CF_3$ | 4-F | $CO_2Me$ | O | Me | O-n-hexyl |
| 4-$CF_3$ | H | $CO_2Me$ | O | Me | O-n-hexyl |
| 4-$CF_3$ | 5-Cl | H | S | Me | O-n-hexyl |
| 4-Cl | 5-Cl | H | S | Me | O-n-hexyl |
| 4-Br | 5-Cl | H | S | Me | O-n-hexyl |
| 4-$CF_3$ | 5-Br | H | S | Me | O-n-hexyl |
| 4-$CF_3$ | 5-F | H | S | Me | O-n-hexyl |
| 4-$CF_3$ | 4-Cl | H | S | Me | O-n-hexyl |
| 4-$CF_3$ | 4-F | H | S | Me | O-n-hexyl |
| 4-$CF_3$ | H | H | S | Me | O-n-hexyl |
| 4-$CF_3$ | 5-Cl | $CO_2Me$ | S | Me | O-n-hexyl |
| 4-$CF_3$ | 5-Br | $CO_2Me$ | S | Me | O-n-hexyl |
| 4-$CF_3$ | 5-F | $CO_2Me$ | S | Me | O-n-hexyl |
| 4-$CF_3$ | 4-Cl | $CO_2Me$ | S | Me | O-n-hexyl |
| 4-$CF_3$ | 4-F | $CO_2Me$ | S | Me | O-n-hexyl |
| 4-$CF_3$ | H | $CO_2Me$ | S | Me | O-n-hexyl |
| 4-$CF_3$ | 5-Br | H | O | Me | O-n-octyl |
| 4-Cl | 5-Br | H | O | Me | O-n-octyl |
| 4-Br | 5-Br | H | O | Me | O-n-octyl |
| 4-$OCF_3$ | 5-Br | H | O | Me | O-n-octyl |
| 4-$CF_3$ | 5-Cl | H | O | Me | O-n-octyl |
| 4-Cl | 5-Cl | H | O | Me | O-n-octyl |
| 4-Br | 5-Cl | H | O | Me | O-n-octyl |
| 4-$CF_3$ | 5-$CF_3$ | H | O | Me | O-n-octyl |
| 4-$CF_3$ | 4-F | H | O | Me | O-n-octyl |
| 4-$CF_3$ | H | H | O | Me | O-n-octyl |
| 4-$CF_3$ | 5-Br | $CO_2Me$ | O | Me | O-n-octyl |
| 4-$CF_3$ | 5-Cl | $CO_2Me$ | O | Me | O-n-octyl |
| 4-$CF_3$ | 5-$CF_3$ | $CO_2Me$ | O | Me | O-n-octyl |
| 4-$CF_3$ | 4-F | $CO_2Me$ | O | Me | O-n-octyl |
| 4-$CF_3$ | H | $CO_2Me$ | O | Me | O-n-octyl |
| 4-$CF_3$ | 5-Cl | H | S | Me | O-n-octyl |
| 4-Cl | 5-Cl | H | S | Me | O-n-octyl |
| 4-Br | 5-Cl | H | S | Me | O-n-octyl |
| 4-$CF_3$ | 5-Br | H | S | Me | O-n-octyl |
| 4-$CF_3$ | 5-F | H | S | Me | O-n-octyl |
| 4-$CF_3$ | 4-Cl | H | S | Me | O-n-octyl |
| 4-$CF_3$ | 4-F | H | S | Me | O-n-octyl |
| 4-$CF_3$ | H | H | S | Me | O-n-octyl |
| 4-$CF_3$ | 5-Cl | $CO_2Me$ | S | Me | O-n-octyl |
| 4-$CF_3$ | 5-Br | $CO_2Me$ | S | Me | O-n-octyl |
| 4-$CF_3$ | 5-F | $CO_2Me$ | S | Me | O-n-octyl |
| 4-$CF_3$ | 4-Cl | $CO_2Me$ | S | Me | O-n-octyl |
| 4-$CF_3$ | 4-F | $CO_2Me$ | S | Me | O-n-octyl |
| 4-$CF_3$ | H | $CO_2Me$ | S | Me | O-n-octyl |
| 4-$CF_3$ | 5-Br | H | O | Me | O-n-decyl |
| 4-Cl | 5-Br | H | O | Me | O-n-decyl |
| 4-Br | 5-Br | H | O | Me | O-n-decyl |
| 4-$OCF_3$ | 5-Br | H | O | Me | O-n-decyl |
| 4-$CF_3$ | 5-Cl | H | O | Me | O-n-decyl |
| 4-Cl | 5-Cl | H | O | Me | O-n-decyl |
| 4-Br | 5-Cl | H | O | Me | O-n-decyl |
| 4-$CF_3$ | 5-$CF_3$ | H | O | Me | O-n-decyl |
| 4-$CF_3$ | 4-F | H | O | Me | O-n-decyl |
| 4-$CF_3$ | H | H | O | Me | O-n-decyl |

TABLE 8-continued

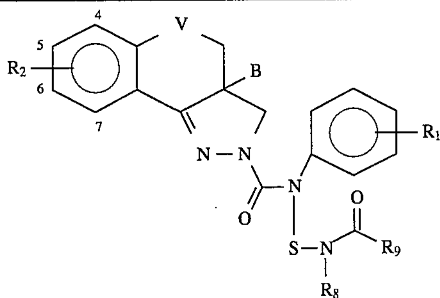

| $R_1$ | $R_2$ | B | V | $R_8$ | $R_9$ |
|---|---|---|---|---|---|
| 4-$CF_3$ | 5-Br | $CO_2Me$ | O | Me | O-n-decyl |
| 4-$CF_3$ | 5-Cl | $CO_2Me$ | O | Me | O-n-decyl |
| 4-$CF_3$ | 5-$CF_3$ | $CO_2Me$ | O | Me | O-n-decyl |
| 4-$CF_3$ | 4-F | $CO_2Me$ | O | Me | O-n-decyl |
| 4-$CF_3$ | H | $CO_2Me$ | O | Me | O-n-decyl |
| 4-$CF_3$ | 5-Cl | H | S | Me | O-n-decyl |
| 4-Cl | 5-Cl | H | S | Me | O-n-decyl |
| 4-Br | 5-Cl | H | S | Me | O-n-decyl |
| 4-$CF_3$ | 5-Br | H | S | Me | O-n-decyl |
| 4-$CF_3$ | 5-F | H | S | Me | O-n-decyl |
| 4-$CF_3$ | 4-Cl | H | S | Me | O-n-decyl |
| 4-$CF_3$ | 4-F | H | S | Me | O-n-decyl |
| 4-$CF_3$ | H | H | S | Me | O-n-decyl |
| 4-$CF_3$ | 5-Cl | $CO_2Me$ | s | Me | O-n-decyl |
| 4-$CF_3$ | 5-Br | $CO_2Me$ | S | Me | O-n-decyl |
| 4-$CF_3$ | 5-F | $CO_2Me$ | S | Me | O-n-decyl |
| 4-$CF_3$ | 4-Cl | $CO_2Me$ | S | Me | O-n-decyl |
| 4-$CF_3$ | 4-F | $CO_2Me$ | S | Me | O-n-decyl |
| 4-$CF_3$ | H | $CO_2Me$ | S | Me | O-n-decyl |
| 4-$CF_3$ | 5-Br | H | O | Me | O-n-dodecyl |
| 4-Cl | 5-Br | H | O | Me | O-n-dodecyl |
| 4-Br | 5-Br | H | O | Me | O-n-dodecyl |
| 4-$OCF_3$ | 5-Br | H | O | Me | O-n-dodecyl |
| 4-$CF_3$ | 5-Cl | H | O | Me | O-n-dodecyl |
| 4-Cl | 5-Cl | H | O | Me | O-n-dodecyl |
| 4-Br | 5-Cl | H | O | Me | O-n-dodecyl |
| 4-$CF_3$ | 5-$CF_3$ | H | O | Me | O-n-dodecyl |
| 4-$CF_3$ | 4-F | H | O | Me | O-n-dodecyl |
| 4-$CF_3$ | H | H | O | Me | O-n-dodecyl |
| 4-$CF_3$ | 5-Br | $CO_2Me$ | O | Me | O-n-dodecyl |
| 4-$CF_3$ | 5-Cl | $CO_2Me$ | O | Me | O-n-dodecyl |
| 4-$CF_3$ | 5-$CF_3$ | $CO_2Me$ | O | Me | O-n-dodecyl |
| 4-$CF_3$ | 4-F | $CO_2Me$ | O | Me | O-n-dodecyl |
| 4-$CF_3$ | H | $CO_2Me$ | O | Me | O-n-dodecyl |
| 4-$CF_3$ | 5-Cl | H | S | Me | O-n-dodecyl |
| 4-Cl | 5-Cl | H | S | Me | O-n-dodecyl |
| 4-Br | 5-Cl | H | S | Me | O-n-dodecyl |
| 4-$CF_3$ | 5-Br | H | S | Me | O-n-dodecyl |
| 4-$CF_3$ | 5-F | H | S | Me | O-n-dodecyl |
| 4-$CF_3$ | 4-Cl | H | S | Me | O-n-dodecyl |
| 4-$CF_3$ | 4-F | H | S | Me | O-n-dodecyl |
| 4-$CF_3$ | H | H | S | Me | O-n-dodecyl |
| 4-$CF_3$ | 5-Cl | $CO_2Me$ | S | Me | O-n-dodecyl |
| 4-$CF_3$ | 5-Br | $CO_2Me$ | S | Me | O-n-dodecyl |
| 4-$CF_3$ | 5-F | $CO_2Me$ | S | Me | O-n-dodecyl |
| 4-$CF_3$ | 4-Cl | $CO_2Me$ | S | Me | O-n-dodecyl |
| 4-$CF_3$ | 4-F | $CO_2Me$ | S | Me | O-n-dodecyl |
| 4-$CF_3$ | H | $CO_2Me$ | S | Me | O-n-dodecyl |
| 4-$CF_3$ | 5-Br | H | O | Me | O-sec-Bu |
| 4-Cl | 5-Br | H | O | Me | O-sec-Bu |
| 4-Br | 5-Br | H | O | Me | O-sec-Bu |
| 4-$OCF_3$ | 5-Br | H | O | Me | O-sec-Bu |
| 4-$CF_3$ | 5-Cl | H | O | Me | O-sec-Bu |
| 4-Cl | 5-Cl | H | O | Me | O-sec-Bu |
| 4-Br | 5-Cl | H | O | Me | O-sec-Bu |
| 4-$CF_3$ | 5-$CF_3$ | H | O | Me | O-sec-Bu |
| 4-$CF_3$ | 4-F | H | O | Me | O-sec-Bu |
| 4-$CF_3$ | H | H | O | Me | O-sec-Bu |
| 4-$CF_3$ | 5-Br | $CO_2Me$ | O | Me | O-sec-Bu |
| 4-$CF_3$ | 5-Cl | $CO_2Me$ | O | Me | O-sec-Bu |
| 4-$CF_3$ | 5-$CF_3$ | $CO_2Me$ | O | Me | O-sec-Bu |
| 4-$CF_3$ | 4-F | $CO_2Me$ | O | Me | O-sec-Bu |
| 4-$CF_3$ | H | $CO_2Me$ | O | Me | O-sec-Bu |

TABLE 8-continued

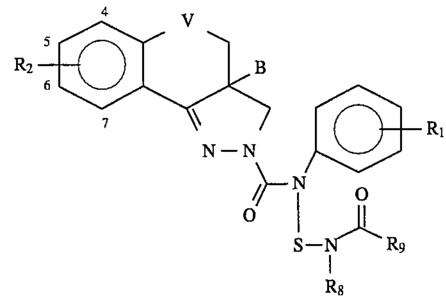

| $R_1$ | $R_2$ | B | V | $R_8$ | $R_9$ |
|---|---|---|---|---|---|
| 4-$CF_3$ | 5-Cl | H | S | Me | O-sec-Bu |
| 4-Cl | 5-Cl | H | S | Me | O-sec-Bu |
| 4-Br | 5-Cl | H | S | Me | O-sec-Bu |
| 4-$CF_3$ | 5-Br | H | S | Me | O-sec-Bu |
| 4-$CF_3$ | 5-F | H | S | Me | O-sec-Bu |
| 4-$CF_3$ | 4-Cl | H | S | Me | O-sec-Bu |
| 4-$CF_3$ | 4-F | H | S | Me | O-sec-Bu |
| 4-$CF_3$ | H | H | S | Me | O-sec-Bu |
| 4-$CF_3$ | 5-Cl | $CO_2Me$ | S | Me | O-sec-Bu |
| 4-$CF_3$ | 5-Br | $CO_2Me$ | S | Me | O-sec-Bu |
| 4-$CF_3$ | 5-F | $CO_2Me$ | S | Me | O-sec-Bu |
| 4-$CF_3$ | 4-Cl | $CO_2Me$ | S | Me | O-sec-Bu |
| 4-$CF_3$ | 4-F | $CO_2Me$ | S | Me | O-sec-Bu |
| 4-$CF_3$ | H | $CO_2Me$ | S | Me | O-sec-Bu |
| 4-$CF_3$ | 5-Br | H | O | Me | O-iPr |
| 4-Cl | 5-Br | H | O | Me | O-iPr |
| 4-Br | 5-Br | H | O | Me | O-iPr |
| 4-$OCF_3$ | 5-Br | H | O | Me | O-iPr |
| 4-$CF_3$ | 5-Cl | H | O | Me | O-iPr |
| 4-Cl | 5-Cl | H | O | Me | O-iPr |
| 4-Br | 5-Cl | H | O | Me | O-iPr |
| 4-$CF_3$ | 5-$CF_3$ | H | O | Me | O-iPr |
| 4-$CF_3$ | 4-F | H | O | Me | O-iPr |
| 4-$CF_3$ | H | H | O | Me | O-iPr |
| 4-$CF_3$ | 5-Br | $CO_2Me$ | O | Me | O-iPr |
| 4-$CF_3$ | 5-Cl | $CO_2Me$ | O | Me | O-iPr |
| 4-$CF_3$ | 5-$CF_3$ | $CO_2Me$ | O | Me | O-iPr |
| 4-$CF_3$ | 4-F | $CO_2Me$ | O | Me | O-iPr |
| 4-$CF_3$ | H | $CO_2Me$ | O | Me | O-iPr |
| 4-$CF_3$ | 5-Cl | H | S | Me | O-iPr |
| 4-Cl | 5-Cl | H | S | Me | O-iPr |
| 4-Br | 5-Cl | H | S | Me | O-iPr |
| 4-$CF_3$ | 5-Br | H | S | Me | O-iPr |
| 4-$CF_3$ | 5-F | H | s | Me | O-iPr |
| 4-$CF_3$ | 4-Cl | H | S | Me | O-iPr |
| 4-$CF_3$ | 4-F | H | S | Me | O-iPr |
| 4-$CF_3$ | H | H | S | Me | O-iPr |
| 4-$CF_3$ | 5-Cl | $CO_2Me$ | S | Me | O-iPr |
| 4-$CF_3$ | 5-Br | $CO_2Me$ | S | Me | O-iPr |
| 4-$CF_3$ | 5-F | $CO_2Me$ | S | Me | O-iPr |
| 4-$CF_3$ | 4-Cl | $CO_2Me$ | S | Me | O-iPr |
| 4-$CF_3$ | 4-F | $CO_2Me$ | S | Me | O-iPr |
| 4-$CF_3$ | H | $CO_2Me$ | S | Me | O-iPr |
| 4-$CF_3$ | 5-Br | H | O | Me | $OCH_2CH_2OEt$ |
| 4-Cl | 5-Br | H | O | Me | $OCH_2CH_2OEt$ |
| 4-Br | 5-Br | H | O | Me | $OCH_2CH_2OEt$ |
| 4-$OCF_3$ | 5-Br | H | O | Me | $OCH_2CH_2OEt$ |
| 4-$CF_3$ | 5-Cl | H | O | Me | $OCH_2CH_2OEt$ |
| 4-Cl | 5-Cl | H | O | Me | $OCH_2CH_2OEt$ |
| 4-Br | 5-Cl | H | O | Me | $OCH_2CH_2OEt$ |
| 4-$CF_3$ | 5-$CF_3$ | H | O | Me | $OCH_2CH_2OEt$ |
| 4-$CF_3$ | 4-F | H | O | Me | $OCH_2CH_2OEt$ |
| 4-$CF_3$ | H | H | O | Me | $OCH_2CH_2OEt$ |
| 4-$CF_3$ | 5-Br | $CO_2Me$ | O | Me | $OCH_2CH_2OEt$ |
| 4-$CF_3$ | 5-Cl | $CO_2Me$ | O | Me | $OCH_2CH_2OEt$ |
| 4-$CF_3$ | 5-$CF_3$ | $CO_2Me$ | O | Me | $OCH_2CH_2OEt$ |
| 4-$CF_3$ | 4-F | $CO_2Me$ | O | Me | $OCH_2CH_2OEt$ |
| 4-$CF_3$ | H | $CO_2Me$ | O | Me | $OCH_2CH_2OEt$ |
| 4-$CF_3$ | 5-Cl | H | S | Me | $OCH_2CH_2OEt$ |
| 4-Cl | 5-Cl | H | S | Me | $OCH_2CH_2OEt$ |
| 4-Br | 5-Cl | H | S | Me | $OCH_2CH_2OEt$ |
| 4-$CF_3$ | 5-Br | H | S | Me | $OCH_2CH_2OEt$ |
| 4-$CF_3$ | 5-F | H | S | Me | $OCH_2CH_2OEt$ |

TABLE 8-continued

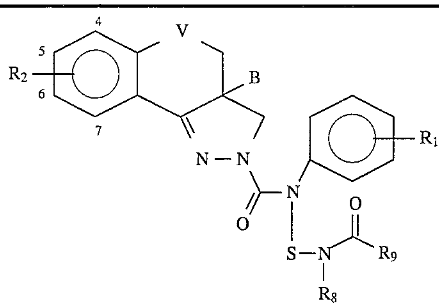

| $R_1$ | $R_2$ | B | V | $R_8$ | $R_9$ |
|---|---|---|---|---|---|
| 4-$CF_3$ | 4-Cl | H | S | Me | $OCH_2CH_2OEt$ |
| 4-$CF_3$ | 4-F | H | S | Me | $OCH_2CH_2OEt$ |
| 4-$CF_3$ | H | H | S | Me | $OCH_2CH_2OEt$ |
| 4-$CF_3$ | 5-Cl | $CO_2Me$ | S | Me | $OCH_2CH_2OEt$ |
| 4-$CF_3$ | 5-Br | $CO_2Me$ | S | Me | $OCH_2CH_2OEt$ |
| 4-$CF_3$ | 5-F | $CO_2Me$ | S | Me | $OCH_2CH_2OEt$ |
| 4-$CF_3$ | 4-Cl | $CO_2Me$ | S | Me | $OCH_2CH_2OEt$ |
| 4-$CF_3$ | 4-F | $CO_2Me$ | S | Me | $OCH_2CH_2OEt$ |
| 4-$CF_3$ | H | $CO_2Me$ | S | Me | $OCH_2CH_2OEt$ |
| 4-$CF_3$ | 5-Br | H | O | Me | $OCH_2CCl_3$ |
| 4-Cl | 5-Br | H | O | Me | $OCH_2CCl_3$ |
| 4-Br | 5-Br | H | O | Me | $OCH_2CCl_3$ |
| 4-$OCF_3$ | 5-Br | H | O | Me | $OCH_2CCl_3$ |
| 4-$CF_3$ | 5-Cl | H | O | Me | $OCH_2CCl_3$ |
| 4-Cl | 5-Cl | H | O | Me | $OCH_2CCl_3$ |
| 4-Br | 5-Cl | H | O | Me | $OCH_2CCl_3$ |
| 4-$CF_3$ | 5-$CF_3$ | H | O | Me | $OCH_2CCl_3$ |
| 4-$CF_3$ | 4-F | H | O | Me | $OCH_2CCl_3$ |
| 4-$CF_3$ | H | H | O | Me | $OCH_2CCl_3$ |
| 4-$CF_3$ | 5-Br | $CO_2Me$ | O | Me | $OCH_2CCl_3$ |
| 4-$CF_3$ | 5-Cl | $CO_2Me$ | O | Me | $OCH_2CCl_3$ |
| 4-$CF_3$ | 5-$CF_3$ | $CO_2Me$ | O | Me | $OCH_2CCl_3$ |
| 4-$CF_3$ | 4-F | $CO_2Me$ | O | Me | $OCH_2CCl_3$ |
| 4-$CF_3$ | H | $CO_2Me$ | O | Me | $OCH_2CCl_3$ |
| 4-$CF_3$ | 5-Cl | H | S | Me | $OCH_2CCl_3$ |
| 4-Cl | 5-Cl | H | S | Me | $OCH_2CCl_3$ |
| 4-Br | 5-Cl | H | S | Me | $OCH_2CCl_3$ |
| 4-$CF_3$ | 5-Br | H | S | Me | $OCH_2CCl_3$ |
| 4-$CF_3$ | 5-F | H | S | Me | $OCH_2CCl_3$ |
| 4-$CF_3$ | 4-Cl | H | S | Me | $OCH_2CCl_3$ |
| 4-$CF_3$ | 4-F | H | S | Me | $OCH_2CCl_3$ |
| 4-$CF_3$ | B | H | S | Me | $OCH_2CCl_3$ |
| 4-$CF_3$ | 5-Cl | $CO_2Me$ | S | Me | $OCH_2CCl_3$ |
| 4-$CF_3$ | 5-Br | $CO_2Me$ | S | Me | $OCH_2CCl_3$ |
| 4-$CF_3$ | 5-F | $CO_2Me$ | S | Me | $OCH_2CCl_3$ |
| 4-$CF_3$ | 4-Cl | $CO_2Me$ | S | Me | $OCH_2CCl_3$ |
| 4-$CF_3$ | 4-F | $CO_2Me$ | S | Me | $OCH_2CCl_3$ |
| 4-$CF_3$ | H | $CO_2Me$ | S | Me | $OCH_2CCl_3$ |
| 4-$CF_3$ | 5-Br | H | O | Me | $OCH_2CF_3$ |
| 4-Cl | 5-Br | H | O | Me | $OCH_2CF_3$ |
| 4-Br | 5-Br | H | O | Me | $OCH_2CF_3$ |
| 4-$OCF_3$ | 5-Br | H | O | Me | $OCH_2CF_3$ |
| 4-$CF_3$ | 5-Cl | H | O | Me | $OCH_2CF_3$ |
| 4-Cl | 5-Cl | H | O | Me | $OCH_2CF_3$ |
| 4-Br | 5-Cl | H | O | Me | $OCH_2CF_3$ |
| 4-$CF_3$ | 5-$CF_3$ | H | O | Me | $OCH_2CF_3$ |
| 4-$CF_3$ | 4-F | H | O | Me | $OCH_2CF_3$ |
| 4-$CF_3$ | H | H | O | Me | $OCH_2CF_3$ |
| 4-$CF_3$ | 5-Br | $CO_2Me$ | O | Me | $OCH_2CF_3$ |
| 4-$CF_3$ | 5-Cl | $CO_2Me$ | O | Me | $OCH_2CF_3$ |
| 4-$CF_3$ | 5-$CF_3$ | $CO_2Me$ | O | Me | $OCH_2CF_3$ |
| 4-$CF_3$ | 4-F | $CO_2Me$ | O | Me | $OCH_2CF_3$ |
| 4-$CF_3$ | H | $CO_2Me$ | O | Me | $OCH_2CF_3$ |
| 4-$CF_3$ | 5-Cl | H | S | Me | $OCH_2CF_3$ |
| 4-Cl | 5-Cl | H | S | Me | $OCH_2CF_3$ |
| 4-Br | 5-Cl | H | S | Me | $OCH_2CF_3$ |
| 4-$CF_3$ | 5-Br | H | S | Me | $OCH_2CF_3$ |
| 4-$CF_3$ | 5-F | H | S | Me | $OCH_2CF_3$ |
| 4-$CF_3$ | 4-Cl | H | S | Me | $OCH_2CF_3$ |
| 4-$CF_3$ | 4-F | H | S | Me | $OCH_2CF_3$ |
| 4-$CF_3$ | H | H | S | Me | $OCH_2CF_3$ |
| 4-$CF_3$ | 5-Cl | $CO_2Me$ | S | Me | $OCH_2CF_3$ |
| 4-$CF_3$ | 5-Br | $CO_2Me$ | S | Me | $OCH_2CF_3$ |

TABLE 8-continued

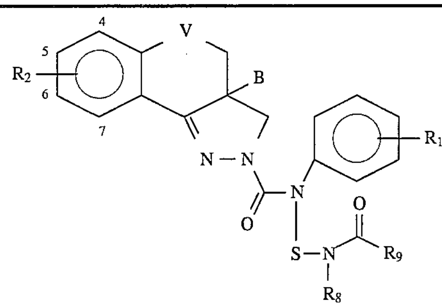

| $R_1$ | $R_2$ | B | V | $R_8$ | $R_9$ |
|---|---|---|---|---|---|
| 4-$CF_3$ | 5-F | $CO_2Me$ | S | Me | $OCH_2CF_3$ |
| 4-$CF_3$ | 4-Cl | $CO_2Me$ | S | Me | $OCH_2CF_3$ |
| 4-$CF_3$ | 4-F | $CO_2Me$ | S | Me | $OCH_2CF_3$ |
| 4-$CF_3$ | H | $CO_2Me$ | S | Me | $OCH_2CF_3$ |
| 4-$CF_3$ | 5-Br | H | O | Me | $OCH_2CO_2Et$ |
| 4-Cl | 5-Br | H | O | Me | $OCH_2CO_2Et$ |
| 4-Br | 5-Br | H | O | Me | $OCH_2CO_2Et$ |
| 4-$OCF_3$ | 5-Br | H | O | Me | $OCH_2CO_2Et$ |
| 4-$CF_3$ | 5-Cl | H | O | Me | $OCH_2CO_2Et$ |
| 4-Cl | 5-Cl | H | O | Me | $OCH_2CO_2Et$ |
| 4-Br | 5-Cl | H | O | Me | $OCH_2CO_2Et$ |
| 4-$CF_3$ | 5-$CF_3$ | H | O | Me | $OCH_2CO_2Et$ |
| 4-$CF_3$ | 4-F | H | O | Me | $OCH_2CO_2Et$ |
| 4-$CF_3$ | H | H | O | Me | $OCH_2CO_2Et$ |
| 4-$CF_3$ | 5-Br | $CO_2Me$ | O | Me | $OCH_2CO_2Et$ |
| 4-$CF_3$ | 4-Cl | $CO_2Me$ | O | Me | $OCH_2CO_2Et$ |
| 4-$CF_3$ | 4-$CF_3$ | $CO_2Me$ | O | Me | $OCH_2CO_2Et$ |
| 4-$CF_3$ | 4-F | $CO_2Me$ | O | Me | $OCH_2CO_2Et$ |
| 4-$CF_3$ | H | $CO_2Me$ | O | Me | $OCH_2CO_2Et$ |
| 4-$CF_3$ | 5-Cl | H | S | Me | $OCH_2CO_2Et$ |
| 4-Cl | 5-Cl | H | S | Me | $OCH_2CO_2Et$ |
| 4-Br | 5-Cl | H | S | Me | $OCH_2CO_2Et$ |
| 4-$CF_3$ | 5-Br | H | S | Me | $OCH_2CO_2Et$ |
| 4-$CF_3$ | 5-F | H | S | Me | $OCH_2CO_2Et$ |
| 4-$CF_3$ | 4-Cl | H | S | Me | $OCH_2CO_2Et$ |
| 4-$CF_3$ | 4-F | H | S | Me | $OCH_2CO_2Et$ |
| 4-$CF_3$ | H | H | S | Me | $OCH_2CO_2Et$ |
| 4-$CF_3$ | 5-Cl | $CO_2Me$ | S | Me | $OCH_2CO_2Et$ |
| 4-$CF_3$ | 5-Br | $CO_2Me$ | S | Me | $OCH_2CO_2Et$ |
| 4-$CF_3$ | 5-F | $CO_2Me$ | S | Me | $OCH_2CO_2Et$ |
| 4-$CF_3$ | 4-Cl | $CO_2Me$ | S | Me | $OCH_2CO_2Et$ |
| 4-$CF_3$ | 4-F | $CO_2Me$ | S | Me | $OCH_2CO_2Et$ |
| 4-$CF_3$ | H | $CO_2Me$ | S | Me | $OCH_2CO_2Et$ |
| 4-$CF_3$ | 5-Br | H | O | Me | F |
| 4-Cl | 5-Br | H | O | Me | F |
| 4-Br | 5-Br | H | O | Me | F |
| 4-$OCF_3$ | 5-Br | H | O | Me | F |
| 4-$CF_3$ | 5-Cl | H | O | Me | F |
| 4-Cl | 5-Cl | H | O | Me | F |
| 4-Br | 5-Cl | H | O | Me | F |
| 4-$CF_3$ | 5-$CF_3$ | H | O | Me | F |
| 4-$CF_3$ | 4-F | H | O | Me | F |
| 4-$CF_3$ | H | H | O | Me | F |
| 4-$CF_3$ | 5-Br | $CO_2Me$ | O | Me | F |
| 4-$CF_3$ | 5-Cl | $CO_2Me$ | O | Me | F |
| 4-$CF_3$ | 5-$CF_3$ | $CO_2Me$ | O | Me | F |
| 4-$CF_3$ | 4-F | $CO_2Me$ | O | Me | F |
| 4-$CF_3$ | H | $CO_2Me$ | O | Me | F |
| 4-$CF_3$ | 5-Cl | H | S | Me | F |
| 4-Cl | 5-Cl | H | S | Me | F |
| 4-Br | 5-Cl | H | S | Me | F |
| 4-$CF_3$ | 5-Br | H | S | Me | F |
| 4-$CF_3$ | 5-F | H | S | Me | F |
| 4-$CF_3$ | 4-Cl | H | S | Me | F |
| 4-$CF_3$ | 4-F | H | S | Me | F |
| 4-$CF_3$ | H | H | S | Me | F |
| 4-$CF_3$ | 5-Cl | $CO_2Me$ | S | Me | F |
| 4-$CF_3$ | 5-Br | $CO_2Me$ | S | Me | F |
| 4-$CF_3$ | 5-F | $CO_2Me$ | S | Me | F |
| 4-$CF_3$ | 4-Cl | $CO_2Me$ | S | Me | F |
| 4-$CF_3$ | 4-F | $CO_2Me$ | S | Me | F |
| 4-$CF_3$ | H | $CO_2Me$ | S | Me | F |
| 4-$CF_3$ | 5-Br | H | O | Me | $NMe_2$ |

TABLE 8-continued

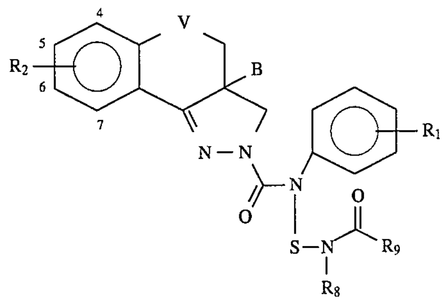

| $R_1$ | $R_2$ | B | V | $R_8$ | $R_9$ |
|---|---|---|---|---|---|
| 4-Cl | 5-Br | H | O | Me | $NMe_2$ |
| 4-Br | 5-Br | H | O | Me | $NMe_2$ |
| 4-$OCF_3$ | 5-Br | H | O | Me | $NMe_2$ |
| 4-$CF_3$ | 5-Cl | H | O | Me | $NMe_2$ |
| 4-Cl | 5-Cl | H | O | Me | $NMe_2$ |
| 4-Br | 5-Cl | H | O | Me | $NMe_2$ |
| 4-$CF_3$ | 5-$CF_3$ | H | O | Me | $NMe_2$ |
| 4-$CF_3$ | 4-F | H | O | Me | $NMe_2$ |
| 4-$CF_3$ | H | H | O | Me | $NMe_2$ |
| 4-$CF_3$ | 5-Br | $CO_2Me$ | O | Me | $NMe_2$ |
| 4-$CF_3$ | 5-Cl | $CO_2Me$ | O | Me | $NMe_2$ |
| 4-$CF_3$ | 5-$CF_3$ | $CO_2Me$ | O | Me | $NMe_2$ |
| 4-$CF_3$ | 4-F | $CO_2Me$ | O | Me | $NMe_2$ |
| 4-$CF_3$ | H | $CO_2Me$ | O | Me | $NMe_2$ |
| 4-$CF_3$ | 5-Cl | H | S | Me | $NMe_2$ |
| 4-Cl | 5-Cl | H | S | Me | $NMe_2$ |
| 4-Br | 5-Cl | H | S | Me | $NMe_2$ |
| 4-$CF_3$ | 5-Br | H | S | Me | $NMe_2$ |
| 4-$CF_3$ | 5-F | H | S | Me | $NMe_2$ |
| 4-$CF_3$ | 4-Cl | H | S | Me | $NMe_2$ |
| 4-$CF_3$ | 4-F | H | S | Me | NMe, |
| 4-$CF_3$ | H | H | S | Me | $NMe_2$ |
| 4-$CF_3$ | 5-Cl | $CO_2Me$ | S | Me | $NMe_2$ |
| 4-$CF_3$ | 5-Br | $CO_2Me$ | S | Me | $NMe_2$ |
| 4-$CF_3$ | 5-F | $CO_2Me$ | S | Me | $NMe_2$ |
| 4-$CF_3$ | 4-Cl | $CO_2Me$ | S | Me | $NMe_2$ |
| 4-$CF_3$ | 4-F | $CO_2Me$ | S | Me | $NMe_2$ |
| 4-$CF_3$ | H | $CO_2Me$ | S | Me | $NMe_2$ |
| 4-$CF_3$ | 5-Br | H | O | Et | O-iPr |
| 4-Cl | 5-Br | H | O | Et | O-iPr |
| 4-Br | 5-Br | H | O | Et | O-iPr |
| 4-$OCF_3$ | 5-Br | H | O | Et | O-iPr |
| 4-$CF_3$ | 5-Cl | H | O | Et | O-iPr |
| 4-Cl | 5-Cl | H | O | Et | O-iPr |
| 4-Br | 5-Cl | H | O | Et | O-iPr |
| 4-$CF_3$ | 5-$CF_3$ | H | O | Et | O-iPr |
| 4-$CF_3$ | 4-F | H | O | Et | O-iPr |
| 4-$CF_3$ | H | H | O | Et | O-iPr |
| 4-$CF_3$ | 5-Br | $CO_2Me$ | O | Et | O-iPr |
| 4-$CF_3$ | 5-Cl | $CO_2Me$ | O | Et | O-iPr |
| 4-$CF_3$ | 5-$CF_3$ | $CO_2Me$ | O | Et | O-iPr |
| 4-$CF_3$ | 4-F | $CO_2Me$ | O | Et | O-iPr |
| 4-$CF_3$ | H | $CO_2Me$ | O | Et | O-iPr |
| 4-$CF_3$ | 5-Cl | H | S | Et | O-iPr |
| 4-Cl | 5-Cl | H | S | Et | O-iPr |
| 4-Br | 5-Cl | H | S | Et | O-iPr |
| 4-$CF_3$ | 5-Br | H | S | Et | O-iPr |
| 4-$CF_3$ | 5-F | H | S | Et | O-iPr |
| 4-$CF_3$ | 4-Cl | H | S | Et | O-iPr |
| 4-$CF_3$ | 4-F | H | S | Et | O-iPr |
| 4-$CF_3$ | H | H | S | Et | O-iPr |
| 4-$CF_3$ | 5-Cl | $CO_2Me$ | S | Et | O-iPr |
| 4-$CF_3$ | 5-Br | $CO_2Me$ | S | Et | O-iPr |
| 4-$CF_3$ | 5-F | $CO_2Me$ | S | Et | O-iPr |
| 4-$CF_3$ | 4-Cl | $CO_2Me$ | S | Et | O-iPr |
| 4-$CF_3$ | 4-F | $CO_2Me$ | S | Et | O-iPr |
| 4-$CF_3$ | H | $CO_2Me$ | S | Et | O-iPr |
| 4-$CF_3$ | 5-Br | H | O | iPr | OEt |
| 4-Cl | 5-Br | H | O | iPr | OEt |
| 4-Br | 5-Br | H | O | iPr | OEt |
| 4-$OCF_3$ | 5-Br | H | O | iPr | OEt |
| 4-$CF_3$ | 5-Cl | H | O | iPr | OEt |
| 4-Cl | 5-Cl | H | O | iPr | OEt |

TABLE 8-continued

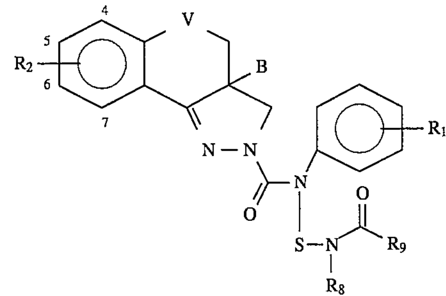

| $R_1$ | $R_2$ | B | V | $R_8$ | $R_9$ |
|---|---|---|---|---|---|
| 4-Br | 5-Cl | H | O | iPr | OEt |
| 4-$CF_3$ | 5-$CF_3$ | H | O | iPr | OEt |
| 4-$CF_3$ | 4-F | H | O | iPr | OEt |
| 4-$CF_3$ | H | H | O | iPr | OEt |
| 4-$CF_3$ | 5-Br | $CO_2Me$ | O | iPr | OEt |
| 4-$CF_3$ | 5-Cl | $CO_2Me$ | O | iPr | OEt |
| 4-$CF_3$ | 5-$CF_3$ | $CO_2Me$ | O | iPr | OEt |
| 4-$CF_3$ | 4-F | $CO_2Me$ | O | iPr | OEt |
| 4-$CF_3$ | H | $CO_2Me$ | O | iPr | OEt |
| 4-$CF_3$ | 5-Cl | H | S | iPr | OEt |
| 4-Cl | 5-Cl | H | S | iPr | OEt |
| 4-Br | 5-Cl | H | S | iPr | OEt |
| 4-$CF_3$ | 5-Br | H | S | iPr | OEt |
| 4-$CF_3$ | 5-F | H | S | iPr | OEt |
| 4-$CF_3$ | 4-Cl | H | S | iPr | OEt |
| 4-$CF_3$ | 4-F | H | S | iPr | OEt |
| 4-$CF_3$ | H | H | S | iPr | OEt |
| 4-$CF_3$ | 5-Cl | $CO_2Me$ | S | iPr | OEt |
| 4-$CF_3$ | 5-Br | $CO_2Me$ | S | iPr | OEt |
| 4-$CF_3$ | 5-F | $CO_2Me$ | S | iPr | OEt |
| 4-$CF_3$ | 4-Cl | $CO_2Me$ | S | iPr | OEt |
| 4-$CF_3$ | 4-F | $CO_2Me$ | S | iPr | OEt |
| 4-$CF_3$ | H | $CO_2Me$ | S | iPr | OEt |
| 4-$CF_3$ | 5-Br | H | O | iPr | O-nBu |
| 4-Cl | 5-Br | H | O | iPr | O-nBu |
| 4-Br | 5-Br | H | O | iPr | O-nBu |
| 4-$OCF_3$ | 5-Br | H | O | iPr | O-nBu |
| 4-$CF_3$ | 5-Cl | H | O | iPr | O-nBu |
| 4-Cl | 5-Cl | H | O | iPr | O-nBu |
| 4-Br | 5-Cl | H | O | iPr | O-nBu |
| 4-$CF_3$ | 5-$CF_3$ | H | O | iPr | O-nBu |
| 4-$CF_3$ | 4-F | H | O | iPr | O-nBu |
| 4-$CF_3$ | H | H | O | iPr | O-nBu |
| 4-$CF_3$ | 5-Br | $CO_2Me$ | O | iPr | O-nBu |
| 4-$CF_3$ | 5-Cl | $CO_2Me$ | O | iPr | O-nBu |
| 4-$CF_3$ | 5-$CF_3$ | $CO_2Me$ | O | iPr | O-nBu |
| 4-$CF_3$ | 4-F | $CO_2Me$ | O | iPr | O-nBu |
| 4-$CF_3$ | H | $CO_2Me$ | O | iPr | O-nBu |
| 4-$CF_3$ | 5-Cl | H | S | iPr | O-nBu |
| 4-Cl | 5-Cl | H | S | iPr | O-nBu |
| 4-Br | 5-Cl | H | S | iPr | O-nBu |
| 4-$CF_3$ | 5-Br | H | S | iPr | O-nBu |
| 4-$CF_3$ | 5-F | H | S | iPr | O-nBu |
| 4-$CF_3$ | 4-Cl | H | S | iPr | O-nBu |
| 4-$CF_3$ | 4-F | H | S | iPr | O-nBu |
| 4-$CF_3$ | H | H | S | iPr | O-nBu |
| 4-$CF_3$ | 5-Cl | $CO_2Me$ | S | iPr | O-nBu |
| 4-$CF_3$ | 5-Br | $CO_2Me$ | S | iPr | O-nBu |
| 4-$CF_3$ | 5-F | $CO_2Me$ | S | iPr | O-nBu |
| 4-$CF_3$ | 4-Cl | $CO_2Me$ | S | iPr | O-nBu |
| 4-$CF_3$ | 4-F | $CO_2Me$ | S | iPr | O-nBu |
| 4-$CF_3$ | H | $CO_2Me$ | S | iPr | O-nBu |
| 4-$CF_3$ | 5-Br | H | O | iPr | $OCH_2CF_3$ |
| 4-Cl | 5-Br | H | O | iPr | $OCH_2CO_2Me$ |
| 4-Br | 5-Br | H | O | iPr | $NMe_2$ |
| 4-$OCF_3$ | 5-Br | H | O | iPr | $NEt_2$ |
| 4-$CF_3$ | 5-Cl | H | O | iPr | piperidino |
| 4-Cl | 5-Cl | H | O | iPr | Et |
| 4-Br | 5-Cl | H | O | iPr | 4-Br-Ph |
| 4-$CF_3$ | 5-$CF_3$ | H | O | $CH_2Ph$ | OEt |
| 4-$CF_3$ | 4-F | H | O | $CH_2Ph$ | O-n-octyl |
| 4-$CF_3$ | H | H | O | $CH_2Ph$ | $OCH_2CO_2Et$ |
| 4-$CF_3$ | 5-Br | $CO_2Me$ | O | $CH_2Ph$ | F |

TABLE 8-continued

| $R_1$ | $R_2$ | B | V | $R_8$ | $R_9$ |
|---|---|---|---|---|---|
| 4-CF$_3$ | 5-Cl | CO$_2$Me | O | CH$_2$Ph | NEt$_2$ |
| 4-CF$_3$ | 5-CF$_3$ | CO$_2$Me | O | CH$_2$Ph | morpholino |
| 4-CF$_3$ | 4-F | CO$_2$Me | O | CH$_2$Ph | 4-Cl-Ph |
| 4-CF$_3$ | H | CO$_2$Me | O | CH$_2$Ph | Et |
| 4-CF$_3$ | 5-Cl | H | S | CH$_2$Ph | Ph |

TABLE 9

| $R_1$ | $R_2$ | B | V | $R_8$ | $R_9$ |
|---|---|---|---|---|---|
| 4-CF$_3$ | 5-Br | H | O | Me | NMe$_2$ |
| 4-Cl | 5-Br | H | O | Me | NMe$_2$ |
| 4-Br | 5-Br | H | O | Me | NMe$_2$ |
| 4-OCF$_3$ | 5-Br | H | O | Me | NMe$_2$ |
| 4-CF$_3$ | 5-Cl | H | O | Me | NMe$_2$ |
| 4-Cl | 5-Cl | H | O | Me | NMe$_2$ |
| 4-Br | 5-Cl | H | O | Me | NMe$_2$ |
| 4-CF$_3$ | 5-CF$_3$ | H | O | Me | NMe$_2$ |
| 4-CF$_3$ | 4-F | H | O | He | NMe$_2$ |
| 4-CF$_3$ | H | H | O | Me | NMe$_2$ |
| 4-CF$_3$ | 5-Br | CO$_2$Me | O | Me | NMe$_2$ |
| 4-CF$_3$ | 5-Cl | CO$_2$Me | O | Me | NMe$_2$ |
| 4-CF$_3$ | 5-CF$_3$ | CO$_2$Me | O | Me | NMe$_2$ |
| 4-CF$_3$ | 4-F | CO$_2$Me | O | Me | NMe$_2$ |
| 4-CF$_3$ | H | CO$_2$Me | O | Me | NMe$_2$ |
| 4-CF$_3$ | 5-Cl | H | S | Me | NMe$_2$ |
| 4-Cl | 5-Cl | H | S | Me | NMe$_2$ |
| 4-Br | 5-Cl | H | S | Me | NMe$_2$ |
| 4-CF$_3$ | 5-Br | H | S | Me | NMe$_2$ |
| 4-CF$_3$ | 5-F | H | S | Me | NMe$_2$ |
| 4-CF$_3$ | 4-Cl | H | S | Me | NMe$_2$ |
| 4-CF$_3$ | 4-F | H | S | Me | NMe$_2$ |
| 4-CF$_3$ | H | H | S | Me | NMe$_2$ |
| 4-CF$_3$ | 5-Cl | CO$_2$Me | S | Me | NMe$_2$ |
| 4-CF$_3$ | 5-Br | CO$_2$Me | S | Me | NMe$_2$ |
| 4-CF$_3$ | 5-F | CO$_2$Me | S | Me | NMe$_2$ |
| 4-CF$_3$ | 4-Cl | CO$_2$Me | S | Me | NMe$_2$ |
| 4-CF$_3$ | 4-F | CO$_2$Me | S | Me | NMe$_2$ |
| 4-CF$_3$ | H | CO$_2$Me | S | Me | NMe$_2$ |
| 4-CF$_3$ | 5-Br | H | O | Me | NEt$_2$ |
| 4-Cl | 5-Br | H | O | Me | NEt$_2$ |
| 4-Br | 5-Br | H | O | Me | NEt$_2$ |
| 4-OCF$_3$ | 5-Br | H | O | Me | NEt$_2$ |
| 4-CF$_3$ | 5-Cl | H | O | Me | NEt$_2$ |
| 4-Cl | 5-Cl | H | O | Me | NEt$_2$ |
| 4-Br | 5-Cl | H | O | Me | NEt$_2$ |
| 4-CF$_3$ | 5-CF$_3$ | H | O | Me | NEt$_2$ |

TABLE 9-continued

| $R_1$ | $R_2$ | B | V | $R_8$ | $R_9$ |
|---|---|---|---|---|---|
| 4-CF$_3$ | 4-F | H | O | Me | NEt$_2$ |
| 4-CF$_3$ | H | H | O | Me | NEt$_2$ |
| 4-CF$_3$ | 5-Br | CO$_2$Me | O | Me | NEt$_2$ |
| 4-CF$_3$ | 5-Cl | CO$_2$Me | O | Me | NEt$_2$ |
| 4-CF$_3$ | 5-CF$_3$ | CO$_2$Me | O | Me | NEt$_2$ |
| 4-CF$_3$ | 4-F | CO$_2$Me | O | Me | NEt$_2$ |
| 4-CF$_3$ | H | CO$_2$Me | O | Me | NEt$_2$ |
| 4-CF$_3$ | 5-Cl | H | S | Me | NEt$_2$ |
| 4-Cl | 5-Cl | H | S | Me | NEt$_2$ |
| 4-Br | 5-Cl | H | S | Me | NEt$_2$ |
| 4-CF$_3$ | 5-Br | H | S | Me | NEt$_2$ |
| 4-CF$_3$ | 5-F | H | S | Me | NEt$_2$ |
| 4-CF$_3$ | 4-Cl | H | S | Me | NEt$_2$ |
| 4-CF$_3$ | 4-F | H | S | Me | NEt$_2$ |
| 4-CF$_3$ | H | H | S | Me | NEt$_2$ |
| 4-CF$_3$ | 5-Cl | CO$_2$Me | S | Me | NEt$_2$ |
| 4-CF$_3$ | 5-Br | CO$_2$Me | S | Me | NEt$_2$ |
| 4-CF$_3$ | 5-F | CO$_2$Me | S | Me | NEt$_2$ |
| 4-CF$_3$ | 4-Cl | CO$_2$Me | S | Me | NEt$_2$ |
| 4-CF$_3$ | 4-F | CO$_2$Me | S | Me | NEt$_2$ |
| 4-CF$_3$ | H | CO$_2$Me | S | Me | NEt$_2$ |
| 4-CF$_3$ | 5-Br | H | O | Me | piperidino |
| 4-Cl | 5-Br | H | O | Me | sec-Bu |
| 4-Br | 5-Br | H | O | Me | n-hexyl |
| 4-OCF$_3$ | 5-Br | H | O | Me | Ph |
| 4-CF$_3$ | 5-Cl | H | O | Me | 4-Cl—Ph |
| 4-Cl | 5-Cl | H | O | Me | 4-Me—Ph |
| 4-Br | 5-Cl | H | O | Me | n-Bu |
| 4-CF$_3$ | 5-CF$_3$ | H | O | Et | NMe$_2$ |
| 4-CF$_3$ | 4-F | H | O | Et | NEt$_2$ |
| 4-CF$_3$ | H | H | O | Et | morpholino |
| 4-CF$_3$ | 5-Br | CO$_2$Me | O | Et | iPr |
| 4-CF$_3$ | 5-Cl | CO$_2$Me | O | Et | n-Bu |
| 4-CF$_3$ | 5-CF$_3$ | CO$_2$Me | O | Et | Ph |
| 4-CF$_3$ | 4-F | CO$_2$Me | O | Et | 4-MeO—Ph |
| 4-CF$_3$ | H | CO$_2$Me | O | Me | NMe$_2$ |
| 4-CF$_3$ | 5-Cl | H | S | Me | NEt$_2$ |
| 4-Cl | 5-Cl | H | S | Me | morpholino |
| 4-Br | 5-Cl | H | S | Me | iPr |
| 4-CF$_3$ | 5-Br | H | S | Me | n-Bu |
| 4-CF$_3$ | 5-F | H | S | Me | Ph |
| 4-CF$_3$ | 4-Cl | H | S | Me | 4-MeO—Ph |
| 4-CF$_3$ | 4-F | H | S | Et | piperidino |
| 4-CF$_3$ | H | H | S | Et | sec-Bu |
| 4-CF$_3$ | 5-Cl | CO$_2$Me | S | Et | n-hexyl |
| 4-CF$_3$ | 5-Br | CO$_2$Me | S | Et | Ph |
| 4-CF$_3$ | 5-F | CO$_2$Me | S | Et | 4-Cl—Ph |
| 4-CF$_3$ | 4-Cl | CO$_2$Me | S | Et | 4-Me—Ph |
| 4-CF$_3$ | 4-F | CO$_2$Me | S | Et | n-Bu |
| 4-CF$_3$ | H | CO$_2$Me | S | Et | 2,6-di-Me-morpholino |
| 4-CF$_3$ | 5-Br | H | O | iPr | NMe$_2$ |
| 4-Cl | 5-Br | H | O | iPr | NMe$_2$ |
| 4-Br | 5-Br | H | O | iPr | NMe$_2$ |
| 4-OCF$_3$ | 5-Br | H | O | iPr | NMe$_2$ |
| 4-CF$_3$ | 5-Cl | H | O | iPr | NMe$_2$ |
| 4-Cl | 5-Cl | H | O | iPr | NMe$_2$ |
| 4-Br | 5-Cl | H | O | iPr | NMe$_2$ |
| 4-CF$_3$ | 5-CF$_3$ | H | O | iPr | NMe$_2$ |
| 4-CF$_3$ | 4-F | H | O | iPr | NMe$_2$ |
| 4-CF$_3$ | H | H | O | iPr | NMe$_2$ |
| 4-CF$_3$ | 5-Br | CO$_2$Me | O | iPr | NMe$_2$ |
| 4-CF$_3$ | 5-Cl | CO$_2$Me | O | iPr | NMe$_2$ |
| 4-CF$_3$ | 5-CF$_3$ | CO$_2$Me | O | iPr | NMe$_2$ |

TABLE 9-continued

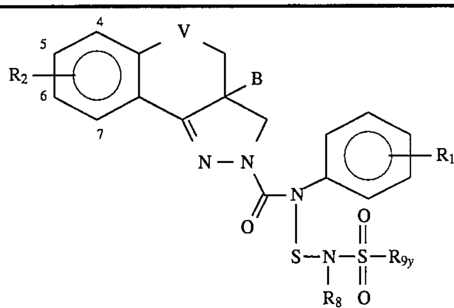

| $R_1$ | $R_2$ | B | V | $R_8$ | $R_9$ |
|---|---|---|---|---|---|
| 4-$CF_3$ | 4-F | $CO_2Me$ | O | iPr | $NMe_2$ |
| 4-$CF_3$ | H | $CO_2Me$ | O | iPr | $NMe_2$ |
| 4-$CF_3$ | 5-Cl | H | S | iPr | $NMe_2$ |
| 4-Cl | 5-Cl | H | S | iPr | $NMe_2$ |
| 4-Br | 5-Cl | H | S | iPr | $NMe_2$ |
| 4-$CF_3$ | 5-Br | H | S | iPr | $NMe_2$ |
| 4-$CF_3$ | 5-F | H | S | iPr | $NMe_2$ |
| 4-$CF_3$ | 4-Cl | H | S | iPr | $NMe_2$ |
| 4-$CF_3$ | 4-F | H | S | iPr | $NMe_2$ |

TABLE 9-continued

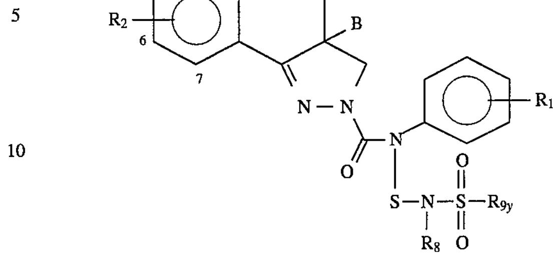

| $R_1$ | $R_2$ | B | V | $R_8$ | $R_9$ |
|---|---|---|---|---|---|
| 4-$CF_3$ | H | H | S | iPr | $NMe_2$ |
| 4-$CF_3$ | 5-Cl | $CO_2Me$ | S | iPr | $NMe_2$ |
| 4-$CF_3$ | 5-Br | $CO_2Me$ | S | iPr | $NMe_2$ |
| 4-$CF_3$ | 5-F | $CO_2Me$ | S | iPr | $NMe_2$ |
| 4-$CF_3$ | 4-Cl | $CO_2Me$ | S | iPr | $NMe_2$ |
| 4-$CF_3$ | 4-F | $CO_2Me$ | S | iPr | $NMe_2$ |
| 4-$CF_3$ | H | $CO_2Me$ | S | iPr | $NMe_2$ |

TABLE 10

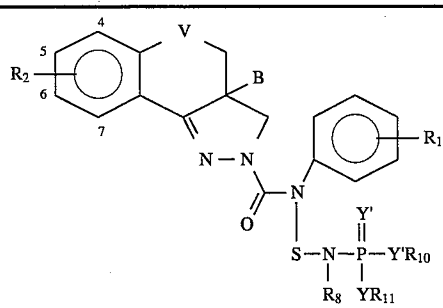

| $R_1$ | $R_2$ | B | V | $R_8$ | Y' | Y'$R_{10}$ | Y'$R_{11}$ |
|---|---|---|---|---|---|---|---|
| 4-$CF_3$ | 5-Br | H | O | tBu | S | OEt | OEt |
| 4-Cl | 5-Br | H | O | tBu | S | OEt | OEt |
| 4-Br | 5-Br | H | O | tBu | S | OEt | OEt |
| 4-$OCF_3$ | 5-Br | H | O | tBu | S | OEt | OEt |
| 4-$CF_3$ | 5-Cl | H | O | tBu | S | OEt | OEt |
| 4-Cl | 5-Cl | H | O | tBu | S | OEt | OEt |
| 4-Br | 5-Cl | H | O | tBu | S | OEt | OEt |
| 4-$CF_3$ | 5-$CF_3$ | H | O | tBu | S | OEt | OEt |
| 4-$CF_3$ | 4-F | H | O | tBu | S | OEt | OEt |
| 4-$CF_3$ | H | H | O | tBu | S | OEt | OEt |
| 4-$CF_3$ | 5-Br | $CO_2Me$ | O | tBu | S | OEt | OEt |
| 4-$CF_3$ | 5-Cl | $CO_2Me$ | O | tBu | S | OEt | OEt |
| 4-$CF_3$ | 5-$CF_3$ | $CO_2Me$ | O | tBu | S | OEt | OEt |
| 4-$CF_3$ | 4-F | $CO_2Me$ | O | tBu | S | OEt | OEt |
| 4-$CF_3$ | H | $CO_2Me$ | O | tBu | S | OEt | OEt |
| 4-$CF_3$ | 5-Cl | H | S | tBu | S | OEt | OEt |
| 4-Cl | 5-Cl | H | S | tBu | S | OEt | OEt |
| 4-Br | 5-Cl | H | S | tBu | S | OEt | OEt |
| 4-$CF_3$ | 5-Br | H | S | tBu | S | OEt | OEt |
| 4-$CF_3$ | 5-F | H | S | tBu | S | OEt | OEt |
| 4-$CF_3$ | 4-Cl | H | S | tBu | S | OEt | OEt |
| 4-$CF_3$ | 4-F | H | S | tBu | S | OEt | OEt |
| 4-$CF_3$ | H | H | S | tBu | S | OEt | OEt |
| 4-$CF_3$ | 5-Cl | $CO_2Me$ | S | tBu | S | OEt | OEt |
| 4-$CF_3$ | 5-Br | $CO_2Me$ | S | tBu | S | OEt | OEt |
| 4-$CF_3$ | 5-F | $CO_2Me$ | S | tBu | S | OEt | OEt |
| 4-$CF_3$ | 4-Cl | $CO_2Me$ | S | tBu | S | OEt | OEt |
| 4-$CF_3$ | 4-F | $CO_2Me$ | S | tBu | S | OEt | OEt |
| 4-$CF_3$ | H | $CO_2Me$ | S | tBu | S | OEt | OEt |
| 4-$CF_3$ | 5-Br | H | O | tBu | S | $-OCH_2C(Me)_2CH_2O-$ | |
| 4-Cl | 5-Br | H | O | tBu | S | $-OCH_2C(Me)_2CH_2O-$ | |
| 4-Br | 5-Br | H | O | tBu | S | $-OCH_2C(Me)_2CH_2O-$ | |

TABLE 10-continued

| $R_1$ | $R_2$ | B | V | $R_8$ | Y' | $Y'R_{10}$ | $Y'R_{11}$ |
|---|---|---|---|---|---|---|---|
| 4-$OCF_3$ | 5-Br | H | O | tBu | S | $-OCH_2C(Me)_2CH_2O-$ | |
| 4-$CF_3$ | 5-Cl | H | O | tBu | S | $-OCH_2C(Me)_2CH_2O-$ | |
| 4-Cl | 5-Cl | H | O | tBu | S | $-OCH_2C(Me)_2CH_2O-$ | |
| 4-Br | 5-Cl | H | O | tBu | S | $-OCH_2C(Me)_2CH_2O-$ | |
| 4-$CF_3$ | 5-$CF_3$ | H | O | tBu | S | $-OCH_2C(Me)_2CH_2O-$ | |
| 4-$CF_3$ | 4-F | H | O | tBu | S | $-OCH_2C(Me)_2CH_2O-$ | |
| 4-$CF_3$ | H | H | O | tBu | S | $-OCH_2C(Me)_2CH_2O-$ | |
| 4-$CF_3$ | 5-Br | $CO_2Me$ | O | tBu | S | $-OCH_2C(Me)_2CH_2O-$ | |
| 4-$CF_3$ | 5-Cl | $CO_2Me$ | O | tBu | S | $-OCH_2C(Me)_2CH_2O-$ | |
| 4-$CF_3$ | 5-$CF_3$ | $CO_2Me$ | O | tBu | S | $-OCH_2C(Me)_2CH_2O-$ | |
| 4-$CF_3$ | 4-F | $CO_2Me$ | O | tBu | S | $-OCH_2C(Me)_2CH_2O-$ | |
| 4-$CF_3$ | H | $CO_2Me$ | O | tBu | S | $-OCH_2C(Me)_2CH_2O-$ | |
| 4-$CF_3$ | 5-Cl | H | S | tBu | S | $-OCH_2C(Me)_2CH_2O-$ | |
| 4-Cl | 5-Cl | H | S | tBu | S | $-OCH_2C(Me)_2CH_2O-$ | |
| 4-Br | 5-Cl | H | S | tBu | S | $-OCH_2C(Me)_2CH_2O-$ | |
| 4-$CF_3$ | 5-Br | H | S | tBu | S | $-OCH_2C(Me)_2CH_2O-$ | |
| 4-$CF_3$ | 5-F | H | S | tBu | S | $-OCH_2C(Me)_2CH_2O-$ | |
| 4-$CF_3$ | 4-Cl | H | S | tBu | S | $-OCH_2C(Me)_2CH_2O-$ | |
| 4-$CF_3$ | 4-F | H | S | tBu | S | $-OCH_2C(Me)_2CH_2O-$ | |
| 4-$CF_3$ | H | H | S | tBu | S | $-OCH_2C(Me)_2CH_2O-$ | |
| 4-$CF_3$ | 5-Cl | $CO_2Me$ | S | tBu | S | $-OCH_2C(Me)_2CH_2O-$ | |
| 4-$CF_3$ | 5-Br | $CO_2Me$ | S | tBu | S | $-OCH_2C(Me)_2CH_2O-$ | |
| 4-$CF_3$ | 5-F | $CO_2Me$ | S | tBu | S | $-OCH_2C(Me)_2CH_2O-$ | |
| 4-$CF_3$ | 4-Cl | $CO_2Me$ | S | tBu | S | $-OCH_2C(Me)_2CH_2O-$ | |
| 4-$CF_3$ | 4-F | $CO_2Me$ | S | tBu | S | $-OCH_2C(Me)_2CH_2O-$ | |
| 4-$CF_3$ | H | $CO_2Me$ | S | tBu | S | $-OCH_2C(Me)_2CH_2O-$ | |
| 4-$CF_3$ | 5-Br | H | O | tBu | S | $-OCH_2CH_2CH_2O-$ | |
| 4-Cl | 5-Br | H | O | tBu | S | $-OCH_2CH_2CH_2O-$ | |
| 4-Br | 5-Br | H | O | tBu | S | $-OCH_2CH_2CH_2O-$ | |
| 4-$OCF_3$ | 5-Br | H | O | tBu | S | $-OCH_2CH_2CH_2O-$ | |
| 4-$CF_3$ | 5-Cl | H | O | tBu | S | $-OCH_2CH_2CH_2O-$ | |
| 4-Cl | 5-Cl | H | O | tBu | S | $-OCH_2CH_2CH_2O-$ | |
| 4-Br | 5-Cl | H | O | tBu | S | $-OCH_2CH_2CH_2O-$ | |
| 4-$CF_3$ | 5-$CF_3$ | H | O | tBu | S | $-OCH_2CH_2CH_2O-$ | |
| 4-$CF_3$ | 4-F | H | O | tBu | S | $-OCH_2CH_2CH_2O-$ | |
| 4-$CF_3$ | H | H | O | tBu | S | $-OCH_2CH_2CH_2O-$ | |
| 4-$CF_3$ | 5-Br | $CO_2Me$ | O | tBu | S | $-OCH_2CH_2CH_2O-$ | |
| 4-$CF_3$ | 5-Cl | $CO_2Me$ | O | tBu | S | $-OCH_2CH_2CH_2O-$ | |
| 4-$CF_3$ | 5-$CF_3$ | $CO_2Me$ | O | tBu | S | $-OCH_2CH_2CH_2O-$ | |
| 4-$CF_3$ | 4-F | $CO_2Me$ | O | tBu | S | $-OCH_2CH_2CH_2O-$ | |
| 4-$CF_3$ | H | $CO_2Me$ | O | tBu | S | $-OCH_2CH_2CH_2O-$ | |
| 4-$CF_3$ | 5-Cl | H | S | tBu | S | $-OCH_2CH_2CH_2O-$ | |
| 4-Cl | 5-Cl | H | S | tBu | S | $-OCH_2CH_2CH_2O-$ | |
| 4-Br | 5-Cl | H | S | tBu | S | $-OCH_2CH_2CH_2O-$ | |
| 4-$CF_3$ | 5-Br | H | S | tBu | S | $-OCH_2CH_2CH_2O-$ | |
| 4-$CF_3$ | 5-F | H | S | tBu | S | $-OCH_2CH_2CH_2O-$ | |
| 4-$CF_3$ | 4-Cl | H | S | tBu | S | $-OCH_2CH_2CH_2O-$ | |
| 4-$CF_3$ | 4-F | H | S | tBu | S | $-OCH_2CH_2CH_2O-$ | |
| 4-$CF_3$ | H | H | S | tBu | S | $-OCH_2CH_2CH_2O-$ | |
| 4-$CF_3$ | 5-Cl | $CO_2Me$ | S | tBu | S | $-OCH_2CH_2CH_2O-$ | |
| 4-$CF_3$ | 5-Br | $CO_2Me$ | S | tBu | S | $-OCH_2CH_2CH_2O-$ | |
| 4-$CF_3$ | 5-F | $CO_2Me$ | S | tBu | S | $-OCH_2CH_2CH_2O-$ | |
| 4-$CF_3$ | 4-Cl | $CO_2Me$ | S | tBu | S | $-OCH_2CH_2CH_2O-$ | |
| 4-$CF_3$ | 4-F | $CO_2Me$ | S | tBu | S | $-OCH_2CH_2CH_2O-$ | |
| 4-$CF_3$ | H | $CO_2Me$ | S | tBu | S | $-OCH_2CH_2CH_2O-$ | |
| 4-$CF_3$ | 5-Br | H | O | tBu | S | $-OCH_2CH_2O-$ | |
| 4-Cl | 5-Br | H | O | tBu | S | $-OCH_2CH_2O-$ | |
| 4-Br | 5-Br | H | O | tBu | S | $-OCH_2CH_2O-$ | |
| 4-$OCF_3$ | 5-Br | H | O | tBu | S | $-OCH_2CH_2O-$ | |
| 4-$CF_3$ | 5-Cl | H | O | tBu | S | $-OCH_2CH_2O-$ | |
| 4-Cl | 5-Cl | H | O | tBu | S | $-OCH_2CH_2O-$ | |
| 4-Br | 5-Cl | H | O | tBu | S | $-OCH_2CH_2O-$ | |
| 4-$CF_3$ | 5-$CF_3$ | H | O | tBu | S | $-OCH_2CH_2O-$ | |

TABLE 10-continued

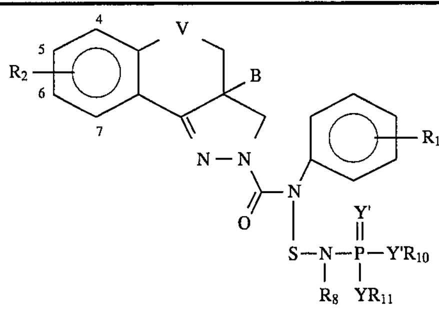

| R1 | R2 | B | V | R8 | Y' | Y'R10 | Y'R11 |
|---|---|---|---|---|---|---|---|
| 4-$CF_3$ | 4-F | H | O | tBu | S | $-OCH_2CH_2O-$ | |
| 4-$CF_3$ | H | H | O | tBu | S | $-OCH_2CH_2O-$ | |
| 4-$CF_3$ | 5-Br | $CO_2Me$ | O | tBu | S | $-OCH_2CH_2O-$ | |
| 4-$CF_3$ | 5-Cl | $CO_2Me$ | O | tBu | S | $-OCH_2CH_2O-$ | |
| 4-$CF_3$ | 5-$CF_3$ | $CO_2Me$ | O | tBu | S | $-OCH_2CH_2O-$ | |
| 4-$CF_3$ | 4-F | $CO_2Me$ | O | tBu | S | $-OCH_2CH_2O-$ | |
| 4-$CF_3$ | H | $CO_2Me$ | O | tBu | S | $-OCH_2CH_2O-$ | |
| 4-$CF_3$ | 5-Cl | H | S | tBu | S | $-OCH_2CH_2O-$ | |
| 4-Cl | 5-Cl | H | S | tBu | S | $-OCH_2CH_2O-$ | |
| 4-Br | 5-Cl | H | S | tBu | S | $-OCH_2CH_2O-$ | |
| 4-$CF_3$ | 5-Br | H | S | tBu | S | $-OCH_2CH_2O-$ | |
| 4-$CF_3$ | 5-Y | H | S | tBu | S | $-OCH_2CH_2O-$ | |
| 4-$CF_3$ | 4-Cl | H | S | tBu | S | $-OCH_2CH_2O-$ | |
| 4-$CF_3$ | 4-F | H | S | tBu | S | $-OCH_2CH_2O-$ | |
| 4-$CF_3$ | H | H | S | tBu | S | $-OCH_2CH_2O-$ | |
| 4-$CF_3$ | 5-Cl | $CO_2Me$ | S | tBu | S | $-OCH_2CH_2O-$ | |
| 4-$CF_3$ | 5-Br | $CO_2Me$ | S | tBu | S | $-OCH_2CH_2O-$ | |
| 4-$CF_3$ | 5-F | $CO_2Me$ | S | tBu | S | $-OCH_2CH_2O-$ | |
| 4-$CF_3$ | 4-Cl | $CO_2Me$ | S | tBu | S | $-OCH_2CH_2O-$ | |
| 4-$CF_3$ | 4-F | $CO_2Me$ | S | tBu | S | $-OCH_2CH_2O-$ | |
| 4-$CF_3$ | H | $CO_2Me$ | S | tBu | S | $-OCH_2CH_2O-$ | |
| 4-$CF_3$ | 5-Br | H | O | iPr | S | OEt | OEt |
| 4-Cl | 5-Br | H | O | iPr | S | OEt | OEt |
| 4-Br | 5-Br | H | O | iPr | S | OEt | OEt |
| 4-$OCF_3$ | 5-Br | H | O | iPr | S | OEt | OEt |
| 4-$CF_3$ | 5-Cl | H | O | iPr | S | OEt | OEt |
| 4-Cl | 5-Cl | H | O | iPr | S | OEt | OEt |
| 4-Br | 5-Cl | H | O | iPr | S | OEt | OEt |
| 4-$CF_3$ | 5-$CF_3$ | H | O | iPr | S | OEt | OEt |
| 4-$CF_3$ | 4-F | H | O | iPr | S | OEt | OEt |
| 4-$CF_3$ | H | H | O | iPr | S | OEt | OEt |
| 4-$CF_3$ | 5-Br | $CO_2Me$ | O | iPr | S | OEt | OEt |
| 4-$CF_3$ | 5-Cl | $CO_2Me$ | O | iPr | S | OEt | OEt |
| 4-$CF_3$ | 5-$CF_3$ | $CO_2Me$ | O | iPr | S | OEt | OEt |
| 4-$CF_3$ | 4-F | $CO_2Me$ | O | iPr | S | OEt | OEt |
| 4-$CF_3$ | H | $CO_2Me$ | O | iPr | S | OEt | OEt |
| 4-$CF_3$ | 5-Cl | H | S | iPr | S | OEt | OEt |
| 4-Cl | 5-Cl | H | S | iPr | S | OEt | OEt |
| 4-Br | 5-Cl | H | S | iPr | S | OEt | OEt |
| 4-$CF_3$ | 5-Br | H | S | iPr | S | OEt | OEt |
| 4-$CF_3$ | 5-F | H | S | iPr | S | OEt | OEt |
| 4-$CF_3$ | 4-Cl | H | S | iPr | S | OEt | OEt |
| 4-$CF_3$ | 4-F | H | S | iPr | S | OEt | OEt |
| 4-$CF_3$ | H | H | S | iPr | S | OEt | OEt |
| 4-$CF_3$ | 5-Cl | $CO_2Me$ | S | iPr | S | OEt | OEt |
| 4-$CF_3$ | 5-Br | $CO_2Me$ | S | iPr | S | OEt | OEt |
| 4-$CF_3$ | 5-F | $CO_2Me$ | S | iPr | S | OEt | OEt |
| 4-$CF_3$ | 4-Cl | $CO_2Me$ | S | iPr | S | OEt | OEt |
| 4-$CF_3$ | 4-F | $CO_2Me$ | S | iPr | S | OEt | OEt |
| 4-$CF_3$ | H | $CO_2Me$ | S | iPr | S | OEt | OEt |
| 4-$CF_3$ | 5-Br | H | O | iPr | S | $-OCH_2C(Me)_2CH_2O-$ | |
| 4-Cl | 5-Br | H | O | iPr | S | $-OCH_2C(Me)_2CH_2O-$ | |
| 4-Br | 5-Br | H | O | iPr | S | $-OCH_2C(Me)_2CH_2O-$ | |
| 4-$OCF_3$ | 5-Br | H | O | iPr | S | $-OCH_2C(Me)_2CH_2O-$ | |
| 4-$CF_3$ | 5-Cl | H | O | iPr | S | $-OCH_2C(Me)_2CH_2O-$ | |
| 4-Cl | 5-Cl | H | O | iPr | S | $-OCH_2C(Me)_2CH_2O-$ | |
| 4-Br | 5-Cl | H | O | iPr | S | $-OCH_2C(Me)_2CH_2O-$ | |
| 4-$CF_3$ | 5-$CF_3$ | H | O | iPr | S | $-OCH_2C(Me)_2CH_2O-$ | |
| 4-$CF_3$ | 4-F | H | O | iPr | S | $-OCH_2C(Me)_2CH_2O-$ | |
| 4-$CF_3$ | H | H | O | iPr | S | $-OCH_2C(Me)_2CH_2O-$ | |
| 4-$CF_3$ | 5-Br | $CO_2Me$ | O | iPr | S | $-OCH_2C(Me)_2CH_2O-$ | |
| 4-$CF_3$ | 5-Cl | $CO_2Me$ | O | iPr | S | $-OCH_2C(Me)_2CH_2O-$ | |
| 4-$CF_3$ | 5-$CF_3$ | $CO_2Me$ | O | iPr | S | $-OCH_2C(Me)_2CH_2O-$ | |

TABLE 10-continued

| $R_1$ | $R_2$ | B | V | $R_8$ | Y' | $Y'R_{10}$ | $Y'R_{11}$ |
|---|---|---|---|---|---|---|---|
| 4-$CF_3$ | 4-F | $CO_2Me$ | O | iPr | S | $-OCH_2C(Me)_2CH_2O-$ | |
| 4-$CF_3$ | H | $CO_2Me$ | O | iPr | S | $-OCH_2C(Me)_2CH_2O-$ | |
| 4-$CF_3$ | 5-Cl | H | S | iPr | S | $-OCH_2C(Me)_2CH_2O-$ | |
| 4-Cl | 5-Cl | H | S | iPr | S | $-OCH_2C(Me)_2CH_2O-$ | |
| 4-Br | 5-Cl | H | S | iPr | S | $-OCH_2C(Me)_2CH_2O-$ | |
| 4-$CF_3$ | 5-Br | H | S | iPr | S | $-OCH_2C(Me)_2CH_2O-$ | |
| 4-$CF_3$ | 5-F | H | S | iPr | S | $-OCH_2C(Me)_2CH_2O-$ | |
| 4-$CF_3$ | 4-Cl | H | S | iPr | S | $-OCH_2C(Me)_2CH_2O-$ | |
| 4-$CF_3$ | 4-F | H | S | iPr | S | $-OCH_2C(Me)_2CH_2O-$ | |
| 4-$CF_3$ | H | H | S | iPr | S | $-OCH_2C(Me)_2CH_2O-$ | |
| 4-$CF_3$ | 5-Cl | $CO_2Me$ | S | iPr | S | $-OCH_2C(Me)_2CH_2O-$ | |
| 4-$CF_3$ | 5-Br | $CO_2Me$ | S | iPr | S | $-OCH_2C(Me)_2CH_2O-$ | |
| 4-$CF_3$ | 5-F | $CO_2Me$ | S | iPr | S | $-OCH_2C(Me)_2CH_2O-$ | |
| 4-$CF_3$ | 4-Cl | $CO_2Me$ | S | iPr | S | $-OCH_2C(Me)_2CH_2O-$ | |
| 4-$CF_3$ | 4-F | $CO_2Me$ | S | iPr | S | $-OCH_2C(Me)_2CH_2O-$ | |
| 4-$CF_3$ | H | $CO_2Me$ | S | iPr | S | $-OCH_2C(Me)_2CH_2O-$ | |
| 4-$CF_3$ | 5-Br | H | O | Me | S | OEt | OEt |
| 4-Cl | 5-Br | H | O | Me | S | OEt | OEt |
| 4-Br | 5-Br | H | O | Me | S | OEt | OEt |
| 4-$OCF_3$ | 5-Br | H | O | Me | S | OEt | OEt |
| 4-$CF_3$ | 5-Cl | H | O | Me | S | OEt | OEt |
| 4-Cl | 5-Cl | H | O | Me | S | OEt | OEt |
| 4-Br | 5-Cl | H | O | Me | S | OEt | OEt |
| 4-$CF_3$ | 5-$CF_3$ | H | O | Me | S | OEt | OEt |
| 4-$CF_3$ | 4-F | H | O | Me | S | OEt | OEt |
| 4-$CF_3$ | H | H | O | Me | S | OEt | OEt |
| 4-$CF_3$ | 5-Br | $CO_2Me$ | O | Me | S | OEt | OEt |
| 4-$CF_3$ | 5-Cl | $CO_2Me$ | O | Me | S | OEt | OEt |
| 4-$CF_3$ | 5-$CF_3$ | $CO_2Me$ | O | Me | S | OEt | OEt |
| 4-$CF_3$ | 4-F | $CO_2Me$ | O | Me | S | OEt | OEt |
| 4-$CF_3$ | H | $CO_2Me$ | O | Me | S | OEt | OEt |
| 4-$CF_3$ | 5-Cl | H | S | Me | S | OEt | OEt |
| 4-Cl | 5-Cl | H | S | Me | S | OEt | OEt |
| 4-Br | 5-Cl | H | S | Me | S | OEt | OEt |
| 4-$CF_3$ | 5-Br | H | S | Me | S | OEt | OEt |
| 4-$CF_3$ | 5-F | H | S | Me | S | OEt | OEt |
| 4-$CF_3$ | 4-Cl | H | S | Me | S | OEt | OEt |
| 4-$CF_3$ | 4-F | H | S | Me | S | OEt | OEt |
| 4-$CF_3$ | H | H | S | Me | S | OEt | OEt |
| 4-$CF_3$ | 5-Cl | $CO_2Me$ | S | Me | S | OEt | OEt |
| 4-$CF_3$ | 5-Br | $CO_2Me$ | S | Me | S | OEt | OEt |
| 4-$CF_3$ | 5-F | $CO_2Me$ | S | Me | S | OEt | OEt |
| 4-$CF_3$ | 4-Cl | $CO_2Me$ | S | Me | S | OEt | OEt |
| 4-$CF_3$ | 4-F | $CO_2Me$ | S | Me | S | OEt | OEt |
| 4-$CF_3$ | H | $CO_2Me$ | S | Me | S | OEt | OEt |
| 4-$CF_3$ | 5-Br | H | O | tBu | O | OEt | OEt |
| 4-Cl | 5-Br | H | O | tBu | O | OEt | OEt |
| 4-Br | 5-Br | H | O | tBu | O | OEt | OEt |
| 4-$OCF_3$ | 5-Br | H | O | tBu | O | OEt | OEt |
| 4-$CF_3$ | 5-Cl | H | O | tBu | O | OEt | OEt |
| 4-Cl | 5-Cl | H | O | tBu | O | OEt | OEt |
| 4-Br | 5-Cl | H | O | tBu | O | OEt | OEt |
| 4-$CF_3$ | 5-$CF_3$ | H | O | tBu | O | OEt | OEt |
| 4-$CF_3$ | 4-F | H | O | tBu | O | OEt | OEt |
| 4-$CF_3$ | H | H | O | tBu | O | OEt | OEt |
| 4-$CF_3$ | 5-Br | $CO_2Me$ | O | tBu | O | OEt | OEt |
| 4-$CF_3$ | 5-Cl | $CO_2Me$ | O | tBu | O | OEt | OEt |
| 4-$CF_3$ | 5-$CF_3$ | $CO_2Me$ | O | tBu | O | OEt | OEt |
| 4-$CF_3$ | 4-F | $CO_2Me$ | O | tBu | O | OEt | OEt |
| 4-$CF_3$ | H | $CO_2Me$ | O | tBu | O | OEt | OEt |
| 4-$CF_3$ | 5-Cl | H | S | tBu | O | OEt | OEt |
| 4-Cl | 5-Cl | H | S | tBu | O | OEt | OEt |
| 4-Br | 5-Cl | H | S | tBu | O | OEt | OEt |

TABLE 10-continued

| $R_1$ | $R_2$ | B | V | $R_8$ | Y' | $Y'R_{10}$ | $Y'R_{11}$ |
|---|---|---|---|---|---|---|---|
| 4-$CF_3$ | 5-Br | H | S | tBu | O | OEt | OEt |
| 4-$CF_3$ | 5-F | H | S | tBu | O | OEt | OEt |
| 4-$CF_3$ | 4-Cl | H | S | tBu | O | OEt | OEt |
| 4-$CF_3$ | 4-F | H | S | tBu | O | OEt | OEt |
| 4-$CF_3$ | H | H | S | tBu | O | OEt | OEt |
| 4-$CF_3$ | 5-Cl | $CO_2Me$ | S | tBu | O | OEt | OEt |
| 4-$CF_3$ | 5-Br | $CO_2Me$ | S | tBu | O | OEt | OEt |
| 4-$CF_3$ | 5-F | $CO_2Me$ | S | tBu | O | OEt | OEt |
| 4-$CF_3$ | 4-Cl | $CO_2Me$ | S | tBu | O | OEt | OEt |
| 4-$CF_3$ | 4-F | $CO_2Me$ | S | tBu | O | OEt | OEt |
| 4-$CF_3$ | H | $CO_2Me$ | S | tBu | O | OEt | OEt |
| 4-$CF_3$ | 5-Br | H | O | tBu | O | $-OCH_2C(Me)_2CH_2O-$ | |
| 4-Cl | 5-Br | H | O | tBu | O | $-OCH_2C(Me)_2CH_2O-$ | |
| 4-Br | 5-Br | H | O | tBu | O | $-OCH_2C(Me)_2CH_2O-$ | |
| 4-$OCF_3$ | 5-Br | H | O | tBu | O | $-OCH_2C(Me)_2CH_2O-$ | |
| 4-$CF_3$ | 5-Cl | H | O | tBu | O | $-OCH_2C(Me)_2CH_2O-$ | |
| 4-Cl | 5-Cl | H | O | tBu | O | $-OCH_2C(Me)_2CH_2O-$ | |
| 4-Br | 5-Cl | H | O | tBu | O | $-OCH_2C(Me)_2CH_2O-$ | |
| 4-$CF_3$ | 5-$CF_3$ | H | O | tBu | O | $-OCH2C(Me)_2CH_2O-$ | |
| 4-$CF_3$ | 4-F | H | O | tBu | O | $-OCH_2C(Me)_2CH_2O-$ | |
| 4-$CF_3$ | H | H | O | tBu | O | $-OCH_2C(Me)_2CH_2O-$ | |
| 4-$CF_3$ | 5-Br | $CO_2Me$ | O | tBu | O | $-OCH_2C(Me)_2CH_2O-$ | |
| 4-$CF_3$ | 5-Cl | $CO_2Me$ | O | tBu | O | $-OCH_2C(Me)_2CH_2O-$ | |
| 4-$CF_3$ | 5-$CF_3$ | $CO_2Me$ | O | tBu | O | $-OCH_2C(Me)_2CH_2O-$ | |
| 4-$CF_3$ | 4-F | $CO_2Me$ | O | tBu | O | $-OCH_2C(Me)_2CH_2O-$ | |
| 4-$CF_3$ | H | $CO_2Me$ | O | tBu | O | $-OCH_2C(Me)_2CH_2O-$ | |
| 4-$CF_3$ | 5-Cl | H | S | tBu | O | $-OCH_2C(Me)_2CH_2O-$ | |
| 4-Cl | 5-Cl | H | S | tBu | O | $-OCH_2C(Me)_2CH_2O-$ | |
| 4-Br | 5-Cl | H | S | tBu | O | $-OCH_2C(Me)_2CH_2O-$ | |
| 4-$CF_3$ | 5-Br | H | S | tBu | O | $-OCH_2C(Me)_2CH_2O-$ | |
| 4-$CF_3$ | 5-F | H | S | tBu | O | $-OCH_2C(Me)_2CH_2O-$ | |
| 4-$CF_3$ | 4-Cl | H | S | tBu | O | $-OCH_2C(Me)_2CH_2O-$ | |
| 4-$CF_3$ | 4-F | H | S | tBu | O | $-OCH_2C(Me)_2CH_2O-$ | |
| 4-$CF_3$ | H | H | S | tBu | O | $-OCH_2C(Me)_2CH_2O-$ | |
| 4-$CF_3$ | 5-Cl | $CO_2Me$ | S | tBu | O | $-OCH_2C(Me)_2CH_2O-$ | |
| 4-$CF_3$ | 5-Br | $CO_2Me$ | S | tBu | O | $-OCH_2C(Me)_2CH_2O-$ | |
| 4-$CF_3$ | 5-F | $CO_2Me$ | S | tBu | O | $-OCH_2C(Me)_2CH_2O-$ | |
| 4-$CF_3$ | 4-Cl | $CO_2Me$ | S | tBu | O | $-OCH_2C(Me)_2CH_2O-$ | |
| 4-$CF_3$ | 4-F | $CO_2Me$ | S | tBu | O | $-OCH_2C(Me)_2CH_2O-$ | |
| 4-$CF_3$ | H | $CO_2Me$ | S | tBu | O | $-OCH_2C(Me)_2CH_2O-$ | |

TABLE 11

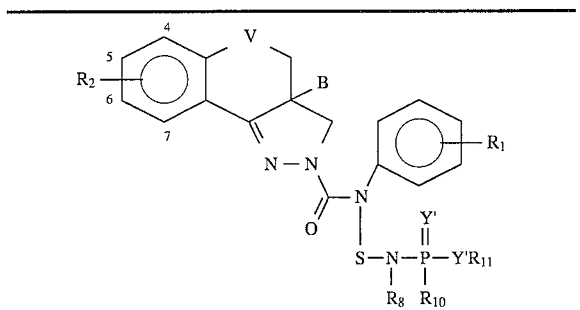

TABLE 11-continued

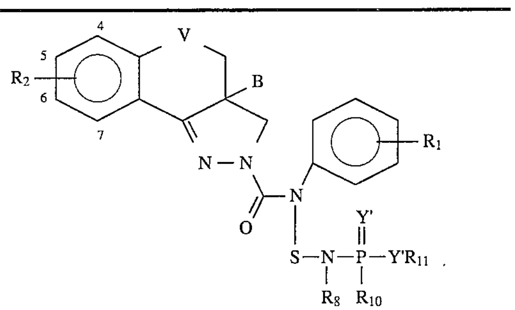

| $R_1$ | $R_2$ | B | V | $R_8$ | Y' | $R_{10}$ | $Y'R_{11}$ |
|---|---|---|---|---|---|---|---|
| 4-$CF_3$ | 5-Br | H | O | iPr | O | Et | OEt |
| 4-Cl | 5-Br | H | O | iPr | O | Et | OEt |
| 4-Br | 5-Br | H | O | iPr | O | Et | OEt |
| 4-$OCF_3$ | 5-Br | H | O | iPr | O | Et | OEt |
| 4-$CF_3$ | 5-Cl | H | O | iPr | O | Et | OEt |
| 4-Cl | 5-Cl | H | O | iPr | O | Et | OEt |
| 4-Br | 5-Cl | H | O | iPr | O | Et | OEt |
| 4-$CF_3$ | 5-$CF_3$ | H | O | iPr | O | Et | OEt |
| 4-$CF_3$ | 4-F | H | O | iPr | O | Et | OEt |
| 4-$CF_3$ | H | H | O | iPr | O | Et | OEt |
| 4-$CF_3$ | 5-Br | $CO_2Me$ | O | iPr | O | Et | OEt |
| 4-$CF_3$ | 5-Cl | $CO_2Me$ | O | iPr | O | Et | OEt |
| 4-$CF_3$ | 5-$CF_3$ | $CO_2Me$ | O | iPr | O | Et | OEt |
| 4-$CF_3$ | 4-F | $CO_2Me$ | O | iPr | O | Et | OEt |
| 4-$CF_3$ | H | $CO_2Me$ | O | iPr | O | Et | OEt |
| 4-$CF_3$ | 5-Cl | H | S | iPr | O | Et | OEt |
| 4-Cl | 5-Cl | H | S | iPr | O | Et | OEt |
| 4-Br | 5-Cl | H | S | iPr | O | Et | OEt |
| 4-$CF_3$ | 5-Br | H | S | iPr | O | Et | OEt |
| 4-$CF_3$ | 5-F | H | S | iPr | O | Et | OEt |
| 4-$CF_3$ | 4-Cl | H | S | iPr | O | Et | OEt |
| 4-$CF_3$ | 4-F | H | S | iPr | O | Et | OEt |
| 4-$CF_3$ | H | H | S | iPr | O | Et | OEt |
| 4-$CF_3$ | 5-Cl | $CO_2Me$ | S | iPr | O | Et | OEt |
| 4-$CF_3$ | 5-Br | $CO_2Me$ | S | iPr | O | Et | OEt |
| 4-$CF_3$ | 5-F | $CO_2Me$ | S | iPr | O | Et | OEt |
| 4-$CF_3$ | 4-Cl | $CO_2Me$ | S | iPr | O | Et | OEt |
| 4-$CF_3$ | 4-F | $CO_2Me$ | S | iPr | O | Et | OEt |
| 4-$CF_3$ | H | $CO_2Me$ | S | iPr | O | Et | OEt |
| 4-$CF_3$ | 5-Br | H | O | iPr | O | Et | O-iPr |
| 4-Cl | 5-Br | H | O | iPr | O | Et | O-iPr |
| 4-Br | 5-Br | H | O | iPr | O | Et | O-iPr |
| 4-$OCF_3$ | 5-Br | H | O | iPr | O | Et | O-iPr |
| 4-$CF_3$ | 5-Cl | H | O | iPr | O | Et | O-iPr |
| 4-Cl | 5-Cl | H | O | iPr | O | Et | O-iPr |
| 4-Br | 5-Cl | H | O | iPr | O | Et | O-iPr |
| 4-$CF_3$ | 5-$CF_3$ | H | O | iPr | O | Et | O-iPr |
| 4-$CF_3$ | 4-F | H | O | iPr | O | Et | O-iPr |
| 4-$CF_3$ | H | H | O | iPr | O | Et | O-iPr |
| 4-$CF_3$ | 5-Br | $CO_2Me$ | O | iPr | O | Et | O-iPr |
| 4-$CF_3$ | 5-Cl | $CO_2Me$ | O | iPr | O | Et | O-iPr |
| 4-$CF_3$ | 5-$CF_3$ | $CO_2Me$ | O | iPr | O | Et | O-iPr |
| 4-$CF_3$ | 4-F | $CO_2Me$ | O | iPr | O | Et | O-iPr |
| 4-$CF_3$ | H | $CO_2Me$ | O | iPr | O | Et | O-iPr |
| 4-$CF_3$ | 5-Cl | H | S | iPr | O | Et | O-iPr |
| 4-Cl | 5-Cl | H | S | iPr | O | Et | O-iPr |
| 4-Br | 5-Cl | H | S | iPr | O | Et | O-iPr |
| 4-$CF_3$ | 5-Br | H | S | iPr | O | Et | O-iPr |
| 4-$CF_3$ | 5-F | H | S | iPr | O | Et | O-iPr |
| 4-$CF_3$ | 4-Cl | H | S | iPr | O | Et | O-iPr |
| 4-$CF_3$ | 4-F | H | S | iPr | O | Et | O-iPr |
| 4-$CF_3$ | H | H | S | iPr | O | Et | O-iPr |
| 4-$CF_3$ | 5-Cl | $CO_2Me$ | S | iPr | O | Et | O-iPr |
| 4-$CF_3$ | 5-Br | $CO_2Me$ | S | iPr | O | Et | O-iPr |
| 4-$CF_3$ | 5-F | $CO_2Me$ | S | iPr | O | Et | O-iPr |
| 4-$CF_3$ | 4-Cl | $CO_2Me$ | S | iPr | O | Et | O-iPr |
| 4-$CF_3$ | 4-F | $CO_2Me$ | S | iPr | O | Et | O-iPr |
| 4-$CF_3$ | H | $CO_2Me$ | S | iPr | O | Et | O-iPr |
| 4-$CF_3$ | 5-Br | H | O | iPr | O | Et | OPh |
| 4-Cl | 5-Br | H | O | iPr | O | Et | OPh |
| 4-Br | 5-Br | H | O | iPr | O | Et | OPh |
| 4-$OCF_3$ | 5-Br | H | O | iPr | O | Et | OPh |
| 4-$CF_3$ | 5-Cl | H | O | iPr | O | Et | OPh |
| 4-Cl | 5-Cl | H | O | iPr | O | Et | OPh |
| 4-Br | 5-Cl | H | O | iPr | O | Et | OPh |
| 4-$CF_3$ | 5-$CF_3$ | H | O | iPr | O | Et | OPh |
| 4-$CF_3$ | 4-F | H | O | iPr | O | Et | OPh |
| 4-$CF_3$ | H | H | O | iPr | O | Et | OPh |
| 4-$CF_3$ | 5-Br | $CO_2Me$ | O | iPr | O | Et | OPh |
| 4-$CF_3$ | 5-Cl | $CO_2Me$ | O | iPr | O | Et | OPh |
| 4-$CF_3$ | 5-$CF_3$ | $CO_2Me$ | O | iPr | O | Et | OPh |
| 4-$CF_3$ | 4-F | $CO_2Me$ | O | iPr | O | Et | OPh |
| 4-$CF_3$ | H | $CO_2Me$ | O | iPr | O | Et | OPh |
| 4-$CF_3$ | 5-Cl | H | S | iPr | O | Et | OPh |
| 4-Cl | 5-Cl | H | S | iPr | O | Et | OPh |
| 4-Br | 5-Cl | H | S | iPr | O | Et | OPh |
| 4-$CF_3$ | 5-Br | H | S | iPr | O | Et | OPh |
| 4-$CF_3$ | 5-F | H | S | iPr | O | Et | OPh |
| 4-$CF_3$ | 4-Cl | H | S | iPr | O | Et | OPh |
| 4-$CF_3$ | 4-F | H | S | iPr | O | Et | Oph |
| 4-$CF_3$ | H | H | S | iPr | O | Et | OPh |
| 4-$CF_3$ | 5-Cl | $CO_2Me$ | S | iPr | O | Et | OPh |
| 4-$CF_3$ | 5-Br | $CO_2Me$ | S | iPr | O | Et | OPh |
| 4-$CF_3$ | 5-F | $CO_2Me$ | S | iPr | O | Et | OPh |
| 4-$CF_3$ | 4-Cl | $CO_2Me$ | S | iPr | O | Et | OPh |
| 4-$CF_3$ | 4-F | $CO_2Me$ | S | iPr | O | Et | OPh |
| 4-$CF_3$ | H | $CO_2Me$ | S | iPr | O | Et | OPh |
| 4-$CF_3$ | 5-Br | H | O | iPr | O | Ph | OEt |
| 4-Cl | 5-Br | H | O | iPr | O | Ph | OEt |
| 4-Br | 5-Br | H | O | iPr | O | Ph | OEt |
| 4-$OCF_3$ | 5-Br | H | O | iPr | O | Ph | OEt |
| 4-$CF_3$ | 5-Cl | H | O | iPr | O | Ph | OEt |
| 4-Cl | 5-Cl | H | O | iPr | O | Ph | OEt |
| 4-Br | 5-Cl | H | O | iPr | O | Ph | OEt |
| 4-$CF_3$ | 5-$CF_3$ | H | O | iPr | O | Ph | OEt |
| 4-$CF_3$ | 4-F | H | O | iPr | O | Ph | OEt |
| 4-$CF_3$ | H | H | O | iPr | O | Ph | OEt |
| 4-$CF_3$ | 5-Br | $CO_2Me$ | O | iPr | O | Ph | OEt |
| 4-$CF_3$ | 5-Cl | $CO_2Me$ | O | iPr | O | Ph | OEt |
| 4-$CF_3$ | 5-$CF_3$ | $CO_2Me$ | O | iPr | O | Ph | OEt |
| 4-$CF_3$ | 4-F | $CO_2Me$ | O | iPr | O | Ph | OEt |
| 4-$CF_3$ | H | $CO_2Me$ | O | iPr | O | Ph | OEt |
| 4-$CF_3$ | 5-Cl | H | S | iPr | O | Ph | OEt |
| 4-Cl | 5-Cl | H | S | iPr | O | Ph | OEt |
| 4-Br | 5-Cl | H | S | iPr | O | Ph | OEt |
| 4-$CF_3$ | 5-Br | H | S | iPr | O | Ph | OEt |
| 4-$CF_3$ | 5-F | H | S | iPr | O | Ph | OEt |
| 4-$CF_3$ | 4-Cl | H | S | iPr | O | Ph | OEt |
| 4-$CF_3$ | 4-F | H | S | iPr | O | Ph | OEt |
| 4-$CF_3$ | H | H | S | iPr | O | Ph | OEt |
| 4-$CF_3$ | 5-Cl | $CO_2Me$ | S | iPr | O | Ph | OEt |
| 4-$CF_3$ | 5-Br | $CO_2Me$ | S | iPr | O | Ph | OEt |
| 4-$CF_3$ | 5-F | $CO_2Me$ | S | iPr | O | Ph | OEt |
| 4-$CF_3$ | 4-Cl | $CO_2Me$ | S | iPr | O | Ph | OEt |
| 4-$CF_3$ | 4-F | $CO_2Me$ | S | iPr | O | Ph | OEt |
| 4-$CF_3$ | H | $CO_2Me$ | S | iPr | O | Ph | OEt |
| 4-$CF_3$ | 5-Br | H | O | tBu | O | Et | OEt |
| 4-Cl | 5-Br | H | O | tBu | O | Et | OEt |
| 4-Br | 5-Br | H | O | tBu | O | Et | OEt |
| 4-$OCF_3$ | 5-Br | H | O | tBu | O | Et | OEt |
| 4-$CF_3$ | 5-Cl | H | O | tBu | O | Et | OEt |
| 4-Cl | 5-Cl | H | O | tBu | O | Et | OEt |
| 4-Br | 5-Cl | H | O | tBu | O | Et | OEt |
| 4-$CF_3$ | 5-$CF_3$ | H | O | tBu | O | Et | OEt |
| 4-$CF_3$ | 4-F | H | O | tBu | O | Et | OEt |
| 4-$CF_3$ | H | H | O | tBu | O | Et | OEt |

TABLE 11-continued

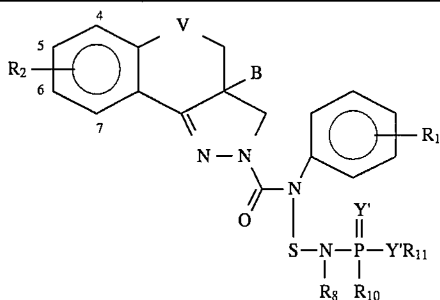

| $R_1$ | $R_2$ | B | V | $R_8$ | Y' | $R_{10}$ | Y'$R_{11}$ |
|---|---|---|---|---|---|---|---|
| 4-$CF_3$ | 5-Br | $CO_2Me$ | O | tBu | O | Et | OEt |
| 4-$CF_3$ | 5-Cl | $CO_2Me$ | O | tBu | O | Et | OEt |
| 4-$CF_3$ | 5-$CF_3$ | $CO_2Me$ | O | tBu | O | Et | OEt |
| 4-$CF_3$ | 4-F | $CO_2Me$ | O | tBu | O | Et | OEt |
| 4-$CF_3$ | H | $CO_2Me$ | O | tBu | O | Et | OEt |
| 4-$CF_3$ | 5-Cl | H | S | tBu | O | Et | OEt |
| 4-Cl | 5-Cl | H | S | tBu | O | Et | OEt |
| 4-Br | 5-Cl | H | S | tBu | O | Et | OEt |
| 4-$CF_3$ | 5-Br | H | S | tBu | O | Et | OEt |
| 4-$CF_3$ | 5-F | H | S | tBu | O | Et | OEt |
| 4-$CF_3$ | 4-Cl | H | S | tBu | O | Et | OEt |
| 4-$CF_3$ | 4-F | H | S | tBu | O | Et | OEt |
| 4-$CF_3$ | H | H | S | tBu | O | Et | OEt |
| 4-$CF_3$ | 5-Cl | $CO_2Me$ | S | tBu | O | Et | OEt |
| 4-$CF_3$ | 5-Br | $CO_2Me$ | S | tBu | O | Et | OEt |
| 4-$CF_3$ | 5-F | $CO_2Me$ | S | tBu | O | Et | OEt |
| 4-$CF_3$ | 4-Cl | $CO_2Me$ | S | tBu | O | Et | OEt |
| 4-$CF_3$ | 4-F | $CO_2Me$ | S | tBu | O | Et | OEt |
| 4-$CF_3$ | H | $CO_2Me$ | S | tBu | O | Et | OEt |
| 4-Cl | 5-Br | H | O | iPr | S | Et | O-iPr |
| 4-Br | 5-Br | H | O | iPr | S | Et | OPh |
| 4-$OCF_3$ | 5-Br | H | O | iPr | S | Ph | OEt |
| 4-$CF_3$ | 5-Cl | H | O | iPr | S | Ph | O-iPr |
| 4-Cl | 5-Cl | H | O | iPr | S | Ph | OPh |
| 4-Br | 5-Cl | H | O | tBu | S | Et | OEt |
| 4-$CF_3$ | 5-$CF_3$ | H | O | tBu | S | Et | O-iPr |
| 4-$CF_3$ | 4-F | H | O | tBu | S | Et | OPh |
| 4-$CF_3$ | H | H | O | tBu | S | Ph | OEt |
| 4-$CF_3$ | 5-Br | $CO_2Me$ | O | tBu | S | Ph | O-iPr |
| 4-$CF_3$ | 5-Cl | $CO_2Me$ | O | tBu | S | Ph | OPh |
| 4-$CF_3$ | 5-Br | H | S | iPr | S | iPr | OEt |
| 4-$CF_3$ | 5-F | H | S | iPr | S | iPr | O-iPr |
| 4-$CF_3$ | 4-Cl | H | S | iPr | S | iPr | OPh |
| 4-$CF_3$ | 4-F | H | S | iPr | S | nPr | OEt |
| 4-$CF_3$ | H | H | S | iPr | S | nPr | O-iPr |
| 4-$CF_3$ | 5-Cl | $CO_2Me$ | S | iPr | S | nPr | OPh |
| 4-$CF_3$ | 5-Br | $CO_2Me$ | S | tBu | S | Me | OEt |
| 4-$CF_3$ | 5-F | $CO_2Me$ | S | tBu | S | Me | O-iPr |
| 4-$CF_3$ | 4-Cl | $CO_2Me$ | S | tBu | S | Me | OPh |
| 4-$CF_3$ | 4-F | $CO_2Me$ | S | tBu | S | Me | O-sec-Bu |
| 4-$CF_3$ | H | $CO_2Me$ | S | tBu | S | Me | O-nPr |

TABLE 12

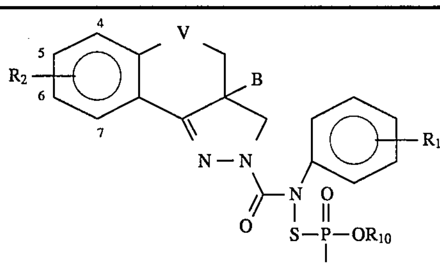

| $R_1$ | $R_2$ | B | V | $R_{10}$ | $R_{11}$ |
|---|---|---|---|---|---|
| 4-$CF_3$ | 5-Br | H | O | Et | Et |
| 4-Cl | 5-Br | H | O | Et | Et |

TABLE 12-continued

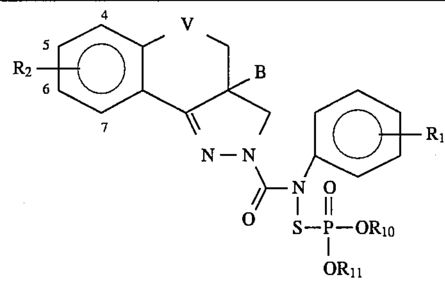

| $R_1$ | $R_2$ | B | V | $R_{10}$ | $R_{11}$ |
|---|---|---|---|---|---|
| 4-Br | 5-Br | H | O | Et | Et |
| 4-$OCF_3$ | 5-Br | H | O | Et | Et |
| 4-$CF_3$ | 5-Cl | H | O | Et | Et |
| 4-Cl | 5-Cl | H | O | Et | Et |
| 4-Br | 5-Cl | H | O | Et | Et |
| 4-$CF_3$ | 5-$CF_3$ | H | O | Et | Et |
| 4-$CF_3$ | 4-F | H | O | Et | Et |
| 4-$CF_3$ | H | H | O | Et | Et |
| 4-$CF_3$ | 5-Br | $CO_2Me$ | O | Et | Et |
| 4-$CF_3$ | 5-Cl | $CO_2Me$ | O | Et | Et |
| 4-$CF_3$ | 5-$CF_3$ | $CO_2Me$ | O | Et | Et |
| 4-$CF_3$ | 4-F | $CO_2Me$ | O | Et | Et |
| 4-$CF_3$ | H | $CO_2Me$ | O | Et | Et |
| 4-$CF_3$ | 5-Cl | H | S | Et | Et |
| 4-Cl | 5-Cl | H | S | Et | Et |
| 4-Br | 5-Cl | H | S | Et | Et |
| 4-$CF_3$ | 5-Br | H | S | Et | Et |
| 4-$CF_3$ | 5-F | H | S | Et | Et |
| 4-$CF_3$ | 4-Cl | H | S | Et | Et |
| 4-$CF_3$ | 4-F | H | S | Et | Et |
| 4-$CF_3$ | H | H | S | Et | Et |
| 4-$CF_3$ | 5-Cl | $CO_2Me$ | S | Et | Et |
| 4-$CF_3$ | 5-Br | $CO_2Me$ | S | Et | Et |
| 4-$CF_3$ | 5-F | $CO_2Me$ | S | Et | Et |
| 4-$CF_3$ | 4-Cl | $CO_2Me$ | S | Et | Et |
| 4-$CF_3$ | 4-F | $CO_2Me$ | S | Et | Et |
| 4-$CF_3$ | H | $CO_2Me$ | S | Et | Et |

TABLE 13

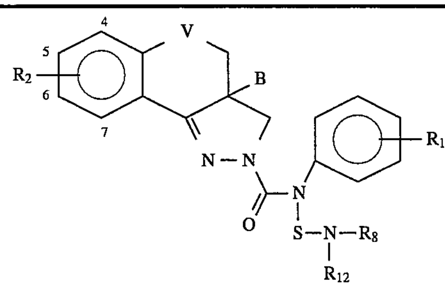

| $R_1$ | $R_2$ | B | V | $R_8$ | $R_{12}$ |
|---|---|---|---|---|---|
| 4-$CF_3$ | 5-Br | H | O | nBu | nBu |
| 4-Cl | 5-Br | H | O | nBu | nBu |
| 4-Br | 5-Br | H | O | nBu | nBu |
| 4-$OCF_3$ | 5-Br | H | O | nBu | nBu |
| 4-$CF_3$ | 5-Cl | H | O | nBu | nBu |
| 4-Cl | 5-Cl | H | O | nBu | nBu |
| 4-Br | 5-Cl | H | O | nBu | nBu |
| 4-$CF_3$ | 5-$CF_3$ | H | O | nBu | nBu |
| 4-$CF_3$ | 4-F | H | O | nBu | nBu |
| 4-$CF_3$ | H | H | O | nBu | nBu |
| 4-$CF_3$ | 5-Br | $CO_2Me$ | O | nBu | nBu |
| 4-$CF_3$ | 5-Cl | $CO_2Me$ | O | nBu | nBu |
| 4-$CF_3$ | 5-$CF_3$ | $CO_2Me$ | O | nBu | nBu |
| 4-$CF_3$ | 4-F | $CO_2Me$ | O | nBu | nBu |
| 4-$CF_3$ | H | $CO_2Me$ | O | nBu | nBu |
| 4-$CF_3$ | 5-Cl | H | S | nBu | nBu |
| 4-Cl | 5-Cl | H | S | nBu | nBu |

TABLE 13-continued

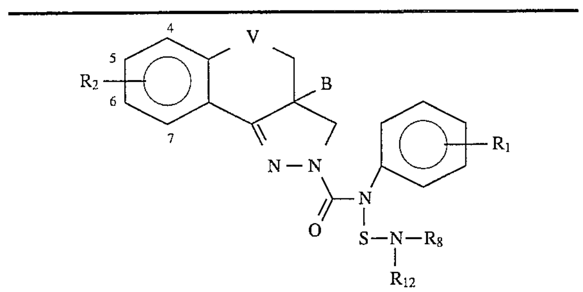

| $R_1$ | $R_2$ | B | V | $R_8$ | $R_{12}$ |
|---|---|---|---|---|---|
| 4-Br | 5-Cl | H | S | nBu | nBu |
| 4-$CF_3$ | 5-Br | H | S | nBu | nBu |
| 4-$CF_3$ | 5-F | H | S | nBu | nBu |
| 4-$CF_3$ | 4-Cl | H | S | nBu | nBu |
| 4-$CF_3$ | 4-F | H | S | nBu | nBu |
| 4-$CF_3$ | H | H | S | nBu | nBu |
| 4-$CF_3$ | 5-Cl | $CO_2Me$ | S | nBu | nBu |
| 4-$CF_3$ | 5-Br | $CO_2Me$ | S | nBu | nBu |
| 4-$CF_3$ | 5-F | $CO_2Me$ | S | nBu | nBu |
| 4-$CF_3$ | 4-Cl | $CO_2Me$ | S | nBu | nBu |
| 4-$CF_3$ | 4-F | $CO_2Me$ | S | nBu | nBu |
| 4-$CF_3$ | H | $CO_2Me$ | S | nBu | nBu |
| 4-$CF_3$ | 5-Br | H | O | $-CH_2CH_2CH_2CH_2CH_2-$ | |
| 4-Cl | 5-Br | H | O | $-CH_2CH_2CH_2CH_2CH_2-$ | |
| 4-Br | 5-Br | H | O | $-CH_2CH_2CH_2CH_2CH_2-$ | |
| 4-$OCF_3$ | 5-Br | H | O | $-CH_2CH_2CH_2CH_2CH_2-$ | |
| 4-$CF_3$ | 5-Cl | H | O | $-CH_2CH_2CH_2CH_2CH_2-$ | |
| 4-Cl | 5-Cl | H | O | $-CH_2CH_2CH_2CH_2CH_2-$ | |
| 4-Br | 5-Cl | H | O | $-CH_2CH_2CH_2CH_2CH_2-$ | |
| 4-$CF_3$ | 5-$CF_3$ | H | O | $-CH_2CH_2CH_2CH_2CH_2-$ | |
| 4-$CF_3$ | 4-F | H | O | $-CH_2CH_2CH_2CH_2CH_2-$ | |
| 4-$CF_3$ | H | H | O | $-CH_2CH_2CH_2CH_2CH_2-$ | |
| 4-$CF_3$ | 5-Br | $CO_2Me$ | O | $-CH_2CH_2CH_2CH_2CH_2-$ | |
| 4-$CF_3$ | 5-Cl | $CO_2Me$ | O | $-CH_2CH_2CH_2CH_2CH_2-$ | |
| 4-$CF_3$ | 5-$CF_3$ | $CO_2Me$ | O | $-CH_2CH_2CH_2CH_2CH_2-$ | |
| 4-$CF_3$ | 4-F | $CO_2Me$ | O | $-CH_2CH_2CH_2CH_2CH_2-$ | |
| 4-$CF_3$ | H | $CO_2Me$ | O | $-CH_2CH_2CH_2CH_2CH_2-$ | |
| 4-$CF_3$ | 5-Cl | H | S | $-CH_2CH_2CH_2CH_2CH_2-$ | |
| 4-Cl | 5-Cl | H | S | $-CH_2CH_2CH_2CH_2CH_2-$ | |
| 4-Br | 5-Cl | H | S | $-CH_2CH_2CH_2CH_2CH_2-$ | |
| 4-$CF_3$ | 5-Br | H | S | $-CH_2CH_2CH_2CH_2CH_2-$ | |
| 4-$CF_3$ | 5-F | H | S | $-CH_2CH_2CH_2CH_2CH_2-$ | |
| 4-$CF_3$ | 4-Cl | H | S | $-CH_2CH_2CH_2CH_2CH_2-$ | |
| 4-$CF_3$ | 4-F | H | S | $-CH_2CH_2CH_2CH_2CH_2-$ | |
| 4-$CF_3$ | H | H | S | $-CH_2CH_2CH_2CH_2CH_2-$ | |
| 4-$CF_3$ | 5-Cl | $CO_2Me$ | S | $-CH_2CH_2CH_2CH_2CH_2-$ | |
| 4-$CF_3$ | 5-Br | $CO_2Me$ | S | $-CH_2CH_2CH_2CH_2CH_2-$ | |
| 4-$CF_3$ | 5-F | $CO_2Me$ | S | $-CH_2CH_2CH_2CH_2CH_2-$ | |
| 4-$CF_3$ | 4-Cl | $CO_2Me$ | S | $-CH_2CH_2CH_2CH_2CH_2-$ | |
| 4-$CF_3$ | 4-F | $CO_2Me$ | S | $-CH_2CH_2CH_2CH_2CH_2-$ | |
| 4-$CF_3$ | H | $CO_2Me$ | S | $-CH_2CH_2CH_2CH_2CH_2-$ | |
| 4-$CF_3$ | 5-Br | H | O | $-CH_2CH_2OCH_2CH_2-$ | |
| 4-Cl | 5-Br | H | O | $-CH_2CH_2OCH_2CH_2-$ | |
| 4-Br | 5-Br | H | O | $-CH_2CH_2OCH_2CH_2-$ | |
| 4-$OCF_3$ | 5-Br | H | O | $-CH_2CH_2OCH_2CH_2-$ | |
| 4-$CF_3$ | 5-Cl | H | O | $-CH_2CH_2OCH_2CH_2-$ | |
| 4-Cl | 5-Cl | H | O | $-CH_2CH_2OCH_2CH_2-$ | |
| 4-Br | 5-Cl | H | O | $-CH_2CH_2OCH_2CH_2-$ | |
| 4-$CF_3$ | 5-$CF_3$ | H | O | $-CH_2CH_2OCH_2CH_2-$ | |
| 4-$CF_3$ | 4-F | H | O | $-CH_2CH_2OCH_2CH_2-$ | |
| 4-$CF_3$ | H | H | O | $-CH_2CH_2OCH_2CH_2-$ | |
| 4-$CF_3$ | 5-Br | $CO_2Me$ | O | $-CH_2CH_2OCH_2CH_2-$ | |
| 4-$CF_3$ | 5-Cl | $CO_2Me$ | O | $-CH_2CH_2OCH_2CH_2-$ | |
| 4-$CF_3$ | 5-$CF_3$ | $CO_2Me$ | O | $-CH_2CH_2OCH_2CH_2-$ | |
| 4-$CF_3$ | 4-F | $CO_2Me$ | O | $-CH_2CH_2OCH_2CH_2-$ | |
| 4-$CF_3$ | H | $CO_2Me$ | O | $-CH_2CH_2OCH_2CH_2-$ | |
| 4-$CF_3$ | 5-Cl | H | S | $-CH_2CH_2OCH_2CH_2-$ | |
| 4-Cl | 5-Cl | H | S | $-CH_2CH_2OCH_2CH_2-$ | |
| 4-Br | 5-Cl | H | S | $-CH_2CH_2OCH_2CH_2-$ | |
| 4-$CF_3$ | 5-Br | H | S | $-CH_2CH_2OCH_2CH_2-$ | |
| 4-$CF_3$ | 5-F | H | S | $-CH_2CH_2OCH_2CH_2-$ | |
| 4-$CF_3$ | 4-Cl | H | S | $-CH_2CH_2OCH_2CH_2-$ | |
| 4-$CF_3$ | 4-F | H | S | $-CH_2CH_2OCH_2CH_2-$ | |
| 4-$CF_3$ | H | H | S | $-CH_2CH_2OCH_2CH_2-$ | |

TABLE 13-continued

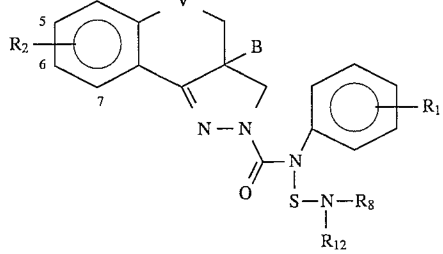

| $R_1$ | $R_2$ | B | V | $R_8$ | $R_{12}$ |
|---|---|---|---|---|---|
| 4-$CF_3$ | 5-Cl | $CO_2Me$ | S | $-CH_2CH_2OCH_2CH_2-$ | |
| 4-$CF_3$ | 5-Br | $CO_2Me$ | S | $-CH_2CH_2OCH_2CH_2-$ | |
| 4-$CF_3$ | 5-F | $CO_2Me$ | S | $-CH_2CH_2OCH_2CH_2-$ | |
| 4-$CF_3$ | 4-Cl | $CO_2Me$ | S | $-CH_2CH_2OCH_2CH_2-$ | |
| 4-$CF_3$ | 4-F | $CO_2Me$ | S | $-CH_2CH_2OCH_2CH_2-$ | |
| 4-$CF_3$ | H | $CO_2Me$ | S | $-CH_2CH_2OCH_2CH_2-$ | |
| 4-$CF_3$ | 5-Br | H | O | $-CH_2CHMeOCHMeCH_2-$ | |
| 4-Cl | 5-Br | H | O | $-CH_2CHMeOCHMeCH_2-$ | |
| 4-Br | 5-Br | H | O | $-CH_2CHMeOCHMeCH_2-$ | |
| 4-$OCF_3$ | 5-Br | H | O | $-CH_2CHMeOCHMeCH_2-$ | |
| 4-$CF_3$ | 5-Cl | H | O | $-CH_2CHMeOCHMeCH_2-$ | |
| 4-Cl | 5-Cl | H | O | $-CH_2CHMeOCHMeCH_2-$ | |
| 4-Br | 5-Cl | H | O | $-CH_2CHMeOCHMeCH_2-$ | |
| 4-$CF_3$ | 5-$CF_3$ | H | O | $-CH_2CHMeOCHMeCH_2-$ | |
| 4-$CF_3$ | 4-F | H | O | $-CH_2CHMeOCHMeCH_2-$ | |
| 4-$CF_3$ | H | H | O | $-CH_2CHMeOCHMeCH_2-$ | |
| 4-$CF_3$ | 5-Br | $CO_2Me$ | O | $-CH_2CHMeOCHMeCH_2-$ | |
| 4-$CF_3$ | 5-Cl | $CO_2Me$ | O | $-CH_2CHMeOCHMeCH_2-$ | |
| 4-$CF_3$ | 5-$CF_3$ | $CO_2Me$ | O | $-CH_2CHMeOCHMeCH_2-$ | |
| 4-$CF_3$ | 4-F | $CO_2Me$ | O | $-CH_2CHMeOCHMeCH_2-$ | |
| 4-$CF_3$ | H | $CO_2Me$ | O | $-CH_2CHMeOCHMeCH_2-$ | |
| 4-$CF_3$ | 5-Cl | H | S | $-CH_2CHMeOCHMeCH_2-$ | |
| 4-Cl | 5-Cl | H | S | $-CH_2CHMeOCHMeCH_2-$ | |
| 4-Br | 5-Cl | H | S | $-CH_2CHMeOCHMeCH_2-$ | |
| 4-$CF_3$ | 5-Br | H | S | $-CH_2CHMeOCHMeCH_2-$ | |
| 4-$CF_3$ | 5-F | H | S | $-CH_2CHMeOCHMeCH_2-$ | |
| 4-$CF_3$ | 4-Cl | H | S | $-CH_2CHMeOCHMeCH_2-$ | |
| 4-$CF_3$ | 4-F | H | S | $-CH_2CHMeOCHMeCH_2-$ | |
| 4-$CF_3$ | H | H | S | $-CH_2CHMeOCHMeCH_2-$ | |
| 4-$CF_3$ | 5-Cl | $CO_2Me$ | S | $-CH_2CHMeOCHMeCH_2-$ | |
| 4-$CF_3$ | 5-Br | $CO_2Me$ | S | $-CH_2CHMeOCHMeCH_2-$ | |
| 4-$CF_3$ | 5-F | $CO_2Me$ | S | $-CH_2CHMeOCHMeCH_2-$ | |
| 4-$CF_3$ | 4-Cl | $CO_2Me$ | S | $-CH_2CHMeOCHMeCH_2-$ | |
| 4-$CF_3$ | 4-F | $CO_2Me$ | S | $-CH_2CHMeOCHMeCH_2-$ | |
| 4-$CF_3$ | H | $CO_2Me$ | S | $-CH_2CHMeOCHMeCH_2-$ | |
| 4-$CF_3$ | 5-Br | H | O | Et | cyclo-$C_6H_{11}$ |
| 4-Cl | 5-Br | H | O | Et | cyclo-$C_6H_{11}$ |
| 4-Br | 5-Br | H | O | Et | cyclo-$C_6H_{11}$ |
| 4-$OCF_3$ | 5-Br | H | O | Et | cyclo-$C_6H_{11}$ |
| 4-$CF_3$ | 5-Cl | H | O | Et | cyclo-$C_6H_{11}$ |
| 4-Cl | 5-Cl | H | O | Et | cyclo-$C_6H_{11}$ |
| 4-Br | 5-Cl | H | O | Et | cyclo-$C_6H_{11}$ |
| 4-$CF_3$ | 5-$CF_3$ | H | O | Et | cyclo-$C_6H_{11}$ |
| 4-$CF_3$ | 4-F | H | O | Et | cyclo-$C_6H_{11}$ |
| 4-$CF_3$ | H | H | O | Et | cyclo-$C_6H_{11}$ |
| 4-$CF_3$ | 5-Br | $CO_2Me$ | O | Et | cyclo-$C_6H_{11}$ |
| 4-$CF_3$ | 5-Cl | $CO_2Me$ | O | Et | cyclo-$C_6H_{11}$ |
| 4-$CF_3$ | 5-$CF_3$ | $CO_2Me$ | O | Et | cyclo-$C_6H_{11}$ |
| 4-$CF_3$ | 4-F | $CO_2Me$ | O | Et | cyclo-$C_6H_{11}$ |
| 4-$CF_3$ | H | $CO_2Me$ | O | Et | cyclo-$C_6H_{11}$ |
| 4-$CF_3$ | 5-Cl | H | S | Et | cyclo-$C_6H_{11}$ |
| 4-Cl | 5-Cl | H | S | Et | cyclo-$C_6H_{11}$ |
| 4-Br | 5-Cl | H | S | Et | cyclo-$C_6H_{11}$ |
| 4-$CF_3$ | 5-Br | H | S | Et | cyclo-$C_6H_{11}$ |
| 4-$CF_3$ | 5-F | H | S | Et | cyclo-$C_6H_{11}$ |
| 4-$CF_3$ | 4-Cl | H | S | Et | cyclo-$C_6H_{11}$ |
| 4-$CF_3$ | 4-F | H | S | Et | cyclo-$C_6H_{11}$ |
| 4-$CF_3$ | H | H | S | Et | cyclo-$C_6H_{11}$ |
| 4-$CF_3$ | 5-Cl | $CO_2Me$ | S | Et | cyclo-$C_6H_{11}$ |
| 4-$CF_3$ | 5-Br | $CO_2Me$ | S | Et | cyclo-$C_6H_{11}$ |
| 4-$CF_3$ | 5-F | $CO_2Me$ | S | Et | cyclo-$C_6H_{11}$ |
| 4-$CF_3$ | 4-Cl | $CO_2Me$ | S | Et | cyclo-$C_6H_{11}$ |
| 4-$CF_3$ | 4-F | $CO_2Me$ | S | Et | cyclo-$C_6H_{11}$ |
| 4-$CF_3$ | H | $CO_2Me$ | S | Et | cyclo-$C_6H_{11}$ |

TABLE 13-continued

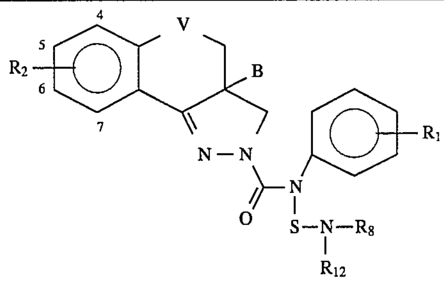

| $R_1$ | $R_2$ | B | V | $R_8$ | $R_{12}$ |
|---|---|---|---|---|---|
| 4-$CF_3$ | 5-Br | H | O | iPr | $CH_2CH_2CO_2Et$ |
| 4-Cl | 5-Br | H | O | iPr | $CH_2CH_2CO_2Et$ |
| 4-Br | 5-Br | H | O | iPr | $CH_2CH_2CO_2Et$ |
| 4-$OCF_3$ | 5-Br | H | O | iPr | $CH_2CH_2CO_2Et$ |
| 4-$CF_3$ | 5-Cl | H | O | iPr | $CH_2CH_2CO_2Et$ |
| 4-Cl | 5-Cl | H | O | iPr | $CH_2CH_2CO_2Et$ |
| 4-Br | 5-Cl | H | O | iPr | $CH_2CH_2CO_2Et$ |
| 4-$CF_3$ | 5-$CF_3$ | H | O | iPr | $CH_2CH_2CO_2Et$ |
| 4-$CF_3$ | 4-F | H | O | iPr | $CH_2CH_2CO_2Et$ |
| 4-$CF_3$ | H | H | O | iPr | $CH_2CH_2CO_2Et$ |
| 4-$CF_3$ | 5-Br | $CO_2Me$ | O | iPr | $CH_2CH_2CO_2Et$ |
| 4-$CF_3$ | 5-Cl | $CO_2Me$ | O | iPr | $CH_2CH_2CO_2Et$ |
| 4-$CF_3$ | 5-$CF_3$ | $CO_2Me$ | O | iPr | $CH_2CH_2CO_2Et$ |
| 4-$CF_3$ | 4-F | $CO_2Me$ | O | iPr | $CH_2CH_2CO_2Et$ |
| 4-$CF_3$ | H | $CO_2Me$ | O | iPr | $CH_2CH_2CO_2Et$ |
| 4-$CF_3$ | 5-Cl | H | S | iPr | $CH_2CH_2CO_2Et$ |
| 4-Cl | 5-Cl | H | S | iPr | $CH_2CH_2CO_2Et$ |
| 4-Br | 5-Cl | H | S | iPr | $CH_2CH_2CO_2Et$ |
| 4-$CF_3$ | 5-Br | H | S | iPr | $CH_2CH_2CO_2Et$ |
| 4-$CF_3$ | 5-F | H | S | iPr | $CH_2CH_2CO_2Et$ |
| 4-$CF_3$ | 4-Cl | H | S | iPr | $CH_2CH_2CO_2Et$ |
| 4-$CF_3$ | 4-F | H | S | iPr | $CH_2CH_2CO_2Et$ |
| 4-$CF_3$ | H | H | S | iPr | $CH_2CH_2CO_2Et$ |
| 4-$CF_3$ | 5-Cl | $CO_2Me$ | S | iPr | $CH_2CH_2CO_2Et$ |
| 4-$CF_3$ | 5-Br | $CO_2Me$ | S | iPr | $CH_2CH_2CO_2Et$ |
| 4-$CF_3$ | 5-F | CO Me | S | iPr | $CH_2CH_2CO_2Et$ |
| 4-$CF_3$ | 4-Cl | $CO_2Me$ | S | iPr | $CH_2CH_2CO_2Et$ |
| 4-$CF_3$ | 4-F | $CO_2Me$ | S | iPr | $CH_2CH_2CO_2Et$ |
| 4-$CF_3$ | H | $CO_2Me$ | S | iPr | $CH_2CH_2CO_2Et$ |

TABLE 14

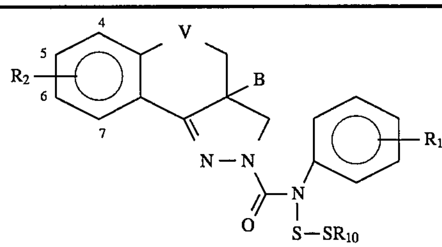

| $R_1$ | $R_2$ | B | V | $R_{10}$ |
|---|---|---|---|---|
| 4-$CF_3$ | 5-Br | H | O | tBu |
| 4-Cl | 5-Br | H | O | tBu |
| 4-Br | 5-Br | H | O | tBu |
| 4-$OCF_3$ | 5-Br | H | O | tBu |
| 4-$CF_3$ | 5-Cl | H | O | tBu |
| 4-Cl | 5-Cl | H | O | tBu |
| 4-Br | 5-Cl | H | O | tBu |
| 4-$CF_3$ | 5-$CF_3$ | H | O | tBu |
| 4-$CF_3$ | 4-F | H | O | tBu |
| 4-$CF_3$ | H | H | O | tBu |
| 4-$CF_3$ | 5-Br | $CO_2Me$ | O | tBu |
| 4-$CF_3$ | 5-Cl | $CO_2Me$ | O | tBu |
| 4-$CF_3$ | 5-$CF_3$ | $CO_2Me$ | O | tBu |
| 4-$CF_3$ | 4-F | $CO_2Me$ | O | tBu |
| 4-$CF_3$ | H | $CO_2Me$ | O | tBu |
| 4-$CF_3$ | 5-Cl | H | S | tBu |

TABLE 14-continued

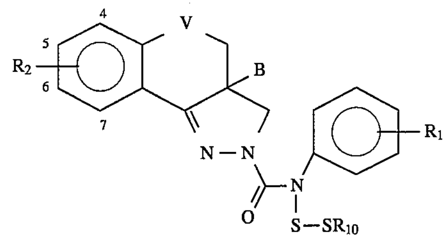

| $R_1$ | $R_2$ | B | V | $R_{10}$ |
|---|---|---|---|---|
| 4-Cl | 5-Cl | H | S | tBu |
| 4-Br | 5-Cl | H | S | tBu |
| 4-$CF_3$ | 5-Br | H | S | tBu |
| 4-$CF_3$ | 5-F | H | S | tBu |
| 4-$CF_3$ | 4-Cl | H | S | tBu |
| 4-$CF_3$ | 4-F | H | S | tBu |
| 4-$CF_3$ | H | H | S | tBu |
| 4-$CF_3$ | 5-Cl | $CO_2Me$ | S | tBu |
| 4-$CF_3$ | 5-Br | $CO_2Me$ | S | tBu |
| 4-$CF_3$ | 5-F | $CO_2Me$ | S | tBu |
| 4-$CF_3$ | 4-Cl | $CO_2Me$ | S | tBu |
| 4-$CF_3$ | 4-F | $CO_2Me$ | S | tBu |
| 4-$CF_3$ | H | $CO_2Me$ | S | tBu |
| 4-Br | 5-Cl | H | S | sec-Bu |
| 4-$CF_3$ | 5-Br | H | S | sec-Bu |
| 4-$CF_3$ | 5-F | H | S | sec-Bu |
| 4-$CF_3$ | 4-Cl | H | S | sec-Bu |
| 4-$CF_3$ | 4-F | H | S | sec-Bu |
| 4-$CF_3$ | H | H | S | sec-Bu |
| 4-$CF_3$ | 5-Cl | $CO_2Me$ | S | sec-Bu |
| 4-$CF_3$ | 5-Br | $CO_2Me$ | S | sec-Bu |
| 4-$CF_3$ | 5-F | $CO_2Me$ | S | sec-Bu |
| 4-$CF_3$ | 4-Cl | $CO_2Me$ | S | sec-Bu |
| 4-$CF_3$ | 4-F | $CO_2Me$ | S | sec-Bu |
| 4-$CF_3$ | H | $CO_2Me$ | S | sec-Bu |
| 4-$CF_3$ | 5-Br | H | O | Ph |
| 4-Cl | 5-Br | H | O | Ph |
| 4-Br | 5-Br | H | O | Ph |
| 4-$OCF_3$ | 5-Br | H | O | Ph |
| 4-$CF_3$ | 5-Cl | H | O | Ph |
| 4-Cl | 5-Cl | H | O | Ph |
| 4-Br | 5-Cl | H | O | Ph |
| 4-$CF_3$ | 5-$CF_3$ | H | O | Ph |
| 4-$CF_3$ | 4-F | H | O | Ph |
| 4-$CF_3$ | H | H | O | Ph |
| 4-$CF_3$ | 5-Br | $CO_2Me$ | O | Ph |
| 4-$CF_3$ | 5-Cl | $CO_2Me$ | O | Ph |
| 4-$CF_3$ | 5-$CF_3$ | $CO_2Me$ | O | Ph |
| 4-$CF_3$ | 4-F | $CO_2Me$ | O | Ph |
| 4-$CF_3$ | H | $CO_2Me$ | O | Ph |
| 4-$CF_3$ | 5-Cl | H | S | Ph |
| 4-Cl | 5-Cl | H | S | Ph |
| 4-Br | 5-Cl | H | S | Ph |
| 4-$CF_3$ | 5-Br | H | S | Ph |
| 4-$CF_3$ | 5-F | H | S | Ph |
| 4-$CF_3$ | 4-Cl | H | S | Ph |
| 4-$CF_3$ | 4-F | H | S | Ph |
| 4-$CF_3$ | H | H | S | Ph |
| 4-$CF_3$ | 5-Cl | $CO_2Me$ | S | Ph |
| 4-$CF_3$ | 5-Br | $CO_2Me$ | S | Ph |
| 4-$CF_3$ | 5-F | $CO_2Me$ | S | Ph |
| 4-$CF_3$ | 4-Cl | $CO_2Me$ | S | Ph |
| 4-$CF_3$ | 4-F | $CO_2Me$ | S | Ph |
| 4-$CF_3$ | H | $CO_2Me$ | S | Ph |
| 4-$CF_3$ | 5-Br | H | O | 4-Cl—Ph |
| 4-Cl | 5-Br | H | O | 4-Cl—Ph |
| 4-Br | 5-Br | H | O | 4-Cl—Ph |
| 4-$OCF_3$ | 5-Br | H | O | 4-Cl—Ph |
| 4-$CF_3$ | 5-Cl | H | O | 4-Cl—Ph |
| 4-Cl | 5-Cl | H | O | 4-Cl—Ph |
| 4-Br | 5-Cl | H | O | 4-Cl—Ph |
| 4-$CF_3$ | 5-$CF_3$ | H | O | 4-Cl—Ph |
| 4-$CF_3$ | 4-F | H | O | 4-Cl—Ph |
| 4-$CF_3$ | 11 | H | O | 4-Cl—Ph |
| 4-$CF_3$ | 5-Br | $CO_2Me$ | O | 4-Cl—Ph |
| 4-CF | 5-Cl | $CO_2Me$ | O | 4-Cl—Ph |

TABLE 14-continued

| $R_1$ | $R_2$ | B | V | $R_{10}$ |
|---|---|---|---|---|
| 4-$CF_3$ | 5-$CF_3$ | $CO_2Me$ | O | 4-Cl−Ph |
| 4-$CF_3$ | 4-F | $CO_2Me$ | O | 4-Cl−Ph |
| 4-$CF_3$ | H | $CO_2Me$ | O | 4-Cl−Ph |
| 4-$CF_3$ | 5-Cl | H | S | 4-Cl−Ph |
| 4-Cl | 5-Cl | H | S | 4-Cl−Ph |
| 4-Br | 5-Cl | H | S | 4-Cl−Ph |
| 4-$CF_3$ | 5-Br | H | S | 4-Cl−Ph |
| 4-$CF_3$ | 5-F | H | S | 4-Cl−Ph |
| 4-$CF_3$ | 4-Cl | H | S | 4-Cl−Ph |
| 4-$CF_3$ | 4-F | H | S | 4-Cl−Ph |
| 4-$CF_3$ | H | H | S | 4-Cl−Ph |
| 4-$CF_3$ | 5-Cl | $CO_2Me$ | S | 4-Cl−Ph |
| 4-$CF_3$ | 5-Br | $CO_2Me$ | S | 4-Cl−Ph |
| 4-$CF_3$ | 5-F | $CO_2Me$ | S | 4-Cl−Ph |
| 4-$CF_3$ | 4-Cl | $CO_2Me$ | S | 4-Cl−Ph |
| 4-$CF_3$ | 4-F | $CO_2Me$ | S | 4-Cl−Ph |
| 4-$CF_3$ | H | $CO_2Me$ | S | 4-Cl−Ph |

TABLE 15

| $R_1$ | $R_2$ | $R_{13}^a$ | $R_{13}^b$ | V | $R_8$ | $R_9$ |
|---|---|---|---|---|---|---|
| 4-$CF_3$ | 5-F | Me | Me | S | Me | OEt |
| 4-$CF_3$ | 5-Cl | Me | Me | S | Me | OEt |
| 4-$CF_3$ | 4-F | Me | Me | S | Me | OEt |
| 4-$CF_3$ | 5-Br | Ph | H | O | Me | OEt |
| 4-$CF_3$ | 5-Br | $CO_2Me$ | H | O | Me | OEt |
| 4-$CF_3$ | 5-Br | Me | Me | O | Me | OEt |
| 4-$CF_3$ | 5-Cl | Me | Me | O | Me | OEt |
| 4-$CF_3$ | 5-F | Me | Me | S | Me | O-nBu |
| 4-$CF_3$ | 5-Cl | Me | Me | S | Me | O-nBu |
| 4-$CF_3$ | 4-F | Me | Me | S | Me | O-nBu |
| 4-$CF_3$ | 5-Br | Ph | H | O | Me | O-nBu |
| 4-$CF_3$ | 5-Br | $CO_2Me$ | H | O | Me | O-nBu |
| 4-$CF_3$ | 5-Br | Me | Me | O | Me | O-nBu |
| 4-$CF_3$ | 5-Cl | Me | Me | O | Me | O-nBu |
| 4-$CF_3$ | 5-F | Me | Me | S | Me | O-nHexyl |
| 4-$CF_3$ | 5-Cl | Me | Me | S | Me | O-nHexyl |
| 4-$CF_3$ | 4-F | Me | Me | S | Me | O-nHexyl |
| 4-$CF_3$ | 5-Br | Ph | H | O | Me | O-nHexyl |
| 4-$CF_3$ | 5-Br | $CO_2Me$ | H | O | Me | O-nHexyl |
| 4-$CF_3$ | 5-Br | Me | Me | O | Me | O-nHexyl |
| 4-$CF_3$ | 5-Cl | Me | Me | O | Me | O-nHexyl |
| 4-$CF_3$ | 5-F | Me | Me | S | Me | O-sec-Bu |
| 4-$CF_3$ | 5-Cl | Me | Me | S | Me | O-sec-Bu |
| 4-$CF_3$ | 4-F | Me | Me | S | Me | O-sec-Bu |
| 4-$CF_3$ | 5-Br | Ph | H | O | Me | O-sec-Bu |
| 4-$CF_3$ | 5-Br | $CO_2Me$ | H | O | Me | O-sec-Bu |

TABLE 15-continued

| $R_1$ | $R_2$ | $R_{13}^a$ | $R_{13}^b$ | V | $R_8$ | $R_9$ |
|---|---|---|---|---|---|---|
| 4-$CF_3$ | 5-Br | Me | Me | O | Me | O-sec-Bu |
| 4-$CF_3$ | 5-Cl | Me | Me | O | Me | O-sec-Bu |
| 4-$CF_3$ | 5-F | Me | Me | S | Me | O-iPr |
| 4-$CF_3$ | 5-Cl | Me | Me | S | Me | O-iPr |
| 4-$CF_3$ | 4-F | Me | Me | S | Me | O-iPr |
| 4-$CF_3$ | 5-Br | Ph | H | O | Me | O-iPr |
| 4-$CF_3$ | 5-Br | $CO_2Me$ | H | O | Me | O-iPr |
| 4-$CF_3$ | 5-Br | Me | Me | O | Me | O-iPr |
| 4-$CF_3$ | 5-Cl | Me | Me | O | Me | O-iPr |
| 4-$CF_3$ | 5-F | Me | Me | S | Me | $OCH_2CH_2OEt$ |
| 4-$CF_3$ | 5-Cl | Me | Me | S | Me | $OCH_2CH_2OEt$ |
| 4-$CF_3$ | 4-F | Me | Me | S | Me | $OCH_2CH_2OEt$ |
| 4-$CF_3$ | 5-Br | Ph | H | O | Me | $OCH_2CH_2OEt$ |
| 4-$CF_3$ | 5-Br | $CO_2Me$ | H | O | Me | $OCH_2CH_2OEt$ |
| 4-$CF_3$ | 5-Br | Me | Me | O | Me | $OCH_2CH_2OEt$ |
| 4-$CF_3$ | 5-Cl | Me | Me | O | Me | $OCH_2CH_2OEt$ |
| 4-$CF_3$ | 5-F | Me | Me | S | Me | F |
| 4-$CF_3$ | 5-Cl | Me | Me | S | Me | F |
| 4-$CF_3$ | 4-F | Me | Me | S | Me | F |
| 4-$CF_3$ | 5-Br | Ph | H | O | Me | F |
| 4-$CF_3$ | 5-Br | $CO_2Me$ | H | O | Me | F |
| 4-$CF_3$ | 5-Br | Me | Me | O | Me | F |
| 4-$CF_3$ | 5-Cl | Me | Me | O | Me | F |
| 4-$CF_3$ | 5-F | Me | Me | S | Me | $NMe_2$ |
| 4-$CF_3$ | 5-Cl | Me | Me | S | Me | $NMe_2$ |
| 4-$CF_3$ | 4-F | Me | Me | S | Me | $NMe_2$ |
| 4-$CF_3$ | 5-Br | Ph | H | O | Me | $NMe_2$ |
| 4-$CF_3$ | 5-Br | $CO_2Me$ | H | O | Me | $NMe_2$ |
| 4-$CF_3$ | 5-Br | Me | Me | O | Me | $NMe_2$ |
| 4-$CF_3$ | 5-Cl | Me | Me | O | Me | $NMe_2$ |
| 4-$CF_3$ | 5-F | Me | Me | S | Et | O-iPr |
| 4-$CF_3$ | 5-Cl | Me | Me | S | Et | O-iPr |
| 4-$CF_3$ | 4-F | Me | Me | S | Et | O-iPr |
| 4-$CF_3$ | 5-Br | Ph | H | O | Et | O-iPr |
| 4-$CF_3$ | 5-Br | $CO_2Me$ | H | O | Et | O-iPr |
| 4-$CF_3$ | 5-Br | Me | Me | O | Et | O-iPr |
| 4-$CF_3$ | 5-Cl | Me | Me | O | Et | O-iPr |
| 4-$CF_3$ | 5-F | Me | Me | S | iPr | OEt |
| 4-$CF_3$ | 5-Cl | Me | Me | S | iPr | OEt |
| 4-$CF_3$ | 4-F | Me | Me | S | iPr | OEt |
| 4-$CF_3$ | 5-Br | Ph | H | O | iPr | OEt |
| 4-$CF_3$ | 5-Br | $CO_2Me$ | H | O | iPr | OEt |
| 4-$CF_3$ | 5-Br | Me | Me | O | iPr | OEt |
| 4-$CF_3$ | 5-Cl | Me | Me | O | iPr | OEt |
| 4-$CF_3$ | 5-F | Me | Me | S | iPr | $OCH_2CF_3$ |
| 4-$CF_3$ | 5-Cl | Me | Me | S | iPr | $OCH_2CF_3$ |
| 4-$CF_3$ | 4-F | Me | Me | S | iPr | $OCH_2CF_3$ |
| 4-$CF_3$ | 5-Br | Ph | H | O | iPr | $OCH_2CF_3$ |
| 4-$CF_3$ | 5-Br | $CO_2Me$ | H | O | iPr | $OCH_2CF_3$ |
| 4-$CF_3$ | 5-Br | Me | Me | O | iPr | $OCH_2CF_3$ |
| 4-$CF_3$ | 5-Cl | Me | Me | O | iPr | $OCH_2CF_3$ |
| 4-$CF_3$ | 5-F | Me | Me | S | iPr | $OCH_2CO_2Me$ |
| 4-$CF_3$ | 5-Cl | Me | Me | S | iPr | $OCH_2CO_2Me$ |
| 4-$CF_3$ | 4-F | Me | Me | S | iPr | $OCH_2CO_2Me$ |
| 4-$CF_3$ | 5-Br | Ph | H | O | iPr | $OCH_2CO_2Me$ |
| 4-$CF_3$ | 5-Br | $CO_2Me$ | H | O | iPr | $OCH_2CO_2Me$ |
| 4-$CF_3$ | 5-Br | Me | Me | O | iPr | $OCH_2CO_2Me$ |
| 4-$CF_3$ | 5-Cl | Me | Me | O | iPr | $OCH_2CO_2Me$ |

TABLE 16

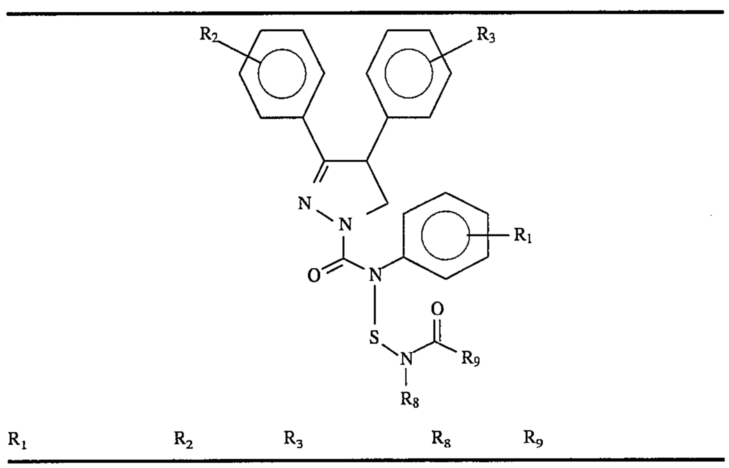

| $R_1$ | $R_2$ | $R_3$ | $R_8$ | $R_9$ |
|---|---|---|---|---|
| 4-$CF_3$ | 4-Cl | H | Me | OEt |
| 4-Cl | 4-Cl | H | Me | OEt |
| 4-Br | 4-Cl | H | Me | OEt |
| 4-$OCF_3$ | 4-Cl | H | Me | OEt |
| 4-$OCF_2H$ | 4-Cl | H | Me | OEt |
| 3,4-$CH_2C(Me)_2O$ | 4-Cl | H | Me | OEt |
| 4-$CF_3$ | 4-F | H | Me | OEt |
| 4-Cl | 4-F | H | Me | OEt |
| 4-Br | 4-F | H | Me | OEt |
| 4-$OCF_3$ | 4-F | H | Me | OEt |
| 4-$OCF_2H$ | 4-F | H | Me | OEt |
| 3,4-$CH_2C(Me)_2O$ | 4-F | H | Me | OEt |
| 4-$CF_3$ | 4-$OCF_2H$ | H | Me | OEt |
| 4-Cl | 4-$OCF_2H$ | H | Me | OEt |
| 4-Br | 4-$OCF_2H$ | H | Me | OEt |
| 4-$OCF_3$ | 4-$OCF_2H$ | H | Me | OEt |
| 4-$OCF_2H$ | 4-$OCF_2H$ | H | Me | OEt |
| 3,4-$CH_2C(Me)_2O$ | 4-$OCF_2H$ | H | Me | OEt |
| 4-$CF_3$ | 4-Br | H | Me | OEt |
| 4-$CF_3$ | 4-Cl | 4-Cl | Me | OEt |
| 4-Cl | 4-Cl | 4-Cl | Me | OEt |
| 4-Br | 4-Cl | 4-Cl | Me | OEt |
| 4-$OCF_3$ | 4-Cl | 4-Cl | Me | OEt |
| 4-$OCF_2H$ | 4-Cl | 4-Cl | Me | OEt |
| 3,4-$CH_2C(Me)_2O$ | 4-Cl | 4-Cl | Me | OEt |
| 4-$CF_3$ | 4-F | 4-Cl | Me | OEt |
| 4-$OCF_3$ | 4-F | 4-Cl | Me | OEt |
| 4-$CF_3$ | 4-$OCF_2H$ | 4-Cl | Me | OEt |
| 4-$OCF_3$ | 4-$OCF_2H$ | 4-Cl | Me | OEt |
| 4-$CF_3$ | 4-Cl | 4-CN | Me | OEt |
| 4-Cl | 4-Cl | 4-CN | Me | OEt |
| 4-$OCF_3$ | 4-Cl | 4-CN | Me | OEt |
| 4-$CF_3$ | 4-F | 4-CN | Me | OEt |
| 4-$OCF_3$ | 4-F | 4-CN | Me | OEt |
| 4-$CF_3$ | 4-Cl | 4-$CO_2Me$ | Me | OEt |
| 4-$CF_3$ | 4-Cl | H | Me | O-n-Bu |
| 4-$OCF_3$ | 4-Cl | H | Me | O-n-Bu |
| 4-$CF_3$ | 4-F | H | Me | O-n-Bu |
| 4-$OCF_3$ | 4-F | H | Me | O-n-Bu |
| 3,4-$CH_2C(Me)_2O$ | 4-F | H | Me | O-n-Bu |
| 4-$CF_3$ | 4-$OCF_2H$ | H | Me | O-n-Bu |
| 4-Cl | 4-$OCF_2H$ | H | Me | O-n-Bu |
| 4-Br | 4-$OCF_2H$ | H | Me | O-n-Bu |
| 4-$OCF_3$ | 4-$OCF_2H$ | H | Me | O-n-Bu |
| 4-$CF_3$ | 4-Br | H | Me | O-n-Bu |
| 4-$CF_3$ | 4-Cl | 4-Cl | Me | O-n-Bu |
| 4-Cl | 4-Cl | 4-Cl | Me | O-n-Bu |
| 4-Br | 4-Cl | 4-Cl | Me | O-n-Bu |
| 4-$OCF_3$ | 4-Cl | 4-Cl | Me | O-n-Bu |
| 4-$CF_3$ | 4-F | 4-Cl | Me | O-n-Bu |
| 4-$OCF_3$ | 4-F | 4-Cl | Me | O-n-Bu |
| 4-$CF_3$ | 4-$OCF_2H$ | 4-Cl | Me | O-n-Bu |
| 4-Cl | 4-$OCF_2H$ | 4-Cl | Me | O-n-Bu |
| 4-Br | 4-$OCF_2H$ | 4-Cl | Me | O-n-Bu |
| 4-$OCF_3$ | 4-$OCF_2H$ | 4-Cl | Me | O-n-Bu |
| 4-$CF_3$ | 4-Cl | 4-CN | Me | O-n-Bu |
| 4-$OCF_3$ | 4-Cl | 4-CN | Me | O-n-Bu |
| 4-$CF_3$ | 4-F | 4-CN | Me | O-n-Bu |

TABLE 16-continued

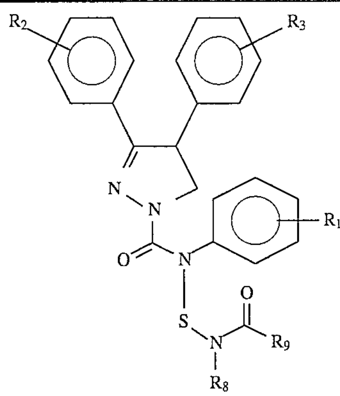

| $R_1$ | $R_2$ | $R_3$ | $R_8$ | $R_9$ |
|---|---|---|---|---|
| 4-$OCF_3$ | 4-F | 4-CN | Me | O-n-Bu |
| 4-$CF_3$ | 4-Cl | 4-$CO_2Me$ | Me | O-n-Bu |
| 4-$CF_3$ | 4-OMe | 4-Cl | Me | O-n-Bu |
| 4-Cl | 4-OPh | 4-Cl | Me | O-n-Bu |
| 4-Br | 4-$SCF_2H$ | 4-Cl | Me | O-n-Bu |
| 4-$OCF_3$ | 4-$NO_2$ | 4-Cl | Me | O-n-Bu |
| 4-$OCF_2H$ | 4-SMe | 4-Cl | Me | O-n-Bu |
| 3,4-$CH_2C(Me)_2O$ | 4-$SO_2Me$ | 4-Cl | Me | O-n-Bu |
| 4-$CF_3$ | 4-CN | 4-Cl | Me | O-n-Bu |
| 4-Cl | 3-Cl | 4-Cl | Me | O-n-Bu |
| 4-Br | 3-F | 4-Cl | Me | O-n-Bu |
| 4-$OCF_3$ | 4-Me | 4-Cl | Me | O-n-Bu |
| 4-$OCF_2H$ | 4-allyl | 4-Cl | Me | O-n-Bu |
| 3,4-$CH_2C(Me)_2O$ | 4-$CF_3$ | 4-Cl | Me | O-n-Bu |
| 4-$CF_3$ | 4-Cl | 4-$CO_2Et$ | Me | O-n-Bu |
| 4-Cl | 4-Cl | 4-OMe | Me | O-n-Bu |
| 4-Br | 4-Cl | 4-$SCF_2CF_2H$ | Me | O-n-Bu |
| 4-$OCF_3$ | 4-Cl | 4-$OCF_2CF_2H$ | Me | O-n-Bu |
| 4-$OCF_2H$ | 4-Cl | 4-OPh | Me | O-n-Bu |
| 3,4-$CH_2C(Me)_2O$ | 4-$CF_3$ | 4-$CF_3$ | Me | O-n-Bu |
| 4-$CF_3$ | 4-Cl | 4-$CF_3$ | Me | O-n-Bu |
| 4-Cl | 4-Cl | 4-Me | Me | O-n-Bu |
| 4-Br | 4-Cl | 3-Cl | Me | O-n-Bu |
| 4-$OCF_3$ | 4-Cl | 3-Br | Me | O-n-Bu |
| 4-$OCF_2H$ | 4-Cl | 4-$NO_2$ | Me | O-n-Bu |
| 4-$CF_3$ | 4-Cl | H | Me | O-n-hexyl |
| 4-$CF_3$ | 4-F | H | Me | O-n-hexyl |
| 4-$CF_3$ | 4-$OCF_2H$ | H | Me | O-n-hexyl |
| 4-$OCF_3$ | 4-$OCF_2H$ | H | Me | O-n-octyl |
| 4-CF | 4-Br | H | Me | O-n-octyl |
| 4-$CF_3$ | 4-Cl | 4-Cl | Me | O-n-octyl |
| 4-Cl | 4-Cl | 4-Cl | Me | O-n-octyl |
| 4-Br | 4-Cl | 4-Cl | Me | O-n-octyl |
| 4-$OCF_3$ | 4-Cl | 4-Cl | Me | O-n-octyl |
| 4-$CF_3$ | 4-F | 4-Cl | Me | O-n-decyl |
| 4-Cl | 4-F | 4-Cl | Me | O-n-decyl |
| 4-$OCF_3$ | 4-F | 4-Cl | Me | O-n-decyl |
| 4-$CF_3$ | 4-$OCF_2H$ | 4-Cl | Me | O-n-decyl |
| 4-$OCF_3$ | 4-$OCF_2H$ | 4-Cl | Me | O-n-decyl |
| 4-$CF_3$ | 4-Cl | 4-CN | Me | O-n-decyl |
| 4-Cl | 4-Cl | 4-CN | Me | O-n-decyl |
| 4-Br | 4-Cl | 4-CN | Me | O-n-decyl |
| 4-$OCF_3$ | 4-Cl | 4-CN | Me | O-n-dodecyl |
| 4-$CF_3$ | 4-F | 4-CN | Me | O-n-dodecyl |
| 4-$OCF_3$ | 4-F | 4-CN | Me | O-n-dodecyl |
| 4-$CF_3$ | 4-Cl | 4-$CO_2Me$ | Me | O-n-dodecyl |
| 4-$CF_3$ | 4-Cl | H | Me | O-sec-Bu |
| 4-Cl | 4-Cl | H | Me | O-sec-Bu |
| 4-$OCF_3$ | 4-Cl | H | Me | O-sec-Bu |
| 4-$CF_3$ | 4-F | H | Me | O-sec-Bu |
| 4-$OCF_3$ | 4-F | H | Me | O-sec-Bu |
| 4-$CF_3$ | 4-$OCF_2H$ | H | Me | O-sec-Bu |
| 4-$OCF_3$ | 4-$OCF_2H$ | H | Me | O-sec-Bu |
| 4-$CF_3$ | 4-Br | H | Me | O-sec-Bu |
| 4-$CF_3$ | 4-Cl | 4-Cl | Me | O-sec-Bu |
| 4-Cl | 4-Cl | 4-Cl | Me | O-sec-Bu |
| 4-Br | 4-Cl | 4-Cl | Me | O-sec-Bu |
| 4-$OCF_3$ | 4-Cl | 4-Cl | Me | O-sec-Bu |

TABLE 16-continued

| $R_1$ | $R_2$ | $R_3$ | $R_8$ | $R_9$ |
|---|---|---|---|---|
| 4-$CF_3$ | 4-F | 4-Cl | Me | O-sec-Bu |
| 4-Cl | 4-F | 4-Cl | Me | O-sec-Bu |
| 4-$OCF_3$ | 4-F | 4-Cl | Me | O-sec-Bu |
| 4-$CF_3$ | 4-$OCF_2H$ | 4-Cl | Me | O-sec-Bu |
| 4-$OCF_3$ | 4-$OCF_2H$ | 4-Cl | Me | O-sec-Bu |
| 4-$CF_3$ | 4-Cl | 4-CN | Me | O-sec-Bu |
| 4-Cl | 4-Cl | 4-CN | Me | O-sec-Bu |
| 4-$OCF_3$ | 4-Cl | 4-CN | Me | O-sec-Bu |
| 4-$CF_3$ | 4-F | 4-CN | Me | O-sec-Bu |
| 4-$OCF_3$ | 4-F | 4-CN | Me | O-sec-Bu |
| 4-$CF_3$ | 4-Cl | 4-$CO_2Me$ | Me | O-sec-Bu |
| 4-CF | 4-CN | 4-Cl | Me | O-sec-Bu |
| 4-Cl | 3-Cl | 4-Cl | Me | O-sec-Bu |
| 4-Br | 3-F | 4-Cl | Me | O-sec-Bu |
| 4-$OCF_3$ | 4-Me | 4-Cl | Me | O-sec-Bu |
| 4-$CF_3$ | 4-Cl | 4-$CO_2Et$ | Me | O-sec-Bu |
| 4-Cl | 4-Cl | 4-OMe | Me | O-sec-Bu |
| 4-Br | 4-Cl | 4-$SCF_2CF_2H$ | Me | O-sec-Bu |
| 4-$OCF_3$ | 4-Cl | 4-$OCF_2CF_2H$ | Me | O-sec-Bu |
| 4-$OCF_2$ | 4-Cl | 4-OPh | Me | O-sec-Bu |
| 3,4-$CH_2C(Me)_2O$ | 4-Cl | 4-$CF_3$ | Me | O-sec-Bu |
| 4-CF | 4-Cl | 4-CF | Me | O-sec-Bu |
| 4-Cl | 4-Cl | 4-Me | Me | O-sec-Bu |
| 4-Br | 4-Cl | 3-Cl | Me | O-sec-Bu |
| 4-$OCF_3$ | 4-Cl | 3-Br | Me | O-sec-Bu |
| 4-$OCF_2H$ | 4-Cl | 4-$NO_2$ | Me | O-sec-Bu |
| 4-$CF_3$ | 4-Cl | H | Me | O-iPr |
| 4-OCF | 4-Cl | H | Me | O-iPr |
| 4-$CF_3$ | 4-F | H | Me | O-iPr |
| 4-$OCF_3$ | 4-F | H | Me | O-iPr |
| 4-$CF_3$ | 4-$OCF_2H$ | H | Me | O-iPr |
| 4-$OCF_3$ | 4-$OCF_2H$ | H | Me | O-iPr |
| 4-$CF_3$ | 4-Br | H | Me | O-iPr |
| 4-OCF | 4-Br | H | Me | O-iPr |
| 4-$CF_3$ | 4-Cl | 4-Cl | Me | O-iPr |
| 4-$OCF_3$ | 4-Cl | 4-Cl | Me | O-iPr |
| 4-$CF_3$ | 4-F | 4-Cl | Me | O-iPr |
| 4-$OCF_3$ | 4-F | 4-Cl | Me | O-iPr |
| 4-CF | 4-Cl | 4-CN | Me | O-iPr |
| 4-$OCF_3$ | 4-Cl | 4-CN | Me | O-iPr |
| 4-$CF_3$ | 4-F | 4-CN | Me | O-iPr |
| 4-$OCF_3$ | 4-F | 4-CN | Me | O-iPr |
| 4-$CF_3$ | 4-Cl | 4-$CO_2Me$ | Me | O-iPr |
| 4-CF | 4-Cl | H | Me | $OCH_2CH_2OEt$ |
| 4-$CF_3$ | 4-F | H | He | $OCH_2CH_2OEt$ |
| 4-$CF_3$ | 4-$OCF_2H$ | H | Me | $OCH_2CH_2OEt$ |
| 4-$OCF_3$ | 4-$OCF_2H$ | H | Me | $OCH_2CCl_3$ |
| 4-$CF_3$ | 4-Br | H | Me | $OCH_2CCl_3$ |
| 4-CF | 4-Cl | 4-Cl | Me | $OCH_2CCl_3$ |
| 4-Cl | 4-Cl | 4-Cl | Me | $OCH_2CCl_3$ |
| 4-$OCF_3$ | 4-Cl | 4-Cl | Me | $OCH_2CCl_3$ |
| 4-$CF_3$ | 4-F | 4-Cl | Me | $OCH_2CF_3$ |
| 4-$OCF_3$ | 4-F | 4-Cl | Me | $OCH_2CF_3$ |
| 4-CF | 4-$OCF_2H$ | 4-Cl | Me | $OCH_2CF_3$ |
| 4-$OCF_3$ | 4-$OCF_2H$ | 4-Cl | Me | $OCH_2CF_3$ |
| 4-$CF_3$ | 4-Cl | 4-CN | Me | $OCH_2CF_3$ |
| 4-$OCF_3$ | 4-Cl | 4-CN | Me | $OCH_2CO_2Et$ |
| 4-$CF_3$ | 4-F | 4-CN | Me | $OCH_2CO_2Et$ |

TABLE 16-continued

| $R_1$ | $R_2$ | $R_3$ | $R_8$ | $R_9$ |
|---|---|---|---|---|
| 4-$OCF_3$ | 4-F | 4-CN | Me | $OCH_2CO_2Et$ |
| 4-$CF_3$ | 4-Cl | 4-$CO_2Me$ | Me | $OCH_2CO_2Et$ |
| 4-$CF_3$ | 4-Cl | H | Me | F |
| 4-Cl | 4-Cl | H | Me | F |
| 4-$OCF_3$ | 4-Cl | H | Me | F |
| 4-$CF_3$ | 4-F | H | Me | F |
| 4-$OCF_3$ | 4-F | H | Me | F |
| 4-$CF_3$ | 4-$OCF_2H$ | H | Me | F |
| 4-$OCF_3$ | 4-$OCF_2H$ | H | Me | $NMe_2$ |
| 4-$CF_3$ | 4-Br | H | Me | $NMe_2$ |
| 4-$CF_3$ | 4-Cl | 4-Cl | Me | $NMe_2$ |
| 4-Cl | 4-Cl | 4-Cl | Me | $NMe_2$ |
| 4-$OCF_3$ | 4-Cl | 4-Cl | Me | $NMe_2$ |
| 4-$CF_3$ | 4-F | 4-Cl | Me | $NEt_2$ |
| 4-$OCF_3$ | 4-F | 4-Cl | Me | $NEt_2$ |
| 4-$CF_3$ | 4-$OCF_2H$ | 4-Cl | Me | piperidino |
| 4-$OCF_3$ | 4-$OCF_2H$ | 4-Cl | Me | morpholino |
| 4-$CF_3$ | 4-Cl | 4-CN | Me | n-Pr |
| 4-$OCF_3$ | 4-Cl | 4-CN | Me | n-Pr |
| 4-$CF_3$ | 4-F | 4-CN | Me | Sec-Bu |
| 4-$OCF_3$ | 4-F | 4-CN | Me | 4-Cl—Ph |
| 4-$CF_3$ | 4-Cl | 4-$CO_2Me$ | Me | Ph |
| 4-$CF_3$ | 4-Cl | H | Et | O-iPr |
| 4-Cl | 4-Cl | H | Et | O-iPr |
| 4-$OCF_3$ | 4-Cl | H | Et | O-iPr |
| 4-$CF_3$ | 4-F | H | Et | O-iPr |
| 4-$OCF_3$ | 4-F | H | Et | O-iPr |
| 4-$CF_3$ | 4-$OCF_2H$ | H | Et | O-iPr |
| 4-$OCF_3$ | 4-$OCF_2H$ | H | Et | O-iPr |
| 4-$CF_3$ | 4-Br | H | Et | O-iPr |
| 4-$CF_3$ | 4-Cl | 4-Cl | Et | O-iPr |
| 4-$OCF_3$ | 4-Cl | 4-Cl | Et | O-iPr |
| 4-$CF_3$ | 4-F | 4-Cl | Et | OEt |
| 4-$OCF_3$ | 4-F | 4-Cl | Et | OEt |
| 4-$CF_3$ | 4-$OCF_2H$ | 4-Cl | Et | $OCH_2CCl_3$ |
| 4-$OCF_3$ | 4-$OCF_2H$ | 4-Cl | Et | $NEt_2$ |
| 4-$CF_3$ | 4-Cl | 4-CN | Et | 2,6-di-Me-morpholino |
| 4-$OCF_3$ | 4-Cl | 4-CN | Et | 2,6-di-Me-morpholino |
| 4-$CF_3$ | 4-F | 4-CN | Et | iPr |
| 4-$OCF_3$ | 4-F | 4-CN | Et | Ph |
| 3,4-$CH_2C(Me)_2O$ | 4-F | 4-CN | Et | Ph |
| 4-$CF_3$ | 4-Cl | H | iPr | OEt |
| 4-$OCF_3$ | 4-Cl | H | iPr | OEt |
| 4-$CF_3$ | 4-F | H | iPr | OEt |
| 4-$CF_3$ | 4-$OCF_2H$ | H | iPr | OEt |
| 4-$OCF_3$ | 4-$OCF_2H$ | H | iPr | OEt |
| 4-$CF_3$ | 4-Br | H | iPr | OEt |
| 4-$CF_3$ | 4-Cl | 4-Cl | iPr | OEt |
| 4-Cl | 4-Cl | 4-Cl | iPr | OEt |
| 4-Br | 4-Cl | 4-Cl | iPr | OEt |
| 4-$OCF_3$ | 4-Cl | 4-Cl | iPr | OEt |
| 4-$CF_3$ | 4-F | 4-Cl | iPr | OEt |
| 4-$OCF_3$ | 4-F | 4-Cl | iPr | OEt |
| 4-$CF_3$ | 4-$OCF_2H$ | 4-Cl | iPr | OEt |
| 4-$OCF_3$ | 4-$OCF_2H$ | 4-Cl | iPr | OEt |
| 4-$CF_3$ | 4-Cl | 4-CN | iPr | OEt |
| 4-$OCF_3$ | 4-Cl | 4-CN | iPr | OEt |
| 4-$CF_3$ | 4-F | 4-CN | iPr | OEt |

TABLE 16-continued

| $R_1$ | $R_2$ | $R_3$ | $R_8$ | $R_9$ |
|---|---|---|---|---|
| 4-$OCF_3$ | 4-F | 4-CN | iPr | OEt |
| 4-CF | 4-Cl | 4-$CO_2Me$ | iPr | OEt |
| 4-$CF_3$ | 4-CN | 4-Cl | iPr | OEt |
| 4-Cl | 3-Cl | 4-Cl | iPr | OEt |
| 4-Br | 3-F | 4-Cl | iPr | OEt |
| 4-$OCF_3$ | 4-Me | 4-Cl | iPr | OEt |
| 4-$OCF_2H$ | 4-o-allyl | 4-Cl | iPr | OEt |
| 3,4-$CH_2C(Me)_2O$ | 4-$CF_3$ | 4-Cl | iPr | OEt |
| 4-$CF_3$ | 4-Cl | 4-$CO_2Et$ | iPr | OEt |
| 4-Cl | 4-Cl | 4-OMe | iPr | OEt |
| 4-Br | 4-Cl | 4-$SCF_2CF_2H$ | iPr | OEt |
| 4-$OCF_3$ | 4-Cl | 4-$OCF_2CF_2H$ | iPr | OEt |
| 4-$OCF_2H$ | 4-Cl | 4-OPh | iPr | OEt |
| 3,4-$CH_2C(Me)_2O$ | 4-Cl | 4-$CF_3$ | iPr | OEt |
| 4-$CF_3$ | 4-Cl | 4-CF 3 | iPr | OEt |
| 4-Br | 4-Cl | 3-Cl | iPr | OEt |
| 4-$OCF_3$ | 4-Cl | 3-Br | iPr | OEt |
| 4-$OCF_2H$ | 4-Cl | 4-$NO_2$ | iPr | OEt |
| 4-$CF_3$ | 4-Cl | H | iPr | O-n-Bu |
| 4-Cl | 4-Cl | H | iPr | O-n-Bu |
| 4-Br | 4-Cl | H | iPr | O-n-Bu |
| 4-$OCF_3$ | 4-Cl | H | iPr | O-n-Bu |
| 4-$CF_3$ | 4-F | H | iPr | O-n-Bu |
| 4-$OCF_3$ | 4-F | H | iPr | O-n-Bu |
| 4-$CF_3$ | 4-$OCF_2H$ | H | iPr | O-n-Bu |
| 4-$OCF_3$ | 4-$OCF_2H$ | H | iPr | O-n-Bu |
| 4-$CF_3$ | 4-Br | H | iPr | O-n-Bu |
| 4-$CF_3$ | 4-Cl | 4-Cl | iPr | O-n-Bu |
| 4-Br | 4-Cl | 4-Cl | iPr | O-n-Bu |
| 4-$OCF_3$ | 4-Cl | 4-Cl | iPr | O-n-Bu |
| 4-$CF_3$ | 4-F | 4-Cl | iPr | $OCH_2CF_3$ |
| 4-$OCF_3$ | 4-F | 4-Cl | iPr | $OCH_2CF_3$ |
| 4-$CF_3$ | 4-$OCF_2H$ | 4-Cl | lPr | $OCH_2CO_2Me$ |
| 4-$OCF_3$ | 4-$OCF_2H$ | 4-Cl | iPr | $NMe_2$ |
| 4-$CF_3$ | 4-Cl | 4-CN | iPr | $NEt_2$ |
| 4-$OCF_3$ | 4-Cl | 4-CN | iPr | $NEt_2$ |
| 4-$CF_3$ | 4-F | 4-CN | iPr | piperidino |
| 4-$OCF_3$ | 4-F | 4-CN | iPr | Et |
| 4-$CF_3$ | 4-Cl | 4-$CO_2Me$ | iPr | Ph |
| 3,4-$CH_2C(Me)_2O$ | 4-Cl | 4-$CO_2Me$ | iPr | Ph |
| 4-$CF_3$ | 4-Cl | H | $CH_2Ph$ | OEt |
| 4-$CF_3$ | 4-$OCF_2H$ | H | $CH_2Ph$ | piperidino |
| 4-$CF_3$ | 4-Br | H | CH Ph | $OCH_2CH_2OEt$ |
| 4-$CF_3$ | 4-Cl | 4-Cl | $CH_2Ph$ | Me |

TABLE 17

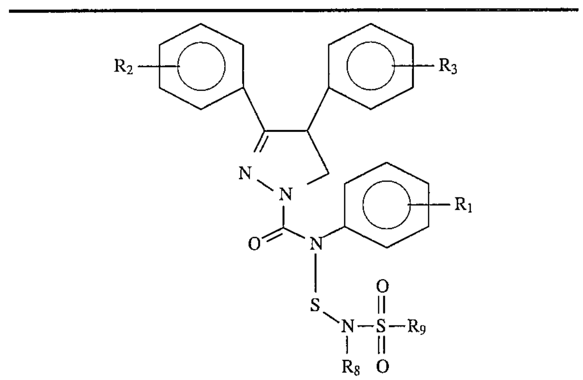

| $R_1$ | $R_2$ | $R_3$ | $R_8$ | $R_9$ |
|---|---|---|---|---|
| 4-$CF_3$ | 4-Cl | H | Me | $NMe_2$ |
| 4-$OCF_3$ | 4-Cl | H | Me | $NMe_2$ |
| 4-$CF_3$ | 4-F | H | Me | NMe |
| 4-$OCF_3$ | 4-F | H | Me | $NMe_2$ |
| 4-$CF_3$ | 4-$OCF_2H$ | H | Me | $NMe_2$ |
| 4-$OCF_3$ | 4-$OCF_2H$ | H | Me | $NMe_2$ |
| 4-$CF_3$ | 4-Cl | 4-Cl | Me | $NMe_2$ |
| 4-Cl | 4-Cl | 4-Cl | Me | NMe |
| 4-Br | 4-Cl | 4-Cl | Me | $NMe_2$ |
| 4-$OCF_3$ | 4-Cl | 4-Cl | Me | $NMe_2$ |
| 4-$CF_3$ | 4-F | 4-Cl | Me | $NMe_2$ |
| 4-$OCF_3$ | 4-F | 4-Cl | Me | $NMe_2$ |
| 4-$CF_3$ | 4-$OCF_2H$ | 4-Cl | Me | $NMe_2$ |
| 4-$OCF_3$ | 4-$OCF_2H$ | 4-Cl | Me | $NMe_2$ |
| 4-$CF_3$ | 4-Cl | 4-CN | Me | $NMe_2$ |
| 4-Cl | 4-Cl | 4-CN | Me | $NMe_2$ |
| 4-Br | 4-Cl | 4-CN | Me | $NMe_2$ |
| 4-$OCF_3$ | 4-Cl | 4-CN | Me | $NMe_2$ |
| 4-$CF_3$ | 4-F | 4-CN | Me | $NMe_2$ |
| 4-$OCF_3$ | 4-F | 4-CN | Me | $NMe_2$ |
| 4-$CF_3$ | 4-Cl | 4-$CO_2Me$ | Me | $NMe_2$ |
| 4-$CF_3$ | 4-Cl | H | Me | $NEt_2$ |
| 3,4-$CH_2C(Me)_2O$ | 4-Cl | H | Me | $NEt_2$ |
| 4-$CF_3$ | 4-F | H | Me | $NEt_2$ |
| 4-$OCF_3$ | 4-F | H | Me | $NEt_2$ |
| 4-$CF_3$ | 4-$OCF_2H$ | H | Me | $NEt_2$ |
| 4-$OCF_3$ | 4-$OCF_2H$ | H | Me | $NEt_2$ |
| 4-$CF_3$ | 4-Br | H | Me | $NEt_2$ |
| 3,4-$CH_2C(Me)_2O$ | 4-Br | H | Me | $NEt_2$ |
| 4-$CF_3$ | 4-Cl | 4-Cl | Me | $NEt_2$ |
| 4-Cl | 4-Cl | 4-Cl | Me | $NEt_2$ |
| 4-Br | 4-Cl | 4-Cl | Me | $NEt_2$ |
| 4-$OCF_3$ | 4-Cl | 4-Cl | Me | $NEt_2$ |
| 4-$CF_3$ | 4-F | 4-Cl | Me | $NEt_2$ |
| 4-$OCF_3$ | 4-F | 4-Cl | Me | $NEt_2$ |
| 4-$CF_3$ | 4-$OCF_2H$ | 4-Cl | Me | $NEt_2$ |
| 4-$OCF_3$ | 4-$OCF_2H$ | 4-Cl | Me | $NEt_2$ |
| 4-$OCF_2H$ | 4-$OCF_2H$ | 4-Cl | Me | $NEt_2$ |
| 3,4-$CH_2C(Me)_2O$ | 4-$OCF_2H$ | 4-Cl | Me | $NEt_2$ |
| 4-$CF_3$ | 4-Cl | 4-CN | Me | $NEt_2$ |
| 4-$OCF_3$ | 4-Cl | 4-CN | Me | $NEt_2$ |
| 4-$CF_3$ | 4-F | 4-CN | Me | $NEt_2$ |
| 4-$OCF_3$ | 4-F | 4-CN | Me | $NEt_2$ |
| 4-$CF_3$ | 4-Cl | 4-$CO_2Me$ | Me | $NEt_2$ |
| 4-$CF_3$ | 4-Cl | H | Me | piperidino |
| 4-$OCF_3$ | 4-Cl | H | Me | piperidino |
| 4-$CF_3$ | 4-F | H | Me | Sec-Bu |
| 4-$OCF_3$ | 4-F | H | Me | n-hexyl |
| 4-$CF_3$ | 4-$OCF_2H$ | H | Me | Ph |
| 4-$OCF_3$ | 4-$OCF_2H$ | H | Me | Ph |
| 4-$CF_3$ | 4-Br | H | Me | 4-Cl−Ph |
| 4-Cl | 4-Br | H | Me | 4-Cl−Ph |
| 4-$CF_3$ | 4-Cl | 4-Cl | Me | n-Bu |
| 4-Cl | 4-Cl | 4-Cl | Me | n-Bu |
| 4-Br | 4-Cl | 4-Cl | Me | n-Bu |
| 4-$OCF_3$ | 4-Cl | 4-Cl | Me | n-Bu |
| 4-$CF_3$ | 4-F | 4-Cl | Et | $NMe_2$ |
| 4-$OCF_3$ | 4-F | 4-Cl | Et | $NMe_2$ |
| 4-$CF_3$ | 4-$OCF_2H$ | 4-Cl | Et | $NEt_2$ |

TABLE 17-continued

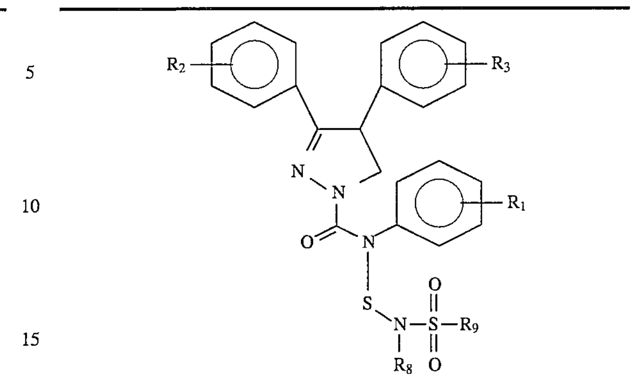

| $R_1$ | $R_2$ | $R_3$ | $R_8$ | $R_9$ |
|---|---|---|---|---|
| 4-$OCF_3$ | 4-$OCF_2H$ | 4-Cl | Et | morpholino |
| 4-$CF_3$ | 4-Cl | 4-CN | Et | iPr |
| 3,4-$CH_2C(Me)_2O$ | 4-Cl | 4-CN | Et | n-Bu |
| 4-$CF_3$ | 4-F | 4-CN | Et | n-Bu |
| 4-$CF_3$ | 4-Cl | 4-$CO_2Me$ | Et | 4-MeO-Ph |
| 4-$CF_3$ | 4-Cl | H | iPr | $NMe_2$ |
| 4-Cl | 4-Cl | H | iPr | $NMe_2$ |
| 4-Br | 4-Cl | H | iPr | $NMe_2$ |
| 4-$OCF_3$ | 4-Cl | H | iPr | $NMe_2$ |
| 4-$CF_3$ | 4-F | H | iPr | $NMe_2$ |
| 4-$OCF_3$ | 4-F | H | iPr | $NMe_2$ |
| 4-$CF_3$ | 4-$OCF_2H$ | H | iPr | $NMe_2$ |
| 4-$OCF_3$ | 4-$OCF_2H$ | H | iPr | $NMe_2$ |
| 3,4-$CH_2C(Me)_2O$ | 4-$OCF_2H$ | H | iPr | $NMe_2$ |
| 4-$CF_3$ | 4-Br | H | iPr | $NMe_2$ |
| 4-$CF_3$ | 4-Cl | 4-Cl | iPr | $NMe_2$ |
| 4-Cl | 4-Cl | 4-Cl | iPr | $NMe_2$ |
| 4-Br | 4-Cl | 4-Cl | iPr | $NMe_2$ |
| 4-$OCF_3$ | 4-Cl | 4-Cl | iPr | $NMe_2$ |
| 4-$CF_3$ | 4-F | 4-Cl | iPr | $NEt_2$ |
| 4-$OCF_3$ | 4-F | 4-Cl | iPr | $NEt_2$ |
| 4-$CF_3$ | 4-$OCF_2H$ | 4-Cl | iPr | 2,6-di-Me-morpholino |
| 4-$OCF_3$ | 4-$OCF_2H$ | 4-Cl | iPr | piperidino |
| 4-$CF_3$ | 4-Cl | 4-CN | iPr | Et |
| 4-$OCF_3$ | 4-Cl | 4-CN | iPr | Et |
| 4-$CF_3$ | 4-F | 4-CN | iPr | n-Bu |
| 4-$OCF_3$ | 4-F | 4-CN | iPr | Ph |
| 4-$CF_3$ | 4-Cl | 4-$CO_2Me$ | iPr | 4-Cl−Ph |

TABLE 18

| $R_1$ | $R_2$ | $R_3$ | $R_8$ | $Y^1$ | $Y^1R_{10}$ | $Y^1R_{11}$ |
|---|---|---|---|---|---|---|
| 4-$CF_3$ | 4-Cl | H | tBu | S | OEt | OEt |
| 4-$OCF_3$ | 4-Cl | H | tBu | S | OEt | OEt |
| 4-$CF_3$ | 4-F | H | tBu | S | OEt | OEt |
| 4-$OCF_3$ | 4-F | H | tBu | S | OEt | OEt |
| 4-$CF_3$ | 4-$OCF_2H$ | H | tBu | S | OEt | OEt |
| 4-$OCF_3$ | 4-$OCF_2H$ | H | tBu | S | OEt | OEt |
| 4-$CF_3$ | 4-Br | H | tBu | S | OEt | OEt |

TABLE 18-continued

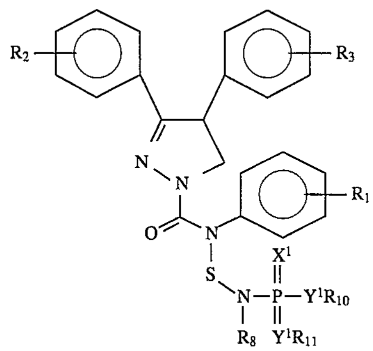

| $R_1$ | $R_2$ | $R_3$ | $R_8$ | $Y^1$ | $Y^1R_{10}$ | $Y^1R_{11}$ |
|---|---|---|---|---|---|---|
| 4-$CF_3$ | 4-Cl | 4-Cl | tBu | S | OEt | OEt |
| 4-Cl | 4-Cl | 4-Cl | tBu | S | OEt | OEt |
| 4-Br | 4-Cl | 4-Cl | tBu | S | OEt | OEt |
| 4-$OCF_3$ | 4-Cl | 4-Cl | tBu | S | OEt | OEt |
| 4-$CF_3$ | 4-F | 4-Cl | tBu | S | OEt | OEt |
| 4-$OCF_3$ | 4-F | 4-Cl | tBu | S | OEt | OEt |
| 4-$CF_3$ | 4-$OCF_2H$ | 4-Cl | tBu | S | OEt | OEt |
| 4-Br | 4-$OCF_2H$ | 4-Cl | tBu | S | OEt | OEt |
| 4-$OCF_3$ | 4-$OCF_2H$ | 4-Cl | tBu | S | OEt | OEt |
| 4-$CF_3$ | 4-Cl | 4-CN | tBu | S | OEt | OEt |
| 4-$OCF_3$ | 4-Cl | 4-CN | tBu | S | OEt | OEt |
| 4-$CF_3$ | 4-F | 4-CN | tBu | S | OEt | OEt |
| 4-$OCF_3$ | 4-F | 4-CN | tBu | S | OEt | OEt |
| 4-$CF_3$ | 4-Cl | 4-$CO_2$Me | tBu | S | OEt | OEt |
| 4-$CF_3$ | 4-Cl | H | tBu | S | $OCH_2C(Me)_2CH_2O$ | |
| 4-$OCF_3$ | 4-Cl | H | tBu | S | $OCH_2C(Me)_2CH_2O$ | |
| 4-$CF_3$ | 4-F | H | tBu | S | $OCH_2C(Me)_2CH_2O$ | |
| 4-Cl | 4-F | H | tBu | S | $OCH_2C(Me)_2CH_2O$ | |
| 4-$OCF_3$ | 4-F | H | tBu | S | $OCH_2C(Me)_2CH_2O$ | |
| 4-$CF_3$ | 4-$OCF_2H$ | H | tBu | S | $OCH_2C(Me)_2CH_2O$ | |
| 4-$OCF_3$ | 4-$OCF_2H$ | H | tBu | S | $OCH_2C(Me)_2CH_2O$ | |
| 4-$CF_3$ | 4-Br | H | tBu | S | $OCH_2C(Me)_2CH_2O$ | |
| 4-$CF_3$ | 4-Cl | 4-Cl | tBu | S | $OCH_2C(Me)_2CH_2O$ | |
| 4-Cl | 4-Cl | 4-Cl | tBu | S | $OCH_2C(Me)_2CH_2O$ | |
| 4-Br | 4-Cl | 4-Cl | tBu | S | $OCH_2C(Me)_2CH_2O$ | |
| 4-$OCF_3$ | 4-Cl | 4-Cl | tBu | S | $OCH_2C(Me)_2CH_2O$ | |
| 4-$CF_3$ | 4-F | 4-Cl | tBu | S | $OCH_2C(Me)_2CH_2O$ | |
| 4-$OCF_3$ | 4-F | 4-Cl | tBu | S | $OCH_2C(Me)_2CH_2O$ | |
| 4-$CF_3$ | 4-$OCF_2H$ | 4-Cl | tBu | S | $OCH_2C(Me)_2CH_2O$ | |
| 4-$OCF_3$ | 4-$OCF_2H$ | 4-Cl | tBu | S | $OCH_2C(Me)_2CH_2O$ | |
| 4-$CF_3$ | 4-Cl | 4-CN | tBu | S | $OCH_2C(Me)_2CH_2O$ | |
| 4-$OCF_3$ | 4-Cl | 4-CN | tBu | S | $OCH_2C(Me)_2CH_2O$ | |
| 4-$CF_3$ | 4-F | 4-CN | tBu | S | $OCH_2C(Me)_2CH_2O$ | |
| 4-$OCF_3$ | 4-F | 4-CN | tBu | S | $OCH_2C(Me)_2CH_2O$ | |
| 4-$CF_3$ | 4-Cl | 4-$CO_2$Me | tBu | S | $OCH_2C(Me)_2CH_2O$ | |
| 4-$CF_3$ | 4-Cl | H | iPr | S | OEt | OEt |
| 4-Cl | 4-Cl | H | iPr | S | OEt | OEt |
| 4-$OCF_3$ | 4-Cl | H | iPr | S | OEt | OEt |
| 4-$CF_3$ | 4-F | H | iPr | S | OEt | OEt |
| 4-$OCF_3$ | 4-F | H | iPr | S | OEt | OEt |
| 4-$CF_3$ | 4-$OCF_2H$ | H | iPr | S | OEt | OEt |
| 4-$OCF_3$ | 4-$OCF_2H$ | H | iPr | S | OEt | OEt |
| 4-CF | 4-Br | H | iPr | S | OEt | OEt |
| 4-$CF_3$ | 4-Cl | 4-Cl | iPr | S | OEt | OEt |
| 4-$OCF_3$ | 4-Cl | 4-Cl | iPr | S | OEt | OEt |
| 4-$CF_3$ | 4-F | 4-Cl | iPr | S | OEt | OEt |
| 4-$OCF_3$ | 4-F | 4-Cl | iPr | S | OEt | OEt |
| 4-$CF_3$ | 4-$OCF_2H$ | 4-Cl | iPr | S | OEt | OEt |
| 4-$OCF_3$ | 4-$OCF_2H$ | 4-Cl | iPr | S | OEt | OEt |
| 4-$CF_3$ | 4-Cl | 4-CN | iPr | S | OEt | OEt |
| 4-$OCF_3$ | 4-Cl | 4-CN | iPr | S | OEt | OEt |
| 4-$CF_3$ | 4-F | 4-CN | iPr | S | OEt | OEt |
| 4-$OCF_3$ | 4-F | 4-CN | iPr | S | OEt | OEt |
| 4-$CF_3$ | 4-Cl | 4-$CO_2$Me | iPr | S | OEt | OEt |
| 4-$CF_3$ | 4-Cl | H | iPr | S | $OCH_2C(Me)_2CH_2O$ | |
| 4-$OCF_3$ | 4-Cl | H | iPr | S | $OCH_2C(Me)_2CH_2O$ | |
| 4-$CF_3$ | 4-F | H | iPr | S | $OCH_2C(Me)_2CH_2O$ | |
| 4-$OCF_3$ | 4-F | H | iPr | S | $OCH_2C(Me)_2CH_2O$ | |
| 4-$CF_3$ | 4-$OCF_2H$ | H | iPr | S | $OCH_2C(Me)_2CH_2O$ | |
| 4-$CF_3$ | 4-Br | H | iPr | S | $OCH_2C(Me)_2CH_2O$ | |

TABLE 18-continued

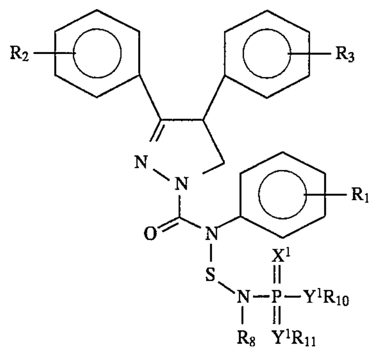

| $R_1$ | $R_2$ | $R_3$ | $R_8$ | $Y^1$ | $Y^1R_{10}$ | $Y^1R_{11}$ |
|---|---|---|---|---|---|---|
| 4-$CF_3$ | 4-Cl | 4-Cl | iPr | S | $OCH_2C(Me)_2CH_2O$ | |
| 4-Cl | 4-Cl | 4-Cl | iPr | S | $OCH_2C(Me)_2CH_2O$ | |
| 4-Br | 4-Cl | 4-Cl | iPr | S | $OCH_2C(Me)_2CH_2O$ | |
| 4-OCF | 4-Cl | 4-Cl | iPr | S | $OCH_2C(Me)_2CH_2O$ | |
| 4-$OCF_2H$ | 4-Cl | 4-Cl | iPr | S | $OCH_2C(Me)_2CH_2O$ | |
| 4-$CF_3$ | 4-F | 4-Cl | iPr | S | $OCH_2C(Me)_2CH_2O$ | |
| 4-Br | 4-F | 4-Cl | iPr | S | $OCH_2C(Me)_2CH_2O$ | |
| 4-$OCF_3$ | 4-F | 4-Cl | iPr | S | $OCH_2C(Me)_2CH_2O$ | |
| 4-$CF_3$ | 4-$OCF_2H$ | 4-Cl | iPr | S | $OCH_2C(Me)_2CH_2O$ | |
| 4-$OCF_3$ | 4-$OCF_2H$ | 4-Cl | iPr | S | $OCH_2C(Me)_2CH_2O$ | |
| 4-$CF_3$ | 4-Cl | 4-CN | iPr | S | $OCH_2C(Me)_2CH_2O$ | |
| 4-$OCF_3$ | 4-Cl | 4-CN | iPr | S | $OCH_2C(Me)_2CH_2O$ | |
| 4-$CF_3$ | 4-F | 4-CN | iPr | S | $OCH_2C(Me)_2CH_2O$ | |
| 4-$OCF_3$ | 4-F | 4-CN | iPr | S | $OCH_2C(Me)_2CH_2O$ | |
| 4-$CF_3$ | 4-Cl | 4-$CO_2$Me | iPr | S | $OCH_2C(Me)_2CH_2O$ | |
| 4-$CF_3$ | 4-Cl | H | tBu | S | OiPr | OiPr |
| 4-$CF_3$ | 4-F | H | tBu | S | OiPr | OiPr |
| 4-$CF_3$ | 4-$OCF_2H$ | H | tBu | S | $OCH_2CH_2CH_2O$ | |
| 4-$OCF_3$ | 4-$OCF_2H$ | H | tBu | S | $OCH_2CH_2CH_2O$ | |
| 4-$CF_3$ | 4-Br | H | tBu | S | $OCH_2CH_2CH_2O$ | |
| 4-$CF_3$ | 4-Cl | 4-Cl | tBu | S | $OCH_2CH_2O$ | |
| 4-Br | 4-Cl | 4-Cl | tBu | S | $OCH_2CH_2O$ | |
| 4-$OCF_3$ | 4-Cl | 4-Cl | tBu | S | $OCH_2CH_2O$ | |
| 4-$CF_3$ | 4-F | 4-Cl | Me | S | OEt | OEt |
| 4-$OCF_3$ | 4-F | 4-Cl | Me | S | OEt | OEt |
| 4-$CF_3$ | 4-$OCF_2H$ | 4-Cl | Me | S | OEt | OEt |
| 4-Cl | 4-$OCF_2H$ | 4-Cl | Me | S | OEt | OEt |
| 4-$CF_3$ | 4-F | 4-CN | tBu | O | OEt | OEt |
| 4-$OCF_3$ | 4-F | 4-CN | tBu | O | OEt | OEt |
| 4-$CF_3$ | 4-Cl | 4-$CO_2$Me | tBu | O | $OCH_2C(Me)_2CH_2O$ | |

TABLE 19

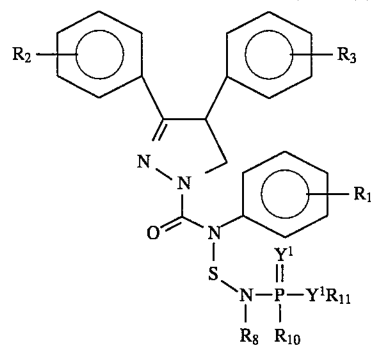

| $R_1$ | $R_2$ | $R_3$ | $R_8$ | $Y^1$ | $R_{10}$ | $Y^1R_{11}$ |
|---|---|---|---|---|---|---|
| 4-$CF_3$ | 4-Cl | H | iPr | O | Et | OEt |
| 4-$OCF_3$ | 4-Cl | H | iPr | O | Et | OEt |
| 4-$CF_3$ | 4-F | H | iPr | O | Et | OEt |
| 4-$OCF_3$ | 4-F | H | iPr | O | Et | OEt |
| 4-$CF_3$ | 4-$OCF_2H$ | H | iPr | O | Et | OEt |
| 4-$OCF_3$ | 4-$OCF_2H$ | H | iPr | O | Et | OEt |
| 4-$CF_3$ | 4-Br | H | iPr | O | Et | OEt |

TABLE 19-continued

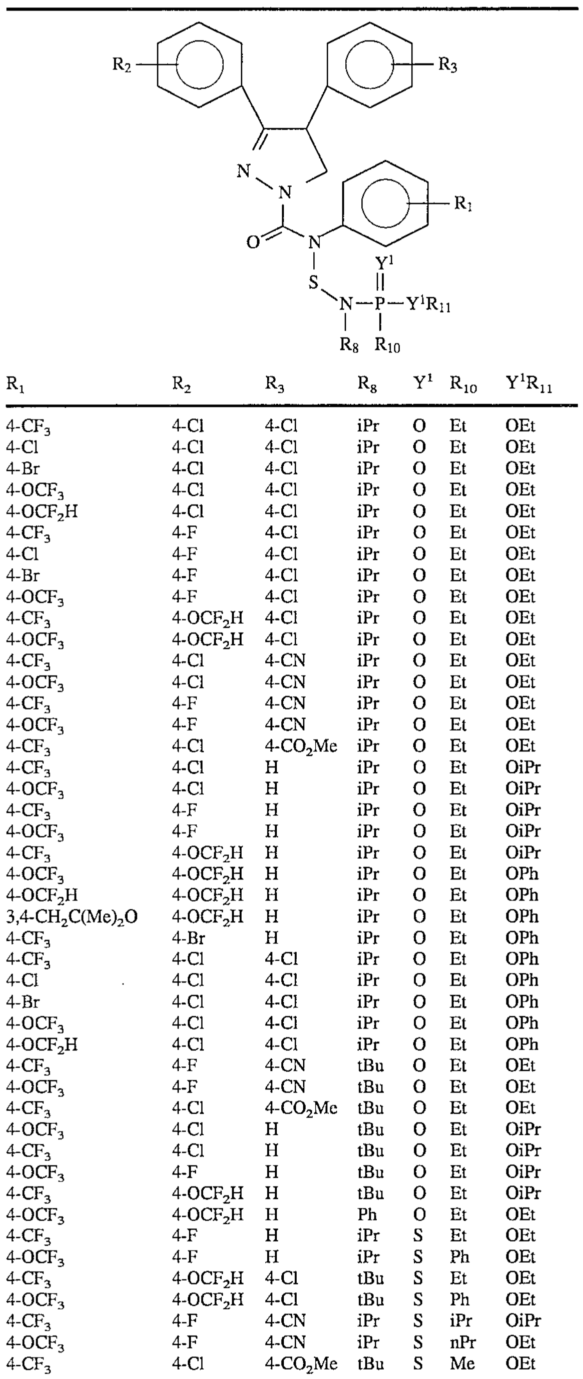

| $R_1$ | $R_2$ | $R_3$ | $R_8$ | $Y^1$ | $R_{10}$ | $Y^1R_{11}$ |
|---|---|---|---|---|---|---|
| 4-CF$_3$ | 4-Cl | 4-Cl | iPr | O | Et | OEt |
| 4-Cl | 4-Cl | 4-Cl | iPr | O | Et | OEt |
| 4-Br | 4-Cl | 4-Cl | iPr | O | Et | OEt |
| 4-OCF$_3$ | 4-Cl | 4-Cl | iPr | O | Et | OEt |
| 4-OCF$_2$H | 4-Cl | 4-Cl | iPr | O | Et | OEt |
| 4-CF$_3$ | 4-F | 4-Cl | iPr | O | Et | OEt |
| 4-Cl | 4-F | 4-Cl | iPr | O | Et | OEt |
| 4-Br | 4-F | 4-Cl | iPr | O | Et | OEt |
| 4-OCF$_3$ | 4-F | 4-Cl | iPr | O | Et | OEt |
| 4-CF$_3$ | 4-OCF$_2$H | 4-Cl | iPr | O | Et | OEt |
| 4-OCF$_3$ | 4-OCF$_2$H | 4-Cl | iPr | O | Et | OEt |
| 4-CF$_3$ | 4-Cl | 4-CN | iPr | O | Et | OEt |
| 4-OCF$_3$ | 4-Cl | 4-CN | iPr | O | Et | OEt |
| 4-CF$_3$ | 4-F | 4-CN | iPr | O | Et | OEt |
| 4-OCF$_3$ | 4-F | 4-CN | iPr | O | Et | OEt |
| 4-CF$_3$ | 4-Cl | 4-CO$_2$Me | iPr | O | Et | OEt |
| 4-CF$_3$ | 4-Cl | H | iPr | O | Et | OiPr |
| 4-OCF$_3$ | 4-Cl | H | iPr | O | Et | OiPr |
| 4-CF$_3$ | 4-F | H | iPr | O | Et | OiPr |
| 4-OCF$_3$ | 4-F | H | iPr | O | Et | OiPr |
| 4-CF$_3$ | 4-OCF$_2$H | H | iPr | O | Et | OiPr |
| 4-OCF$_3$ | 4-OCF$_2$H | H | iPr | O | Et | OPh |
| 4-OCF$_2$H | 4-OCF$_2$H | H | iPr | O | Et | OPh |
| 3,4-CH$_2$C(Me)$_2$O | 4-OCF$_2$H | H | iPr | O | Et | OPh |
| 4-CF$_3$ | 4-Br | H | iPr | O | Et | OPh |
| 4-CF$_3$ | 4-Cl | 4-Cl | iPr | O | Et | OPh |
| 4-Cl | 4-Cl | 4-Cl | iPr | O | Et | OPh |
| 4-Br | 4-Cl | 4-Cl | iPr | O | Et | OPh |
| 4-OCF$_3$ | 4-Cl | 4-Cl | iPr | O | Et | OPh |
| 4-OCF$_2$H | 4-Cl | 4-Cl | iPr | O | Et | OPh |
| 4-CF$_3$ | 4-F | 4-CN | tBu | O | Et | OEt |
| 4-OCF$_3$ | 4-F | 4-CN | tBu | O | Et | OEt |
| 4-CF$_3$ | 4-Cl | 4-CO$_2$Me | tBu | O | Et | OEt |
| 4-OCF$_3$ | 4-Cl | H | tBu | O | Et | OiPr |
| 4-CF$_3$ | 4-Cl | H | tBu | O | Et | OiPr |
| 4-OCF$_3$ | 4-F | H | tBu | O | Et | OiPr |
| 4-CF$_3$ | 4-OCF$_2$H | H | tBu | O | Et | OiPr |
| 4-OCF$_3$ | 4-OCF$_2$H | H | Ph | O | Et | OEt |
| 4-CF$_3$ | 4-F | H | iPr | S | Et | OEt |
| 4-OCF$_3$ | 4-F | H | iPr | S | Ph | OEt |
| 4-CF$_3$ | 4-OCF$_2$H | 4-Cl | tBu | S | Et | OEt |
| 4-OCF$_3$ | 4-OCF$_2$H | 4-Cl | tBu | S | Ph | OEt |
| 4-CF$_3$ | 4-F | 4-CN | iPr | S | iPr | OiPr |
| 4-OCF$_3$ | 4-F | 4-CN | iPr | S | nPr | OEt |
| 4-CF$_3$ | 4-Cl | 4-CO$_2$Me | tBu | S | Me | OEt |

TABLE 20

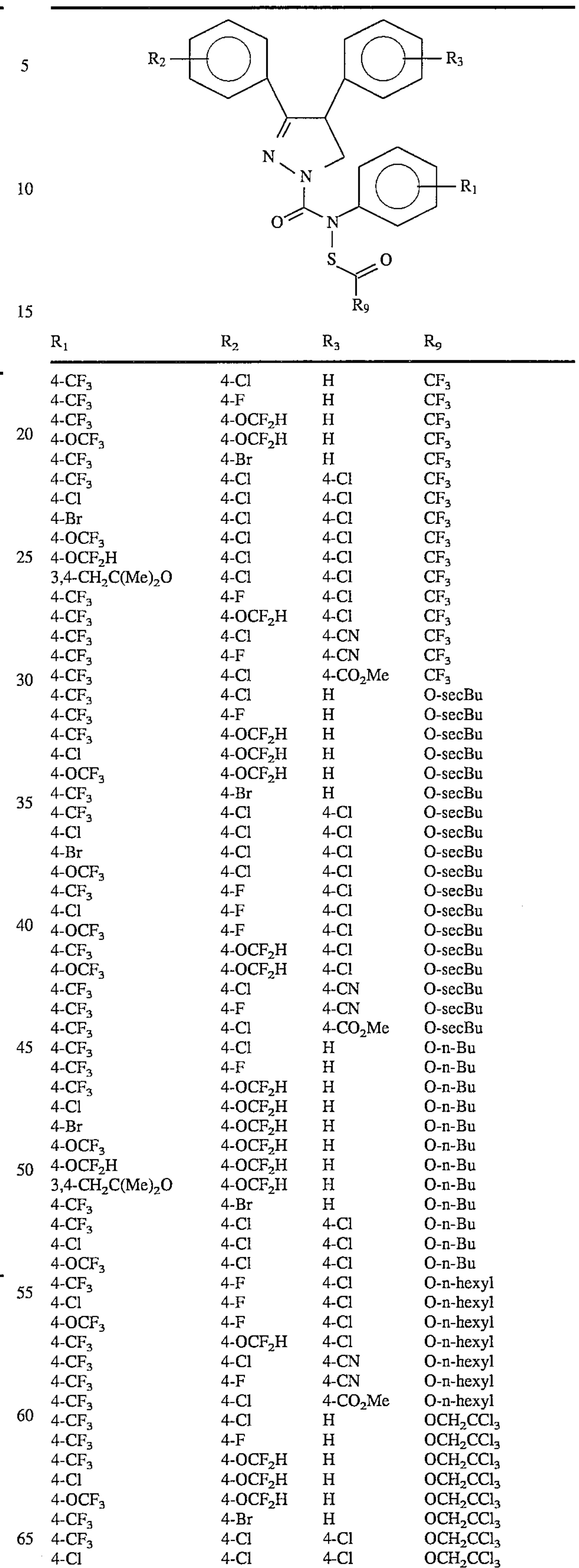

| $R_1$ | $R_2$ | $R_3$ | $R_9$ |
|---|---|---|---|
| 4-CF$_3$ | 4-Cl | H | CF$_3$ |
| 4-CF$_3$ | 4-F | H | CF$_3$ |
| 4-CF$_3$ | 4-OCF$_2$H | H | CF$_3$ |
| 4-OCF$_3$ | 4-OCF$_2$H | H | CF$_3$ |
| 4-CF$_3$ | 4-Br | H | CF$_3$ |
| 4-CF$_3$ | 4-Cl | 4-Cl | CF$_3$ |
| 4-Cl | 4-Cl | 4-Cl | CF$_3$ |
| 4-Br | 4-Cl | 4-Cl | CF$_3$ |
| 4-OCF$_3$ | 4-Cl | 4-Cl | CF$_3$ |
| 4-OCF$_2$H | 4-Cl | 4-Cl | CF$_3$ |
| 3,4-CH$_2$C(Me)$_2$O | 4-Cl | 4-Cl | CF$_3$ |
| 4-CF$_3$ | 4-F | 4-Cl | CF$_3$ |
| 4-CF$_3$ | 4-OCF$_2$H | 4-Cl | CF$_3$ |
| 4-CF$_3$ | 4-Cl | 4-CN | CF$_3$ |
| 4-CF$_3$ | 4-F | 4-CN | CF$_3$ |
| 4-CF$_3$ | 4-Cl | 4-CO$_2$Me | CF$_3$ |
| 4-CF$_3$ | 4-Cl | H | O-secBu |
| 4-CF$_3$ | 4-F | H | O-secBu |
| 4-CF$_3$ | 4-OCF$_2$H | H | O-secBu |
| 4-Cl | 4-OCF$_2$H | H | O-secBu |
| 4-OCF$_3$ | 4-OCF$_2$H | H | O-secBu |
| 4-CF$_3$ | 4-Br | H | O-secBu |
| 4-CF$_3$ | 4-Cl | 4-Cl | O-secBu |
| 4-Cl | 4-Cl | 4-Cl | O-secBu |
| 4-Br | 4-Cl | 4-Cl | O-secBu |
| 4-OCF$_3$ | 4-Cl | 4-Cl | O-secBu |
| 4-CF$_3$ | 4-F | 4-Cl | O-secBu |
| 4-Cl | 4-F | 4-Cl | O-secBu |
| 4-OCF$_3$ | 4-F | 4-Cl | O-secBu |
| 4-CF$_3$ | 4-OCF$_2$H | 4-Cl | O-secBu |
| 4-OCF$_3$ | 4-OCF$_2$H | 4-Cl | O-secBu |
| 4-CF$_3$ | 4-Cl | 4-CN | O-secBu |
| 4-CF$_3$ | 4-F | 4-CN | O-secBu |
| 4-CF$_3$ | 4-Cl | 4-CO$_2$Me | O-secBu |
| 4-CF$_3$ | 4-Cl | H | O-n-Bu |
| 4-CF$_3$ | 4-F | H | O-n-Bu |
| 4-CF$_3$ | 4-OCF$_2$H | H | O-n-Bu |
| 4-Cl | 4-OCF$_2$H | H | O-n-Bu |
| 4-Br | 4-OCF$_2$H | H | O-n-Bu |
| 4-OCF$_3$ | 4-OCF$_2$H | H | O-n-Bu |
| 4-OCF$_2$H | 4-OCF$_2$H | H | O-n-Bu |
| 3,4-CH$_2$C(Me)$_2$O | 4-OCF$_2$H | H | O-n-Bu |
| 4-CF$_3$ | 4-Br | H | O-n-Bu |
| 4-CF$_3$ | 4-Cl | 4-Cl | O-n-Bu |
| 4-Cl | 4-Cl | 4-Cl | O-n-Bu |
| 4-OCF$_3$ | 4-Cl | 4-Cl | O-n-Bu |
| 4-CF$_3$ | 4-F | 4-Cl | O-n-hexyl |
| 4-Cl | 4-F | 4-Cl | O-n-hexyl |
| 4-OCF$_3$ | 4-F | 4-Cl | O-n-hexyl |
| 4-CF$_3$ | 4-OCF$_2$H | 4-Cl | O-n-hexyl |
| 4-CF$_3$ | 4-Cl | 4-CN | O-n-hexyl |
| 4-CF$_3$ | 4-F | 4-CN | O-n-hexyl |
| 4-CF$_3$ | 4-Cl | 4-CO$_2$Me | O-n-hexyl |
| 4-CF$_3$ | 4-Cl | H | OCH$_2$CCl$_3$ |
| 4-CF$_3$ | 4-F | H | OCH$_2$CCl$_3$ |
| 4-CF$_3$ | 4-OCF$_2$H | H | OCH$_2$CCl$_3$ |
| 4-Cl | 4-OCF$_2$H | H | OCH$_2$CCl$_3$ |
| 4-OCF$_3$ | 4-OCF$_2$H | H | OCH$_2$CCl$_3$ |
| 4-CF$_3$ | 4-Br | H | OCH$_2$CCl$_3$ |
| 4-CF$_3$ | 4-Cl | 4-Cl | OCH$_2$CCl$_3$ |
| 4-Cl | 4-Cl | 4-Cl | OCH$_2$CCl$_3$ |

TABLE 20-continued

| $R_1$ | $R_2$ | $R_3$ | $R_9$ |
|---|---|---|---|
| 4-$OCF_3$ | 4-Cl | 4-Cl | $OCH_2CCl_3$ |
| 4-$CF_3$ | 4-F | 4-Cl | $OCH_2CH_2OEt$ |
| 4-$CF_3$ | 4-$OCF_2H$ | 4-Cl | $OCH_2CH_2OEt$ |
| 4-$CF_3$ | 4-Cl | 4-CN | $OCH_2CH_2OEt$ |
| 4-$CF_3$ | 4-F | 4-CN | $OCH_2CH_2OEt$ |
| 4-$CF_3$ | 4-Cl | 4-$CO_2Me$ | $OCH_2CH_2OEt$ |

TABLE 21

| $R_1$ | $R_2$ | $R_3$ | $R_{10}$ | $R_{11}$ |
|---|---|---|---|---|
| 4-$CF_3$ | 4-Cl | H | Et | Et |
| 4-$CF_3$ | 4-F | H | Et | Et |
| 4-$CF_3$ | 4-$OCF_2H$ | H | Et | Et |
| 4-$CF_3$ | 4-Br | H | Et | Et |
| 4-$CF_3$ | 4-Cl | 4-Cl | Et | Et |
| 4-Cl | 4-Cl | 4-Cl | Et | Et |
| 4-Br | 4-Cl | 4-Cl | Et | Et |
| 4-$OCF_3$ | 4-Cl | 4-Cl | Et | Et |
| 4-$OCF_2H$ | 4-Cl | 4-Cl | Et | Et |
| 3,4-$CH_2C(Me)_2O$ | 4-Cl | 4-Cl | Et | Et |
| 4-$CF_3$ | 4-F | 4-Cl | Et | Et |
| 4-Cl | 4-F | 4-Cl | Et | Et |
| 4-Br | 4-F | 4-Cl | Et | Et |

TABLE 21-continued

| $R_1$ | $R_2$ | $R_3$ | $R_{10}$ | $R_{11}$ |
|---|---|---|---|---|
| 4-$OCF_3$ | 4-F | 4-Cl | Et | Et |
| 4-$OCF_2H$ | 4-F | 4-Cl | Et | Et |
| 3,4-$CH_2C(Me)_2O$ | 4-F | 4-Cl | Et | Et |
| 4-$CF_3$ | 4-$OCF_2H$ | 4-Cl | Et | Et |
| 4-$CF_3$ | 4-Cl | 4-CN | Et | Et |
| 4-$CF_3$ | 4-F | 4-CN | Et | Et |
| 4-$CF_3$ | 4-Cl | 4-$CO_2Me$ | Et | Et |
| 4-$CF_3$ | 4-Cl | H | $-CH_2CH_2-$ | |
| 4-$CF_3$ | 4-F | H | $-CH_2CH_2-$ | |
| 4-$CF_3$ | 4-$OCF_2H$ | H | $-CH_2CH_2-$ | |
| 4-$CF_3$ | 4-Br | H | $-CH_2CH_2-$ | |
| 4-$CF_3$ | 4-Cl | 4-Cl | $-CH_2CH_2-$ | |
| 4-Cl | 4-Cl | 4-Cl | $-CH_2CH_2-$ | |
| 4-$OCF_3$ | 4-Cl | 4-Cl | $-CH_2CH_2-$ | |
| 4-$CF_3$ | 4-F | 4-Cl | $-CH_2CH_2CH_2-$ | |
| 4-Cl | 4-F | 4-Cl | $-CH_2CH_2CH_2-$ | |
| 4-$OCF_3$ | 4-F | 4-Cl | $-CH_2CH_2CH_2-$ | |
| 4-$CF_3$ | 4-$OCF_2H$ | 4-Cl | $-CH_2CH_2CH_2-$ | |
| 4-Cl | 4-$OCF_2H$ | 4-Cl | $-CH_2CH_2CH_2-$ | |
| 4-$OCF_3$ | 4-$OCF_2H$ | 4-Cl | $-CH_2CH_2CH_2-$ | |
| 4-$CF_3$ | 4-Cl | 4-CN | $-CH_2CH_2CH_2-$ | |
| 4-$CF_3$ | 4-F | 4-CN | $-CH_2CH_2CH_2-$ | |
| 4-$CF_3$ | 4-Cl | 4-$CO_2Me$ | $-CH_2CH_2CH_2-$ | |
| 4-$CF_3$ | 4-Cl | H | $-CH_2C(Me)_2CH_2-$ | |
| 4-$CF_3$ | 4-F | H | $-CH_2C(Me)_2CH_2-$ | |
| 4-$CF_3$ | 4-$OCF_2H$ | H | $-CH_2C(Me)_2CH_2-$ | |
| 4-$CF_3$ | 4-Br | H | $-CH_2C(Me)_2CH_2-$ | |
| 4-$CF_3$ | 4-Cl | 4-Cl | $-CH_2C(Me)_2CH_2-$ | |
| 4-Cl | 4-Cl | 4-Cl | $-CH_2C(Me)_2CH_2-$ | |
| 4-Br | 4-Cl | 4-Cl | $-CH_2C(Me)_2CH_2-$ | |
| 4-$OCF_3$ | 4-Cl | 4-Cl | $-CH_2C(Me)_2CH_2-$ | |
| 4-$OCF_2H$ | 4-Cl | 4-Cl | $-CH_2C(Me)_2CH_2-$ | |
| 3,4-$CH_2C(Me)_2O$ | 4-Cl | 4-Cl | $-CH_2C(Me)_2CH_2-$ | |
| 4-$CF_3$ | 4-F | 4-Cl | Ph | Ph |
| 4-$CF_3$ | 4-$OCF_2H$ | 4-Cl | Ph | Ph |
| 4-$CF_3$ | 4-Cl | 4-CN | Ph | Ph |
| 4-$CF_3$ | 4-F | 4-CN | Ph | Ph |
| 4-$CF_3$ | 4-Cl | 4-$CO_2Me$ | Ph | Ph |

TABLE 22

| $R_1$ | $R_2$ | $R_3$ | $R_8$ | $R_{12}$ |
|---|---|---|---|---|
| 4-$CF_3$ | 4-Cl | H | nBu | nBu |
| 4-Cl | 4-Cl | H | nBu | nBu |
| 4-$OCF_3$ | 4-Cl | H | nBu | nBu |
| 4-$CF_3$ | 4-F | H | nBu | nBu |
| 4-$CF_3$ | 4-$OCF_2H$ | H | nBu | nBu |
| 4-$OCF_3$ | 4-$OCF_2H$ | H | nBu | nBu |
| 4-$CF_3$ | 4-Br | H | nBu | nBu |
| 4-$CF_3$ | 4-Cl | 4-Cl | nBu | nBu |
| 4-Cl | 4-Cl | 4-Cl | nBu | nBu |
| 4-Br | 4-Cl | 4-Cl | nBu | nBu |
| 4-$OCF_3$ | 4-Cl | 4-Cl | nBu | nBu |
| 4-$CF_3$ | 4-F | 4-Cl | $-CH_2CH_2CH_2CH_2CH_2-$ | |
| 4-$CF_3$ | 4-$OCF_2H$ | 4-Cl | $-CH_2CH_2CH_2CH_2CH_2-$ | |
| 4-$CF_3$ | 4-Cl | 4-CN | $-CH_2CH_2CH_2CH_2CH_2-$ | |
| 4-$CF_3$ | 4-F | 4-CN | $-CH_2CH_2CH_2CH_2CH_2-$ | |
| 4-$CF_3$ | 4-Cl | 4-$CO_2Me$ | $-CH_2CH_2CH_2CH_2CH_2-$ | |
| 4-$CF_3$ | 4-Cl | H | $-CH_2CH_2OCH_2CH_2-$ | |
| 4-$OCF_3$ | 4-Cl | H | $-CH_2CH_2OCH_2CH_2-$ | |
| 4-$CF_3$ | 4-F | H | $-CH_2CH_2OCH_2CH_2-$ | |
| 4-$OCF_3$ | 4-F | H | $-CH_2CH_2OCH_2CH_2-$ | |
| 4-$CF_3$ | 4-$OCF_2H$ | H | $-CH_2CH_2OCH_2CH_2-$ | |
| 4-$OCF_3$ | 4-$OCF_2H$ | H | $-CH_2CH_2OCH_2CH_2-$ | |
| 4-$CF_3$ | 4-Br | H | $-CH_2CH_2OCH_2CH_2-$ | |
| 4-$CF_3$ | 4-Cl | 4-Cl | $-CH_2CH_2OCH_2CH_2-$ | |
| 4-Cl | 4-Cl | 4-Cl | $-CH_2CH_2OCH_2CH_2-$ | |
| 4-Br | 4-Cl | 4-Cl | $-CH_2CH_2OCH_2CH_2-$ | |
| 4-$OCF_3$ | 4-Cl | 4-Cl | $-CH_2CH_2OCH_2CH_2-$ | |
| 4-$CF_3$ | 4-F | 4-Cl | $-CH_2CHMeOCHMeCH_2-$ | |
| 4-$CF_3$ | 4-$OCF_2H$ | 4-Cl | $-CH_2CHMeOCHMeCH_2-$ | |
| 4-$CF_3$ | 4-Cl | 4-CN | $-CH_2CHMeOCHMeCH_2-$ | |
| 4-$CF_3$ | 4-F | 4-CN | $-CH_2CHMeOCHMeCH_2-$ | |
| 4-$CF_3$ | 4-Cl | 4-$CO_2Me$ | $-CH_2CHMeOCHMeCH_2-$ | |
| 4-$CF_3$ | 4-Cl | H | Et | cyclo-$C_6H_{11}$ |
| 4-$CF_3$ | 4-F | H | Et | cyclo-$C_6H_{11}$ |
| 4-$CF_3$ | 4-$OCF_2H$ | H | Et | cyclo-$C_6H_{11}$ |
| 4-$CF_3$ | 4-Br | H | Et | cyclo-$C_6H_{11}$ |
| 4-$CF_3$ | 4-Cl | 4-Cl | Et | cyclo-$C_6H_{11}$ |
| 4-Cl | 4-Cl | 4-Cl | Et | cyclo-$C_6H_{11}$ |
| 4-Br | 4-Cl | 4-Cl | Et | cyclo-$C_6H_{11}$ |
| 4-$OCF_3$ | 4-Cl | 4-Cl | Et | cyclo-$C_6H_{11}$ |
| 4-$CF_3$ | 4-F | 4-Cl | iPr | $-CH_2CH_2CO_2ET$ |
| 4-Cl | 4-F | 4-Cl | iPr | $-CH_2CH_2CO_2ET$ |
| 4-$OCF_3$ | 4-F | 4-Cl | iPr | $-CH_2CH_2CO_2ET$ |
| 4-$CF_3$ | 4-$OCF_2H$ | 4-Cl | iPr | $-CH_2CH_2CO_2ET$ |
| 4-Cl | 4-$OCF_2H$ | 4-Cl | iPr | $-CH_2CH_2CO_2ET$ |
| 4-Br | 4-$OCF_2H$ | 4-Cl | iPr | $-CH_2CH_2CO_2ET$ |
| 4-$OCF_3$ | 4-$OCF_2H$ | 4-Cl | iPr | $-CH_2CH_2CO_2ET$ |
| 4-$OCF_2H$ | 4-$OCF_2H$ | 4-Cl | iPr | $-CH_2CH_2CO_2ET$ |
| 3,4-$CH_2C(Me)_2O$ | 4-$OCF_2H$ | 4-Cl | iPr | $-CH_2CH_2CO_2ET$ |
| 4-$CF_3$ | 4-Cl | 4-CN | iPr | $-CH_2CH_2CO_2ET$ |
| 4-Cl | 4-Cl | 4-CN | iPr | $-CH_2CH_2CO_2ET$ |
| 4-$OCF_3$ | 4-Cl | 4-CN | $CF_3$ | 2,4-di-Cl$-$Ph |
| 4-$CF_3$ | 4-F | 4-CN | $CF_3$ | 2,4-di-Cl$-$Ph |
| 4-$CF_3$ | 4-Cl | 4-$CO_2Me$ | $CF_3$ | 2,4-di-Cl$-$Ph |

TABLE 23

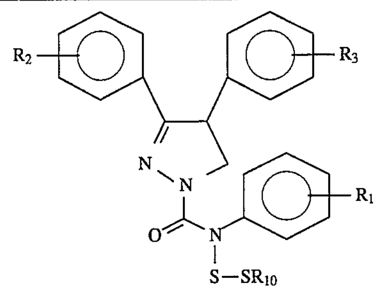

| $R_1$ | $R_2$ | $R_3$ | $R_{10}$ |
|---|---|---|---|
| 4-$CF_3$ | 4-Cl | H | tBu |
| 4-$OCF_3$ | 4-Cl | H | tBu |
| 4-$CF_3$ | 4-F | H | tBu |
| 4-$CF_3$ | 4-$OCF_2H$ | H | tBu |
| 4-$OCF_3$ | 4-$OCF_2H$ | H | tBu |
| 4-$CF_3$ | 4-Br | H | tBu |
| 4-$CF_3$ | 4-Cl | 4-Cl | tBu |
| 4-Cl | 4-Cl | 4-Cl | tBu |
| 4-Br | 4-Cl | 4-Cl | tBu |
| 4-$OCF_3$ | 4-Cl | 4-Cl | tBu |
| 4-$OCF_2H$ | 4-Cl | 4-Cl | tBu |
| 4-$CF_3$ | 4-F | 4-Cl | tBu |
| 4-$CF_3$ | 4-$OCF_2H$ | 4-Cl | tBu |
| 4-Cl | 4-$OCF_2H$ | 4-Cl | tBu |
| 4-$OCF_3$ | 4-$OCF_2H$ | 4-Cl | tBu |
| 4-$CF_3$ | 4-Cl | 4-CN | tBu |
| 4-$CF_3$ | 4-F | 4-CN | tBu |
| 4-$CF_3$ | 4-Cl | 4-$CO_2Me$ | tBu |
| 4-$CF_3$ | 4-Cl | H | sec-Bu |
| 4-$OCF_3$ | 4-Cl | H | sec-Bu |
| 4-$CF_3$ | 4-F | H | sec-Bu |
| 4-$OCF_3$ | 4-F | H | sec-Bu |
| 4-$CF_3$ | 4-$OCF_2H$ | H | sec-Bu |
| 4-Cl | 4-$OCF_2H$ | H | sec-Bu |
| 4-$OCF_3$ | 4-$OCF_2H$ | H | Ph |
| 4-$OCF_2H$ | 4-$OCF_2H$ | H | Ph |
| 3,4-$CH_2C(Me)_2O$ | 4-$OCF_2H$ | H | Ph |
| 4-$CF_3$ | 4-Br | H | Ph |
| 4-$CF_3$ | 4-Cl | 4-Cl | Ph |
| 4-Cl | 4-Cl | 4-Cl | Ph |
| 4-Br | 4-Cl | 4-Cl | Ph |
| 4-$OCF_3$ | 4-Cl | 4-Cl | Ph |
| 4-$OCF_2H$ | 4-Cl | 4-Cl | Ph |
| 3,4-$CH_2C(Me)_2O$ | 4-Cl | 4-Cl | Ph |
| 4-$CF_3$ | 4-F | 4-Cl | 4-Cl—Ph |
| 4-Cl | 4-F | 4-Cl | 4-Cl—Ph |
| 4-Br | 4-F | 4-Cl | 4-Cl—Ph |
| 4-$OCF_3$ | 4-F | 4-Cl | 4-Cl—Ph |
| 4-$OCF_2H$ | 4-F | 4-Cl | 4-Cl—Ph |
| 3,4-$CH_2C(Me)_2O$ | 4-F | 4-Cl | 4-Cl—Ph |
| 4-$CF_3$ | 4-$OCF_2H$ | 4-Cl | 4-Cl—Ph |
| 4-$CF_3$ | 4-Cl | 4-CN | 4-Cl—Ph |
| 4-$OCF_3$ | 4-Cl | 4-CN | 2-Me-4-t-Bu—Ph |
| 4-$CF_3$ | 4-F | 4-CN | 2-Me-4-t-Bu—Ph |
| 4-$OCF_3$ | 4-F | 4-CN | 2-Me-4-t-Bu—Ph |
| 4-$CF_3$ | 4-Cl | 4-$CO_2He$ | 2-Me-4-t-Bu—Ph |
| 4-$CF_3$ | 4-Cl | H | 2-$NO_2$—Ph |
| 4-$OCF_3$ | 4-Cl | H | 2-$NO_2$—Ph |
| 4-$CF_3$ | 4-F | H | 2-$NO_2$—Ph |
| 4-$CF_3$ | 4-$OCF_2H$ | H | 2-$NO_2$—Ph |
| 4-$OCF_3$ | 4-$OCF_2H$ | H | 2-$NO_2$—Ph |
| 4-$CF_3$ | 4-Br | H | 2-$NO_2$—Ph |
| 4-$CF_3$ | 4-Cl | 4-Cl | 2-$NO_2$—Ph |
| 4-Cl | 4-Cl | 4-Cl | 2-$NO_2$—Ph |
| 4-Br | 4-Cl | 4-Cl | 2-$NO_2$—Ph |
| 4-$OCF_3$ | 4-Cl | 4-Cl | 2-$NO_2$—Ph |
| 4-$CF_3$ | 4-F | 4-Cl | 2-$NO_2$Ph |
| 4-Cl | 4-F | 4-Cl | 2-$NO_2$Ph |
| 4-$OCF_3$ | 4-F | 4-Cl | 2-$NO_2$Ph |
| 4-$CF_3$ | 4-$OCF_2H$ | 4-Cl | 2-$NO_2$Ph |
| 4-$OCF_3$ | 4-$OCF_2H$ | 4-Cl | 2-$NO_2$Ph |
| 4-$CF_3$ | 4-Cl | 4-CN | 2-$NO_2$Ph |
| 4-$OCF_3$ | 4-Cl | 4-CN | 2-$NO_2$Ph |

TABLE 23-continued

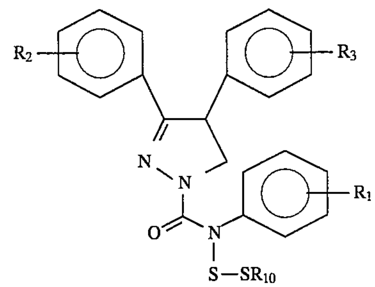

| $R_1$ | $R_2$ | $R_3$ | $R_{10}$ |
|---|---|---|---|
| 4-$CF_3$ | 4-F | 4-CN | 2-$NO_2$Ph |
| 4-$CF_3$ | 4-Cl | 4-$CO_2Me$ | 2-$NO_2$Ph |

TABLE 24

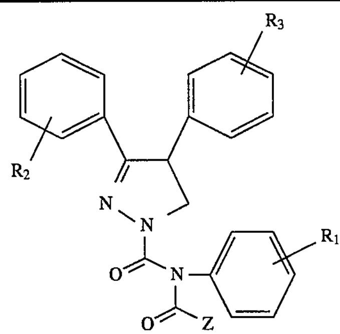

| $R_1$ | $R_2$ | $R_3$ | Z |
|---|---|---|---|
| 4-$CF_3$ | 4-H | 4-H | $CH_3$ |
| 4-$CF_3$ | 4-H | 4-Cl | $CH_3$ |
| 4-$CF_3$ | 4-H | 4-F | $CH_3$ |
| 4-$CF_3$ | 4-F | 4-H | $CH_3$ |
| 4-$CF_3$ | 4-F | 4-Cl | $CH_3$ |
| 4-$CF_3$ | 4-F | 4-F | $CH_3$ |
| 4-$CF_3$ | 4-Cl | 4-H | $CH_3$ |
| 4-$CF_3$ | 4-Cl | 4-Cl | $CH_3$ |
| 4-$CF_3$ | 4-Cl | 4-F | $CH_3$ |
| 4-$CF_3$ | 4-$OCHF_2$ | 4-H | $CH_3$ |
| 4-$CF_3$ | 4-$OCHF_2$ | 4-Cl | $CH_3$ |
| 4-$CF_3$ | 4-$OCHF_2$ | 4-F | $CH_3$ |
| 4-$OCF_3$ | 4-H | 4-H | $CH_3$ |
| 4-$OCF_3$ | 4-H | 4-Cl | $CH_3$ |
| 4-$OCF_3$ | 4-H | 4-F | $CH_3$ |
| 4-$OCF_3$ | 4-F | 4-H | $CH_3$ |
| 4-$OCF_3$ | 4-F | 4-Cl | $CH_3$ |
| 4-$OCF_3$ | 4-F | 4-F | $CH_3$ |
| 4-$OCF_3$ | 4-Cl | 4-H | $CH_3$ |
| 4-$OCF_3$ | 4-Cl | 4-Cl | $CH_3$ |
| 4-$OCF_3$ | 4-Cl | 4-F | $CH_3$ |
| 4-Cl | 4-H | 4-H | $CH_3$ |
| 4-Cl | 4-H | 4-Cl | $CH_3$ |
| 4-Cl | 4-H | 4-F | $CH_3$ |
| 4-Cl | 4-Cl | 4-H | $CH_3$ |
| 4-Cl | 4-Cl | 4-Cl | $CH_3$ |
| 4-Cl | 4-Cl | 4-F | $CH_3$ |
| 4-Cl | 4-F | 4-H | $CH_3$ |
| 4-Cl | 4-F | 4-Cl | $CH_3$ |
| 4-Cl | 4-F | 4-F | $CH_3$ |
| 4-Br | 4-H | 4-H | $CH_3$ |
| 4-Br | 4-H | 4-F | $CH_3$ |
| 4-Br | 4-H | 4-Cl | $CH_3$ |
| 4-Br | 4-Cl | 4-H | $CH_3$ |
| 4-Br | 4-Cl | 4-F | $CH_3$ |
| 4-Br | 4-Cl | 4-Cl | $CH_3$ |
| 4-Br | 4-F | 4-H | $CH_3$ |
| 4-Br | 4-F | 4-F | $CH_3$ |
| 4-Br | 4-F | 4-Cl | $CH_3$ |

TABLE 24-continued

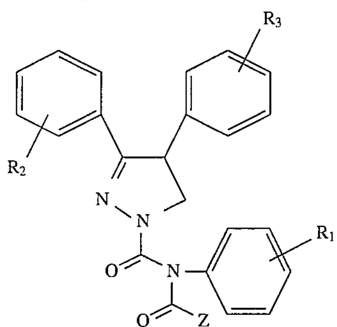

| $R_1$ | $R_2$ | $R_3$ | Z |
|---|---|---|---|
| 4-$OCHF_2$ | 4-H | 4-H | $CH_3$ |
| 4-$OCHF_2$ | 4-H | 4-F | $CH_3$ |
| 4-$OCHF_2$ | 4-H | 4-Cl | $CH_3$ |
| 4-$OCHF_2$ | 4-F | 4-H | $CH_3$ |
| 4-$OCHF_2$ | 4-F | 4-F | $CH_3$ |
| 4-$OCHF_2$ | 4-F | 4-Cl | $CH_3$ |
| 4-$OCHF_2$ | 4-Cl | 4-H | $CH_3$ |
| 4-$OCHF_2$ | 4-Cl | 4-F | $CH_3$ |
| 4-$OCHF_2$ | 4-Cl | 4-Cl | $CH_3$ |
| 4-$CF_3$ | 4-H | 4-H | $CH_3CH_2$ |
| 4-$CF_3$ | 4-H | 4-Cl | $CH_3CH_2$ |
| 4-$CF_3$ | 4-H | 4-F | $CH_3CH_2$ |
| 4-$CF_3$ | 4-F | 4-H | $CH_3CH_2$ |
| 4-$CF_3$ | 4-F | 4-Cl | $CH_3CH_2$ |
| 4-$CF_3$ | 4-F | 4-F | $CH_3CH_2$ |
| 4-$CF_3$ | 4-Cl | 4-H | $CH_3CH_2$ |
| 4-$CF_3$ | 4-Cl | 4-Cl | $CH_3CH_2$ |
| 4-$CF_3$ | 4-Cl | 4-F | $CH_3CH_2$ |
| 4-$CF_3$ | 4-$OCHF_2$ | 4-H | $CH_3CH_2$ |
| 4-$CF_3$ | 4-$OCHF_2$ | 4-Cl | $CH_3CH_2$ |
| 4-$CF_3$ | 4-$OCHF_2$ | 4-F | $CH_3CH_2$ |
| 4-$OCF_3$ | 4-H | 4-H | $CH_3CH_2$ |
| 4-$OCF_3$ | 4-H | 4-Cl | $CH_3CH_2$ |
| 4-$OCF_3$ | 4-H | 4-F | $CH_3CH_2$ |
| 4-$OCF_3$ | 4-F | 4-H | $CH_3CH_2$ |
| 4-$OCF_3$ | 4-F | 4-Cl | $CH_3CH_2$ |
| 4-$OCF_3$ | 4-F | 4-F | $CH_3CH_2$ |
| 4-$OCF_3$ | 4-Cl | 4-H | $CH_3CH_2$ |
| 4-$OCF_3$ | 4-Cl | 4-Cl | $CH_3CH_2$ |
| 4-$OCF_3$ | 4-Cl | 4-F | $CH_3CH_2$ |
| 4-Cl | 4-H | 4-H | $CH_3CH_2$ |
| 4-Cl | 4-H | 4-Cl | $CH_3CH_2$ |
| 4-Cl | 4-H | 4-F | $CH_3CH_2$ |
| 4-Cl | 4-Cl | 4-H | $CH_3CH_2$ |
| 4-Cl | 4-Cl | 4-Cl | $CH_3CH_2$ |
| 4-Cl | 4-Cl | 4-F | $CH_3CH_2$ |
| 4-Cl | 4-F | 4-H | $CH_3CH_2$ |
| 4-Cl | 4-F | 4-Cl | $CH_3CH_2$ |
| 4-Cl | 4-F | 4-F | $CH_3CH_2$ |
| 4-$CF_3$ | 4-H | 4-H | $C_6H_5$ |
| 4-$CF_3$ | 4-H | 4-Cl | $C_6H_5$ |
| 4-$CF_3$ | 4-H | 4-F | $C_6H_5$ |
| 4-$CF_3$ | 4-F | 4-H | $C_6H_5$ |
| 4-$CF_3$ | 4-F | 4-Cl | $C_6H_5$ |
| 4-$CF_3$ | 4-F | 4-F | $C_6H_5$ |
| 4-$CF_3$ | 4-Cl | 4-H | $C_6H_5$ |
| 4-$CF_3$ | 4-Cl | 4-Cl | $C_6H_5$ |
| 4-$CF_3$ | 4-Cl | 4-F | $C_6H_5$ |
| 4-$CF_3$ | 4-$OCHF_2$ | 4-H | $C_6H_5$ |
| 4-$CF_3$ | 4-$OCHF_2$ | 4-Cl | $C_6H_5$ |
| 4-$CF_3$ | 4-$OCHF_2$ | 4-F | $C_6H_5$ |
| 4-$OCF_3$ | 4-H | 4-H | $C_6H_5$ |
| 4-$OCF_3$ | 4-H | 4-Cl | $C_6H_5$ |
| 4-$OCF_3$ | 4-H | 4-F | $C_6H_5$ |
| 4-$OCF_3$ | 4-F | 4-H | $C_6H_5$ |
| 4-$OCF_3$ | 4-F | 4-Cl | $C_6H_5$ |
| 4-$OCF_3$ | 4-F | 4-F | $C_6H_5$ |
| 4-$OCF_3$ | 4-Cl | 4-H | $C_6H_5$ |
| 4-$OCF_3$ | 4-Cl | 4-Cl | $C_6H_5$ |
| 4-$OCF_3$ | 4-Cl | 4-F | $C_6H_5$ |
| 4-Cl | 4-H | 4-H | $C_6H_5$ |

TABLE 24-continued

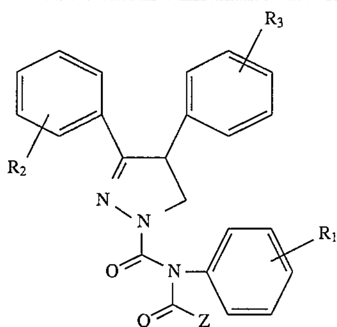

| $R_1$ | $R_2$ | $R_3$ | Z |
|---|---|---|---|
| 4-Cl | 4-H | 4-Cl | $C_6H_5$ |
| 4-Cl | 4-H | 4-F | $C_6H_5$ |
| 4-Cl | 4-F | 4-H | $C_6H_5$ |
| 4-Cl | 4-F | 4-Cl | $C_6H_5$ |
| 4-Cl | 4-F | 4-F | $C_6H_5$ |
| 4-$CF_3$ | 4-H | 4-H | $CH_3O$ |
| 4-$CF_3$ | 4-H | 4-Cl | $CH_3O$ |
| 4-$CF_3$ | 4-H | 4-F | $CH_3O$ |
| 4-$CF_3$ | 4-F | 4-H | $CH_3O$ |
| 4-$CF_3$ | 4-F | 4-Cl | $CH_3O$ |
| 4-$CF_3$ | 4-F | 4-F | $CH_3O$ |
| 4-$CF_3$ | 4-Cl | 4-H | $CH_3O$ |
| 4-$CF_3$ | 4-Cl | 4-Cl | $CH_3O$ |
| 4-$CF_3$ | 4-Cl | 4-F | $CH_3O$ |
| 4-$CF_3$ | 4-$OCHF_2$ | 4-H | $CH_3O$ |
| 4-$CF_3$ | 4-$OCHF_2$ | 4-Cl | $CH_3O$ |
| 4-$CF_3$ | 4-$OCHF_2$ | 4-F | $CH_3O$ |
| 4-$OCF_3$ | 4-H | 4-H | $CH_3O$ |
| 4-$OCF_3$ | 4-H | 4-Cl | $CH_3O$ |
| 4-$OCF_3$ | 4-H | 4-F | $CH_3O$ |
| 4-$OCF_3$ | 4-F | 4-H | $CH_3O$ |
| 4-$OCF_3$ | 4-F | 4-Cl | $CH_3O$ |
| 4-$OCF_3$ | 4-F | 4-F | $CH_3O$ |
| 4-$OCF_3$ | 4-Cl | 4-H | $CH_3O$ |
| 4-$OCF_3$ | 4-Cl | 4-Cl | $CH_3O$ |
| 4-$OCF_3$ | 4-Cl | 4-F | $CH_3O$ |
| 4-Cl | 4-H | 4-H | $CH_3O$ |
| 4-Cl | 4-H | 4-Cl | $CH_3O$ |
| 4-Cl | 4-H | 4-F | $CH_3O$ |
| 4-Cl | 4-Cl | 4-H | $CH_3O$ |
| 4-Cl | 4-Cl | 4-Cl | $CH_3O$ |
| 4-Cl | 4-Cl | 4-F | $CH_3O$ |
| 4-Cl | 4-F | 4-H | $CH_3O$ |
| 4-Cl | 4-F | 4-Cl | $CH_3O$ |
| 4-Cl | 4-F | 4-F | $CH_3O$ |
| 4-$CF_3$ | 4-H | 4-H | H |
| 4-$CF_3$ | 4-H | 4-Cl | H |
| 4-$CF_3$ | 4-H | 4-F | H |
| 4-$CF_3$ | 4-F | 4-H | H |
| 4-$CF_3$ | 4-F | 4-Cl | H |
| 4-$CF_3$ | 4-F | 4-F | H |
| 4-$CF_3$ | 4-Cl | 4-H | H |
| 4-$CF_3$ | 4-Cl | 4-Cl | H |
| 4-$CF_3$ | 4-Cl | 4-F | H |
| 4-$CF_3$ | 4-$OCHF_2$ | 4-H | H |
| 4-$CF_3$ | 4-$OCHF_2$ | 4-Cl | H |
| 4-$CF_3$ | 4-$OCHF_2$ | 4-F | H |
| 4-$OCF_3$ | 4-H | 4-H | H |
| 4-$OCF_3$ | 4-H | 4-Cl | H |
| 4-$OCF_3$ | 4-H | 4-F | H |
| 4-$OCF_3$ | 4-F | 4-H | H |
| 4-$OCF_3$ | 4-F | 4-Cl | H |
| 4-$OCF_3$ | 4-F | 4-F | H |
| 4-$OCF_3$ | 4-Cl | 4-H | H |
| 4-$OCF_3$ | 4-Cl | 4-Cl | H |
| 4-$OCF_3$ | 4-Cl | 4-F | H |
| 4-Cl | 4-H | 4-H | H |
| 4-Cl | 4-H | 4-Cl | H |
| 4-Cl | 4-H | 4-F | H |
| 4-Cl | 4-Cl | 4-H | H |
| 4-Cl | 4-Cl | 4-Cl | H |

TABLE 24-continued

| $R_1$ | $R_2$ | $R_3$ | Z |
|---|---|---|---|
| 4-Cl | 4-Cl | 4-F | H |
| 4-Cl | 4-F | 4-H | H |
| 4-Cl | 4-F | 4-Cl | H |
| 4-Cl | 4-F | 4-F | H |
| 4-$CF_3$ | 4-Cl | 4-Cl | $BrCH_2$ |
| 4-$CF_3$ | 4-Cl | 4-Cl | $ClCH_2$ |
| 4-$CF_3$ | 4-Cl | 4-Cl | $CF_3$ |
| 4-$CF_3$ | 4-Cl | 4-Cl | benzyl |
| 4-$CF_3$ | 4-Cl | 4-Cl | $CH_3CH_2CH_2$ |
| 4-$CF_3$ | 4-Cl | 4-Cl | $CH_3(CH_2)_3$ |
| 4-$CF_3$ | 4-Cl | 4-Cl | $CH_3(CH_2)_4$ |
| 4-$CF_3$ | 4-Cl | 4-Cl | $CH_3(CH_2)_5$ |
| 4-$CF_3$ | 4-Cl | 4-Cl | $CH_3(CH_2)_6$ |
| 4-$CF_3$ | 4-Cl | 4-Cl | $CH_3(CH_2)_7$ |
| 4-$CF_3$ | 4-Cl | 4-Cl | $CH_3(CH_2)_9$ |
| 4-$CF_3$ | 4-Cl | 4-Cl | $CH_3(CH_2)_{10}$ |
| 4-$CF_3$ | 4-Cl | 4-Cl | $Cl_3C$ |
| 4-$CF_3$ | 4-Cl | 4-Cl | i-Pr |
| 4-$CF_3$ | 4-Cl | 4-Cl | t-Bu |
| 4-$CF_3$ | 4-Cl | 4-Cl | $MeO_2C$ |

TABLE 24-continued

| $R_1$ | $R_2$ | $R_3$ | Z |
|---|---|---|---|
| 4-$CF_3$ | 4-Cl | 4-Cl | $EtO_2C$ |
| 4-$CF_3$ | 4-Cl | 4-Cl | 2-Cl-phenyl |
| 4-$CF_3$ | 4-Cl | 4-Cl | 3-Cl-phenyl |
| 4-$CF_3$ | 4-Cl | 4-Cl | 4-Cl-phenyl |
| 4-$CF_3$ | 4-Cl | 4-Cl | $CH_3CH2O$ |
| 4-$CF_3$ | 4-Cl | 4-Cl | $CH_3(CH_2)_2O$ |
| 4-$CF_3$ | 4-Cl | 4-Cl | $CH_3(CH_2)_4O$ |
| 4-$CF_3$ | 4-Cl | 4-Cl | $CH_3(CH_2)_6O$ |
| 4-$CF_3$ | 4-Cl | 4-Cl | $CH_3(CH_2)_8O$ |
| 4-$CF_3$ | 4-Cl | 4-Cl | $CH_3(CH_2)_{10}O$ |
| 4-$CF_3$ | 4-Cl | 4-Cl | phenyl-O |
| 4-$CF_3$ | 4-Cl | 4-Cl | 4-Cl-phenyl-O |
| 4-$CF_3$ | 4-Cl | 4-Cl | benzyl-O |
| 4-Cl | 4-Cl | 4-Cl | $ClCH_2$ |
| 4-Cl | 4-Cl | 4-Cl | $CF_3$ |
| 4-Cl | 4-Cl | 4-Cl | benzyl |
| 4-Cl | 4-Cl | 4-Cl | $CH_3(CH_2)_3$ |
| 4-Cl | 4-Cl | 4-Cl | $CH_3O_2C$ |
| 4-Cl | 4-Cl | 4-Cl | $CH_3CH_2O$ |

TABLE 25

| $R_1$ | $R_2$ | $R_3$ | $R_8$ | $R_9$ |
|---|---|---|---|---|
| 4-$CF_3$ | 4-Cl | H | Me | O-nBu |
| 4-$OCF_3$ | 4-Cl | H | Me | O-nBu |
| 4-$CF_3$ | 4-F | H | Me | O-nBu |
| 4-$OCF_3$ | 4-F | H | Me | O-nBu |
| 4-$CF_3$ | 4-$OCF_2H$ | H | Me | O-nBu |
| 4-$CF_3$ | 4-Br | H | Me | O-nBu |
| 4-$CF_3$ | 4-Cl | 4-Cl | Me | O-nBu |
| 4-Cl | 4-Cl | 4-Cl | Me | O-nBu |
| 4-Br | 4-Cl | 4-Cl | Me | O-nBu |
| 4-$OCF_3$ | 4-Cl | 4-Cl | Me | O-nBu |
| 4-$CF_3$ | 4-F | 4-Cl | Me | O-nBu |
| 4-$CF_3$ | 4-$OCF_2H$ | 4-Cl | Me | O-nBu |
| 4-$CF_3$ | 4-Cl | 4-CN | Me | O-nBu |
| 4-$CF_3$ | 4-F | 4-CN | Me | O-nBu |
| 4-$CF_3$ | 4-Cl | 4-$CO_2Me$ | Me | O-nBu |
| 4-$CF_3$ | 4-Cl | H | Me | O-n-hexyl |

TABLE 25-continued

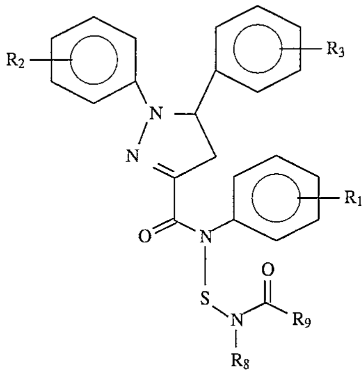

| $R_1$ | $R_2$ | $R_3$ | $R_8$ | $R_9$ |
|---|---|---|---|---|
| 4-$CF_3$ | 4-F | H | Me | O-n-hexyl |
| 4-$CF_3$ | 4-$OCF_2H$ | H | Me | O-n-octyl |
| 4-$CF_3$ | 4-Br | H | Me | O-n-decyl |
| 4-$CF_3$ | 4-Cl | 4-Cl | Me | O-n-dodecyl |
| 4-Cl | 4-Cl | 4-Cl | Me | O-n-dodecyl |
| 4-Br | 4-Cl | 4-Cl | Me | O-n-dodecyl |
| 4-$OCF_3$ | 4-Cl | 4-Cl | Me | O-n-dodecyl |
| 4-$CF_3$ | 4-F | 4-Cl | Me | O-sec-Bu |
| 4-Cl | 4-F | 4-Cl | Me | O-sec-Bu |
| 4-Br | 4-F | 4-Cl | Me | O-sec-Bu |
| 4-$OCF_3$ | 4-F | 4-Cl | Me | O-sec-Bu |
| 4-$CF_3$ | 4-$OCF_2H$ | 4-Cl | Me | O-sec-Bu |
| 4-$CF_3$ | 4-Cl | 4-CN | Me | O-iPr |
| 4-$CF_3$ | 4-F | 4-CN | Me | $OCH_2CH_2OEt$ |
| 4-$CF_3$ | 4-Cl | 4-$CO_2Me$ | Me | $OCH_2CF_3$ |
| 4-$CF_3$ | 4-Cl | H | Me | F |
| 4-$CF_3$ | 4-F | H | Me | $NMe_2$ |
| 4-$CF_3$ | 4-$OCF_2H$ | H | Me | $NEt_2$ |
| 4-$CF_3$ | 4-Br | H | Me | morpholino |
| 4-$OCF_3$ | 4-Br | H | Me | n-Pr |
| 4-$CF_3$ | 4-Cl | 4-Cl | Me | sec-Bu |
| 4-Br | 4-Cl | 4-Cl | Me | Ph |
| 4-$OCF_3$ | 4-Cl | 4-Cl | Me | Ph |
| 4-$CF_3$ | 4-F | 4-Cl | Et | O-iPr |
| 4-$CF_3$ | 4-$OCF_2H$ | 4-Cl | Et | O-iPr |
| 4-$CF_3$ | 4-Cl | 4-CN | Et | $OCH_2CCl_3$ |
| 4-$OCF_3$ | 4-Cl | 4-CN | Et | $NEt_2$ |
| 4-$CF_3$ | 4-F | 4-CN | Et | 2,6-di-Me-morpholino |
| 4-Cl | 4-F | 4-CN | Et | 2,6-di-Me-morpholino |
| 4-$CF_3$ | 4-Cl | 4-$CO_2Me$ | Et | Ph |
| 4-$CF_3$ | 4-Cl | H | iPr | OEt |
| 4-$CF_3$ | 4-F | H | iPr | OEt |
| 4-$CF_3$ | 4-$OCF_2H$ | H | iPr | OEt |
| 4-Cl | 4-$OCF_2H$ | H | iPr | OEt |
| 4-Br | 4-$OCF_2H$ | H | iPr | OEt |
| 4-$OCF_3$ | 4-$OCF_2H$ | H | iPr | OEt |
| 4-$OCF_2H$ | 4-$OCF_2H$ | H | iPr | OEt |
| 3,4-$CH_2C(Me)_2O$ | 4-$OCF_2H$ | H | iPr | OEt |
| 4-$CF_3$ | 4-Br | H | iPr | OEt |
| 4-$CF_3$ | 4-Cl | 4-Cl | iPr | OEt |
| 4-$OCF_3$ | 4-Cl | 4-Cl | iPr | OEt |
| 4-$CF_3$ | 4-F | 4-Cl | iPr | OEt |
| 4-$OCF_3$ | 4-F | 4-Cl | iPr | OEt |
| 4-$CF_3$ | 4-$OCF_2H$ | 4-Cl | iPr | OEt |
| 4-$OCF_3$ | 4-$OCF_2H$ | 4-Cl | iPr | OEt |
| 4-$CF_3$ | 4-Cl | 4-CN | iPr | OEt |
| 4-$OCF_3$ | 4-Cl | 4-CN | iPr | OEt |
| 4-$CF_3$ | 4-F | 4-CN | iPr | OEt |
| 4-$CF_3$ | 4-Cl | 4-$CO_2Me$ | iPr | OEt |
| 4-$OCF_3$ | 4-Cl | 4-$CO_2Me$ | iPr | OEt |
| 4-$CF_3$ | 4-OMe | 4-Cl | iPr | OEt |
| 4-Cl | 4-OPh | 4-Cl | iPr | OEt |
| 4-Br | 4-$SCF_2H$ | 4-Cl | iPr | OEt |
| 4-$OCF_3$ | 4-$NO_2$ | 4-Cl | iPr | OEt |
| 4-$OCF_2H$ | 4-SMe | 4-Cl | iPr | OEt |
| 3,4-$CH_2C(Me)_2O$ | 4-$SO_2Me$ | 4-Cl | iPr | OEt |
| 4-$CF_3$ | 4-CN | 4-Cl | iPr | OEt |
| 4-Cl | 3-Cl | 4-Cl | iPr | OEt |
| 4-Br | 3-F | 4-Cl | iPr | OEt |

TABLE 25-continued

| $R_1$ | $R_2$ | $R_3$ | $R_8$ | $R_9$ |
|---|---|---|---|---|
| 4-$OCF_3$ | 4-Me | 4-Cl | iPr | OEt |
| 4-$OCF_2H$ | 4-O-allyl | 4-Cl | iPr | OEt |
| 3,4-$CH_2C(Me)_2O$ | 4-$CF_3$ | 4-Cl | iPr | OEt |
| 4-$CF_3$ | 4-Cl | 4-$CO_2Et$ | iPr | OEt |
| 4-Cl | 4-Cl | 4-OMe | iPr | OEt |
| 4-Br | 4-Cl | 4-$SCF_2CF_2H$ | iPr | OEt |
| 4-$OCF_3$ | 4-Cl | 4-$OCF_2CF_2H$ | iPr | OEt |
| 4-$CF_3$ | 4-Cl | 4-$CF_3$ | iPr | OEt |
| 4-Cl | 4-Cl | 4-Me | iPr | OEt |
| 4-Br | 4-Cl | 3-Cl | iPr | OEt |
| 4-$OCF_3$ | 4-Cl | 3-Br | iPr | OEt |
| 4-$OCF_2H$ | 4-Cl | 4-$NO_2$ | iPr | OEt |
| 4-$CF_3$ | 4-Cl | H | iPr | O-n-Bu |
| 4-$CF_3$ | 4-F | H | iPr | O-n-Bu |
| 4-$OCF_3$ | 4-F | H | iPr | $OCH_2CO_2Me$ |
| 4-$CF_3$ | 4-$OCF_2H$ | H | iPr | $NMe_2$ |
| 4-$OCF_3$ | 4-$OCF_2H$ | H | iPr | piperidino |
| 3,4-$CH_2C(Me)_2O$ | 4-$OCF_2H$ | H | iPr | Et |
| 4-$CF_3$ | 4-Br | H | iPr | Et |
| 4-$OCF_3$ | 4-Br | H | $CH_2Ph$ | OEt |
| 4-$CF_3$ | 4-Cl | 4-$CO_2Me$ | $CH_2Ph$ | $NME_2$ |

TABLE 26

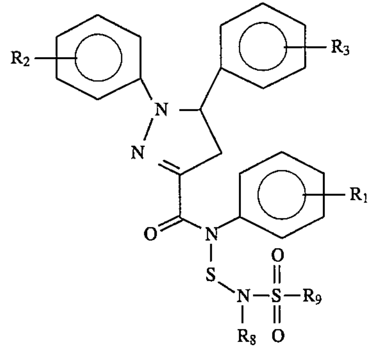

| $R_1$ | $R_2$ | $R_3$ | $R_8$ | $R_9$ |
|---|---|---|---|---|
| 4-$CF_3$ | 4-Cl | H | Me | $NMe_2$ |
| 4-$CF_3$ | 4-F | H | Me | $NEt_2$ |
| 4-$CF_3$ | 4-$OCF_2H$ | H | Me | n-hexyl |
| 4-$OCF_3$ | 4-$OCF_2H$ | H | Me | Ph |
| 4-$CF_3$ | 4-Br | H | Me | 4-Me−Ph |
| 4-$CF_3$ | 4-Cl | 4-Cl | Et | morpholino |
| 4-Cl | 4-Cl | 4-Cl | Et | iPr |
| 4-Br | 4-Cl | 4-Cl | Et | n-Bu |
| 4-$OCF_3$ | 4-Cl | 4-Cl | Et | Ph |

TABLE 26-continued

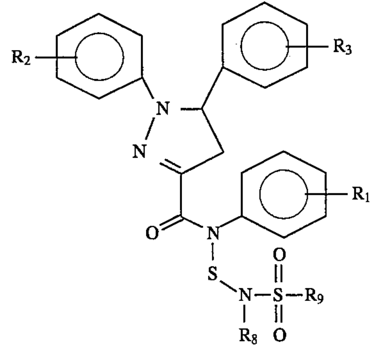

| $R_1$ | $R_2$ | $R_3$ | $R_8$ | $R_9$ |
|---|---|---|---|---|
| 4-$CF_3$ | 4-F | 4-Cl | iPr | $NMe_2$ |
| 4-$CF_3$ | 4-$OCF_2H$ | 4-Cl | iPr | piperidino |
| 4-Cl | 4-$OCF_2H$ | 4-Cl | iPr | Et |
| 4-Br | 4-$OCF_2H$ | 4-Cl | iPr | n-Bu |
| 4-$OCF_3$ | 4-$OCF_2H$ | 4-Cl | iPr | Ph |
| 4-$OCF_2H$ | 4-$OCF_2H$ | 4-Cl | iPr | 4-Cl−Ph |

TABLE 27

| $R_1$ | $R_2$ | $R_3$ | $R_8$ | $Y^1$ | $Y^1R_{10}$ | $Y^1R_{11}$ |
|---|---|---|---|---|---|---|
| 4-$CF_3$ | 4-Cl | H | tBu | S | OEt | OEt |
| 4-Cl | 4-Cl | H | tBu | S | OEt | OEt |
| 4-Br | 4-Cl | H | tBu | S | OEt | OEt |
| 4-$OCF_3$ | 4-Cl | H | tBu | S | OEt | OEt |
| 4-$OCF_2H$ | 4-Cl | H | tBu | S | OEt | OEt |
| 3,4-$CH_2C(Me)_2O$ | 4-Cl | H | tBu | S | OEt | OEt |
| 4-$CF_3$ | 4-F | H | tBu | S | OEt | OEt |
| 4-Cl | 4-F | H | tBu | S | OEt | OEt |
| 4-Br | 4-F | H | tBu | S | OEt | OEt |
| 4-OCF | 4-F | H | tBu | S | $OCH_2C(Me)_2CH_2O$ | |
| 4-$OCF_2H$ | 4-F | H | tBu | S | $OCH_2C(Me)_2CH_2O$ | |
| 3,4-$CH_2C(Me)_2O$ | 4-F | H | tBu | S | $OCH_2C(Me)_2CH_2O$ | |
| 4-$CF_3$ | 4-$OCF_2H$ | H | tBu | S | $OCH_2C(Me)_2CH_2O$ | |
| 4-Cl | 4-$OCF_2H$ | H | tBu | S | $OCH_2C(Me)_2CH_2O$ | |
| 4-Br | 4-$OCF_2H$ | H | tBu | S | $OCH_2C(Me)_2CH_2O$ | |
| 4-$OCF_3$ | 4-$OCF_2H$ | H | tBu | S | $OCH_2C(Me)_2CH_2O$ | |
| 4-$OCF_2H$ | 4-$OCF_2H$ | H | tBu | S | $OCH_2C(Me)_2CH_2O$ | |
| 3,4-$CH_2C(Me)_2O$ | 4-$OCF_2H$ | H | tBu | S | $OCH_2C(Me)_2CH_2O$ | |
| 4-$CF_3$ | 4-Br | H | tBu | S | $OCH_2C(Me)_2CH_2O$ | |
| 4-Cl | 4-Br | H | iPr | S | OEt | OEt |
| 4-Br | 4-Br | H | iPr | S | OEt | OEt |
| 4-$OCF_3$ | 4-Br | H | iPr | S | OEt | OEt |
| 4-$OCF_2H$ | 4-Br | H | iPr | S | OEt | OEt |
| 3,4-$CH_2C(Me)_2O$ | 4-Br | H | iPr | S | OEt | OEt |
| 4-$CF_3$ | 4-Cl | 4-Cl | iPr | S | OEt | OEt |
| 4-Cl | 4-Cl | 4-Cl | iPr | S | OEt | OEt |
| 4-Br | 4-Cl | 4-Cl | iPr | S | OEt | OEt |
| 4-$OCF_3$ | 4-Cl | 4-Cl | iPr | S | oEt | OEt |
| 4-$OCF_2H$ | 4-Cl | 4-Cl | iPr | S | OEt | OEt |
| 3,4-$CH_2C(Me)_2O$ | 4-Cl | 4-Cl | iPr | S | OEt | OEt |
| 4-$CF_3$ | 4-F | 4-Cl | iPr | S | $OCH_2C(Me)_2CH_2O$ | |
| 4-Cl | 4-F | 4-Cl | iPr | S | $OCH_2C(Me)_2CH_2O$ | |
| 4-Br | 4-F | 4-Cl | iPr | S | $OCH_2C(Me)_2CH_2O$ | |
| 4-$OCF_3$ | 4-F | 4-Cl | iPr | S | $OCH_2C(Me)_2CH_2O$ | |
| 4-$OCF_2H$ | 4-F | 4-Cl | iPr | S | $OCH_2C(Me)_2CH_2O$ | |
| 3,4-$CH_2C(Me)_2O$ | 4-F | 4-Cl | iPr | S | $OCH_2C(Me)_2CH_2O$ | |
| 4-$CF_3$ | 4-$OCF_2H$ | 4-Cl | tBu | S | OiPr | OiPr |
| 4-Cl | 4-$OCF_2H$ | 4-Cl | tBu | S | OiPr | OiPr |
| 4-Br | 4-$OCF_2H$ | 4-Cl | tBu | S | OiPr | OiPr |
| 4-$OCF_3$ | 4-$OCF_2H$ | 4-Cl | tBu | S | OiPr | OiPr |
| 4-$OCF_2H$ | 4-$OCF_2H$ | 4-Cl | tBu | S | OiPr | OiPr |
| 3,4-$CH_2C(Me)_2O$ | 4-$OCF_2H$ | 4-Cl | tBu | S | OiPr | OiPr |
| 4-$CF_3$ | 4-Cl | 4-CN | tBu | S | $OCH_2CH_2CH_2O$ | |
| 4-Cl | 4-Cl | 4-CN | tBu | S | $OCH_2CH_2CH_2O$ | |
| 4-Br | 4-Cl | 4-CN | tBu | S | $OCH_2CH_2CH_2O$ | |
| 4-$OCF_3$ | 4-Cl | 4-CN | tBu | S | $OCH_2CH_2CH_2O$ | |
| 4-$OCF_2H$ | 4-Cl | 4-CN | tBu | S | $OCH_2CH_2CH_2O$ | |
| 3,4-$CH_2C(Me)_2O$ | 4-Cl | 4-CN | tBu | S | $OCH_2CH_2O$ | |
| 4-$CF_3$ | 4-F | 4-CN | tBu | S | $OCH_2CH_2O$ | |
| 4-Cl | 4-F | 4-CN | tBu | S | $OCH_2CH_2O$ | |
| 4-Br | 4-F | 4-CN | tBu | S | $OCH_2CH_2O$ | |
| 4-$OCF_3$ | 4-F | 4-CN | Me | S | OEt | OEt |
| 4-$OCF_2H$ | 4-F | 4-CN | Me | S | OEt | OEt |
| 3,4-$CH_2C(Me)_2O$ | 4-F | 4-CN | Me | S | OEt | OEt |
| 4-Br | 4-Cl | 4-$CO_2Me$ | tBu | O | OEt | OEt |
| 4-$OCF_3$ | 4-Cl | 4-$CO_2Me$ | tBu | O | OEt | OEt |
| 4-$OCF_2H$ | 4-Cl | 4-$CO_2Me$ | tBu | O | $OCH_2C(Me)_2CH_2O$ | |
| 3,4-$CH_2C(Me)_2O$ | 4-Cl | 4-$CO_2Me$ | tBu | O | $OCH_2C(Me)_2CH_2O$ | |

TABLE 28

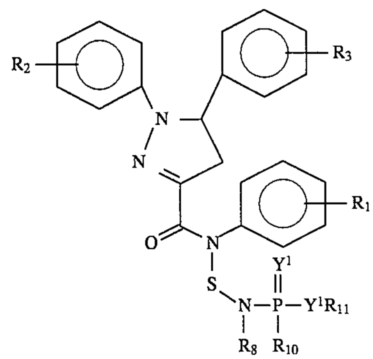

| $R_1$ | $R_2$ | $R_3$ | $R_8$ | $Y^1$ | $R_{10}$ | $Y^1R_{11}$ |
|---|---|---|---|---|---|---|
| 4-$CF_3$ | 4-Cl | H | iPr | O | Et | OEt |
| 4-Cl | 4-Cl | H | iPr | O | Et | OEt |
| 4-$OCF_3$ | 4-Cl | H | iPr | O | Et | OEt |
| 4-$CF_3$ | 4-F | H | iPr | O | Et | O-iPr |
| 4-OCF | 4-F | H | iPr | O | Et | O-iPr |
| 4-$CF_3$ | 4-$OCF_2H$ | H | iPr | O | Et | O-iPr |
| 4-$OCF_3$ | 4-$OCF_2H$ | H | iPr | O | Et | OPh |
| 4-$CF_3$ | 4-Br | H | iPr | O | Et | OPh |
| 4-$CF_3$ | 4-Cl | 4-Cl | iPr | O | Ph | OEt |
| 4-Cl | 4-Cl | 4-Cl | iPr | O | Ph | OEt |
| 4-Br | 4-Cl | 4-Cl | iPr | O | Ph | OEt |
| 4-$OCF_3$ | 4-Cl | 4-Cl | iPr | O | Ph | OEt |
| 4-$CF_3$ | 4-F | 4-Cl | tBu | O | Et | OEt |
| 4-$OCF_3$ | 4-F | 4-Cl | tBu | O | Et | OEt |
| 4-$CF_3$ | 4-$OCF_2H$ | 4-Cl | tBu | O | Et | O-iPr |
| 4-$OCF_3$ | 4-$OCF_2H$ | 4-Cl | tBu | O | Et | O-iPr |
| 4-$CF_3$ | 4-Cl | 4-CN | Ph | O | Et | OEt |
| 4-$OCF_3$ | 4-Cl | 4-CN | Ph | O | Et | OEt |
| 4-$CF_3$ | 4-F | 4-CN | iPr | S | Ph | O-iPr |
| 4-$OCF_3$ | 4-F | 4-CN | tBu | S | Et | OEt |

TABLE 29

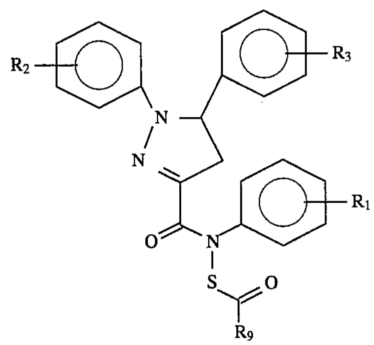

| $R_1$ | $R_2$ | $R_3$ | $R_9$ |
|---|---|---|---|
| 4-$CF_3$ | 4-Cl | H | $CF_3$ |
| 4-$CF_3$ | 4-F | H | $CF_3$ |
| 4-$OCF_3$ | 4-F | H | O-sec-Bu |
| 4-$CF_3$ | 4-$OCF_2H$ | H | O-sec-Bu |
| 4-Br | 4-$OCF_2H$ | H | O-sec-Bu |
| 4-$OCF_3$ | 4-$OCF_2H$ | H | O-sec-Bu |
| 4-$CF_3$ | 4-Br | H | O-n-Bu |
| 4-$CF_3$ | 4-Cl | 4-Cl | O-n-Bu |
| 4-Cl | 4-Cl | 4-Cl | O-n-Bu |

TABLE 29-continued

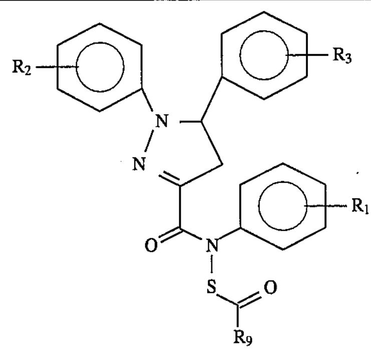

| $R_1$ | $R_2$ | $R_3$ | $R_9$ |
|---|---|---|---|
| 4-Br | 4-Cl | 4-Cl | O-n-Bu |
| 4-$OCF_3$ | 4-Cl | 4-Cl | O-n-Bu |
| 4-$CF_3$ | 4-F | 4-Cl | O-n-hexyl |
| 4-$CF_3$ | 4-$OCF_2H$ | 4-Cl | O-n-hexyl |
| 4-$OCF_3$ | 4-$OCF_2H$ | 4-Cl | O-n-hexyl |
| 4-$CF_3$ | 4-Cl | 4-CN | $OCH_2CCl_3$ |
| 4-$OCF_3$ | 4-Cl | 4-CN | $OCH_2CCl_3$ |
| 4-$CF_3$ | 4-F | 4-CN | $OCH_2CCl_3$ |
| 4-$CF_3$ | 4-Cl | 4-$CO_2Me$ | $OCH_2CH_2OEt$ |

TABLE 30

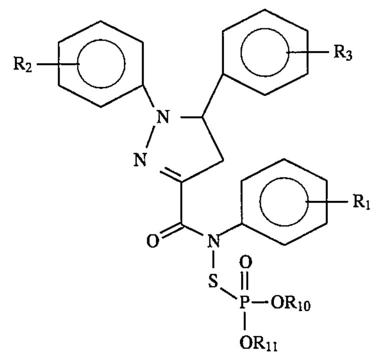

| $R_1$ | $R_2$ | $R_3$ | $R_{10}$ | $R_{11}$ |
|---|---|---|---|---|
| 4-$CF_3$ | 4-Cl | H | Et | Et |
| 4-$CF_3$ | 4-F | H | Et | Et |
| 4-$CF_3$ | 4-$OCF_2H$ | H | Et | Et |
| 4-$OCF_3$ | 4-$OCF_2H$ | H | $-CH_2CH_2-$ | |
| 4-$CF_3$ | 4-Br | H | $-CH_2CH_2-$ | |
| 4-$CF_3$ | 4-Cl | 4-Cl | $-CH_2CH_2-$ | |
| 4-Cl | 4-Cl | 4-Cl | $-CH_2CH_2-$ | |
| 4-$OCF_3$ | 4-Cl | 4-Cl | $-CH_2CH_2-$ | |
| 4-$CF_3$ | 4-F | 4-Cl | $-CH_2CH_2CH_2-$ | |
| 4-$OCF_3$ | 4-F | 4-Cl | $-CH_2CH_2CH_2-$ | |
| 4-$CF_3$ | 4-$OCF_2H$ | 4-Cl | $-CH_2CH_2CH_2-$ | |
| 4-$OCF_3$ | 4-$OCF_2H$ | 4-Cl | $-CH_2C(Me)_2CH_2-$ | |
| 4-$CF_3$ | 4-Cl | 4-CN | $-CH_2C(Me)_2CH_2-$ | |
| 4-$OCF_3$ | 4-Cl | 4-CN | $-CH_2C(Me)_2CH_2-$ | |
| 4-$CF_3$ | 4-F | 4-CN | Ph | Ph |
| 4-$CF_3$ | 4-Cl | 4-$CO_2Me$ | Ph | Ph |

TABLE 31

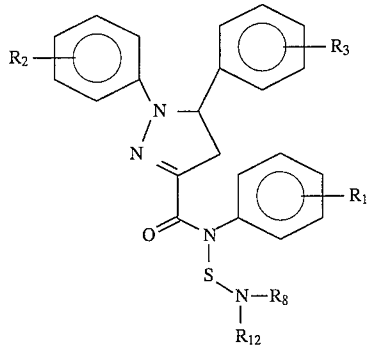

| $R_1$ | $R_2$ | $R_3$ | $R_8$ | $R_{12}$ |
|---|---|---|---|---|
| 4-$CF_3$ | 4-Cl | H | nBu | nBu |
| 4-$CF_3$ | 4-F | H | nBu | nBu |
| 4-$CF_3$ | 4-$OCF_2H$ | H | nBu | nBu |
| 4-$OCF_3$ | 4-$OCF_2H$ | H | $-CH_2CH_2CH_2CH_2CH_2-$ | |
| 4-$CF_3$ | 4-Br | H | $-CH_2CH_2CH_2CH_2CH_2-$ | |
| 4-$CF_3$ | 4-Cl | 4-Cl | $-CH_2CH_2OCH_2CH_2-$ | |
| 4-Cl | 4-Cl | 4-Cl | $-CH_2CH_2OCH_2CH_2-$ | |
| 4-$OCF_3$ | 4-Cl | 4-Cl | $-CH_2CH_2OCH_2CH_2-$ | |
| 4-$CF_3$ | 4-F | 4-Cl | $-CH_2CH(Me)OCH(Me)CH-$ | |
| 4-$OCF_3$ | 4-F | 4-Cl | $-CH_2CH(Me)OCH(Me)CH-$ | |
| 4-$CF_3$ | 4-$OCF_2H$ | 4-Cl | Et | cyclo-$C_6H_{11}$ |
| 4-$OCF_3$ | 4-$OCF_2H$ | 4-Cl | Et | cyclo-$C_6H_{11}$ |
| 4-$CF_3$ | 4-Cl | 4-CN | Et | cyclo-$C_6H_{11}$ |
| 4-$CF_3$ | 4-F | 4-CN | iPr | $-CH_2CH_2CO_2Et$ |
| 4-$CF_3$ | 4-Cl | 4-$CO_2Me$ | $CF_3$ | 2,4-di-Cl-Ph |

TABLE 32

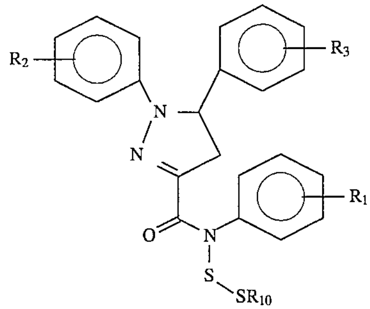

| $R_1$ | $R_2$ | $R_3$ | $R_{10}$ |
|---|---|---|---|
| 4-$CF_3$ | 4-Cl | H | tBu |
| 4-$CF_3$ | 4-F | H | tBu |
| 4-$CF_3$ | 4-$OCF_2H$ | H | sec-Bu |
| 4-$OCF_3$ | 4-$OCF_2H$ | H | sec-Bu |
| 4-$CF_3$ | 4-Br | H | sec-Bu |
| 4-$CF_3$ | 4-Cl | 4-Cl | Ph |
| 4-Cl | 4-Cl | 4-Cl | Ph |
| 4-$OCF_3$ | 4-Cl | 4-Cl | Ph |
| 4-$CF_3$ | 4-F | 4-Cl | 4-Cl-Ph |
| 4-Cl | 4-F | 4-Cl | 4-Cl-Ph |
| 4-$OCF_3$ | 4-F | 4-Cl | 4-Cl-Ph |
| 4-$CF_3$ | 4-$OCF_2H$ | 4-Cl | 4-Cl-Ph |
| 4-$OCF_3$ | 4-$OCF_2H$ | 4-Cl | 2-Me-4-t-Bu-Ph |
| 4-$CF_3$ | 4-Cl | 4-CN | 2-Me-4-t-Bu-Ph |
| 4-$CF_3$ | 4-F | 4-CN | 2-$NO_2$-Ph |
| 4-$CF_3$ | 4-Cl | 4-$CO_2Me$ | 2-$NO_2$-Ph |

Formulation and Use

The compounds of this invention will generally be used in formulation with a carrier comprising a liquid or solid diluent or an organic solvent. Useful formulations of the compounds of this invention are prepared in conventional ways. They include dusts, baits, traps, granules, pellets, solutions, suspensions, emulsions, wettable powders, emulsifiable concentrates, dry flowables and the like. Many of these can be applied directly. Sprayable formulations can be extended in suitable media and used at spray volumes of from about one to several hundred liters per hectare. High strength compositions are primarily used as intermediates for further formulation. The formulations, broadly, contain about 1% to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 25–90 | 0–74 | 0–10 |
| Oil Suspensions, Emulsions, Solutions (including Emulsifiable Concentrates) | 1–50 | 40–95 | 0–35 |
| Dusts | 1–25 | 70–99 | 0–5 |
| Granules, Baits and Pellets | 0.01–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers," 2nd Ed., Dorland Books, Caldwell, N.J. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual," Allured Publ. Corp., Ridgewood, N.J., as well as Sisely and Wood, "Encyclopedia of Surface Active Agents," Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, griding as in a hammer or fluid energy mill. Suspensions are prepared by wet-milling (see, for example, U.S. Pat. No. 3,060,084). Granules and pellets can be made by spraying the active material upon preformed granular carriers or by agglomeration techniques. See Browning, "Agglomeration," *Chemical Engineering*, Dec. 4, 1967, pages 147 and following, and "Perry's Chemical Engineer's Handbook," 4th Ed., McGraw-Hill, New York, 1963, pages 8 to 59 and following.

Many of the compounds of the invention are most efficacious when applied in the form of an emulsifiable concentrate mixed with a spray oil or spray oil concentrate. Although any oil can be used as a spray oil, spray oils usually have these characteristics: they are not phytotoxic to the crop sprayed, and they have appropriate viscosity. Petroleum based oils are commonly used for spraying. In some areas, crop oils are preferred such as the following:

| Common Crop Oils Used as Spray Oils | |
|---|---|
| Corn Oil | Linseed Oil |
| Cottonseed Oil | Soybean Oil |
| Coconut Oil | Sunflower Oil |
| Rapeseed Oil | Olive Oil |
| Peanut Oil | Palm Oil |
| Safflower Oil | Sesame Oil |
| Mustardseed Oil | Castor Oil |

The following oils also meet the criteria for a spray oil: mineral, fish and cod liver oil. Spray oil concentrates comprise a spray oil together with one or more additional ingredients such as emulsifiers and wetting agents. A number of useful spray oil and spray oil concentrates can be found in "A Guide to Agricultural Spray Adjuvants Used in the United States" by Thomson, Thomson Publications, California, 1986.

Examples of useful arthropodicidal formulations of compounds of the present invention are as follows.

EXAMPLE A

Emulsifiable Concentrate

| | |
|---|---|
| methyl 4-[3-(4-chlorophenyl)-1-[[(ethoxycarbonyl)(1-methylethyl)amino]thio]-N-[4-(trifluoromethyl)phenyl]-amino]carbonyl]-4,5-di-hydro-1H-pyrazol-4-yl]benzoate. | 20% |
| blend of oil soluble sulfonates and polyoxyethylene ethers | 10% |
| isophorone | 70% |

The ingredients are combined and stirred with gentle warming to speed solution. A fine screen filter is included in packaging operation to insure the substantial absence of extraneous undissolved material in the product.

EXAMPLE B

Wettable Powder

| | |
|---|---|
| methyl 4-[3-(4-chlorophenyl)-1-[[(ethoxycarbonyl)(1-methylethyl)amino]thio])-N-[4-(trifluoromethyl)phenyl]-amino]carbonyl]-4,5-di-hydro-1H-pyrazol-4-yl]benzoate. | 30% |
| sodium alkylnaphthalenesulfonate | 2% |
| sodium ligninsulfonate | 2% |
| synthetic amorphous silica | 3% |
| kaolinite | 63% |

The active ingredient is mixed with the inert materials in a blender. After grinding in a hammer-mill, the material is reblended and sifted through a 5-mesh screen.

EXAMPLE C

Dust

| | |
|---|---|
| methyl 4-[3-(4-chlorophenyl)-1-[[(ethoxycarbonyl)(1-methylethyl)amino]thio]-N-[4-(trifluoromethyl)phenyl]-amino]carbonyl]-4,5-di-hydro-1H-pyrazol-4-yl]benzoate. | |
| Wettable powder of Example B | 10% |
| pyrophyllite (powder) | 90% |

The wettable powder and the pyrophyllite diluent are thoroughly blended and then packaged. The product is suitable for use as a dust.

EXAMPLE D

Granule

| | |
|---|---|
| methyl 4-[3-(4-chlorophenyl)-1-[[(ethoxycarbonyl)-(1-methylethyl)amino]thio]-N-[4-(trifluoro-methyl)phenyl]amino]carbonyl]-4,5-di-hydro-1H-pyrazol-4-yl]benzoate. | 10% |
| attapulgite granules (low volative matter, 0.71/9/30 mm; U.S.S. No. 25–50 sieves) | 90% |

The active ingredient is dissolved in a volatile solvent such as acetone and sprayed upon dedusted and pre-warmed attapulgite granules in a double cone blender. The acetone is then driven off by heating. The granules are then allowed to cool and are packaged.

EXAMPLE E

Emulsifiable Concentrate

| | |
|---|---|
| methyl 4-[3-(4-chlorophenyl)-1-[[(ethoxycarbonyl)(1-methylethyl)amino]thio]-N-[4-(trifluoromethyl)phenyl]-amino]carbonyl]-4,5-di-hydro-1H-pyrazol-4-yl]benzoate. | 10% |
| blend of oil soluble sulfonates and polyoxyethylene ethers | 4% |
| isophorone | 86% |

The ingredients are combined and stirred with gentle warming to speed solution. A fine screen filter is included in packaging operation to insure the absence of any extraneous undissolved material in the product.

EXAMPLE F

Wettable Powder

| | |
|---|---|
| methyl 4-[3-(4-chlorophenyl)-1-[[(ethoxycarbonyl)(1-methylethyl)amino]thio]-N-[4-(trifluoromethyl)phenyl]-amino]carbonyl]-4,5-di-hydro-1H-pyrazol-4-yl]benzoate. | 80% |
| sodium alkylnaphthalenesulfonate | 2% |
| sodium ligninsulfonate | 2% |
| synthetic amorphous silica | 3% |
| kaolinite | 3% |

The active ingredient is blended with the inert materials in a blender. After grinding in a hammermill, the material is reblended an sifted through a U.S.S. 50-mesh screen and packaged.

EXAMPLE G

Dust

| Dust | |
|---|---|
| wettable powder of Example F | 5% |
| pyrophyllite (powder) | 95% |

The wettable powder and the pyrophyllite diluent are thoroughly blended and then packaged. The product is suitable for use as a dust.

EXAMPLE H

Granule

| | |
|---|---|
| methyl 4-[3-(4-chlorophenyl)-1-[[(ethoxycarbonyl)(1-methylethyl)amino]thio]-N-[4-(trifluoromethyl)phenyl]- | 10% |

-continued

| | |
|---|---|
| amino]carbonyl]-4,5-di-hydro-1H-pyrazol-4-yl]benzoate. | |
| attapulgite granules (low volative matter, 0.71/0.30 mm; U.S.S. No. 25-50 sieves) | 90% |

The active ingredient is dissolved in a suitable solvent and sprayed onto dedusted attapulgite granules in a double cone blender. The granules are warmed to drive off solvent, cooled and packaged.

EXAMPLE I

| Granule | |
|---|---|
| wettable powder of Example F | 15% |
| gypsum | 69% |
| potassium sulfate | 16% |

The ingredients are blended in a rotating mixer and water is sprayed on to accomplish granulation. When most of the material has reached the desired range of 0.1 to 0.42 mm (U.S.S. No. 18 to 40 sieves), the granules are removed, dried, and screened. Oversize material is crushed to produce additional material in the desired range. These granules contain 12% active ingredient.

EXAMPLE J

Solution

| | |
|---|---|
| methyl 4-[3-(4-chlorophenyl)-1-[[(ethoxycarbonyl)(1-methylethyl)amino]thio]-N-[4-(trifluoromethyl)phenyl]-amino]carbonyl]-4,5-di-hydro-1H-pyrazol-4-yl]benzoate. | 15% |
| 4-butyrolactone | 85% |

The ingredients are combined and stirred to produce a solution suitable for direct, low volume application.

EXAMPLE K

Oil Suspension.

| | |
|---|---|
| methyl 4-[3-(4-chlorophenyl)-1-[[(ethoxycarbonyl)(1-methylethyl)amino]thio]-N-[4-(trifluoromethyl)phenyl]-amino]carbonyl]-4,5-di-hydro-1H-pyrazol-4-yl]benzoate. | 20% |
| sodium alkylnaphthalenesulfonate | 4% |
| sodium ligninsulfonate | 4% |
| low viscosity methyl cellulose | 3% |
| attapulgite | 69% |

The active ingredient is blended with the inert materials in a blender. After grinding in a hammermill to produce particles substantially all below 100 microns, the material is reblended and sifted through a U.S.S. 50-mesh screen and packaged.

EXAMPLE L

Aqueous Suspension

| | |
|---|---|
| methyl 4-[3-(4-chlorophenyl)-1-[[(ethoxycarbonyl)-(1-methylethyl)amino]thio]-N-[4-(trifluoromethyl)-phenyl]amino]carbonyl]-4,5-dihydro-1H-pyrazol-4-yl]benzoate. | 40% |
| polyacrylic acid thickener | 0.3% |
| dodecyclophenol polyethylene glycol ether | 0.5% |
| disodium phosphate | 1.0% |

-continued

| | |
|---|---|
| monosodium phosphate | 0.5% |
| polyvinyl alcohol | 1.0% |
| water | 56.7% |

The ingredient's are blended and ground together in a sand mill to produce particles substantially all under 5 microns in size.

EXAMPLE M

Oil Suspension

| | |
|---|---|
| methyl 4-[3-(4-chlorophenyl)-1-[[(ethoxycarbonyl)-(1-methylethyl)amino]thio]-N-[4-(trifluoromethyl)-phenyl]amino]carbonyl]-4,5-dihydro-1H-pyrazol-4-yl]benzoate. | 35.0% |
| blend of polyalcohol carboxylic esters and oil soluble petroleum sulfonates | 6.0% |
| xylene range solvent | 59.0% |

The ingredients are combined and ground together in a sand mill to produce particles substantially all below 5 microns. The product can be used directly, extended with oils, or emulsified in water.

EXAMPLE N

Emulsifiable Concentrate

| | |
|---|---|
| methyl 7-chloro-2-[[N-[[[(hexyloxy)carbonyl]-methyl-amino]-thio]-N-[4-(trifluoromethyl)-phenyl]amino]-carbonyl]-3,3a,4,5-tetrahydro-2H-benz[g]indazole-3a-carboxylate. | 5% |
| blend of oil soluble sulfonates and polyoxyethylene ethers | 4% |
| xylene | 91% |

The ingredients are combined and stirred with gentle warming to speed solution. A fine screen filter is included in packaging operation to insure the absence of any extraneous undissolved material in the product.

EXAMPLE O

Wettable Powder

| | |
|---|---|
| methyl 7-chloro-2-[[N-[[[(hexyloxy)carbonyl]-methyl-amino]-thio]-N-[4-(trifluoromethyl)-phenyl]amino]-carbonyl]-3,3a,4,5-tetrahydro-2H-benz[g]indazole-3a-carboxylate. | 30% |
| sodium alkylnaphthalenesulfonate | 2% |
| sodium ligninsulfonate | 2% |
| synthetic amorphous silica | 3% |
| kaolinite | 63% |

The active ingredient, warmed to reduce viscosity, is sprayed onto the inert materials in a blender. After grinding in a hammer-mill, the material is reblended and sifted through a 50 mesh screen.

EXAMPLE P

Solution

| | |
|---|---|
| methyl 7-chloro-2-[[N-[[[(hexyloxy)carbonyl]-methyl-amino]-thio]-N-[4-(trifluoromethyl)-phenyl]amino]-carbonyl]-3,3a,4,5-tetrahydro-2H-benz[g]indazole-3a- | 10% |

-continued

| | |
|---|---|
| carboxylate. | |
| isophorone | 90% |

The ingredients are combined and stirred to produce a solution suitable for direct, low volume application.

EXAMPLE Q

Bait Granules

| | |
|---|---|
| methyl 4-[3-(4-chlorophenyl)-1-[[(ethoxycarbonyl)-(1-methylethyl)amino]thio]-N-[4-(trifluoromethyl)-phenyl]amino]carbonyl]-4,5-dihydro-1H-pyrazol-4-yl]benzoate. | 3.0% |
| blend of polyethoxylated nonyl-phenols an sodium dodecylbenzene benzene sulfonates | 9.0% |
| ground up corn cobs | 88.0% |

The active ingredient and surfactant blend are dissolved in a suitable solvent such as acetone and sprayed onto the ground corn cobs. The granules are then dried and packaged. Compounds of Formula I, II and/or III can also be mixed with one or more other insecticides, fungicides, nematocides, bactericides, acaricides, or other biologically active compounds to form a multi-component pesticide giving an even broader spectrum of effective pesticide protection. Examples of other agricultural protectants with which compounds of the present invention can be mixed or formulated are as follows.

Insecticides:

3-hydroxy-N-methylcrotonamide(dimethylphosphate)ester (monocrotophos)

methylcarbamic acid, ester with 2,3-dihydro-2,2-dimethyl-7-benzofuranol (carbofuran)

O-[2,4,5-trichloro-α-(chloromethyl)benzyl]ophosphoric acid, O',O'-dimethyl ester (tetrachlorvinphos)

2-mercaptosuccinic acid, diethyl ester, S-ester with thionophosphoric acid, dimethyl ester (malathion)

phosphorothioic acid, O,O-dimethyl, O-p-nitrophenyl ester (methyl parathion)

methylcarbamic acid, ester with α-naphthol (carbaryl) methyl O-(methylcarbamoyl)thiolacetohydroxamate (methomyl)

N'-(4-chloro-o-tolyl)-N,N-dimethylformamidine (chlordimeform)

O,O-diethyl-O-(2-isopropyl-4-methyl-6-pyrimidylphosphorothioate (diazinon) octachlorocamphene (toxaphene)

O-ethyl O-p-nitrophenyl phenylphosphonothioate (EPN) (S)-a-cyano-m-phenoxybenzyl(1R,3R)-3-(2,2-dibromovinyl)-2,2-dimethylcyclopropanecarboxylate (deltamethrin) Methyl N',N'-dimethyl-N-[(methylcarbamoyl)oxy]-1-thiooxamimidate (oxamyl)

cyano(3-phenoxyphenyl)-methyl-4-chloro-a-(1-methylethyl)benzeneacetate (fenvalerate)

(3-phenoxyphenyl)methyl(±)-cis,trans-3-(2,2-dichloro ethenyl)-2,2-dimethylcyclopropanecarboxylate (permethrin)

a-cyano-3-phenoxybenzyl 3-(2,2-dichlorovinyl)-2,2-dimethylcyclopropane carboxylate (cypermethrin)

-ethyl-S-(p-chlorophenyl)ethylphosphonodithioate (profenofos)

phosphorothiolothionic acid,

O-ethyl-O-[4-(methylthio)-phenyl]-S-n-propyl ester (sulprofos).

Additional insecticides are listed hereafter by their common names: triflumuron, diflubenzureon, methoprene, buprofezin, thiodicarb, acephate, azinphosmethyl, chlorpyrifos, dimethoate, fonophos, isofenphos, methidathio, methamidiphos, monocrotphos, phosmet, phosphamidon, phosalone, pirimicarb, phorate, profenofos, terbufos, trichlorfon, methoxychlor, bifenthrin, biphenate, cyfluthrin, fenpropathrin, fluvalinate, flucythrinate, tralomethrin, metaldehyde and rotenone.

Fungicides:

methyl 2-benzimidazolecarbamate (carbendazim)

tetramethylthiuram disulfide (thiuram)

n-dodecylguanidine acetate (dodine)

manganese ethylenebisdithiocarbamate (maneb)

1,4-dichloro-2,5-dimethoxybenzene (chloroneb)

methyl 1-(butylcarbamoly)-2-benzimidazolecarbamate (benomyl)

1-[2-(2,4-dichlorophenyl)-4-propyl-1,3-dioxolan-2-ylmethyl]-1H-1,2,4-triazole (propiconazole)

2-cyano-N-ethylcarbamoy-2-methoxyiminoacetamide (cymoxanil)

1-(4-chlorophenoxy)-3,3-dimethyl-1-(1H-1,2,4-triazol-1-yl)-2-butanone (triadimefon)

N-(trichloromethylthio)tetrahydrophthalimide (captan)

N-(trichloromethylthio)phthalimide (folpet)

1-[[[bis(4-fluorophenyl)][methyl]silyl]methyl]-1H-1,2,4-triazole.

Nematocides:

S-methyl 1-(dimethylcarbamoyl)-N-(methylcarbamoyloxy)thioformimidate

S-methyl 1-carbamoyl-N-(methylcarbamoyloxy)thioformimidate

N-isopropylphosphoramidic acid, O-ethyl

O'-[4-(methylthio)-m-tolyl]diester (fenamiphos)

Bactericides:

tribasic copper sulfate streptomycin sulfate

Acaricides:

senecioic acid, ester with 2-sec-butyl-4,6-dinitrophenol (binapacryl)

6-methyl-1,3-cithiolo[4,5-β]quinoxalin-2-one (oxythioquinox)

ethyl 4,4'-dichlorobenzilate (chlorobenzilate)

1,1-bis(p-chlorophenyl)-2,2,2-trichloroethanol (dicofol)

bis(pentachloro-2,4-cyclopentadien-1-yl) (dienochlor)

tricyclohexyltin hydroxide (cyhexatin)

trans-5-(4-chlorophenyl)-N-cyclohexyl-4-methyl-2-oxothiazolidine-3-carboxamide (hexythiazox)

amitraz propargite fenbutatin-oxide

Biological

*Bacillus thuringiensis*

Avermectin B.

Utility

The compounds of the present invention exhibit activity against a wide spectrum of foliar and soil-inhabiting, livestock, household and public health arthropods. Those skilled in the art will recognize that not all compounds will be equally effective against all arthropods but the compounds of this invention display activity against economically important pest species, such as grasshoppers and cockroaches including German or American roaches; thrips; hemipterans: plant bugs (Miridae) such as tarnished plant bugs, lace bugs (Tingidae), seed bugs (Lygaeidae) such as cinch bugs, stink bugs (Pentatomidae), leaf-footed bugs (Coreidae) such as squash bug, and red bugs and stainers (Pyrrocoridae) such as cotton stainer; also homopterans such as whiteflies, aphids such as the green peach aphid, greenbug and cotton aphid, leafhoppers, spittlebugs and planthoppers such as aster leafhopper, potato leafhopper and rice planthoppers, psyllids such as pear psylla, scales (coccids and diaspidids) and mealybugs; coleopterans including weevils such as boll weevil and rice water weevil, grain borers, chrysomellid beetles such as Colorado potato beetle, flea beetles and other leaf beetles, coccinellid beetles such as Mexican bean beetle.

Activity is also shown against soil insects such as southern corn rootworm and wireworm; lepidopterous larvae including noctuids such as fall armyworm, beet armyworm, other Spodoptera spp., Heliothis spp. such as virescens, Heliothis zea, cabbage looper, green cloverworm, velvetbean caterpillar, cotton leafworm, black cut- worm, and other noctuid cutworms and including pyralids such as European corn borer, navel orange- worm, and. stalk/stem borers and including tortricids like codling moth and grape berry moth as well as other lepidopterous larvae such as pink bollworm and diamodback moth; and dipterans such as leaf-miner, soil maggots, midges, and tephritid fruit flies; house fly, *Musca domestica*; stable fly, *Stomoxys calcitrans*; black blow fly, *Phormia regina*; face fly, *Musca autumnalis*; black fly, *Simulum meridionale*; yellow fever mosquito, *Aedes egypti*; German cockroach, *Blattella germanica*; carpenter ants, *Camponotus pennsylvanicus* and eastern subterranean termite, *Reticulitermes flavipes*. The pest control afforded by the compounds of the present invention is not limited, however, to these species.

The specific species, for which control is exemplified below, are: fall armyworm, *Spodoptera frugiperda*; tobacco budworm, *Heliothis virescens*; southern corn rootworm, *Diabrotica undecimpunctata* howardi; aster leafhopper, *Macrosteles fascifrons*. The pest control afforded by the compounds of the present invention is not limited, however, to these species.

Application

Arthropods are controlled in agricultural crops and animals and humans are protected by applying one or more of the compounds of this invention, in an effective amount, to the locus of infestation, to the area to be protected, directly to the pests to be controlled, or to their environment. A preferred method of application is by spraying with spray equipment that distributes the compound on the foliage, in the soil, or to the plant part that is infested or needs to be protected. Alternatively, granular formulations of these compounds can be applied to soil or foliage or, optionally, incorporated into the soil. Either aerial or ground application can be used. Because of the diversity of behavior patterns and habitats of the animal and human health species, many different methods of application are employed. These include direct and residual sprays, baits, ear tags, soil treatment and many others.

The pyrazoline compound(s) of this invention can be applied directly, but most often application will be of a formulation comprising one or more compounds of this invention, in an agriculturally suitable carrier or diluent. A most preferred method of application involves spraying a water dispersion or refined oil solution of the compounds. The compound(s) can also be incorporated into baits which are consumed or in devices such as traps and the like that entice the arthropod to ingest or otherwise contact the toxicant compound(s).

The rate of application of Formula I, II or III compounds required for effective control will depend on such factors as the species of arthropod to be controlled, the pest's life stage, its size, its location, the host crop, time of year of application, ambient moisture, temperature conditions, and the like. In general, application rates of 0.01 to 2 kg of active ingredient per hectare are sufficient to provide effective control in large scale field operations under normal circumstances, but as little as 0.001 kg/hectare may be sufficient or as much as 8 kg/hectare may be required for agricultural use, or 0.1 mg/ft$^2$ to 20 mg/ft$^2$ for home use, depending upon the factors listed above.

The following Examples demonstrate the control efficacy of compounds of Formulae I, II and III on specific arthropod pests wherein Compounds 1 through 55 are depicted in the Examples and Tables A, B and C and summarized in Table D, respectively.

TABLE D

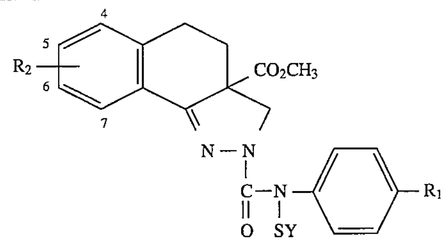

| CMPD | $R_1$ | $R_2$ | Y |
|---|---|---|---|
| 1 | $CF_3$ | H | $N(CH[CH_3]_2)CO_2Et$ |
| 2 | $CF_3$ | H | $CO_2$s-Bu |
| 3 | $CF_3$ | H | $N(n\text{-}Bu)_2$ |
| 4 | $CF_3$ | 5-Cl | $N(CH_3)CO_2$n-hexyl |
| 5 | $CF_3$ | H | $N(CH_3)CO_2$n-Bu |
| 6 | $CF_3$ | H | $N(CH_3)CO_2Et$ |
| 7 | $CF_3$ | 4-F | $N(CH_3)CO_2$n-Bu |
| 8 | $CF_3$ | H | $N(CH_3)CO_2$cyclohexyl |
| 9 | $CF_3$ | H | $N(CH_3)CO_2$n-octyl |
| 10 | $CF_3$ | H | $N(CH_3)CO_2$n-decyl |
| 11 | $CF_3$ | 4-F | $N[CH(CH_3)_2]CO_2Et$ |
| 12 | $CF_3$ | H | $N(CH_3)CO_2$n-dodecyl |
| 13 | $CF_3$ | H | $N(CH_3)CO_2$n-hexyl |
| 14 | $CF_3$ | 5-Cl | $CO_2$s-Bu |
| 15 | $CF_3$ | 5-Cl | $N[CH(CH_3)_2]CO_2Et$ |
| 16 | $CF_3$ | 5-Cl | $N(CH_3)CO_2Et$ |
| 17 | $CF_3$ | 5-Cl | $N(CH_3)CO_2$n-octyl |
| 18 | $CF_3$ | 4-F | $CO_2$s-Bu |
| 19 | $CF_3$ | 5-Cl | $N(CH_3)CO_2$n-Bu |
| 20 | $CF_3$ | 5-Cl | $N[CH_3(CH_3)_2]CO_2$n-Bu |
| 21 | $CF_3$ | 5-Cl | $N(CH_3)CO_2$n-dodecyl |
| 22 | $CF_3$ | 5-Cl | $N(CH_3)CO_2$cyclohexyl |
| 23 | $CF_3$ | 5-Cl | $N(CH_3)CO_2(CH_2)_2OBu$ |
| 24 | $CF_3$ | 5-Cl | $N(CH_3)CO_2C_{14}H_{29}$ |
| 25 | $CF_3$ | 5-Cl | $N(CH_3)CO_2C_{16}H_{33}$ |
| 26 | $CF_3$ | 5-Cl | $N(CH_3)CO_2C_{18}H_{37}$ |

TABLE D-continued

| | | | |
|---|---|---|---|
| 27 | $CF_3$ | 5-Cl | $N(CH_3)CO_2C_{22}H_{45}$ |
| 28 | $CF_3$ | 5-Cl | $N(CH_3)CO_2(CH_2)_2O(CH_2)_2OBu$ |

| CMPD | $R_1$ | $R_2$ | R3 | Y |
|---|---|---|---|---|
| 29 | $CF_3$ | 4-Cl | 4-F | $N[CH(CH_3)_2]CO_2Et$ |
| 31 | $CF_3$ | 4-Cl | 4-F | $N[CH(CH_3)_2]CO_2Bu$ |
| 32 | $CF_3$ | 4-Cl | 4-F | $N[CH(CH_3)CH_2CH_3]CO_2Et$ |
| 33 | $CF_3$ | 4-Cl | 4-F | $CO_2$s-Bu |
| 34 | $CF_3$ | 4-Cl | 4-F | $N(CH_3)CO_2$cyclohexyl |

| CMPD | $R_1$ | $R_2$ | R3 | Q |
|---|---|---|---|---|
| 30 | $CF_3$ | 4-Cl | 4-Cl | $SN[CH(CH_3)_2]CO_2Et$ |
| 35 | $CF_3$ | 4-Cl | 4-Cl | $SN(CH_3)CO_2$s-Bu |
| 36 | $CF_3$ | 4-Cl | 4-Cl | $SCO_2$s-Bu |
| 37 | Cl | 4-Cl | 4-Cl | $SCO_2$s-Bu |
| 38 | $CF_3$ | 4-Cl | 4-Cl | $CO_2CH_3$ |
| 39 | $CF_3$ | 4-Cl | 4-F | $COCH_3$ |
| 40 | $CF_3$ | 4-Cl | 4-Cl | $SN[CH(CH_3)_2]CO_2Et$ |
| 41 | $CF_3$ | 4-Cl | 4-Cl | $COCH_3$ |
| 42 | 4-Cl | 4-Cl | 4-F | $COCH_3$ |
| 43 | Br | 4-Cl | 4-F | $COCH_3$ |
| 44 | $CF_3$ | 4-Cl | 4-F | $CO_2CH_3$ |
| 45 | $CF_3$ | 4-Cl | 4-F | COPh |
| 46 | $CF_3$ | 4-Cl | 4-Cl | $COCH_2CH_3$ |
| 47 | $CF_3$ | 4-Cl | 4-Cl | $COCOCH_2CH_3$ |
| 48 | $CF_3$ | 4-Cl | 4-Cl | COn-Bu |
| 49 | Cl | 4-Cl | 4-Cl | $COCH_3$ |
| 50 | Cl | 4-Cl | 4-Cl | $COCH_2CH_3$ |
| 51 | Cl | 4-Cl | 4-Cl | $CO_2CH_3$ |
| 52 | $CF_3$ | 4-Cl | 4-Cl | CO-4-Cl−Ph |
| 53 | $CF_3$ | 4-Cl | 4-Cl | COt-Bu |
| 54 | $CF_3$ | 4-Cl | 4-Cl | $CO_2Ph$ |

EXAMPLE 56

Fall Armyworm

Test units, each consisting of an 8-ounce plastic cup containing a layer of wheat germ diet, approx. 0.5 cm thick, were prepared. Ten third-instar larvae of fall armyworm (*Spodoptera frugiperda*) were placed into each cup. Solutions of each of the test compounds (acetone/distilled water 75/25 solvent) were sprayed onto the cups, a single solution per set of three cups. Spraying was accomplished by passing the cups, on a conveyor belt, directly beneath a flat fan hydraulic nozzle which discharged the spray at a rate of 0.5 pounds of active ingredient per acre (about 0.55 kg/ha) at 30 p.s.i. The cups were then covered and held at 27 C. and 50% relative humidity for 72 hours, after which time mortality readings were taken.

Of the compounds tested on fall armyworm, the following resulted in greater than or equal to 80% mortality: 1, 2, 4, 5, 6, 7, 9, 10, 11, 12, 13, 16, 17, 19, 20, 21, 22, 23, 24, 25, 26, 27, 28, 29, 30, 31, 32, 33, 35, 36, 38, 41, 42, 43, 44, 45, 46, 47, 48, 49, 50, 51, 52, 53, and 54.

EXAMPLE 57

Tobacco Budworm

The test procedure of Example 56 was repeated for efficacy against third-instar larvae of the tobacco budworm (*Heliothis virescens*) except that mortality was assessed at 48 hours. Of the compounds tested on tobacco budworm, the following resulted in greater than or equal to 80% mortality: 2, 4, 7, 11, 16, 17, 19, 20, 21, 22, 23, 24, 25, 26, 27, 28, 29, 30, 31, 32, 33, 35, 36, 38, 41, 42, 43, 44, 45, 46, 48, 49, 50, 51, 52, 53 and 54.

EXAMPLE 58

European Corn Borer

Test units, each consisting of an 8-ounce plastic cup containing a one-inch square of wheat germ/soyflour diet, were prepared. Five third-instar larvae of the European corn borer (*Ostrinia nubilalis*) were placed into each cup. Sets of three test units were sprayed as described in Example 56 with individual solutions of the test compounds. The cups were then covered and held at 27 C. and 50% relative humidity for 48 hours, after which time mortality readings were taken. Of the compounds tested on European corn borer, the following resulted in greater than or equal to 80% mortality: no testing.

EXAMPLE 59

Southern Corn Rootworm

Test units, each consisting of an 8-ounce plastic containing 1 sprouted corn (*Zea mays*) see, were prepared. Sets of three test units were sprayed as described in Example 56 with individual solutions of the test compounds. After the spray on the cups had dried, five third-instar larvae of the southern corn rootworm (*Diabrotica undecimpunctata howardi*) were placed into each cup. A moistened dental wick was inserted into each sup to prevent drying and the cups were then covered. The cups were then held at 27 C. and 50% relative humidity for 48 hours, after which time mortality readings were taken.

Of the compounds tested on southern corn rootworm, the following resulted in greater than or equal to 80% mortality: 1, 2, 3, 4, 6, 7, 9, 10, 11, 13, 16, 17, 19, 20, 21, 22, 23, 24, 25, 26, 27, 28, 29, 30, 31, 32, 35, 36, 38, 41, 42, 44, 45, 47, 48, 49 and 51.

EXAMPLE 60

Aster Leafhopper

Test units were prepared from a series of 12-ounce cups, each containing oat (*Avena sativa*) seedlings in a 1-inch layer of sterilized soil. Sets of three test units were sprayed as described in Example 56 with individual solutions of the below-listed compounds. After the oats had dried from the spraying, between 10 and 15 adult aster leafhoppers (*Mas-*

*crosteles fascifroms*) were aspirated into each of the cups. The cups were held at 27 C. and 50% relative humidity for 48 hours, after which time mortality readings were taken.

Of the compounds tested on aster leafhopper, the following resulted in greater than or equal to 80% mortality: 1, 2, 3, 4, 6, 7, 8, 9, 10, 11, 12, 13, 16, 17, 19, 20, 21, 22, 23, 24, 25, 26, 28, 30, 31, 35, 36, 38, 41, 42, 43, 44, 45, 47, 49, 50 and 51.

EXAMPLE 61

Boll Weevil

Five adult boll weevils (*Anthonomus grandis*) were placed into each of a series of 9-ounce cups. The test procedure employed was then otherwise the same as in Example 56 with three cups per treatment. Mortality readings were taken 48 hours after treatment.

Of the compounds tested on boll weevil, the following resulted in greater than or equal to 80% mortality: 16, 21, 22, 23, 24, 25, 26, 27, 28, 30, 35, 36, 38, 41, 42, 43, 44, 46, 48, 49, 50, 51, 52 and 54.

What is claimed is:

1. A compound of the formula:

I wherein $R_1$ is $C_1$ to $C_6$ haloalkylthio, $C_1$ to $C_6$ haloalkylsulfinyl or $C_1$ to $C_6$ haloalkylsulfonyl;

$R_2$, and $R_3$ are independently selected from $R_4$, halogen, CN, $N_3$, SCN, $NO_2$, $OR_4$, $SR_4$, $S(O)R_4$, $S(O)_2R_4$, $OC(O)R_4$, $OS(O)_2R_4$, $CO_2R_4$, $C(O)R_4$, $C(O)NR_4R_5$, $S(O)_2NR_4R_5$, $NR_4R_5$, $NR_5C(O)R_4$, $OC(O)NHR_4$, $NR_5C(O)NHR_4$ and $NR_5S(O)_2R_4$;

$R_4$ is selected from H, $C_1$ to $C_6$ alkyl, $C_3$ to $C_6$ cycloalkyl, $C_3$ to $C_8$ alkoxycarbonylalkyl, $C_3$ to $C_6$ alkenyl, $C_3$ to $C_6$ alkynyl, $C_1$ to $C_6$ haloalkyl, $C_3$ to $C_6$ haloalkenyl, $C_1$ to $C_6$ alkyl substituted with CN, $CO_2CH_3$, $CO_2CH_2CH_3$, $OCH_3$, $OCH_2CH_3$, $SCH_3$, $SCH_2CH_3$ or $NO_2$, or $R_4$ is phenyl or benzyl, either optionally substituted with W; or $R_4$ and $R_5$ can be taken together as $(CH_2)_4$, or $(CH_2)_5$;

$R_5$ is selected from H, $C_1$ to $C_4$ alkyl, $C_3$ to $C_4$ alkenyl, $C_3$ to $C_4$ alkynyl or $C_1$ to $C_4$ haloalkyl;

m, n and p are independently 1 to 3;

W is halogen, CN, $NO_2$, $C_1$ to $C_2$ alkyl, $C_1$ to $C_2$ haloalkyl, $C_1$ to $C_2$ alkoxy, $C_1$ to $C_2$ haloalkoxy, $C_1$ to $C_2$ alkylthio, $C_1$ to $C_2$ haloalkylthio, $C_1$ to $C_2$ alkylsulfonyl or $C_1$ to $C_2$ haloalkylsulfonyl; and Q is $C_2$ to $C_{22}$ alkoxycarbonyl, $C_2$ to $C_{22}$ haloalkoxycarbonyl, $C_7$ to $C_{15}$ phenoxycarbonyl optionally substituted with 1 to 3 substituents selected from W; $C_7$ to $C_{15}$ phenyl carbonyl optionally substituted with 1 to 3 substituents independently selected from W; $C_2$ to $C_{22}$ alkyl carbonyl, $C_2$ to $C_{22}$ haloalkyl carbonyl, CHO, $C(O)CO_2R_5$, or $C_8$ to $C_{12}$ benzyloxycarbonyl optionally substituted with 1 to 3 substituents independently selected from W; with the proviso that $R_3$ is other than $CO_2R_4$, $C(O)R_4$, $SO_2NR_4R_5$ or $CONR_4R_5$.

2. A compound according to claim 1 wherein:

$R_2$ is H, halogen, CN, $NO_2$, $OCH_3$, $OCF_2H$, $OCH_2CF_3$, $OCF_3$, $SCH_3$, $SCF_2H$, $SCF_3$, $CF_3$, $OCF_2CF_2H$ or phenoxy;

$R_3$ is independently $R_2$ or $CO_2R_4$;

Q is $C_2$ to $C_4$ alkyoxycarbonyl, $C_2$ to $C_4$ alkylcarbonyl, $C_7$ to $C_8$ phenylcarbonyl or CHO; and m, n or p are independently 1 to 2 and one substituent is in the 4-position.

3. An arthropodicidal composition comprising an arthropodicidally effective amount of a compound according to claims 1 or 2 and a carrier therefor.

4. A method for controlling arthropods comprising applying to them or to their environment an arthropodicidally effective amount of a compound according to claims 1 or 2.

* * * * *